US012692269B2

(12) United States Patent
Crawford et al.

(10) Patent No.: US 12,692,269 B2
(45) Date of Patent: Jul. 28, 2026

(54) THERAPEUTIC COMPOUNDS

(71) Applicant: Genentech, Inc., South San Francisco, CA (US)

(72) Inventors: James John Crawford, San Carlos, CA (US); Jason Robert Zbieg, Montara, CA (US)

(73) Assignee: Genentech, Inc., South San Francisco, CA (US)

( * ) Notice: Subject to any disclaimer, the term of this patent is extended or adjusted under 35 U.S.C. 154(b) by 948 days.

(21) Appl. No.: 17/826,102

(22) Filed: May 26, 2022

(65) Prior Publication Data

US 2023/0002396 A1 Jan. 5, 2023

Related U.S. Application Data

(63) Continuation of application No. PCT/US2020/062141, filed on Nov. 25, 2020.

(60) Provisional application No. 62/943,745, filed on Dec. 4, 2019, provisional application No. 62/941,515, filed on Nov. 27, 2019.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .................................................... C07D 487/04
See application file for complete search history.

(56) References Cited

U.S. PATENT DOCUMENTS

| | | | |
|---|---|---|---|
| 8,796,285 B2 | 8/2014 | Zhang et al. |
| 2010/0221211 A1 | 9/2010 | Furuyama et al. |
| 2012/0088775 A1 | 4/2012 | Zhang et al. |
| 2012/0277224 A1 | 11/2012 | McCall et al. |
| 2012/0289496 A1 | 11/2012 | Nagarathnam et al. |

FOREIGN PATENT DOCUMENTS

| | | | |
|---|---|---|---|
| CN | 101321763 A | 12/2008 |
| CN | 101906105 A | 12/2010 |
| CN | 102503945 A | 6/2012 |
| CN | 103596958 A | 2/2014 |
| WO | 2007/048066 A2 | 4/2007 |
| WO | 2007/048066 A3 | 4/2007 |
| WO | 2008/134035 A1 | 11/2008 |
| WO | 2012/149157 A2 | 11/2012 |
| WO | 2014/066795 A1 | 5/2014 |
| WO | 2017/058716 A1 | 4/2017 |
| WO | 2018/165204 A1 | 9/2018 |
| WO | 2018/198077 A2 | 11/2018 |
| WO | 2018/198077 A3 | 11/2018 |
| WO | 2019/232216 A1 | 12/2019 |

OTHER PUBLICATIONS

International Preliminary Report on Patentability—PCT/US2020/062141 issued May 17, 2022, pp. 1-8.
International Search Report with Written Opinion—PCT/US2020/062141 mailed Jan. 2, 2021, pp. 1-10.
Petrova, O.V., et al., "Synthesis of Functionalized 2-(2-Pyrrolyl)pyrazolo[1,5-a]pyrimidines" Russian J Org Chem 39(10):1471-1476 (Oct. 1, 2003).
Song, J., et al., "Research progress on cancer treatment targeting the Hippo-YAP signaling pathway" Chin J Clin Oncol (Chinese w/Eng. Abstract), 42(17):876-880 (Aug. 20, 2015).
"International Preliminary Report on Patentability—PCT/US2019/034660" (Report Issuance Date: Dec. 1, 2020; Chapter I),:pp. 1-8 (Dec. 10, 2020).
"International Search Report—PCT/US2019/034660" (w/Written Opinion),:pp. 1-11 (Aug. 13, 2019).
Neuman Organic Chemistry Textbook "11: Free Radical Substitution and Addition Reactions":1-45 ( 2013).

*Primary Examiner* — John S Kenyon
*Assistant Examiner* — Sara Elizabeth Bell
(74) *Attorney, Agent, or Firm* — Eric E. Silverman

(57) ABSTRACT

The present disclosure relates to compounds of formula (I):

(I)

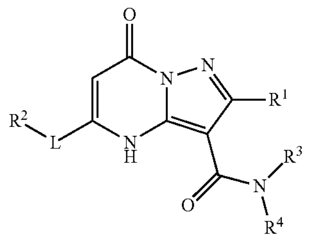

and pharmaceutically acceptable salts thereof, and compositions and uses thereof. The compounds are useful as inhibitors of the YAP:TEAD protein:protein interaction. Also included are pharmaceutical compositions comprising a compound of formula (I) or a pharmaceutically acceptable salt thereof, and methods of using such compounds and salts in the treatment of various YAP:TEAD-mediated disorders, including cancer.

21 Claims, No Drawings

THERAPEUTIC COMPOUNDS

CROSS-REFERENCE TO RELATED APPLICATIONS

This application is a continuation of International Application No. PCT/US2020/062141 having an International filing date of Nov. 25, 2020, which claims benefit of priority to U.S. Application No. 62/941,515, filed on Nov. 27, 2019 and U.S. Application No. 62/943,745, filed on Dec. 4, 2019, the contents of which are incorporated herein by reference in their entirety.

BACKGROUND

The Hippo pathway is a signaling pathway that regulates cell proliferation and cell death and determines organ size. The pathway is believed to play a role as a tumor suppressor in mammals, and disorders of the pathway are often detected in human cancers. The pathway is involved in and/or may regulate the self-renewal and differentiation of stem cells and progenitor cells. In addition, the Hippo pathway may be involved in wound healing and tissue regeneration. Furthermore, it is believed that as the Hippo pathway cross-talks with other signaling pathways such as Wnt, Notch, Hedgehog, and MAPK/ERK, it may influence a wide variety of biological events, and that its dysfunction could be involved in many human diseases in addition to cancer.

The Hippo signaling pathway core consists of a cascade of kinases (Hippo-MST1-2 being upstream of Lats 1-2 and NDRI-2) leading to the phosphorylation of two transcriptional co-activators, YAP (Yes-Associated Protein) and TAZ (Transcription co-activator with PDZ binding motif or tafazzin). Non-phosphorylated, activated YAP is translocated into the cell nucleus where its major target transcription factors are the four proteins of the TEAD-domain-containing family (TEAD1-TEAD4, collectively "TEAD"). YAP together with TEAD (or other transcription factors such as Smad1, RUNX, ErbB4 and p73) has been shown to induce the expression of a variety of genes, including connective tissue growth factor (CTGF), Gli2, Birc5, Birc2, fibroblast growth factor 1 (FGF1), and amphiregulin (AREG). Like YAP, non-phosphorylated TAZ is translocated into the cell nucleus where it interacts with multiple DNA-binding transcription factors, such as peroxisome proliferator-activated receptor γ (PPARγ), thyroid transcription factor-1 (TTF-1), Pax3, TBX5, RUNX, TEAD1 and Smad2/3/4. Many of the genes activated by YAP/TAZ-transcription factor complexes mediate cell survival and proliferation. Therefore, under some conditions YAP and/or TAZ acts as an oncogene and the Hippo pathway acts as a tumor suppressor.

Because the Hippo signaling pathway is a regulator of animal development, organ size control and stem cell regulation, it has been implicated in cancer development. In vitro, the overexpression of YAP or TAZ in mammary epithelial cells induces cell transformation, through interaction of both proteins with the TEAD family of transcription factors. Increased YAP/TAZ transcriptional activity induces oncogenic properties such as epithelial-mesenchymal transition and was also shown to confer stem cells properties to breast cancer cells. In vivo, in mouse liver, the overexpression of YAP or the genetic knockout of its upstream regulators MST1-2 triggers the development of hepatocellular carcinomas. Furthermore, when the tumor suppressor NF2 is inactivated in the mouse liver, the development of hepatocellular carcinomas can be blocked completely by the co-inactivation of YAP.

It is believed that deregulation of the Hippo tumor suppressor pathway is a major event in the development of a wide range of cancer types and malignancies.

Hence, pharmacological targeting of the Hippo cascade through inhibition of YAP, TAZ, TEAD, and/or the YAP:TEAD protein-protein interaction would be a valuable approach for the treatment of cancers that harbor functional alterations of this pathway.

SUMMARY

The present disclosure is directed to compounds of formula (I)

(I)

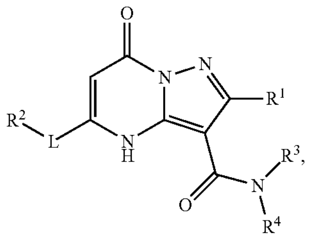

or a pharmaceutically acceptable salt, stereoisomer, tautomer, or deuterated analog thereof, wherein:

$R^1$ is selected from the group consisting of $C(O)N(R^a)(R^b)$, $C_{6-20}$aryl, 5-20 membered heteroaryl, 5-20 membered heterocyclyl, and $C_{1-6}$alkyl, wherein the $C_{6-20}$aryl, 5-20 membered heteroaryl and 5-20 membered heterocyclyl of $R^1$ are independently optionally substituted with one or more substituents selected from the group consisting of halo, OH, cyano, $C_{1-6}$alkyl, $C_{1-6}$haloalkyl, $C_{1-6}$alkoxy, $C_{3-8}$cycloalkyl, and $C_{6-10}$aryl, and wherein the $C_{1-6}$alkyl of $R^1$ is optionally substituted with one or more substituents selected from the group consisting of halogen, OH, cyano, $C_{1-6}$alkyl, $C_{1-6}$haloalkyl, $C_{1-6}$alkoxy, $C_{3-8}$cycloalkyl, and $C_{6-10}$aryl;

$R^a$ and $R^b$ are each independently H or $C_{1-6}$alkyl, wherein the $C_{1-6}$alkyl is optionally substituted with one or more substituents selected from the group consisting of halo, OH, cyano, $C_{1-6}$alkyl, $C_{1-6}$haloalkyl, and $C_{1-6}$alkoxy, or $R^a$ and $R^b$ are taken, together with the atoms to which they attached, to form a 3-10 membered heterocyclyl, wherein the 3-10 membered heterocyclyl is optionally substituted with one or more substituents selected from the group consisting of halo, OH, cyano, $C_{1-6}$alkyl, $C_{1-6}$haloalkyl, and $C_{1-6}$alkoxy;

L is absent or is $*—O—CH_2—**$, $*—CH_2—O—$, or —O—, wherein  denotes the point of attachment to the $R^2$ moiety and * denotes the point of attachment to the remainder of the molecule;

$R^2$ is $C_{2-12}$alkyl, $C_{2-12}$alkenyl, or $C_{6-10}$aryl, wherein the $C_{2-12}$alkyl, $C_{2-12}$alkenyl, and $C_{6-10}$aryl of $R^2$ are independently optionally substituted with one or more substituents selected from the group consisting of halo, OH, cyano, $C_{1-6}$alkyl, $C_{1-6}$haloalkyl, $C_{1-6}$alkoxy, $C_{6-10}$aryl, and $C_{3-10}$cycloalkyl, wherein the $C_{1-6}$alkyl, $C_{1-6}$alkoxy, and $C_{3-10}$cycloalkyl are independently optionally further substituted with one or more halo, $C_{1-6}$haloalkyl, $C_{6-10}$aryl, or $C_{3-10}$cycloalkyl; and $R^3$ and $R^4$ are each independently H or $C_{1-6}$alkyl, wherein the $C_{1-6}$alkyl is optionally substituted with one or more substituents selected from the group consisting of halo, OH, cyano, $C_{1-6}$alkyl, $C_{1-6}$haloalkyl, and $C_{1-6}$alkoxy, or $R^3$ and $R^4$, together with the atoms to which they are attached, form a 3-10 membered heterocyclyl, wherein the 3-10 membered heterocyclyl is optionally substituted with one or more substituents selected from the group consisting of halo, OH, cyano, and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy. Some other embodiments provide pharmaceutical compositions comprising a compound described above, or a pharmaceutically acceptable salt thereof, and a pharmaceutically acceptable carrier, diluent or excipient.

Some other embodiments provide pharmaceutical compositions comprising a compound described above, and a therapeutically inert carrier.

Some other embodiments provide a compound as described above, or a pharmaceutically acceptable salt thereof, for use in medical therapy.

Some other embodiments provide a compound as described above, or a pharmaceutically acceptable salt thereof, for use as a therapeutically active substance.

Some other embodiments provide a compound as described above, or a pharmaceutically acceptable salt thereof, for the treatment or prophylaxis of cancer.

Some other embodiments provide a compound as described above, or a pharmaceutically acceptable salt thereof, for the preparation of a medicament for the treatment or prophylaxis of cancer.

Some other embodiments provide a method for treating cancer in a mammal comprising, administering a therapeutically effective amount of a compound as described above, or a pharmaceutically acceptable salt thereof, to the mammal.

Some other embodiments provide a compound as described above, or a pharmaceutically acceptable salt thereof, for modulating the YAP:TEAD protein-protein interaction.

Some other embodiments provide a compound as described above, or a pharmaceutically acceptable salt thereof, for the treatment or prophylaxis of a disease or condition mediated by YAP:TEAD activity.

Some other embodiments provide a use of a compound as described above, or a pharmaceutically acceptable salt thereof, for the preparation of a medicament for the treatment or prophylaxis of a disease or condition that is mediated by YAP:TEAD activity.

Some other embodiments provide a method for modulating YAP:TEAD activity, comprising contacting YAP:TEAD with a compound as described above, or a pharmaceutically acceptable salt thereof.

Some other embodiments provide a method for treating a disease or condition mediated by YAP:TEAD activity in a mammal, comprising administering a therapeutically effective amount of a compound as described above, or a pharmaceutically acceptable salt thereof, to the mammal.

Also provided are methods of making a compound of Formula (I), or a pharmaceutically acceptable salt, stereoisomer, tautomer, or deuterated compound thereof. Kits comprising a compound detailed herein, or a pharmaceutically acceptable salt, stereoisomer, tautomer, or deuterated compound thereof, and optionally instructions for use are also provided.

DETAILED DESCRIPTION

I. Definitions

Unless otherwise indicated, the following specific terms and phrases used in the description and claims are defined as follows:

The terms “moiety” and “substituent” refer to an atom or group of chemically bonded atoms that is attached to another atom or molecule by one or more chemical bonds thereby forming part of a molecule.

The term “substituted” refers to the replacement of at least one of hydrogen atom of a compound or moiety with another substituent or moiety. Examples of such substituents include, without limitation, halogen, —OH, —CN, oxo, alkoxy, alkyl, aryl, heteroaryl, haloalkyl, haloalkoxy, cycloalkyl and heterocycle. For example, the term “alkyl substituted by halogen” refers to the fact that one or more hydrogen atoms of a alkyl (as defined below) is replaced by one or more halogen atoms (e.g., trifluoromethyl, difluoromethyl, fluoromethyl, chloromethyl, etc.).

The term “alkyl” refers to an aliphatic straight-chain or branched-chain saturated hydrocarbon moiety having 1 to 20 carbon atoms unless provided otherwise. For example, in particular embodiments, the alkyl has 1 to 10 carbon atoms. In particular embodiments the alkyl has 1 to 6 carbon atoms. Alkyl groups may be optionally substituted independently with one or more substituents described herein.

The term “alkoxy” denotes a group of the formula —O—R', wherein R' is an alkyl group. Alkoxy groups may be optionally substituted independently with one or more substituents described herein. Examples of alkoxy moieties include methoxy, ethoxy, isopropoxy, and tert-butoxy.

“Aryl” means a cyclic aromatic hydrocarbon moiety having a mono-, bi- or tricyclic aromatic ring of 5 to 16 carbon ring atoms unless provided otherwise. For example, in particular embodiments the aryl has 6 to 10 carbon atoms. Bicyclic aryl ring systems include fused bicyclics having two fused five-membered aryl rings (denoted as 5-5), having a five-membered aryl ring and a fused six-membered aryl ring (denoted as 5-6 and as 6-5), and having two fused six-membered aryl rings (denoted as 6-6). The aryl group can be optionally substituted as defined herein. Examples of aryl moieties include, but are not limited to, phenyl, naphthyl, phenanthryl, fluorenyl, indenyl, pentalenyl, azulenyl, and the like. The term “aryl” also includes partially hydrogenated derivatives of the cyclic aromatic hydrocarbon moiety provided that at least one ring of the cyclic aromatic hydrocarbon moiety is aromatic, each being optionally substituted.

The term “heteroaryl” denotes an aromatic heterocyclic mono-, bi- or tricyclic ring system of 5 to 16 ring atoms unless provided otherwise, comprising 1, 2, 3 or 4 heteroatoms selected from N, O and S, the remaining ring atoms being carbon. For example, in some aspects, monocyclic heteroaryl rings may be 5-6 membered. In some aspects, heteroaryl rings may contain 5 to 10 carbon atoms. Bicyclic heteroaryl ring systems include fused bicyclics having two fused five-membered heteroaryl rings (denoted as 5-5), having a five-membered heteroaryl ring and a fused six-membered heteroaryl ring (denoted as 5-6 and 6-5), and having two fused six-membered heteroaryl rings (denoted as 6-6). The heteroaryl group can be optionally substituted as defined herein. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms “halo”, “halogen” and “halide”, which may be used interchangeably, refer to a substituent fluoro, chloro, bromo, or iodo.

The term “haloalkyl” denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl or trifluoromethyl.

“Cycloalkyl” means a saturated or partially unsaturated carbocyclic moiety having mono-, bi- (including bridged bicyclic) or tricyclic rings and 3 to 10 carbon atoms in the ring unless provided otherwise. For example, in particular embodiments cycloalkyl contains from 3 to 8 carbon atoms (i.e., ($C_3$-$C_8$)cycloalkyl). In other particular embodiments cycloalkyl contains from 3 to 6 carbon atoms (i.e., ($C_3$-$C_6$) cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl), bicyclo[3.1.0]hexanyl, bicyclo[3.1.0]hexenyl, bicyclo[3.1.1]heptanyl, and bicyclo[3.1.1]heptenyl. The cycloalkyl moiety can be attached in a “spirocycloakyl” fashion such as “spirocyclopropyl”:

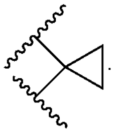

The cycloalkyl moiety can optionally be substituted with one or more substituents.

“Heterocycle” or “heterocyclyl” refers to a 3, 4, 5, 6 and 7-membered monocyclic, 7, 8, 9 and 10-membered bicyclic (including bridged bicyclic) or 10, 11, 12, 13, 14 and 15-membered bicyclic heterocyclic moiety, unless provided otherwise, that is saturated or partially unsaturated, and has one or more (e.g., 1, 2, 3 or 4 heteroatoms selected from oxygen, nitrogen and sulfur in the ring with the remaining ring atoms being carbon. For example, in particular embodiments heterocycle or heterocyclyl refers to a 4, 5, 6 or 7-membered heterocycle. In some aspects, the heterocycle is a heterocycloalkyl. When used in reference to a ring atom of a heterocycle, a nitrogen or sulfur may also be in an oxidized form, and a nitrogen may be substituted with one or more groups such as $C_1$-$C_6$alkyl. The heterocycle can be attached to its pendant group at any heteroatom or carbon atom that results in a stable structure. Any of the heterocycle ring atoms can be optionally substituted with one or more substituents described herein. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, azabicyclo[2.2.1]heptanyl, azabicyclo[3.1.0]hexanyl, azabicyclo[3.1.1]heptanyl, octahydroindolyl, or tetrahydroquinolinyl.

The term “fused bicyclic” denotes a ring system including two fused rings, including bridged cycloalkyl and bridged heterocycloalkyl as defined elsewhere herein. The rings are each independently, aryl, heteroaryl, cycloalkyl, and heterocycle. In some aspects, the rings are each independently, $C_{5-6}$ aryl, 5-6 membered heteroaryl, $C_{3-6}$ cycloalkyl, and 4-6 membered heterocycle. Non-limiting examples of fused bicyclic ring systems include $C_{5-6}$ aryl-$C_{5-6}$ aryl, $C_{5-6}$ aryl-4-6 membered heteroaryl, and $C_{5-6}$ aryl-$C_{5-6}$ cycloalkyl.

Unless otherwise indicated, the term “hydrogen” or “hydro” refers to the moiety of a hydrogen atom (—H) and not $H_2$.

In the description herein, if the stereochemistry of a structure or a portion of a structure is not indicated with, for example, bold wedged, or dashed lines, the structure or portion of the structure is to be interpreted as encompassing all stereoisomers of it. In some cases, however, where more than one chiral center exists, the structures and names may be represented as single enantiomers to help describe the relative stereochemistry.

Unless otherwise indicated, the term “a compound of the formula” or “a compound of formula” or “compounds of the formula” or “compounds of formula” refers to any compound selected from the genus of compounds as defined by the formula (including any pharmaceutically acceptable salt or ester of any such compound if not otherwise noted).

The term “pharmaceutically acceptable salts” refers to those salts which retain the biological effectiveness and properties of the free bases or free acids, which are not biologically or otherwise undesirable. As used herein, “pharmaceutically acceptable” refers to a carrier, diluent or excipient that is compatible with the other ingredients of the formulation and not deleterious to the recipient thereof. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula (I), which can be useful as an intermediate for isolating or purifying a compound of formula (I). The compounds of the present invention can also be present in the form of pharmaceutically acceptable esters (e.g., the methyl and ethyl esters of the acids of formula (I) to be used as prodrugs). The compounds of the present invention can also be solvated, e.g. hydrated. The solvation can be effected in the course of the manufacturing process or can take place e.g. as a consequence of hygroscopic properties of an initially anhydrous compound of formula (I).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, regioisomers and individual isomers (e.g., separate enantiomers) are all intended to be encompassed within the scope of the present invention.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in compounds (l), (m) and (n) for illustrative purposes, while stereochemistry is definitively established, such as from x-ray crystallographic data.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The terms "pharmaceutically acceptable carrier", "pharmaceutically acceptable carrier, adjuvant, or vehicle", or "therapeutically inert carrier" may be used interchangeably throughout and are intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutically acceptable carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The term "patient" or "individual" as used herein, refers to an animal, such as a mammal, such as a human. In one embodiment, patient or individual refers to a human.

In the practice of the method of the present invention, a therapeutically effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

II. Generic and Subgeneric Formulae of Disclosed Compounds

In one aspect, provided is a compound of formula (I):

(I)

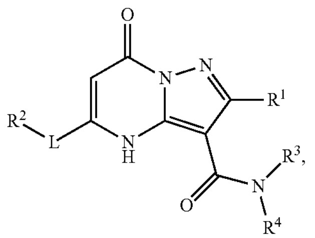

or a pharmaceutically acceptable salt, stereoisomer, tautomer, or deuterated compound thereof, wherein:

$R^1$ is selected from the group consisting of $C(O)N(R^a)(R^b)$, $C_{6-20}$aryl, 5-20 membered heteroaryl, 5-20 membered heterocyclyl, and $C_{1-6}$alkyl, wherein the $C_{6-20}$aryl, 5-20 membered heteroaryl and 5-20 membered heterocyclyl of $R^1$ are independently optionally substituted with one or more substituents selected from the group consisting of halo, OH, cyano, $C_{1-6}$alkyl, $C_{1-6}$haloalkyl, $C_{1-6}$alkoxy, $C_{3-8}$cycloalkyl, and $C_{6-10}$aryl, and wherein the $C_{1-6}$alkyl of $R^1$ is optionally substituted with one or more substituents selected from the group consisting of halogen, OH, cyano, $C_{1-6}$alkyl, $C_{1-6}$haloalkyl, $C_{1-6}$alkoxy, $C_{3-8}$cycloalkyl, and $C_{6-10}$aryl;

$R^a$ and $R^b$ are each independently H or $C_{1-6}$alkyl, wherein the $C_{1-6}$alkyl is optionally substituted with one or more substituents selected from the group consisting of halo, OH, cyano, $C_{1-6}$alkyl, $C_{1-6}$haloalkyl, and $C_{1-6}$alkoxy, or $R^a$ and $R^b$ are taken, together with the atoms to which they attached, to form a 3-10 membered heterocyclyl, wherein the 3-10 membered heterocyclyl is optionally substituted with one or more substituents selected from the group consisting of halo, OH, cyano, $C_{1-6}$alkyl, $C_{1-6}$haloalkyl, and $C_{1-6}$alkoxy;

L is absent or is *—O—$CH_2$—**, *—$CH_2$—O—, or —O—, wherein  denotes the point of attachment to the $R^2$ moiety and * denotes the point of attachment to the remainder of the molecule;

$R^2$ is $C_{2-12}$alkyl, $C_{2-12}$alkenyl, or $C_{6-10}$aryl, wherein the $C_{2-12}$alkyl, $C_{2-12}$alkenyl, and $C_{6-10}$aryl of $R^2$ are independently optionally substituted with one or more substituents selected from the group consisting of halo, OH, cyano, $C_{1-6}$alkyl, $C_{1-6}$haloalkyl, $C_{1-6}$alkoxy, $C_{6-10}$aryl, and $C_{3-10}$cycloalkyl, wherein the $C_{1-6}$alkyl, $C_{1-6}$alkoxy, and $C_{3-10}$cycloalkyl are independently optionally further substituted with one or more halo, $C_{1-6}$haloalkyl, $C_{6-10}$aryl, or $C_{3-10}$cycloalkyl; and $R^3$ and $R^4$ are each independently H or $C_{1-6}$alkyl, wherein the $C_{1-6}$alkyl is optionally substituted with one or more substituents selected from the group consisting of halo, OH, cyano, $C_{1-6}$alkyl, $C_{1-6}$haloalkyl, and $C_{1-6}$alkoxy, or $R^3$ and $R^4$, together with the atoms to which they are attached, form a 3-10 membered heterocyclyl, wherein the 3-10 membered heterocyclyl is optionally substituted with one or more substituents selected from the group consisting of halo, OH, cyano, and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy.

Disclosed compounds are provided as shown in the following embodiments.

In some embodiments, the compound of formula (I) is a deuterated compound.

In some embodiments, $R^1$ is $C(O)N(R^a)(R^b)$, wherein $R^a$ and $R^b$ are each independently H or $C_{1-6}$alkyl, wherein the $C_{1-6}$alkyl is optionally substituted with one or more substituents selected from the group consisting of halo, OH, cyano, $C_{1-6}$alkyl, $C_{1-6}$haloalkyl, and $C_{1-6}$alkoxy.

In some embodiments, $R^1$ is $C(O)N(R^a)(R^b)$, wherein $R^a$ and $R^b$ are each methyl.

In some embodiments, $R^1$ is selected from the group consisting of $C(O)N(R^a)(R^b)$, wherein $R^a$ and $R^b$ are taken, together with the atoms to which they attached, to form a 4-membered heterocyclyl, wherein the 4-membered heterocyclyl is optionally substituted with one or more substituents selected from the group consisting of halo, OH, cyano, $C_{1-6}$alkyl, $C_{1-6}$haloalkyl, and $C_{1-6}$alkoxy.

In some embodiments, $R^1$ is 5-6 membered heteroaryl optionally substituted with one or more substituents selected from the group consisting of halo, OH, cyano, $C_{1-6}$alkyl, $C_{1-6}$haloalkyl, $C_{1-6}$alkoxy, $C_{3-8}$cycloalkyl, and $C_{6-10}$aryl.

In some embodiments, $R^1$ is a 6-membered heteroaryl.

In some embodiments, $R^1$ is 5-6 membered heterocyclyl optionally substituted with one or more substituents selected from the group consisting of halo, OH, cyano, $C_{1-6}$alkyl, $C_{1-6}$haloalkyl, $C_{1-6}$alkoxy, $C_{3-8}$cycloalkyl, and $C_{6-10}$aryl.

In some embodiments, $R^1$ is $C_{1-6}$alkyl optionally substituted with one or more substituents selected from the group consisting of halogen, OH, cyano, $C_{1-6}$alkyl, $C_{1-6}$haloalkyl, $C_{1-6}$alkoxy, $C_{3-8}$cycloalkyl, and $C_{6-10}$aryl.

In some embodiments, L is absent.

In some embodiments, $R^2$ is phenyl optionally substituted with one or more substituents selected from the group consisting of halo, OH, cyano, $C_{1-6}$alkyl, $C_{1-6}$haloalkyl, $C_{1-6}$alkoxy, $C_{6-10}$aryl, and $C_{3-10}$cycloalkyl, wherein the $C_{1-6}$alkyl, $C_{1-6}$alkoxy, and $C_{3-10}$cycloalkyl are independently optionally further substituted with one or more deuterium, halo, $C_{1-6}$haloalkyl, $C_{6-10}$aryl, or $C_{3-10}$cycloalkyl.

In some embodiments, $R^2$ is phenyl substituted with $C_{5-6}$cycloalkyl optionally further substituted with one or more deuterium, halo, $C_{1-6}$haloalkyl, $C_{6-10}$aryl, or $C_{3-10}$cycloalkyl.

In some embodiments, $R^2$ is phenyl substituted with methylene substituted with $C_5$cycloalkyl.

In some embodiments, $R^3$ and $R^4$, together with the atoms to which they are attached, form a 3-10 membered heterocyclyl, wherein the 3-10 membered heterocyclyl is optionally substituted with one or more substituents selected from the group consisting of halo, OH, cyano and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy.

In some embodiments, $R^3$ and $R^4$, together with the atoms to which they are attached, form a 4-membered heterocyclyl optionally substituted with one or more substituents selected from the group consisting of halo, OH, cyano, and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy.

In embodiments, $R^1$ is selected from the group consisting of $C(O)N(R^a)(R^b)$, $C_{6-20}$aryl, 5-20 membered heteroaryl, 5-20 membered heterocyclyl, and $C_{1-6}$alkyl, wherein the $C_{6-20}$aryl, 5-20 membered heteroaryl and 5-20 membered heterocyclyl of $R^1$ are independently optionally substituted with one or more substituents selected from the group consisting of cyano, $C_{1-6}$alkyl, $C_{1-6}$haloalkyl, and $C_{1-6}$alkoxy, and wherein the $C_{1-6}$alkyl of $R^1$ is optionally substituted with one or more substituents selected from the group consisting of halogen and OH; $R^a$ and $R^b$ are each independently $C_{1-6}$alkyl, or $R^a$ and $R^b$ are taken, together with the atoms to which they attached, to form a 3-10 membered heterocyclyl, wherein the 3-10 membered heterocyclyl is optionally substituted with one or more $C_{1-6}$alkyl; L is absent or is —O— or *—O—$CH_2$—, wherein  denotes the point of attachment to the $R^2$ moiety and * denotes the point of attachment to the remainder of the molecule; $R^2$ is $C_{2-12}$alkyl, $C_{2-12}$alkenyl, or $C_{6-10}$aryl, wherein the $C_{2-12}$alkyl, $C_{2-12}$alkenyl, and $C_{6-10}$aryl of $R^2$ are independently optionally substituted with one or more substituents selected from the group consisting of halo, $C_{1-6}$alkyl, $C_{1-6}$alkoxy, $C_{6-10}$aryl, and $C_{3-10}$cycloalkyl, wherein the $C_{1-6}$alkyl, $C_{1-6}$alkoxy, and $C_{3-10}$cycloalkyl are independently optionally further substituted with one or more halo, $C_{6-10}$aryl, or $C_{3-10}$cycloalkyl; and $R^3$ and $R^4$, together with the atoms to which they are attached, form a 3-10 membered heterocyclyl, wherein the 3-10 membered heterocyclyl is optionally substituted with one or more substituents selected from the group consisting of cyano, and $C_{1-6}$alkyl, wherein the $C_{1-6}$alkyl is further optionally substituted with one or more halo.

In some embodiments, L is absent, such that the compound of formula (I) is a compound of formula (IA):

(IA)

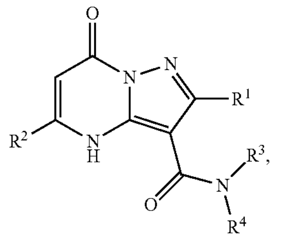

or a pharmaceutically acceptable salt, stereoisomer, tautomer, or deuterated analog thereof.

In embodiments, $R^1$ is 5-20 membered heteroaryl optionally substituted with $C_{1-6}$alkyl.

In embodiments, $R^1$ is 6-membered heteroaryl optionally substituted with $C_{1-6}$alkyl.

In embodiments, $R^1$ is pyrazinyl or pyrimidinyl optionally substituted with methyl.

In embodiments, $R^1$ is pyrazinyl or pyrimidinyl optionally substituted with methyl.

In embodiments, $R^2$ is phenyl optionally substituted with one or more halo and substituted with $C_{5-6}$cycloalkyl optionally further substituted with one or more halo.

In embodiments, $R^2$ is phenyl substituted with $C_{5-6}$cycloalkyl.

In embodiments, $R^2$ is phenyl substituted with cyclohexyl.

In embodiments, $R^2$ is phenyl optionally substituted with one or more fluoro and substituted with $C_{5-6}$cycloalkyl.

In embodiments, $R^2$ is phenyl optionally substituted with one or more fluoro and substituted with cyclohexyl.

In embodiments, $R^2$ is phenyl substituted with $C_{1-6}$alkyl optionally further substituted with $C_{5-6}$cycloalkyl.

In embodiments, $R^2$ is phenyl substituted with methyl optionally further substituted with cyclopentyl.

In embodiments, $R^3$ and $R^4$, together with the atoms to which they are attached, form a 4-membered heterocyclyl, wherein the heterocyclyl is substituted with one or more $C_{1-6}$alkyl, wherein at least one of said $C_{1-6}$alkyl is further substituted with halo.

In embodiments, $R^3$ and $R^4$, together with the atoms to which they are attached, form azetidine, wherein the heterocyclyl is substituted with one or more methyl, wherein one methyl is further substituted with fluoro.

In embodiments, $R^2$ is phenyl optionally substituted with one or more halo and substituted with $C_{5-6}$cycloalkyl optionally further substituted with one or more halo; and $R^3$ and $R^4$, together with the atoms to which they are attached, form a 4-membered heterocyclyl, wherein the heterocyclyl is substituted with one or more $C_{1-6}$alkyl, wherein at least one of said $C_{1-6}$alkyl is further substituted with halo.

In embodiments, $R^2$ is phenyl substituted with $C_{5-6}$cycloalkyl; $R^3$ and $R^4$, together with the atoms to which they are attached, form a 4-membered heterocyclyl, wherein the heterocyclyl is substituted with one or more $C_{1-6}$alkyl, wherein at least one of said $C_{1-6}$alkyl is further substituted with halo.

In embodiments, $R^2$ is phenyl substituted with cyclohexyl; and $R^3$ and $R^4$, together with the atoms to which they are attached, form azetidine, wherein the heterocyclyl is substituted with one or more methyl, wherein one methyl is further substituted with fluoro.

In embodiments, $R^2$ is phenyl optionally substituted with one or more fluoro and substituted with cyclohexyl; and $R^3$ and $R^4$, together with the atoms to which they are attached, form azetidine, wherein the heterocyclyl is substituted with one or more methyl, wherein one methyl is further substituted with fluoro.

In embodiments, $R^2$ is phenyl substituted with $C_{1-6}$alkyl optionally further substituted with $C_{5-6}$cycloalkyl; and $R^3$ and $R^4$, together with the atoms to which they are attached, form azetidine, wherein the heterocyclyl is substituted with one or more methyl, wherein one methyl is further substituted with fluoro.

In embodiments, $R^2$ is phenyl substituted with methyl optionally further substituted with cyclopentyl; and $R^3$ and $R^4$, together with the atoms to which they are attached, form azetidine, wherein the heterocyclyl is substituted with one or more methyl, wherein one methyl is further substituted with fluoro.

In embodiments, $R^1$ is 5-20 membered heteroaryl optionally substituted with $C_{1-6}$alkyl; $R^2$ is phenyl optionally substituted with one or more halo and substituted with $C_{5-6}$cycloalkyl optionally further substituted with one or more halo; and $R^3$ and $R^4$, together with the atoms to which they are attached, form a 4-membered heterocyclyl, wherein the heterocyclyl is substituted with one or more $C_{1-6}$alkyl, wherein at least one of said $C_{1-6}$alkyl is further substituted with halo.

In embodiments, $R^1$ is 6-membered heteroaryl optionally substituted with $C_{1-6}$alkyl; $R^2$ is phenyl substituted with $C_{5-6}$cycloalkyl; $R^3$ and $R^4$, together with the atoms to which they are attached, form a 4-membered heterocyclyl, wherein the heterocyclyl is substituted with one or more $C_{1-6}$alkyl, wherein at least one of said $C_{1-6}$alkyl is further substituted with halo.

In embodiments, $R^1$ is pyrazinyl or pyrimidinyl optionally substituted with methyl; $R^2$ is phenyl substituted with cyclohexyl; and $R^3$ and $R^4$, together with the atoms to which they are attached, form azetidine, wherein the heterocyclyl is substituted with one or more methyl, wherein one methyl is further substituted with fluoro.

In embodiments, $R^1$ is pyrazinyl or pyrimidinyl optionally substituted with methyl; $R^2$ is phenyl optionally substituted with one or more fluoro and substituted with cyclohexyl; and $R^3$ and $R^4$, together with the atoms to which they are attached, form azetidine, wherein the heterocyclyl is substituted with one or more methyl, wherein one methyl is further substituted with fluoro.

In embodiments, $R^1$ is pyrazinyl or pyrimidinyl optionally substituted with methyl; $R^2$ is phenyl substituted with $C_{1-6}$alkyl optionally further substituted with $C_{5-6}$cycloalkyl; and $R^3$ and $R^4$, together with the atoms to which they are attached, form azetidine, wherein the heterocyclyl is substituted with one or more methyl, wherein one methyl is further substituted with fluoro.

In embodiments, $R^1$ is pyrazinyl or pyrimidinyl optionally substituted with methyl; $R^2$ is phenyl substituted with methyl optionally further substituted with cyclopentyl; and $R^3$ and $R^4$, together with the atoms to which they are attached, form azetidine, wherein the heterocyclyl is substituted with one or more methyl, wherein one methyl is further substituted with fluoro.

In some embodiments, the compound of formula (I) is a compound of formula (IB):

(IB)

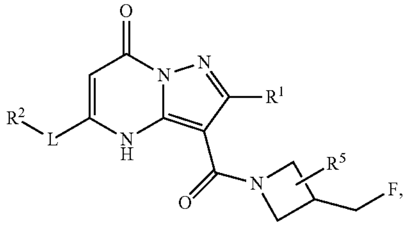

wherein $R^5$ is selected from the group consisting of H, halo, OH, cyano, and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy.

In embodiments, $R^1$ is 5-20 membered heteroaryl optionally substituted with $C_{1-6}$alkyl.

In embodiments, $R^1$ is 6-membered heteroaryl optionally substituted with $C_{1-6}$alkyl.

In embodiments, $R^1$ is pyrazinyl or pyrimidinyl optionally substituted with methyl.

In embodiments, $R^1$ is pyrazinyl or pyrimidinyl optionally substituted with methyl.

In embodiments, $R^2$ is phenyl optionally substituted with one or more halo and substituted with $C_{5-6}$cycloalkyl optionally further substituted with one or more halo.

In embodiments, $R^2$ is phenyl substituted with $C_{5-6}$cycloalkyl.

In embodiments, $R^2$ is phenyl substituted with cyclohexyl.

In embodiments, $R^2$ is phenyl optionally substituted with one or more fluoro and substituted with $C_{5-6}$cycloalkyl.

In embodiments, $R^2$ is phenyl optionally substituted with one or more fluoro and substituted with cyclohexyl.

In embodiments, $R^2$ is phenyl substituted with $C_{1-6}$alkyl optionally further substituted with $C_{5-6}$cycloalkyl.

In embodiments, $R^2$ is phenyl substituted with methyl optionally further substituted with cyclopentyl.

In embodiments, $R^1$ is 5-20 membered heteroaryl optionally substituted with $C_{1-6}$alkyl; and $R^2$ is phenyl optionally substituted with one or more halo and substituted with $C_{5-6}$cycloalkyl optionally further substituted with one or more halo.

In embodiments, $R^1$ is 6-membered heteroaryl optionally substituted with $C_{1-6}$alkyl; and $R^2$ is phenyl substituted with $C_{5-6}$cycloalkyl.

In embodiments, $R^1$ is pyrazinyl or pyrimidinyl optionally substituted with methyl; and $R^2$ is phenyl substituted with cyclohexyl.

In embodiments, $R^1$ is pyrazinyl or pyrimidinyl optionally substituted with methyl; and $R^2$ is phenyl optionally substituted with one or more fluoro and substituted with cyclohexyl.

In embodiments, $R^1$ is pyrazinyl or pyrimidinyl optionally substituted with methyl; and $R^2$ is phenyl substituted with $C_{1-6}$alkyl optionally further substituted with $C_{5-6}$cycloalkyl.

In embodiments, $R^1$ is pyrazinyl or pyrimidinyl optionally substituted with methyl; and $R^2$ is phenyl substituted with methyl optionally further substituted with cyclopentyl.

In embodiments, $R^1$ is 5-20 membered heteroaryl optionally substituted with $C_{1-6}$alkyl; $R^2$ is phenyl optionally substituted with one or more halo and substituted with $C_{5-6}$cycloalkyl optionally further substituted with one or more halo; and $R^5$ is hydrogen or methyl.

In embodiments, $R^1$ is 6-membered heteroaryl optionally substituted with $C_{1-6}$alkyl; $R^2$ is phenyl substituted with $C_{5-6}$cycloalkyl; and $R^5$ is hydrogen or methyl.

In embodiments, $R^1$ is pyrazinyl or pyrimidinyl optionally substituted with methyl; $R^2$ is phenyl substituted with cyclohexyl; and $R^5$ is hydrogen or methyl.

In embodiments, $R^1$ is pyrazinyl or pyrimidinyl optionally substituted with methyl; $R^2$ is phenyl optionally substituted with one or more fluoro and substituted with cyclohexyl; and $R^5$ is hydrogen or methyl.

In embodiments, $R^1$ is pyrazinyl or pyrimidinyl optionally substituted with methyl; $R^2$ is phenyl substituted with $C_{1-6}$alkyl optionally further substituted with $C_{5-6}$cycloalkyl; and $R^5$ is hydrogen or methyl.

In embodiments, $R^1$ is pyrazinyl or pyrimidinyl optionally substituted with methyl; $R^2$ is phenyl substituted with methyl optionally further substituted with cyclopentyl; and $R^5$ is hydrogen or methyl; and $R^5$ is hydrogen or methyl.

In some embodiments, $R^5$ is H, and the compound of formula (IB) is

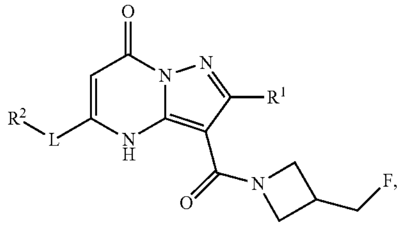

or a pharmaceutically acceptable salt, stereoisomer, tautomer, or deuterated analog thereof.

In some embodiments, $R^5$ is methyl, and the compound of formula (IB) is

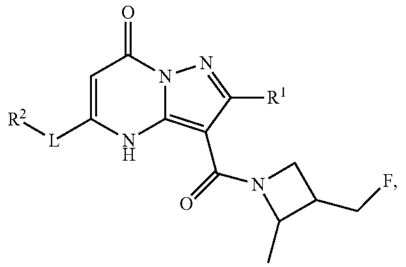

or a pharmaceutically acceptable salt, stereoisomer, tautomer, or deuterated analog thereof.

In some embodiments, the compound of formula (I) is a compound of formula (IC):

(IC)

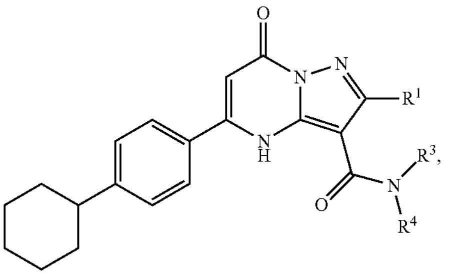

or a pharmaceutically acceptable salt, stereoisomer, tautomer, or deuterated analog thereof.

In embodiments, the compound of formula (IC) is:

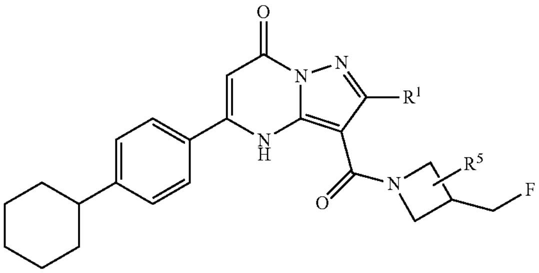

or a pharmaceutically acceptable salt, stereoisomer, tautomer, or deuterated analog thereof, wherein $R^1$ is selected from the group consisting of $C(O)N(R^a)(R^b)$, $C_{6-20}$aryl, 5-20 membered heteroaryl, 5-20 membered heterocyclyl, and $C_{1-6}$alkyl, wherein the $C_{6-20}$aryl, 5-20 membered heteroaryl and 5-20 membered heterocyclyl of $R^1$ are independently optionally substituted with one or more substituents selected from the group consisting of halo, OH, cyano, $C_{1-6}$alkyl, $C_{1-6}$haloalkyl, $C_{1-6}$alkoxy, $C_{3-8}$cycloalkyl, and $C_{6-10}$aryl, and wherein the $C_{1-6}$alkyl of $R^1$ is optionally substituted with one or more substituents selected from the group consisting of halogen, OH, cyano, $C_{1-6}$alkyl, $C_{1-6}$haloalkyl, $C_{1-6}$alkoxy, $C_{3-8}$cycloalkyl, and $C_{6-10}$aryl;

$R^a$ and $R^b$ are each independently H or $C_{1-6}$alkyl, wherein the $C_{1-6}$alkyl is optionally substituted with one or more substituents selected from the group consisting of halo, OH, cyano, $C_{1-6}$alkyl, $C_{1-6}$haloalkyl, and $C_{1-6}$alkoxy, or $R^a$ and $R^b$ are taken, together with the atoms to which they attached, to form a 3-10 membered heterocyclyl, wherein the 3-10 membered heterocyclyl is optionally substituted with one or more substituents selected from the group consisting of halo, OH, cyano, $C_{1-6}$alkyl, $C_{1-6}$haloalkyl, and $C_{1-6}$alkoxy; and $R^5$ is selected from the group consisting of H, halo, OH, cyano, and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy.

In embodiments, $R^1$ is selected from the group consisting of $C(O)N(R^a)(R^b)$, $C_{6-20}$aryl, 5-20 membered heteroaryl, 5-20 membered heterocyclyl, and $C_{1-6}$alkyl, wherein the $C_{6-20}$aryl, 5-20 membered heteroaryl and 5-20 membered heterocyclyl of $R^1$ are independently optionally substituted with one or more substituents selected from the group consisting of cyano, $C_{1-6}$alkyl and $C_{1-6}$alkoxy, and wherein the $C_{1-6}$alkyl of $R^1$ is optionally substituted with one or more substituents selected from the group consisting of halogen and OH; and $R^a$ and $R^b$ are each independently $C_{1-6}$alkyl, or $R^a$ and $R^b$ are taken, together with the atoms to which they attached, to form a 3-10 membered heterocyclyl, wherein the 3-10 membered heterocyclyl is optionally substituted with one or more $C_{1-6}$alkyl.

In embodiments, $R^1$ is 5-20 membered heteroaryl optionally substituted with $C_{1-6}$alkyl.

In embodiments, $R^1$ is 6-membered heteroaryl optionally substituted with $C_{1-6}$alkyl.

In embodiments, $R^1$ is pyrazinyl or pyrimidinyl optionally substituted with methyl.

In embodiments, $R^1$ is pyrazinyl or pyrimidinyl optionally substituted with methyl.

In embodiments, $R^5$ is H.

In embodiments, $R^5$ is methyl.

In embodiments, the compound of formula (I) includes the compounds listed in Table A and stereoisomers thereof, tautomers thereof, and pharmaceutically acceptable salts thereof.

TABLE A

| Compound number | Structure | Chemical name |
|---|---|---|
| 1 | 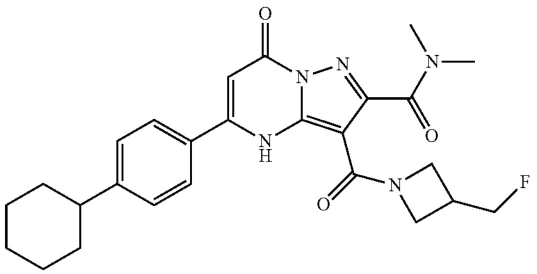 [SMILES: CN(C)C(=O)c1nn2c(=O)cc(-c3ccc(C4CCCCC4)cc3)[nH]c2c1C(=O)N1CC(CF)C1] | 5-(4-Cyclohexylphenyl)-3-(3-(fluoromethyl)azetidine-1-carbonyl)-N,N-dimethyl-7-oxo-4,7-dihydropyrazolo[1,5-a]pyrimidine-2-carboxamide |
| 2 | 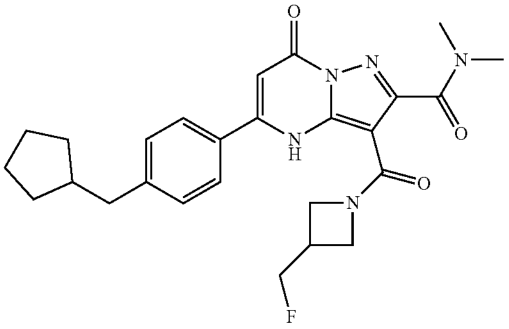 [SMILES: CN(C)C(=O)c1nn2c(=O)cc(-c3ccc(CC4CCCC4)cc3)[nH]c2c1C(=O)N1CC(CF)C1] | 5-(4-(Cyclopentylmethyl)phenyl)-3-(3-(fluoromethyl)azetidine-1-carbonyl)-N,N-dimethyl-7-oxo-4,7-dihydropyrazolo[1,5-a]pyrimidine-2-carboxamide |
| 3 | 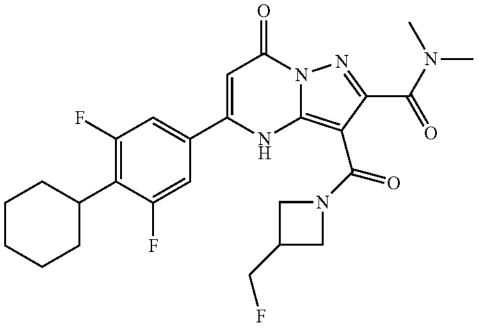 [SMILES: CN(C)C(=O)c1nn2c(=O)cc(-c3cc(F)c(C4CCCCC4)c(F)c3)[nH]c2c1C(=O)N1CC(CF)C1] | 5-(4-Cyclohexyl-3,5-difluorophenyl)-3-(3-(fluoromethyl)azetidine-1-carbonyl)-N,N-dimethyl-7-oxo-4,7-dihydropyrazolo[1,5-a]pyrimidine-2-carboxamide |
| 4 | 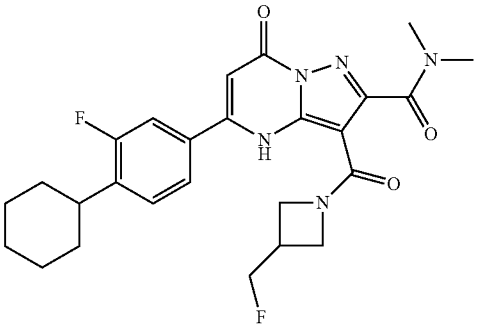 [SMILES: CN(C)C(=O)c1nn2c(=O)cc(-c3ccc(C4CCCCC4)c(F)c3)[nH]c2c1C(=O)N1CC(CF)C1] | 5-(4-Cyclohexyl-3-fluorophenyl)-3-(3-(fluoromethyl)azetidine-1-carbonyl)-N,N-dimethyl-7-oxo-4,7-dihydropyrazolo[1,5-a]pyrimidine-2-carboxamide |

TABLE A-continued

| Compound number | Structure | Chemical name |
|---|---|---|
| 5 | 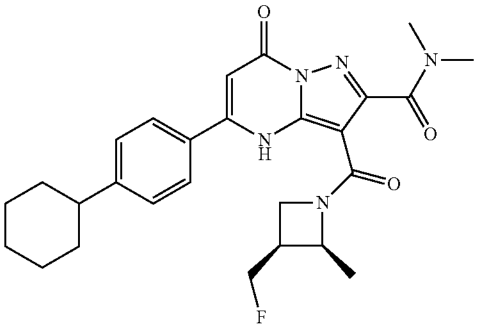 [SMILES: C[C@H]1[C@@H](CF)CN1C(=O)c1c(C(=O)N(C)C)nn2c(=O)cc(-c3ccc(C4CCCCC4)cc3)[nH]c12] | 5-(4-Cyclohexylphenyl)-3-((2S,3S)-3-(fluoromethyl)-2-methylazetidine-1-carbonyl)-N,N-dimethyl-7-oxo-4,7-dihydropyrazolo[1,5-a]pyrimidine-2-carboxamide |
| 6 | 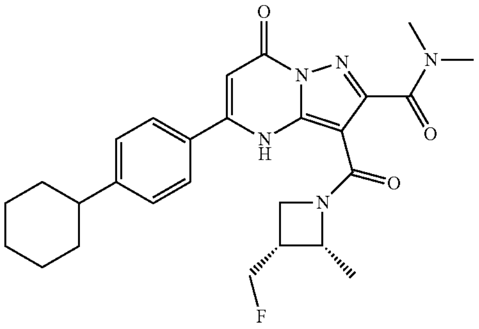 [SMILES: C[C@@H]1[C@H](CF)CN1C(=O)c1c(C(=O)N(C)C)nn2c(=O)cc(-c3ccc(C4CCCCC4)cc3)[nH]c12] | 5-(4-Cyclohexylphenyl)-3-((2R,3R)-3-(fluoromethyl)-2-methylazetidine-1-carbonyl)-N,N-dimethyl-7-oxo-4,7-dihydropyrazolo[1,5-a]pyrimidine-2-carboxamide |
| 7 | 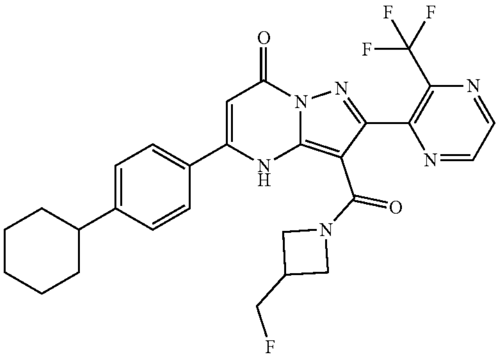 [SMILES: O=C(c1c(-c2nccnc2C(F)(F)F)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(3-(trifluoromethyl)pyrazin-2-yl)pyrazolo[1,5-a]pyrimidin-7(4H)-one |
| 8 | 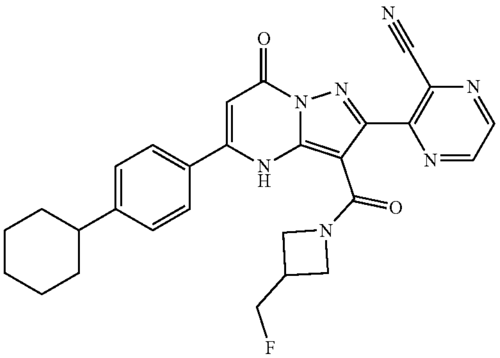 [SMILES: N#Cc1nccnc1-c1nn2c(=O)cc(-c3ccc(C4CCCCC4)cc3)[nH]c2c1C(=O)N1CC(CF)C1] | 3-(5-(4-Cyclohexylphenyl)-3-(3-(fluoromethyl)azetidine-1-carbonyl)-7-oxo-4,7-dihydropyrazolo[1,5-a]pyimidin-2-yl)pyrazine-2-carbonitrile |

TABLE A-continued

| Compound number | Structure | Chemical name |
| --- | --- | --- |
| 9 | 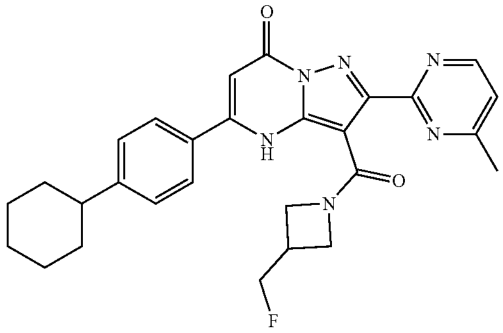 [SMILES: Cc1ccnc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(4-methylpyrimidin-2-yl)pyrazolo[1,5-a]pyrimidin-7(4H)-one |
| 10 | 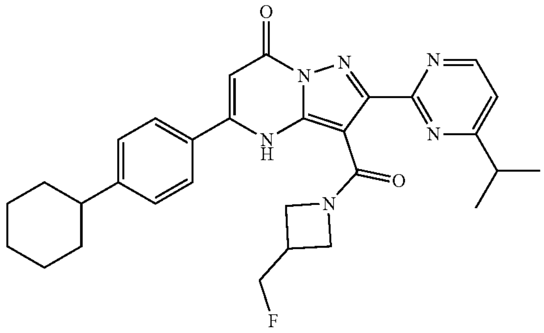 [SMILES: CC(C)c1ccnc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(4-isopropylpyrimidin-2-yl)pyrazolo[1,5-a]pyrimidin-7(4H)-one |
| 11 | 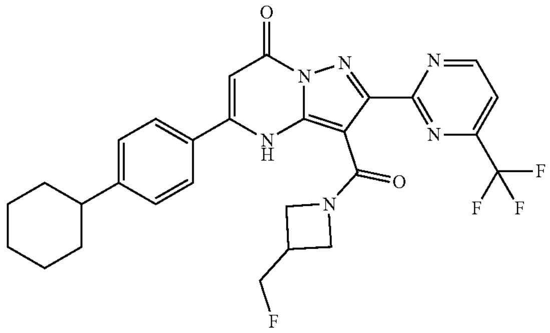 [SMILES: O=C(c1c(-c2nccc(C(F)(F)F)n2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(4-(trifluoromethyl)pyrimidin-2-yl)pyrazolo[1,5-a]pyrimidin-7(4H)-one |
| 12 | 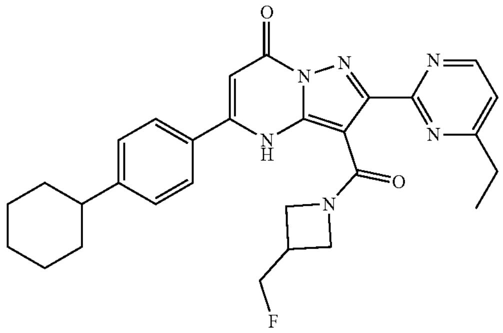 [SMILES: CCc1ccnc(-c2nn3c(=O)cc(-c4ccc(C5CCCCC5)cc4)[nH]c3c2C(=O)N2CC(CF)C2)n1] | 5-(4-Cyclohexylphenyl)-2-(4-ethylpyrimidin-2-yl)-3-(3-(fluoromethyl)azetidine-1-carbonyl)pyrazolo[1,5-a]pyrimidin-7(4H)-one |

TABLE A-continued

| Compound number | Structure | Chemical name |
|---|---|---|
| 13 | 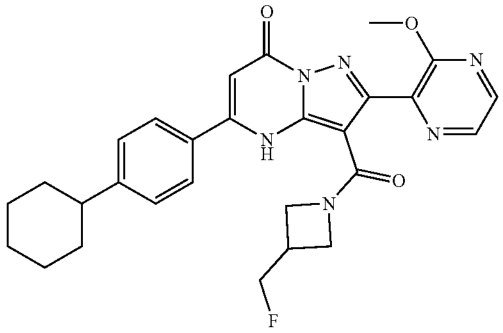 [SMILES: COc1nccnc1-c1nn2c(=O)cc(-c3ccc(C4CCCCC4)cc3)[nH]c2c1C(=O)N1CC(CF)C1] | 5-(4-Cyclohexylphenyl)-3-(3-(fluoromethyl)azetidine-1-carbonyl)-2-(3-methoxypyrazin-2-yl)pyrazolo[1,5-a]pyrimidin-7(4H)-one |
| 14 | 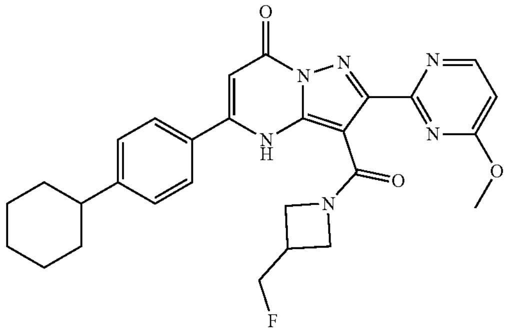 [SMILES: COc1ccnc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(4-methoxypyrimidin-2-yl)pyrazolo[1,5-a]pyrimidin-7(4H)-one |
| 15 | 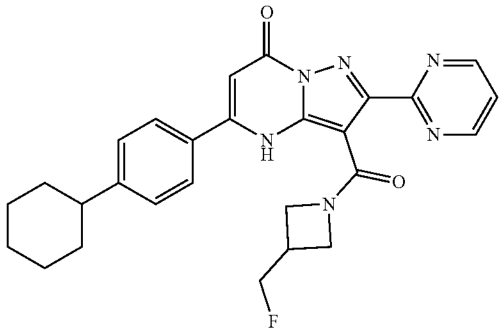 [SMILES: O=C(c1c(-c2ncccn2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(pyrimidin-2-yl)pyrazolo[1,5-a]pyrimidin-7(4H)-one |
| 16 | 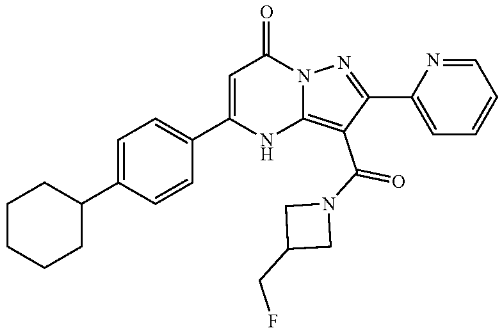 [SMILES: O=C(c1c(-c2ccccn2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(pyridin-2-yl)pyrazolo[1,5-a]pyrimidin-7(4H)-one |

TABLE A-continued

| Compound number | Structure | Chemical name |
|---|---|---|
| 17 | 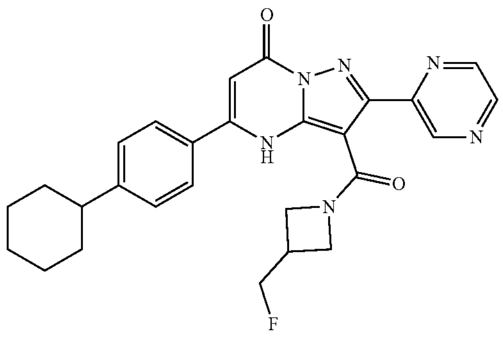 [SMILES: O=C(c1c(-c2cnccn2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(pyrazin-2-yl)pyrazolo[1,5-a]pyrimidin-7(4H)-one |
| 18 | 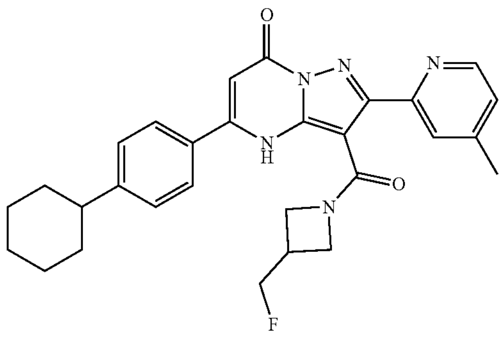 [SMILES: Cc1ccnc(-c2nn3c(=O)cc(-c4ccc(C5CCCCC5)cc4)[nH]c3c2C(=O)N2CC(CF)C2)c1] | 5-(4-Cyclohexylphenyl)-3-(3-(fluoromethyl)azetidine-1-carbonyl)-2-(4-methylpvridin-2-yl)pyrazolo[1,5-a]pyrimidin-7(4H)-one |
| 19 | 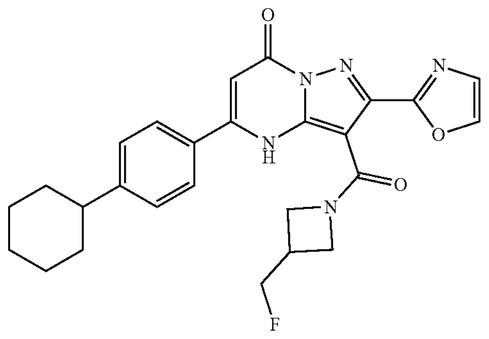 [SMILES: O=C(c1c(-c2ncco2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(oxazol-2-yl)pyrazolo[1,5-a]pyrimidin-7(4H)-one |
| 20 | 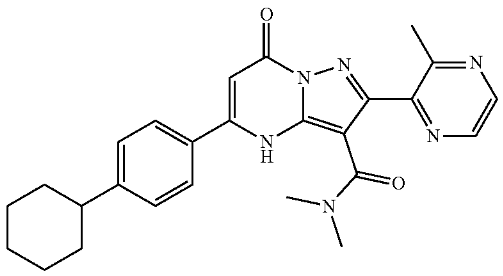 [SMILES: Cc1nccnc1-c1nn2c(=O)cc(-c3ccc(C4CCCCC4)cc3)[nH]c2c1C(=O)N(C)C] | 5-(4-Cyclohexylphenyl)-N,N-dimethyl-2-(3-methylpyrazin-2-yl)-7-oxo-4,7-dihydropyrazolo[1,5-a]pyrimidine-3-carboxamide |

TABLE A-continued

| Compound number | Structure | Chemical name |
|---|---|---|
| 21 | 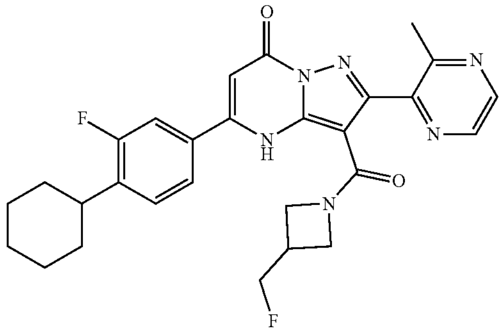 [SMILES: Cc1nccnc1-c1nn2c(=O)cc(-c3ccc(C4CCCCC4)c(F)c3)[nH]c2c1C(=O)N1CC(CF)C1] | 5-(4-cyclohexyl-3-fluorophenyl)-3-(3-(fluoromethyl)azetidine-1-carbonyl)-2-(3-methylpyrazin-2-yl)pyrazolo[1,5-a]pyrimidin-7(4H)-one |
| 22 | 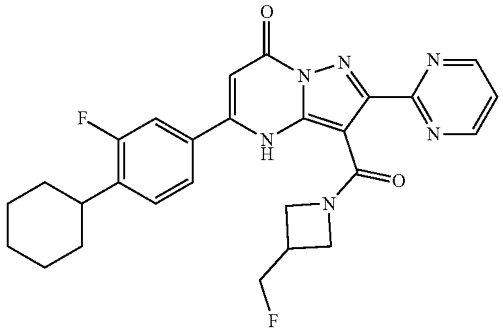 [SMILES: O=C(c1c(-c2ncccn2)nn2c(=O)cc(-c3ccc(C4CCCCC4)c(F)c3)[nH]c12)N1CC(CF)C1] | 5-(4-Cyclohexyl-3-fluorophenyl)-3-(3-(fluoromethyl)azetidine-1-carbonyl)-2-(pyrimidin-2-yl)pyrazolo[1,5-a]pyrimidin-7(4H)-one |
| 23 | 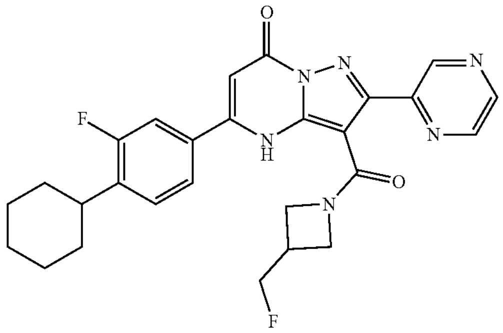 [SMILES: O=C(c1c(-c2cnccn2)nn2c(=O)cc(-c3ccc(C4CCCCC4)c(F)c3)[nH]c12)N1CC(CF)C1] | 5-(4-Cyclohexyl-3-fluorophenyl)-3-(3-(fluoromethyl)azetidine-1-carbonyl)-2-(pyrazin-2-yl)pyrazolo[1,5-a]pyrimidin-7(4H)-one |
| 24 | 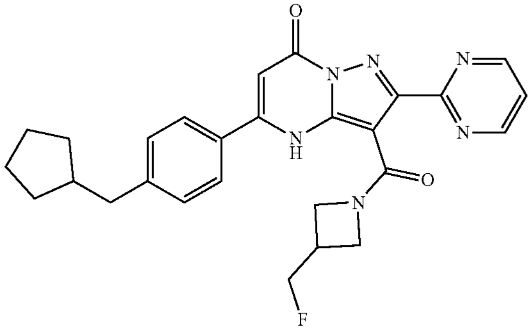 [SMILES: O=C(c1c(-c2ncccn2)nn2c(=O)cc(-c3ccc(CC4CCCC4)cc3)[nH]c12)N1CC(CF)C1] | 5-(4-(Cyclopentylmethyl)phenyl)-3-(3-(fluoromethyl)azetidine-1-carbonyl)-2-(pyrimidin-2-yl) pyrazolo[1,5-a]pyrimidin-7(4H)-one |

TABLE A-continued

| Compound number | Structure | Chemical name |
|---|---|---|
| 25 | 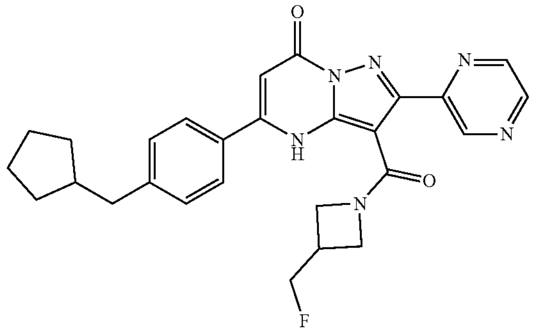 [SMILES: O=C(c1c(-c2cnccn2)nn2c(=O)cc(-c3ccc(CC4CCCC4)cc3)[nH]c12)N1CC(CF)C1] | 5-(4-(Cyclopentylmethyl)phenyl)-3-(3-(fluoromethyl)azetidine-1-carbonyl)-2-(pyrazin-2-yl)pyrazolo[1,5-a]pyrimidin-7(4H)-one |
| 26 | 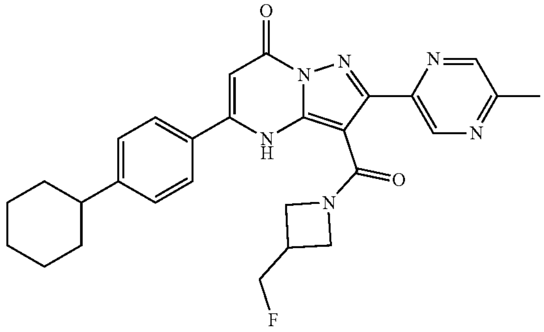 [SMILES: Cc1cnc(-c2nn3c(=O)cc(-c4ccc(C5CCCCC5)cc4)[nH]c3c2C(=O)N2CC(CF)C2)cn1] | 5-(4-Cyclohexylphenyl)-3-(3-(fluoromethyl) azetidine-1-carbonyl)-2-(5-methylpyrazin-2-yl) pyrazolo [1,5-a]pyrimidin-7(4H)-one |
| 27 | 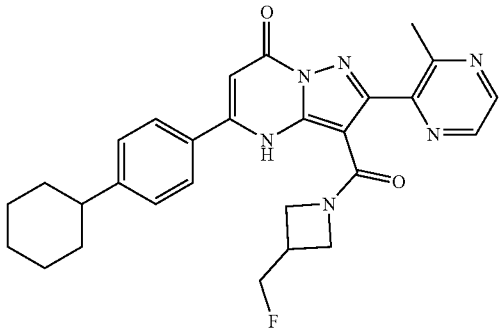 [SMILES: Cc1nccnc1-c1nn2c(=O)cc(-c3ccc(C4CCCCC4)cc3)[nH]c2c1C(=O)N1CC(CF)C1] | 5-(4-Cyclohexylphenyl)-3-(3-(fluoromethyl)azetidine-1-carbonyl)-2-(3-methylpyrazin-2-yl)pyrazolo[1,5-a]pyrimidin-7(4H)-one |
| 28 | 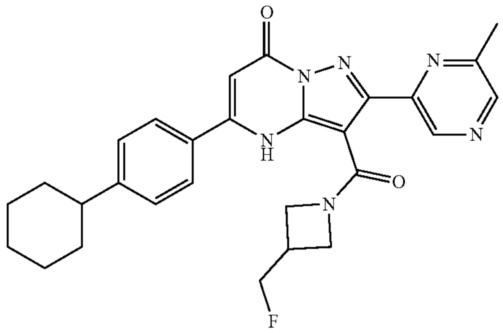 [SMILES: Cc1cncc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(6-methylpyrazin-2-yl)pyrazolo[1,5-a]pyrimidin-7(4H)-one |

TABLE A-continued

| Compound number | Structure | Chemical name |
| --- | --- | --- |
| 29 | 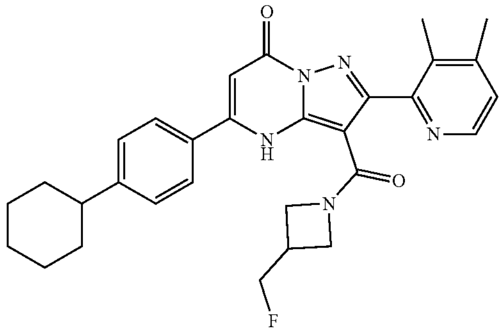 [SMILES: Cc1ccnc(-c2nn3c(=O)cc(-c4ccc(C5CCCCC5)cc4)[nH]c3c2C(=O)N2CC(CF)C2)c1C] | 5-(4-Cyclohexylphenyl)-2-(3,4-dimethylpyridin-2-yl)-3-(3-(fluoromethyl)azetidine-1-carbonyl)pyrazolo[1,5-a]pyrimidin-7(4H)-one |
| 30 | 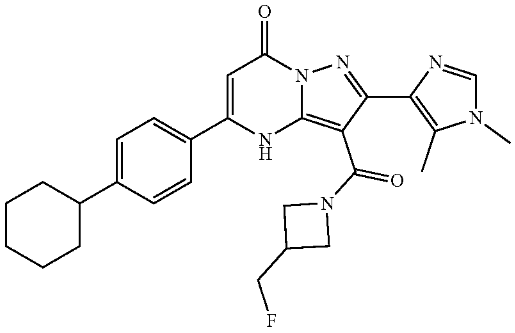 [SMILES: Cc1c(-c2nn3c(=O)cc(-c4ccc(C5CCCCC5)cc4)[nH]c3c2C(=O)N2CC(CF)C2)ncn1C] | 5-(4-Cyclohexylphenyl)-2-(1,5-dimethyl-1H-imidazol-4-yl)-3-(3-(fluoromethyl)azetidine-1-carbonyl)pyrazolo[1,5-a]pyrimidin-7(4H)-one |
| 31 | 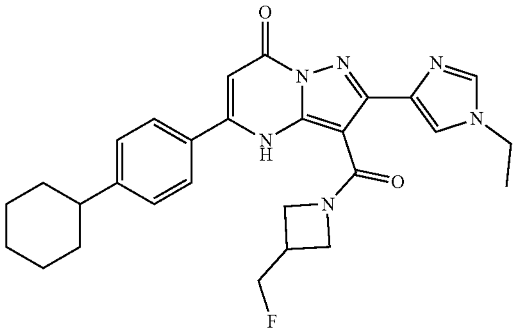 [SMILES: CCn1cnc(-c2nn3c(=O)cc(-c4ccc(C5CCCCC5)cc4)[nH]c3c2C(=O)N2CC(CF)C2)c1] | 5-(4-Cyclohexylphenyl)-2-(1-ethyl-1H-imidazol-4-yl)-3-(3-(fluoromethyl)azetidine-1-carbonyl)pyrazolo[1,5-a]pyrimidin-7(4H)-one |
| 32 | 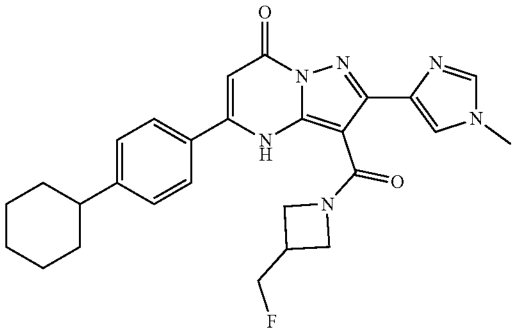 [SMILES: Cn1cnc(-c2nn3c(=O)cc(-c4ccc(C5CCCCC5)cc4)[nH]c3c2C(=O)N2CC(CF)C2)c1] | 5-(4-Cyclohexylphenyl)-3-(3-(fluoromethyl)azetidine-1-carbonyl)-2-(1-methyl-1H-imidazol-4-yl)pyrazolo[1,5-a]pyrimidin-7(4H)-one |

TABLE A-continued

| Compound number | Structure | Chemical name |
|---|---|---|
| 33 | 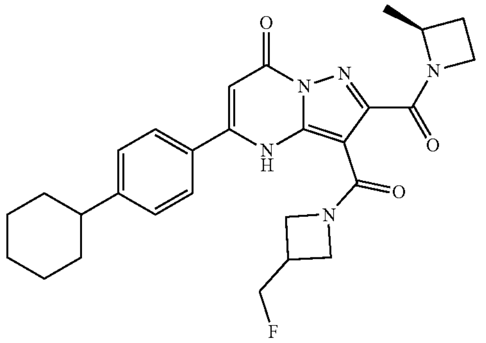 [SMILES: C[C@H]1CCN1C(=O)c1nn2c(=O)cc(-c3ccc(C4CCCCC4)cc3)[nH]c2c1C(=O)N1CC(CF)C1] | (S)-5-(4-cyclohexylphenyl)-3-(3-(fluoromethyl)azetidine-1-carbonyl)-2-(2-methylazetidine-1-carbonyl)pyrazolo[1,5-a]pyrimidin-7(4H)-one |
| 34 | 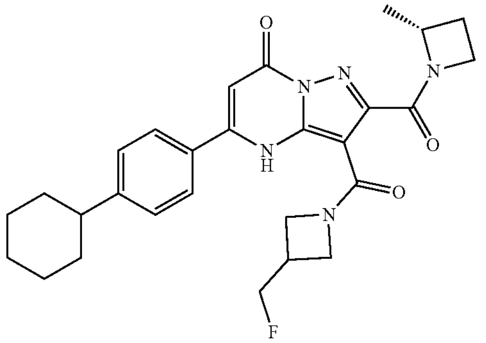 [SMILES: C[C@@H]1CCN1C(=O)c1nn2c(=O)cc(-c3ccc(C4CCCCC4)cc3)[nH]c2c1C(=O)N1CC(CF)C1] | (R)-5-(4-cyclohexylphenyl)-3-(3-(fluoromethyl)azetidine-1-carbonyl)-2-(2-methylazetidine-1-carbonyl)pyrazolo[1,5-a]pyrimidin-7(4H)-one |
| 35 | 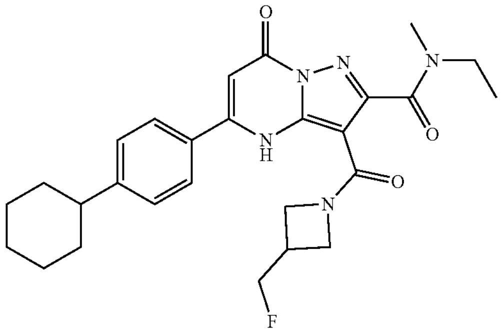 [SMILES: CCN(C)C(=O)c1nn2c(=O)cc(-c3ccc(C4CCCCC4)cc3)[nH]c2c1C(=O)N1CC(CF)C1] | 5-(4-Cyclohexylphenyl)-N-ethyl-3-(3-(fluoromethyl)azetidine-1-carbonyl)-N-methyl-7-oxo-4,7-dihydropyrazolo[1,5-a]pynmidine-2-carboxamide |
| 36 | 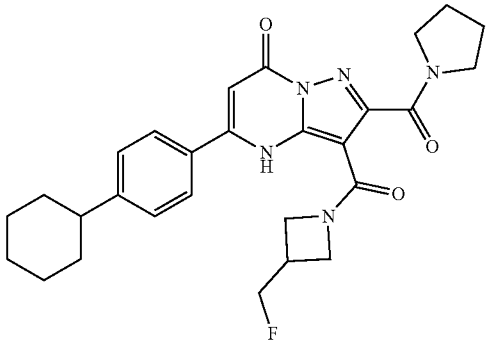 [SMILES: O=C(c1nn2c(=O)cc(-c3ccc(C4CCCCC4)cc3)[nH]c2c1C(=O)N1CC(CF)C1)N1CCCC1] | 5-(4-Cyclohexylphenyl)-3-(3-(fluoromethyl)azetidine-1-carbonyl)-2-(pyrrolidine-1-carbonyl)pyrazolo[1,5-a]pyrimidin-7(4H)-one |

TABLE A-continued

| Compound number | Structure | Chemical name |
|---|---|---|
| 37 | 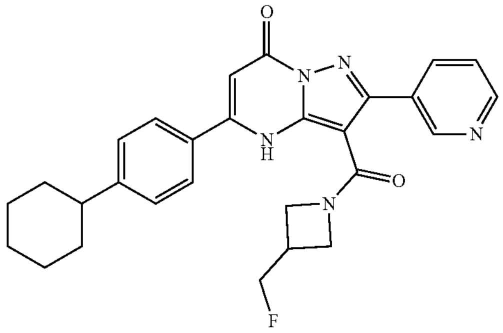 [SMILES: O=C(c1c(-c2cccnc2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(pyridin-3-yl)pyrazolo[1,5-a]pyrimidin-7(4H)-one |
| 38 | 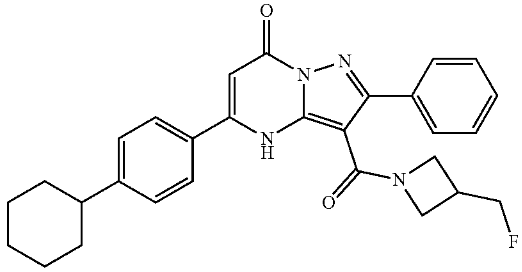 [SMILES: O=C(c1c(-c2ccccc2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-phenylpyrazolo[1,5-a]pyrimidin-7(4H)-one |
| 39 | 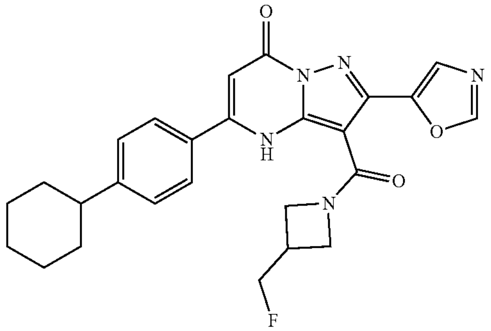 [SMILES: O=C(c1c(-c2cnco2)nn2c(=O)cc(-c3ccc(C4CCCCC4)cc3)[nH]c12)N1CC(CF)C1] | 5-(4-Cyclohexylphenyl)-3-(3-(fluoromethyl)azetidine-1-carbonyl)-2-(oxazol-5-yl)pyrazolo[1,5-a]pyrimidin-7(4H)-one |
| 40 | 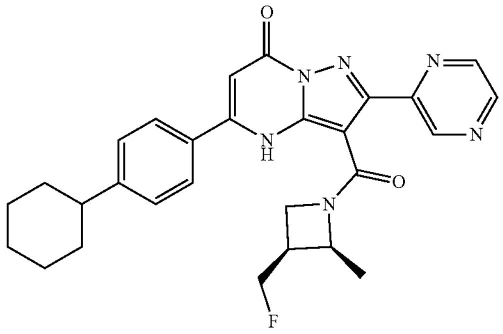 [SMILES: C[C@H]1[C@@H](CF)CN1C(=O)c1c(-c2cnccn2)nn2c(=O)cc(-c3ccc(C4CCCCC4)cc3)[nH]c12] | 5-(4-Cyclohexylphenyl)-3-((2S,3S)-3-(fluoromethyl)-2-methylazetidine-1-carbonyl)-2-(pyrazin-2-yl)pyrazolo[1,5-a]pyrimidin-7(4H)-one |

TABLE A-continued

| Compound number | Structure | Chemical name |
|---|---|---|
| 41 | 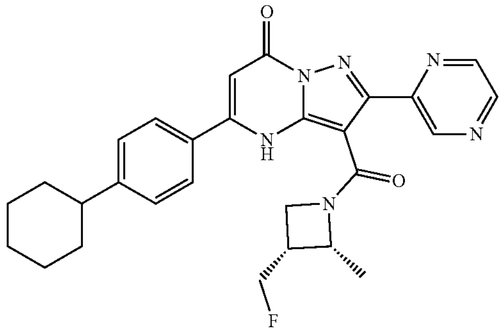 [SMILES: C[C@@H]1[C@H](CF)CN1C(=O)c1c(-c2cnccn2)nn2c(=O)cc(-c3ccc(C4CCCCC4)cc3)[nH]c12] | 5-(4-Cyclohexylphenyl)-3-((2R,3R)-3-(fluoromethyl)-2-methylazetidine-1-carbonyl)-2-(pyrazin-2-yl)pyrazolo[1,5-a]pyrimidin-7(4H)-one |
| 42 | 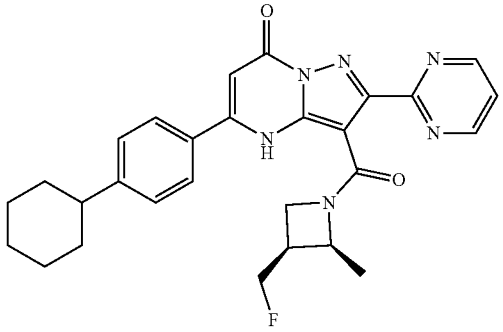 [SMILES: C[C@H]1[C@@H](CF)CN1C(=O)c1c(-c2ncccn2)nn2c(=O)cc(-c3ccc(C4CCCCC4)cc3)[nH]c12] | 5-(4-Cyclohexylphenyl)-3-((2S,3S)-3-(fluoromethyl)-2-methylazetidine-1-carbonyl)-2-(pyrimidin-2-yl)pyrazolo[1,5-a]pyrimidin-7(4H)-one |
| 43 | 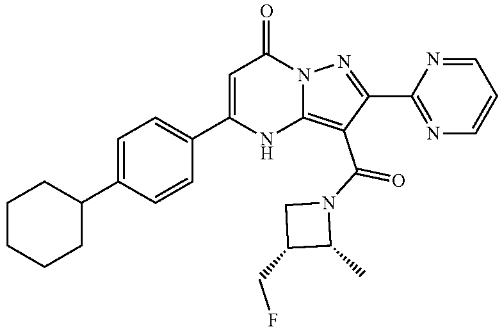 [SMILES: C[C@@H]1[C@H](CF)CN1C(=O)c1c(-c2ncccn2)nn2c(=O)cc(-c3ccc(C4CCCCC4)cc3)[nH]c12] | 5-(4-Cyclohexylphenyl)-3-((2R,3R)-3-(fluoromethyl)-2-methylazetidine-1-carbonyl)-2-(pyrimidin-2-yl)pyrazolo[1,5-a]pyrimidin-7(4H)-one |
| 44 | 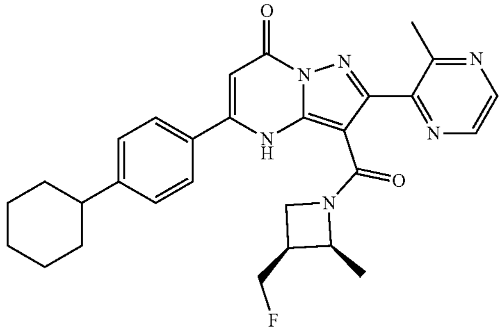 [SMILES: Cc1nccnc1-c1nn2c(=O)cc(-c3ccc(C4CCCCC4)cc3)[nH]c2c1C(=O)N1C[C@H](CF)[C@@H]1C] | 5-(4-Cyclohexylphenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one |

TABLE A-continued

| Compound number | Structure | Chemical name |
|---|---|---|
| 45 | 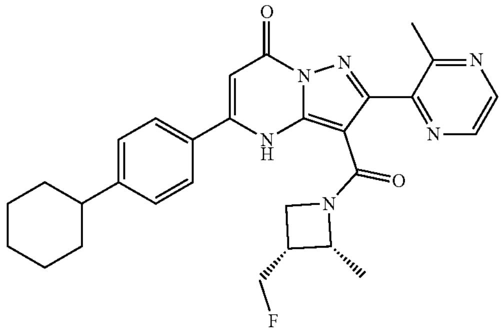 [SMILES: Cc1nccnc1-c1nn2c(=O)cc(-c3ccc(C4CCCCC4)cc3)[nH]c2c1C(=O)N1C[C@@H](CF)[C@H]1C] | 5-(4-cyclo hexylphenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one |
| 46 | 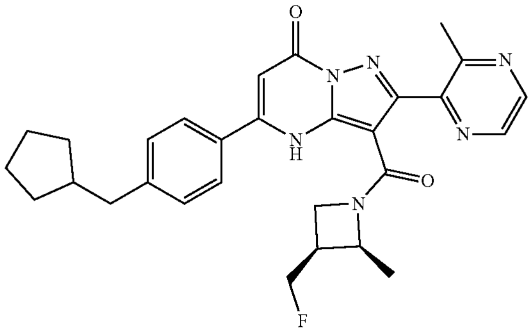 [SMILES: Cc1nccnc1-c1nn2c(=O)cc(-c3ccc(CC4CCCC4)cc3)[nH]c2c1C(=O)N1C[C@H](CF)[C@@H]1C] | 5-(4-(Cyclopentylmethyl)phenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one |
| 47 | 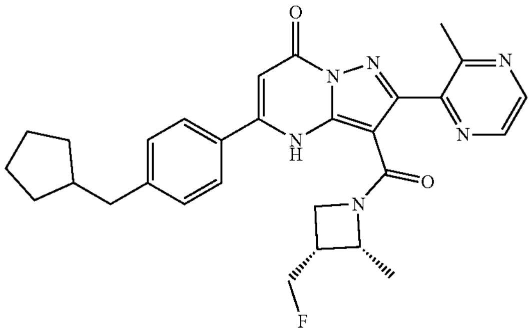 [SMILES: Cc1nccnc1-c1nn2c(=O)cc(-c3ccc(CC4CCCC4)cc3)[nH]c2c1C(=O)N1C[C@@H](CF)[C@H]1C] | 5-(4-(cyclo pentylmethyl)phenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one |
| 48 | 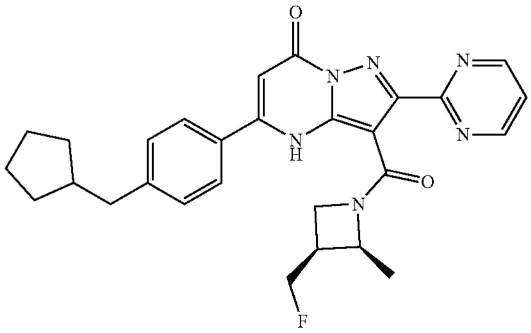 [SMILES: C[C@H]1[C@@H](CF)CN1C(=O)c1c(-c2ncccn2)nn2c(=O)cc(-c3ccc(CC4CCCC4)cc3)[nH]c12] | 5-(4-(Cyclopentylmethyl)phenyl)-3-((2S,3S)-3-(fluoromethyl)-2-methyl azetidine-1-carbonyl)-2-(3-methylpyrazin-2-yl)pyrazolo[1,5-a]pyrimidin-7(4H)-one |

TABLE A-continued

| Compound number | Structure | Chemical name |
|---|---|---|
| 49 | 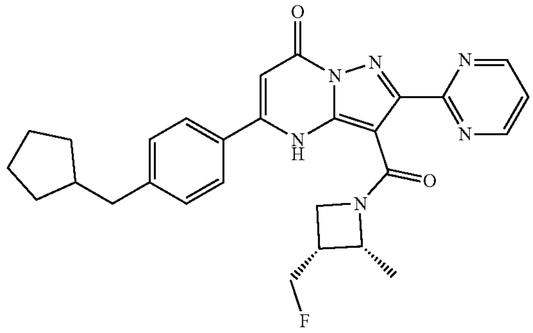 [SMILES: C[C@@H]1[C@H](CF)CN1C(=O)c1c(-c2ncccn2)nn2c(=O)cc(-c3ccc(CC4CCCC4)cc3)[nH]c12] | 5-(4-(cyclopentylmethyl)phenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one |
| 50 | 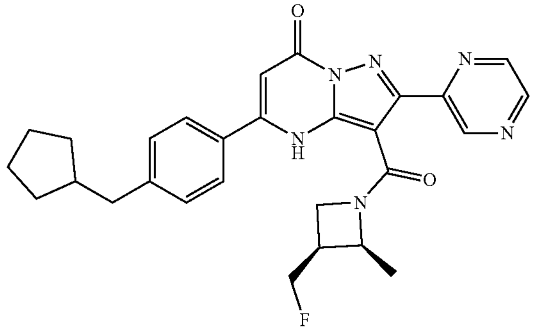 [SMILES: C[C@H]1[C@@H](CF)CN1C(=O)c1c(-c2cnccn2)nn2c(=O)cc(-c3ccc(CC4CCCC4)cc3)[nH]c12] | 5-(4-(cyclopentylmethyl)phenyl)-3-((2S,3S)-3-(fluoromethyl)-2-methylazetidine-1-carbonyl)-2-(pyrazin-2-yl)pyrazolo[1,5-a]pyrimidin-7(4H)-one |
| 51 | 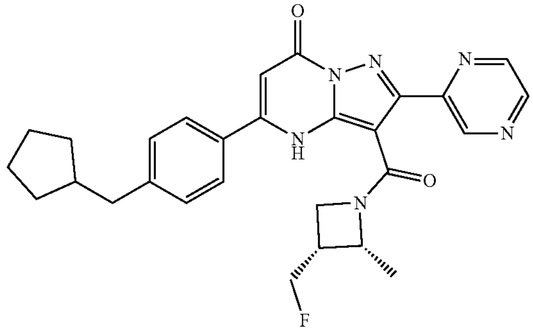 [SMILES: C[C@@H]1[C@H](CF)CN1C(=O)c1c(-c2cnccn2)nn2c(=O)cc(-c3ccc(CC4CCCC4)cc3)[nH]c12] | 5-(4-(cyclopentylmethyl)phenyl)-3-((2R,3R)-3-(fluoromethyl)-2-methylazetidine-1-carbonyl)-2-(pyrazin-2-yl)pyrazolo[1,5-a]pyrimidin-7(4H)-one |
| 52 | 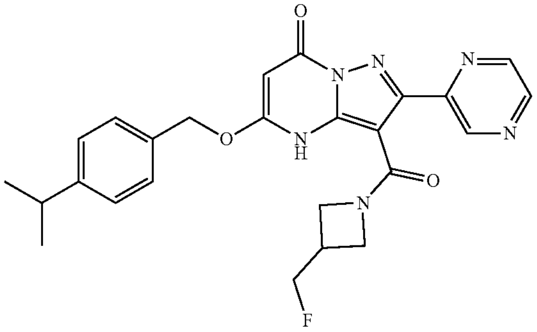 [SMILES: CC(C)c1ccc(COc2cc(=O)n3nc(-c4cnccn4)c(C(=O)N4CC(CF)C4)c3[nH]2)cc1] | 3-(3-(Fluoromethyl)azetidine-1-carbonyl)-5-((4-isopropylbenzyl)oxy)-2-(pyrazin-2-yl)pyrazolo[1,5-a]primidin-7(4H)-one |

TABLE A-continued

| Compound number | Structure | Chemical name |
|---|---|---|
| 53 | 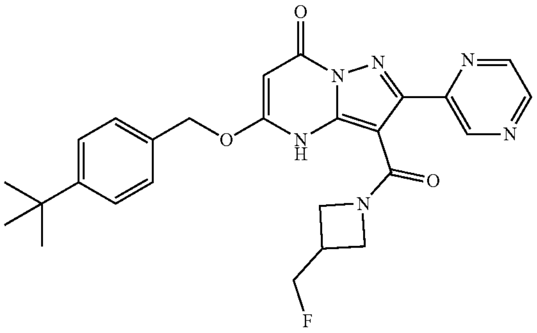 [SMILES: CC(C)(C)c1ccc(COc2cc(=O)n3nc(-c4cnccn4)c(C(=O)N4CC(CF)C4)c3[nH]2)cc1] | 5-((4-(Tert-butyl)benzyl)oxy)-3-(3-(fluoromethyl)azetidine-1-carbonyl)-2-(pyrazin-2-yl)pyrazolo[1,5-a]pyrimidin-7(4H)-one |
| 54 | 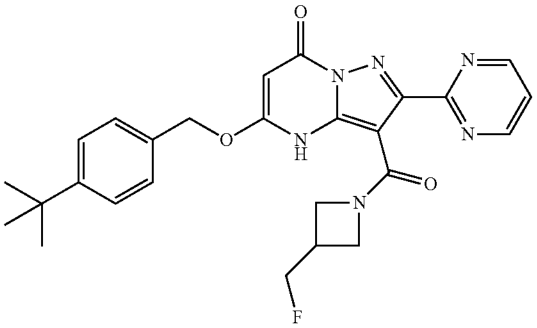 [SMILES: CC(C)(C)c1ccc(COc2cc(=O)n3nc(-c4ncccn4)c(C(=O)N4CC(CF)C4)c3[nH]2)cc1] | 5-((4-(Tert-butyl)benzyl)oxy)-3-(3-(fluoromethyl)azetidine-1-carbonyl)-2-(pyrimidin-2-yl)pyrazolo[1,5-a]pyrimidin-7(4H)-one |
| 55 | 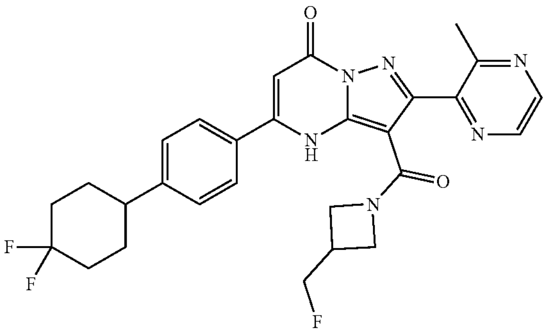 [SMILES: Cc1nccnc1-c1nn2c(=O)cc(-c3ccc(C4CCC(F)(F)CC4)cc3)[nH]c2c1C(=O)N1CC(CF)C1] | 5-(4-(4,4-Difluorocyclohexyl)phenyl)-3-(3-(fluoromethyl)azetidine-1-carbonyl)-2-(3-methylpyrazin-2-yl)pyrazolo[1,5-a]pyrimidin-7(4H)-one |
| 56 | 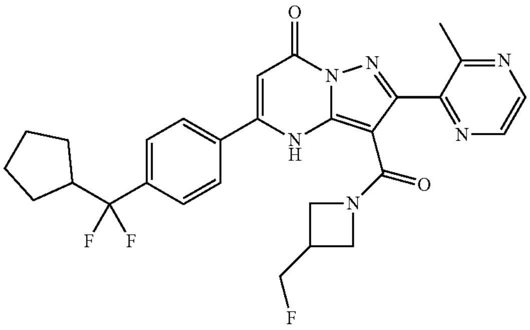 [SMILES: Cc1nccnc1-c1nn2c(=O)cc(-c3ccc(C(F)(F)C4CCCC4)cc3)[nH]c2c1C(=O)N1CC(CF)C1] | 5-(4-(Cyclopentyldifluoromethyl)phenyl)-3-(3-(fluoromethyl)azetidine-1-carbonyl)-2-(3-methylpyrazin-2-yl)pyrazolo[1,5-a]pyrimidin-7(4H)-one |

TABLE A-continued

| Compound number | Structure | Chemical name |
|---|---|---|
| 57 | 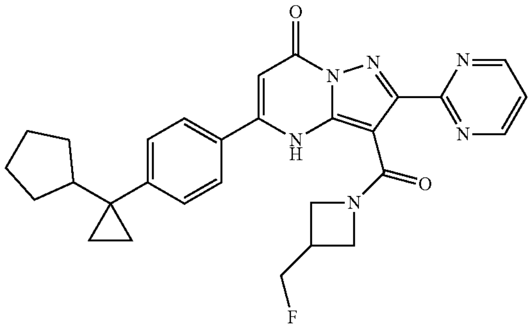 [SMILES: O=C(c1c(-c2ncccn2)nn2c(=O)cc(-c3ccc(C4(C5CCCC5)CC4)cc3)[nH]c12)N1CC(CF)C1] | 5-(4-(1-Cyclopentylcyclopropyl)phenyl)-3-(3-(fluoromethyl)azetidine-1-carbonyl)-2-(pyrimidin-2-yl)pyrazolo[1,5-a]pyrimidin-7(4H)-one |
| 58 | 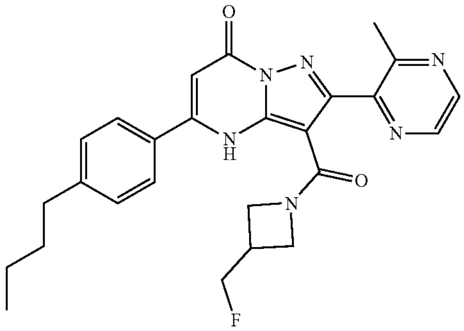 [SMILES: CCCCc1ccc(-c2cc(=O)n3nc(-c4nccnc4C)c(C(=O)N4CC(CF)C4)c3[nH]2)cc1] | 5-(4-Butylphenyl)-3-(3-(fluoromethyl)azetidine-1-carbonyl)-2-(3-methylpyrazin-2-yl)pyrazolo[1,5-a]pyrimidin-7(4H)-one |
| 59 | 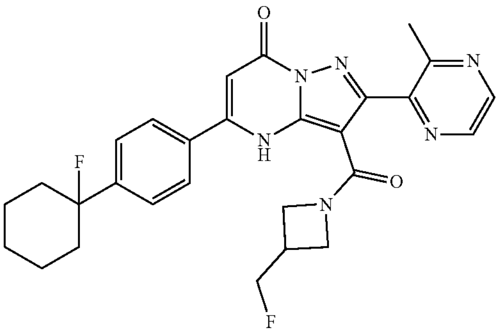 [SMILES: Cc1nccnc1-c1nn2c(=O)cc(-c3ccc(C4(F)CCCCC4)cc3)[nH]c2c1C(=O)N1CC(CF)C1] | 5-(4-(1-Fluorocyclohexyl)phenyl)-3-(3-(fluoromethyl)azetidine-1-carbonyl)-2-(3-methylpyrazin-2-yl)pyrazolo[1,5-a]pyrimidin-7(4H)-one |
| 60 | 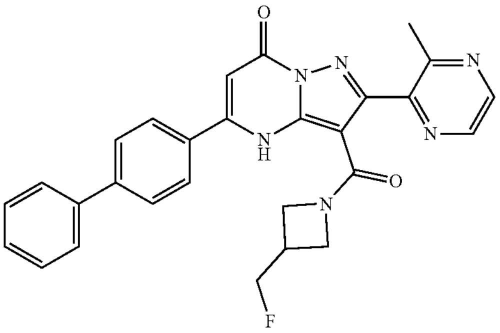 [SMILES: Cc1nccnc1-c1nn2c(=O)cc(-c3ccc(-c4ccccc4)cc3)[nH]c2c1C(=O)N1CC(CF)C1] | 5-([1,1'-Biphenyl]-4-yl)-3-(3-(fluoromethyl)azetidine-1-carbonyl)-2-(3-methylpyrazin-2-yl)pyrazolo[1,5-a]pyrimidin-7(4H)-one |

TABLE A-continued

| Compound number | Structure | Chemical name |
| --- | --- | --- |
| 61 | 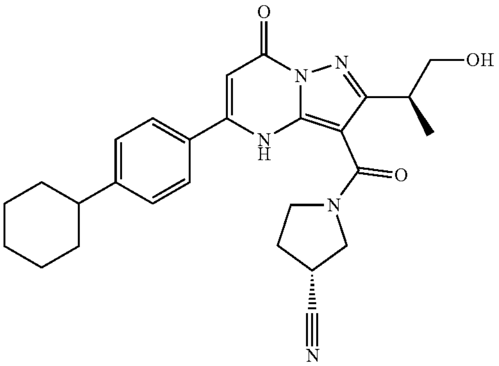 [SMILES: C[C@H](CO)c1nn2c(=O)cc(-c3ccc(C4CCCCC4)cc3)[nH]c2c1C(=O)N1CC[C@@H](C#N)C1] | (R)-1-(5-(4-cyclohexylphenyl)-2-((S)-1-hydroxypropan-2-yl)-7-oxo-4,7-dihydropyrazolo[1,5-a]pyrimidine-3-carbonyl)pyrrolidine-3-carbonitrile |
| 62 | 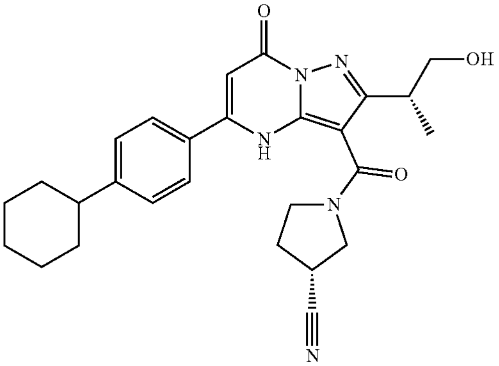 [SMILES: C[C@@H](CO)c1nn2c(=O)cc(-c3ccc(C4CCCCC4)cc3)[nH]c2c1C(=O)N1CC[C@@H](C#N)C1] | (R)-1-(5-(4-cyclohexylphenyl)-2-((R)-1-hydroxypropan-2-yl)-7-oxo-4,7-dihydropyrazolo[1,5-a]pyrimidine-3-carbonyl)pyrrolidine-3-carbonitrile |
| 63 | 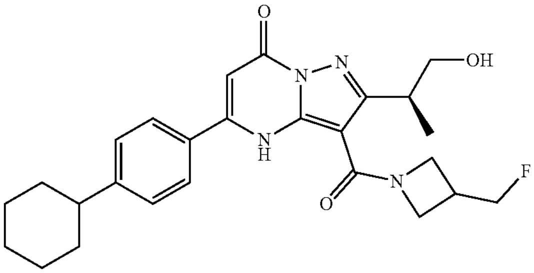 [SMILES: C[C@H](CO)c1nn2c(=O)cc(-c3ccc(C4CCCCC4)cc3)[nH]c2c1C(=O)N1CC(CF)C1] | (S)-5-(4-cyclohexylphenyl)-3-(3-(fluoromethyl)azetidine-1-carbonyl)-2-(1-hydroxypropan-2-yl)pyrazolo[1,5-a]pyrimidin-7(4H)-one |
| 64 | 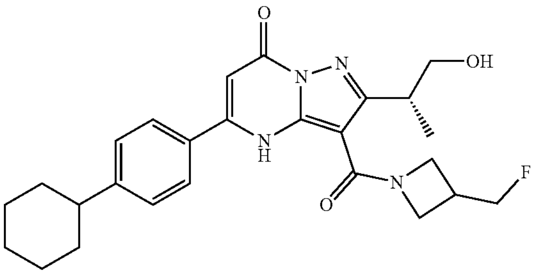 [SMILES: C[C@@H](CO)c1nn2c(=O)cc(-c3ccc(C4CCCCC4)cc3)[nH]c2c1C(=O)N1CC(CF)C1] | (R)-5-(4-cyclohexylphenyl)-3-(3-(fluoromethyl)azetidine-1-carbonyl)-2-(1-hydroxypropan-2-yl)pyrazolo[1,5-a]pyrimidin-7(4H)-one |

TABLE A-continued

| Compound number | Structure | Chemical name |
|---|---|---|
| 65 | 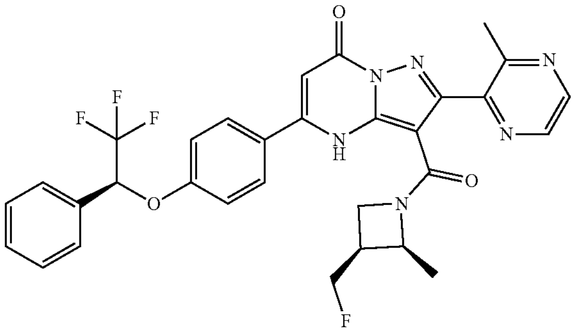 [SMILES: Cc1nccnc1-c1nn2c(=O)cc(-c3ccc(O[C@@H](c4ccccc4)C(F)(F)F)cc3)[nH]c2c1C(=O)N1C[C@H](CF)[C@@H]1C] | 3-((2S,3S)-3-(fluoromethyl)-2-methylazetidine-1-carbonyl)-2-(3-methylpyrazin-2-yl)-5-(4-((5)-2,2,2-trifluoro-1-phenylethoxy)phenyl)pyrazolo[1,5-a]pyrimidin-7(4H)-one |
| 66 | 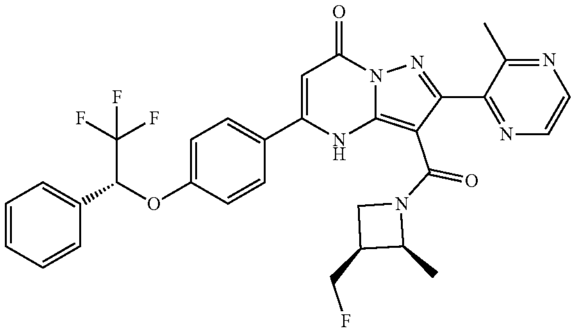 [SMILES: Cc1nccnc1-c1nn2c(=O)cc(-c3ccc(O[C@H](c4ccccc4)C(F)(F)F)cc3)[nH]c2c1C(=O)N1C[C@H](CF)[C@@H]1C] | 3-((2S,3S)-3-(fluoromethyl)-2-methylazetidine-1-carbonyl)-2-(3-methylpyrazin-2-yl)-5-(4-((R)-2,2,2-trifluoro-1-phenylethoxy)phenyl)pyrazolo[1,5-a]pyrimidin-7(4H)-one |
| 67 | 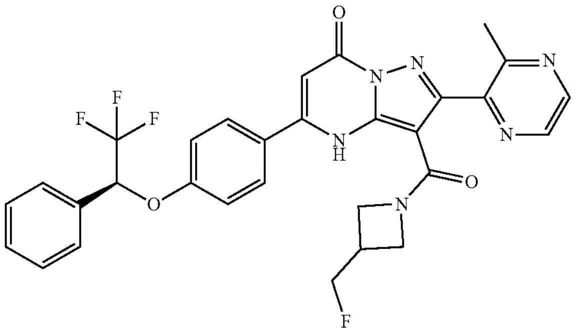 [SMILES: Cc1nccnc1-c1nn2c(=O)cc(-c3ccc(O[C@@H](c4ccccc4)C(F)(F)F)cc3)[nH]c2c1C(=O)N1CC(CF)C1] | (S)-3-(3-(Fluoromethyl)azetidine-1-carbonyl)-2-(3-methylpyrazin-2-yl)-5-(4-(2,2,2-trifluoro-1-phenylethoxy)phenyl)pyrazolo[1,5-a]pyrimidin-7(4H)-one |
| 68 | 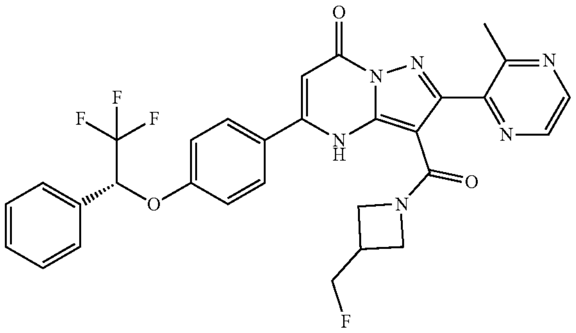 [SMILES: Cc1nccnc1-c1nn2c(=O)cc(-c3ccc(O[C@H](c4ccccc4)C(F)(F)F)cc3)[nH]c2c1C(=O)N1CC(CF)C1] | (R)-3-(3-(Fluoromethyl)azetidine-1-carbonyl)-2-(3-methylpyrazin-2-yl)-5-(4-(2,2,2-trifluoro-1-phenylethoxy)phenyl)pyrazolo[1,5-a]pyrimidin-7(4H)-one |

TABLE A-continued

| Compound number | Structure | Chemical name |
|---|---|---|
| 69 | 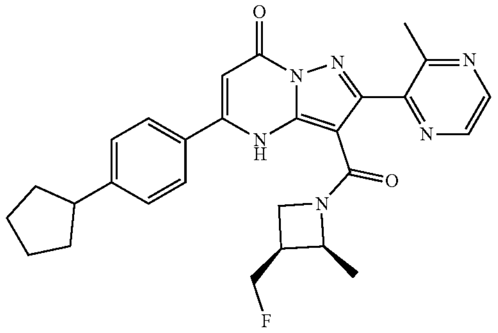 [SMILES: Cc1nccnc1-c1nn2c(=O)cc(-c3ccc(C4CCCC4)cc3)[nH]c2c1C(=O)N1C[C@H](CF)[C@@H]1C] | 5-(4-Cyclopentylphenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one |
| 70 | 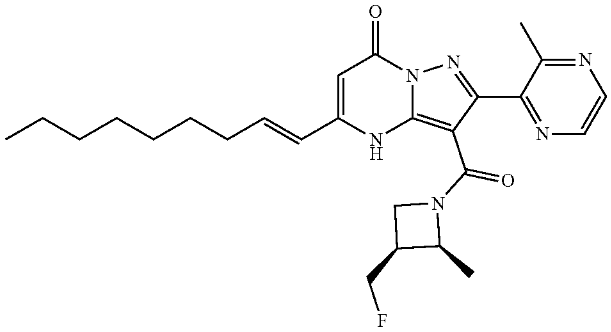 [SMILES: CCCCCCC/C=C/c1cc(=O)n2nc(-c3nccnc3C)c(C(=O)N3C[C@H](CF)[C@@H]3C)c2[nH]1] | 3-((2S,3S)-3-(fluoromethyl)-2-methylazetidine-1-carbonyl)-2-(3-methylpyrazin-2-yl)-5-((E)-non-1-en-1-yl)pyrazolo[1,5-a]pyrimidin-7(4H)-one |
| 71 | 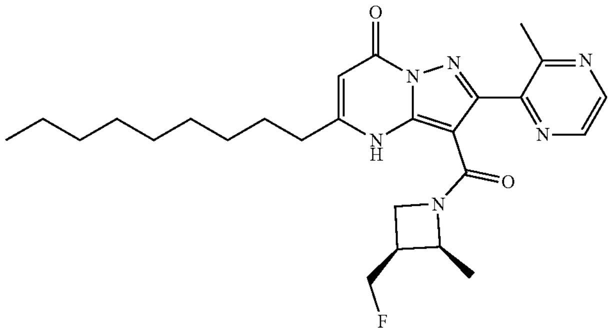 [SMILES: CCCCCCCCCc1cc(=O)n2nc(-c3nccnc3C)c(C(=O)N3C[C@H](CF)[C@@H]3C)c2[nH]1] | 3-((2S,3S)-3-(fluoromethyl)-2-methylazetidine-1-carbonyl)-2-(3-methylpyrazin-2-yl)-5-nonylpyrazolo[1,5-a]pyrimidin-7(4H)-one |
| 72 | 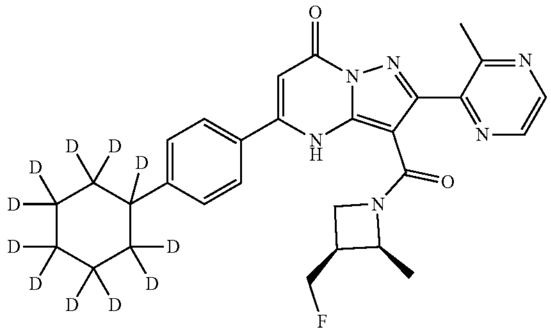 [SMILES: [2H]C1([2H])C([2H])([2H])C([2H])([2H])C([2H])(c2ccc(-c3cc(=O)n4nc(-c5nccnc5C)c(C(=O)N5C[C@H](CF)[C@@H]5C)c4[nH]3)cc2)C([2H])([2H])C1([2H])[2H]] | 3-[(2S,35)-3-(fluoromethyl)-2-methyl-azetidine-1-carbonyl]-2-(3-methylpyrazin-2-yl)-5-[4-(1,2,2,3,3,4,4,5,5,6,6-undecadeuteriocyclohexyl)phenyl]-4H-pyrazolo[1,5-a]pyrimidin-7-one |

TABLE A-continued

| Compound number | Structure | Chemical name |
|---|---|---|
| 73 | 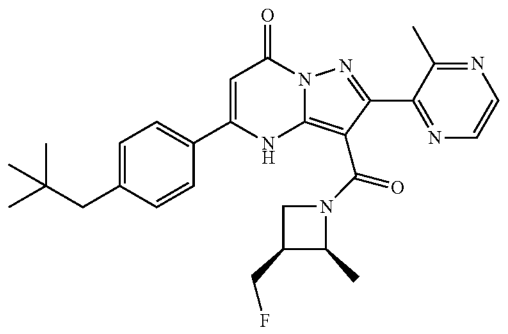 [SMILES: Cc1nccnc1-c1nn2c(=O)cc(-c3ccc(CC(C)(C)C)cc3)[nH]c2c1C(=O)N1C[C@H](CF)[C@@H]1C] | 5-[4-(2,2-dimethylpropyl)phenyl]-2-(3-methylpyrazin-2-yl)-3-[rac-(2S,3S)-3-(fluoromethyl)-2-methyl-azetidine-1-carbonyl]-4H-pyrazolo[1,5-a]pyrimidin-7-one |
| 74 | 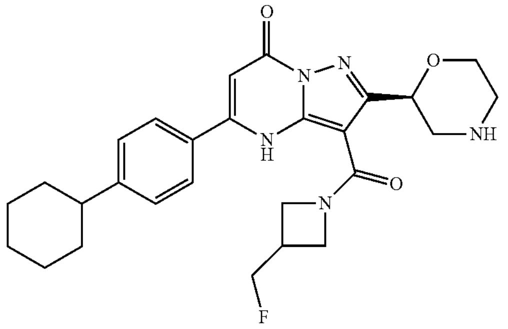 [SMILES: O=C(c1c([C@@H]2CNCCO2)nn2c(=O)cc(-c3ccc(C4CCCCC4)cc3)[nH]c12)N1CC(CF)C1] | (S)-5-(4-cyclohexylphenyl)-3-(3-(fluoromethyl)azetidine-1-carbonyl)-2-(morpholin-2-yl)pyrazolo[1,5-a]pyrimidin-7(4H)-one |
| 75 | 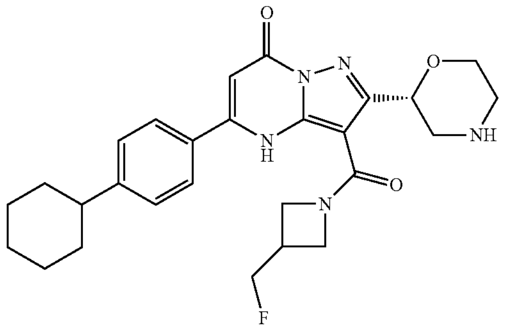 [SMILES: O=C(c1c([C@H]2CNCCO2)nn2c(=O)cc(-c3ccc(C4CCCCC4)cc3)[nH]c12)N1CC(CF)C1] | (R)-5-(4-cyclohexylphenyl)-3-(3-(fluoromethyl)azetidine-1-carbonyl)-2-(morpholin-2-yl)pyrazolo[1,5-a]pyrimidin-7(4H)-one |

In some embodiments, provided herein is a compound selected from the group consisting of 5-(4-cyclohexylphenyl)-3-[3-(fluoromethyl)azetidine-1-carbonyl]-N,N-dimethyl-7-oxo-4H-pyrazolo[1,5-a]pyrimidine-2-carboxamide;

5-[4-(cyclopentylmethyl)phenyl]-3-[3-(fluoromethyl)azetidine-1-carbonyl]-N,N-dimethyl-7-oxo-4H-pyrazolo[1,5-a]pyrimidine-2-carboxamide;

5-(4-cyclohexyl-3,5-difluoro-phenyl)-3-[3-(fluoromethyl)azetidine-1-carbonyl]-N,N-dimethyl-7-oxo-4H-pyrazolo[1,5-a]pyrimidine-2-carboxamide;

5-(4-cyclohexyl-3-fluoro-phenyl)-3-[3-(fluoromethyl)azetidine-1-carbonyl]-N,N-dimethyl-7-oxo-4H-pyrazolo[1,5-a]pyrimidine-2-carboxamide;

5-(4-cyclohexylphenyl)-N,N-dimethyl-7-oxo-3-[3-(fluoromethyl)-2-methyl-azetidine-1-carbonyl]-4H-pyrazolo[1,5-a]pyrimidine-2-carboxamide;

5-(4-cyclohexylphenyl)-N,N-dimethyl-7-oxo-3-[3-(fluoromethyl)-2-methyl-azetidine-1-carbonyl]-4H-pyrazolo[1,5-a]pyrimidine-2-carboxamide;

5-(4-cyclohexylphenyl)-3-[3-(fluoromethyl)azetidine-1-carbonyl]-2-[3-(trifluoromethyl)pyrazin-2-yl]-4H-pyrazolo[1,5-a]pyrimidin-7-one;

3-[5-(4-cyclohexylphenyl)-3-[3-(fluoromethyl)azetidine-1-carbonyl]-7-oxo-4H-pyrazolo[1,5-a]pyrimidin-2-yl]pyrazine-2-carbonitrile;

5-(4-cyclohexylphenyl)-3-[3-(fluoromethyl)azetidine-1-carbonyl]-2-(4-methylpyrimidin-2-yl)-4H-pyrazolo[1,5-a]pyrimidin-7-one;

5-(4-cyclohexylphenyl)-3-[3-(fluoromethyl)azetidine-1-carbonyl]-2-(4-isopropylpyrimidin-2-yl)-4H-pyrazolo[1,5-a]pyrimidin-7-one;

5-(4-cyclohexylphenyl)-3-[3-(fluoromethyl)azetidine-1-carbonyl]-2-[4-(trifluoromethyl)pyrimidin-2-yl]-4H-pyrazolo[1,5-a]pyrimidin-7-one;

5-(4-cyclohexylphenyl)-2-(4-ethylpyrimidin-2-yl)-3-[3-(fluoromethyl)azetidine-1-carbonyl]-4H-pyrazolo[1,5-a]pyrimidin-7-one;

5-(4-cyclohexylphenyl)-3-[3-(fluoromethyl)azetidine-1-carbonyl]-2-(3-methoxypyrazin-2-yl)-4H-pyrazolo[1,5-a]pyrimidin-7-one;

5-(4-cyclohexylphenyl)-3-[3-(fluoromethyl)azetidine-1-carbonyl]-2-(4-methoxypyrimidin-2-yl)-4H-pyrazolo[1,5-a]pyrimidin-7-one;

5-(4-cyclohexylphenyl)-3-[3-(fluoromethyl)azetidine-1-carbonyl]-2-pyrimidin-2-yl-4H-pyrazolo[1,5-a]pyrimidin-7-one;
5-(4-cyclohexylphenyl)-3-[3-(fluoromethyl)azetidine-1-carbonyl]-2-(2-pyridyl)-4H-pyrazolo[1,5-a]pyrimidin-7-one;
5-(4-cyclohexylphenyl)-3-[3-(fluoromethyl)azetidine-1-carbonyl]-2-pyrazin-2-yl-4H-pyrazolo[1,5-a]pyrimidin-7-one;
5-(4-cyclohexylphenyl)-3-[3-(fluoromethyl)azetidine-1-carbonyl]-2-(4-methyl-2-pyridyl)-4H-pyrazolo[1,5-a]pyrimidin-7-one;
5-(4-cyclohexylphenyl)-3-[3-(fluoromethyl)azetidine-1-carbonyl]-2-oxazol-2-yl-4H-pyrazolo[1,5-a]pyrimidin-7-one;
5-(4-cyclohexylphenyl)-N,N-dimethyl-2-(3-methylpyrazin-2-yl)-7-oxo-4H-pyrazolo[1,5-a]pyrimidine-3-carboxamide;
5-(4-cyclohexyl-3-fluoro-phenyl)-3-[3-(fluoromethyl)azetidine-1-carbonyl]-2-(3-methylpyrazin-2-yl)-4H-pyrazolo[1,5-a]pyrimidin-7-one;
5-(4-cyclohexyl-3-fluoro-phenyl)-3-[3-(fluoromethyl)azetidine-1-carbonyl]-2-pyrimidin-2-yl-4H-pyrazolo[1,5-a]pyrimidin-7-one;
5-(4-cyclohexyl-3-fluoro-phenyl)-3-[3-(fluoromethyl)azetidine-1-carbonyl]-2-pyrazin-2-yl-4H-pyrazolo[1,5-a]pyrimidin-7-one;
5-[4-(cyclopentylmethyl)phenyl]-3-[3-(fluoromethyl)azetidine-1-carbonyl]-2-pyrimidin-2-yl-4H-pyrazolo[1,5-a]pyrimidin-7-one;
5-[4-(cyclopentylmethyl)phenyl]-3-[3-(fluoromethyl)azetidine-1-carbonyl]-2-pyrazin-2-yl-4H-pyrazolo[1,5-a]pyrimidin-7-one;
5-(4-cyclohexylphenyl)-3-[3-(fluoromethyl)azetidine-1-carbonyl]-2-(5-methylpyrazin-2-yl)-4H-pyrazolo[1,5-a]pyrimidin-7-one;
5-(4-cyclohexylphenyl)-3-[3-(fluoromethyl)azetidine-1-carbonyl]-2-(3-methylpyrazin-2-yl)-4H-pyrazolo[1,5-a]pyrimidin-7-one;
5-(4-cyclohexylphenyl)-3-[3-(fluoromethyl)azetidine-1-carbonyl]-2-(6-methylpyrazin-2-yl)-4H-pyrazolo[1,5-a]pyrimidin-7-one;
5-(4-cyclohexylphenyl)-2-(3,4-dimethyl-2-pyridyl)-3-[3-(fluoromethyl)azetidine-1-carbonyl]-4H-pyrazolo[1,5-a]pyrimidin-7-one;
5-(4-cyclohexylphenyl)-2-(1,5-dimethylimidazol-4-yl)-3-[3-(fluoromethyl)azetidine-1-carbonyl]-4H-pyrazolo[1,5-a]pyrimidin-7-one;
5-(4-cyclohexylphenyl)-2-(1-ethylimidazol-4-yl)-3-[3-(fluoromethyl)azetidine-1-carbonyl]-4H-pyrazolo[1,5-a]pyrimidin-7-one;
5-(4-cyclohexylphenyl)-3-[3-(fluoromethyl)azetidine-1-carbonyl]-2-(1-methylimidazol-4-yl)-4H-pyrazolo[1,5-a]pyrimidin-7-one;
5-(4-cyclohexylphenyl)-3-[3-(fluoromethyl)azetidine-1-carbonyl]-2-[2-methylazetidine-1-carbonyl]-4H-pyrazolo[1,5-a]pyrimidin-7-one;
5-(4-cyclohexylphenyl)-3-[3-(fluoromethyl)azetidine-1-carbonyl]-2-[2-methylazetidine-1-carbonyl]-4H-pyrazolo[1,5-a]pyrimidin-7-one;
5-(4-cyclohexylphenyl)-N-ethyl-3-[3-(fluoromethyl)azetidine-1-carbonyl]-N-methyl-7-oxo-4H-pyrazolo[1,5-a]pyrimidine-2-carboxamide;
5-(4-cyclohexylphenyl)-3-[3-(fluoromethyl)azetidine-1-carbonyl]-2-(pyrrolidine-1-carbonyl)-4H-pyrazolo[1,5-a]pyrimidin-7-one;
5-(4-cyclohexylphenyl)-3-[3-(fluoromethyl)azetidine-1-carbonyl]-2-(3-pyridyl)-4H-pyrazolo[1,5-a]pyrimidin-7-one;
5-(4-cyclohexylphenyl)-3-[3-(fluoromethyl)azetidine-1-carbonyl]-2-phenyl-4H-pyrazolo[1,5-a]pyrimidin-7-one;
5-(4-cyclohexylphenyl)-3-[3-(fluoromethyl)azetidine-1-carbonyl]-2-oxazol-5-yl-4H-pyrazolo[1,5-a]pyrimidin-7-one;
5-(4-cyclohexylphenyl)-2-pyrazin-2-yl-3-[3-(fluoromethyl)-2-methyl-azetidine-1-carbonyl]-4H-pyrazolo[1,5-a]pyrimidin-7-one;
5-(4-cyclohexylphenyl)-2-pyrazin-2-yl-3-[3-(fluoromethyl)-2-methyl-azetidine-1-carbonyl]-4H-pyrazolo[1,5-a]pyrimidin-7-one;
5-(4-cyclohexylphenyl)-2-pyrimidin-2-yl-3-[3-(fluoromethyl)-2-methyl-azetidine-1-carbonyl]-4H-pyrazolo[1,5-a]pyrimidin-7-one;
5-(4-cyclohexylphenyl)-2-pyrimidin-2-yl-3-[3-(fluoromethyl)-2-methyl-azetidine-1-carbonyl]-4H-pyrazolo[1,5-a]pyrimidin-7-one;
5-(4-cyclohexylphenyl)-2-(3-methylpyrazin-2-yl)-3-[3-(fluoromethyl)-2-methyl-azetidine-1-carbonyl]-4H-pyrazolo[1,5-a]pyrimidin-7-one;
5-(4-cyclohexylphenyl)-2-(3-methylpyrazin-2-yl)-3-[3-(fluoromethyl)-2-methyl-azetidine-1-carbonyl]-4H-pyrazolo[1,5-a]pyrimidin-7-one;
5-[4-(cyclopentylmethyl)phenyl]-2-(3-methylpyrazin-2-yl)-3-[3-(fluoromethyl)-2-methyl-azetidine-1-carbonyl]-4H-pyrazolo[1,5-a]pyrimidin-7-one;
5-[4-(cyclopentylmethyl)phenyl]-2-(3-methylpyrazin-2-yl)-3-[3-(fluoromethyl)-2-methyl-azetidine-1-carbonyl]-4H-pyrazolo[1,5-a]pyrimidin-7-one;
5-[4-(cyclopentylmethyl)phenyl]-2-pyrimidin-2-yl-3-[3-(fluoromethyl)-2-methyl-azetidine-1-carbonyl]-4H-pyrazolo[1,5-a]pyrimidin-7-one;
5-[4-(cyclopentylmethyl)phenyl]-2-pyrimidin-2-yl-3-[3-(fluoromethyl)-2-methyl-azetidine-1-carbonyl]-4H-pyrazolo[1,5-a]pyrimidin-7-one;
5-[4-(cyclopentylmethyl)phenyl]-2-pyrazin-2-yl-3-[3-(fluoromethyl)-2-methyl-azetidine-1-carbonyl]-4H-pyrazolo[1,5-a]pyrimidin-7-one;
5-[4-(cyclopentylmethyl)phenyl]-2-pyrazin-2-yl-3-[3-(fluoromethyl)-2-methyl-azetidine-1-carbonyl]-4H-pyrazolo[1,5-a]pyrimidin-7-one;
3-[3-(fluoromethyl)azetidine-1-carbonyl]-5-[(4-isopropylphenyl)methoxy]-2-pyrazin-2-yl-4H-pyrazolo[1,5-a]pyrimidin-7-one;
5-[(4-tert-butylphenyl)methoxy]-3-[3-(fluoromethyl)azetidine-1-carbonyl]-2-pyrazin-2-yl-4H-pyrazolo[1,5-a]pyrimidin-7-one;
5-[(4-tert-butylphenyl)methoxy]-3-[3-(fluoromethyl)azetidine-1-carbonyl]-2-pyrimidin-2-yl-4H-pyrazolo[1,5-a]pyrimidin-7-one;
5-[4-(4,4-difluorocyclohexyl)phenyl]-3-[3-(fluoromethyl)azetidine-1-carbonyl]-2-(3-methylpyrazin-2-yl)-4H-pyrazolo[1,5-a]pyrimidin-7-one;
5-[4-[cyclopentyl(difluoro)methyl]phenyl]-3-[3-(fluoromethyl)azetidine-1-carbonyl]-2-(3-methylpyrazin-2-yl)-4H-pyrazolo[1,5-a]pyrimidin-7-one;
5-[4-(1-cyclopentylcyclopropyl)phenyl]-3-[3-(fluoromethyl)azetidine-1-carbonyl]-2-pyrimidin-2-yl-4H-pyrazolo[1,5-a]pyrimidin-7-one;
5-(4-butylphenyl)-3-[3-(fluoromethyl)azetidine-1-carbonyl]-2-(3-methylpyrazin-2-yl)-4H-pyrazolo[1,5-a]pyrimidin-7-one;

5-[4-(1-fluorocyclohexyl)phenyl]-3-[3-(fluoromethyl)azetidine-1-carbonyl]-2-(3-methylpyrazin-2-yl)-4H-pyrazolo[1,5-a]pyrimidin-7-one;

3-[3-(fluoromethyl)azetidine-1-carbonyl]-2-(3-methylpyrazin-2-yl)-5-(4-phenylphenyl)-4H-pyrazolo[1,5-a]pyrimidin-7-one;

1-[5-(4-cyclohexylphenyl)-7-oxo-2-[2-hydroxy-1-methyl-ethyl]-4H-pyrazolo[1,5-a]pyrimidine-3-carbonyl]pyrrolidine-3-carbonitrile;

1-[5-(4-cyclohexylphenyl)-7-oxo-2-[2-hydroxy-1-methyl-ethyl]-4H-pyrazolo[1,5-a]pyrimidine-3-carbonyl]pyrrolidine-3-carbonitrile;

5-(4-cyclohexylphenyl)-3-[3-(fluoromethyl)azetidine-1-carbonyl]-2-[2-hydroxy-1-methyl-ethyl]-4H-pyrazolo[1,5-a]pyrimidin-7-one;

5-(4-cyclohexylphenyl)-3-[3-(fluoromethyl)azetidine-1-carbonyl]-2-[2-hydroxy-1-methyl-ethyl]-4H-pyrazolo[1,5-a]pyrimidin-7-one;

2-(3-methylpyrazin-2-yl)-3-[3-(fluoromethyl)-2-methyl-azetidine-1-carbonyl]-5-[4-[2,2,2-trifluoro-1-phenyl-ethoxy]phenyl]-4H-pyrazolo[1,5-a]pyrimidin-7-one;

3-[3-(fluoromethyl)azetidine-1-carbonyl]-2-(3-methylpyrazin-2-yl)-5-[4-[2,2,2-trifluoro-1-phenyl-ethoxy]phenyl]-4H-pyrazolo[1,5-a]pyrimidin-7-one;

2-(3-methylpyrazin-2-yl)-3-[3-(fluoromethyl)-2-methyl-azetidine-1-carbonyl]-5-[4-[2,2,2-trifluoro-1-phenyl-ethoxy]phenyl]-4H-pyrazolo[1,5-a]pyrimidin-7-one;

3-[3-(fluoromethyl)azetidine-1-carbonyl]-2-(3-methylpyrazin-2-yl)-5-[4-[2,2,2-trifluoro-1-phenyl-ethoxy]phenyl]-4H-pyrazolo[1,5-a]pyrimidin-7-one;

5-(4-cyclopentylphenyl)-2-(3-methylpyrazin-2-yl)-3-[3-(fluoromethyl)-2-methyl-azetidine-1-carbonyl]-4H-pyrazolo[1,5-a]pyrimidin-7-one;

2-(3-methylpyrazin-2-yl)-3-[3-(fluoromethyl)-2-methyl-azetidine-1-carbonyl]-5-[non-1-enyl]-4H-pyrazolo[1,5-a]pyrimidin-7-one;

2-(3-methylpyrazin-2-yl)-5-nonyl-3-[3-(fluoromethyl)-2-methyl-azetidine-1-carbonyl]-4H-pyrazolo[1,5-a]pyrimidin-7-one;

2-(3-methylpyrazin-2-yl)-3-[3-(fluoromethyl)-2-methyl-azetidine-1-carbonyl]-5-[4-(1,2,2,3,3,4,4,5,5,6,6-undecadeuteriocyclohexyl)phenyl]-4H-pyrazolo[1,5-a]pyrimidin-7-one;

5-[4-(2,2-dimethylpropyl)phenyl]-2-(3-methylpyrazin-2-yl)-3-[3-(fluoromethyl)-2-methyl-azetidine-1-carbonyl]-4H-pyrazolo[1,5-a]pyrimidin-7-one;

5-(4-cyclohexylphenyl)-3-[3-(fluoromethyl)azetidine-1-carbonyl]-2-[morpholin-2-yl]-4H-pyrazolo[1,5-a]pyrimidin-7-one; and 5-(4-cyclohexylphenyl)-3-[3-(fluoromethyl)azetidine-1-carbonyl]-2-[morpholin-2-yl]-4H-pyrazolo[1,5-a]pyrimidin-7-one, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

In some embodiments, the compounds of formula (I) are isotopically-labeled by having one or more atoms therein replaced by an atom having a different atomic mass or mass number. Such isotopically-labeled (e.g., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements. It is to be understood that any hydrogen ($^{1}H$) atom present in any of the compounds of formula (I) disclosed herein may be replaced by a deuterium ($^{2}H$) atom. In any given compound of formula (I), any number of hydrogen atoms may be replaced by the same number of deuterium atoms.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

In addition to salt forms, the present disclosure provides compounds which are in a prodrug form. As used herein the term "prodrug" refers to those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Prodrugs of the disclosure may include phosphates, phosphate esters, alkyl phosphates, alkyl phosphate esters, acyl ethers, or other prodrug moieties as discussed below. In some embodiments, the prodrug moiety is:

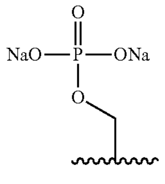
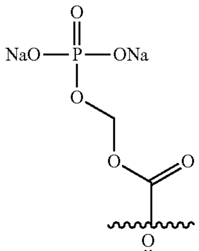
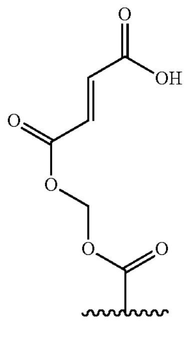
or
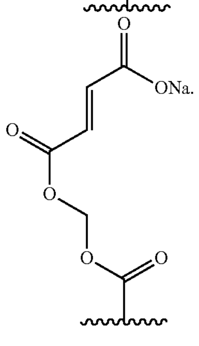

Additional types of prodrugs are also encompassed. For example, where an amino acid residue, or a polypeptide chain of two or more (e.g., two, three or four) amino acid residues, is covalently joined through an amide or ester bond to a free amino, hydroxy or carboxylic acid group of a compound of the present disclosure. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methylalanine, para-benzoylphenylalanine, phenylglycine, propargylglycine, sarcosine, methionine sulfone and tert-butylglycine.

Additional types of prodrugs are also encompassed. For instance, a free carboxyl group of a compound of the disclosure can be derivatized as an amide or alkyl ester. As another example, compounds of this disclosure comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxyl groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, $—P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present disclosure provides for metabolites of compounds of the disclosure. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the disclosure, administering it parenterally in a detectable dose (e.g., greater than about 0.5 mg/kg) to an animal such as rat, mouse, guinea pig, monkey, or to human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure can exist in multiple crystalline or amorphous forms. In general, all physical forms are equivalent for the uses contemplated by the present disclosure and are intended to be within the scope of the present disclosure.

III. Pharmaceutical Compositions and Administration

Also disclosed is a pharmaceutical composition comprising at least one of the disclosed compounds and a therapeutically inert carrier. Another aspect includes a pharmaceutical composition comprising a compound of formula (I) or a pharmaceutically acceptable salt thereof. In one embodiment, the composition further comprises a pharmaceutically acceptable carrier, adjuvant, or vehicle. In another embodiment, the composition further comprises a therapeutically inert carrier. In another embodiment, the composition further comprises an amount of the compound effective to measurably disrupt the YAP:TEAD protein:protein interaction. In certain embodiments, the composition is formulated for administration to a patient in need thereof. In another embodiment, the disclosure provides for a pharmaceutical composition, comprising a therapeutically effective amount of a compound according to formula (I) and a pharmaceutically acceptable carrier, diluent and/or excipient.

Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula (I) or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula (I) or salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula (I) or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound of formula (I) or salt thereof, and optionally, further comprises one or more excipients.

In another embodiment, compositions comprise liquid dosage formulations comprising a compound of formula (I) or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I).

Example dosage forms for topical or transdermal administration of a compound of formula (I) include ointments, pastes, creams, lotions, gels, powders, solutions, sprays, inhalants or patches. The compound of formula (I) or a salt thereof is admixed under sterile conditions with a pharmaceutically acceptable carrier, and optionally preservatives or buffers. Additional formulation examples include an ophthalmic formulation, ear drops, eye drops, and transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula (I) or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula (I) or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

IV. Indications and Combination Therapy

In certain embodiments, the disclosed compounds are inhibitors of YAP:TEAD protein-protein interaction that bind to TEAD and disrupt the YAP:TEAD protein-protein interaction ("YAP:TEAD inhibitors"). In embodiments, the disclosed compounds are useful for the treatment of cancers, including cancers characterized by solid tumors, through their ability to inhibit YAP:TEAD protein-protein interaction. Compounds of the present disclosure are small molecule YAP:TEAD inhibitors. Small molecule YAP:TEAD inhibitors are useful, e.g., for the diagnosis or treatment of cancer, including with no limitations, lung cancer, breast cancer, head and neck cancer, colon cancer, ovarian cancer, liver cancer, brain cancer and prostate cancer, mesotheliomas, sarcomas and/or leukemia. In other embodiments, small molecule YAP:TEAD inhibitors are useful for the diagnosis or treatment of cancers characterized by solid tumors, including with no limitations lung, liver, ovarian, breast and/or squamous cancers. In some embodiments, the solid tumors have YAP/TAZ amplification or Nf2 deletion/mutation.

In some embodiments, the disclosed compounds are for use as therapeutically active substance.

In some embodiments, the disclosed compounds and the disclosed compositions are for the therapeutic and/or prophylactic treatment of cancer.

In some embodiments, the disclosed compounds are for the preparation of a medicament for the therapeutic treatment of cancer.

In some embodiments, the disclosed compounds are for use in the therapeutic treatment of cancer.

The present disclosure is directed to a method for the therapeutic treatment of cancer in a subject. The method comprises administering to the subject an effective amount of one or more of any one of the disclosed compounds.

In some embodiments, the cancer is a solid tumor.

In some embodiments, the cancer is selected from the group consisting of lung, liver, ovarian, breast and squamous cancer.

In some embodiments, the disclosure includes use of any of the compounds of formula (I) disclosed herein for the therapeutic and/or prophylactic treatment of cancer. In other embodiments, the disclosure includes use of any of the compounds of formula (I) disclosed herein for the preparation of a medicament for the therapeutic and/or prophylactic treatment of cancer. In other embodiments, the disclosure includes compounds of formula (I) disclosed herein for the therapeutic and/or prophylactic treatment of cancer.

In some embodiments, the disclosure includes methods for the therapeutic and/or prophylactic treatment of cancer, the method including administering an effective amount of a compound of formula (I) disclosed herein.

In some embodiments, the treatment method includes the co-administration of a compound of formula (I), or stereoisomers, tautomers, or deuterated analogs thereof, or pharmaceutically acceptable salts of any of the foregoing, and at least one mitogen-activated protein kinase (MAPK) inhibitor. In some embodiments, the treatment method includes the co-administration of a compound of formula (I), or stereoisomers, tautomers, or deuterated analogs thereof, or pharmaceutically acceptable salts of any of the foregoing, and at least one inhibitor of the RAS/MAPK pathway. In some embodiments, the treatment method includes the co-administration of a compound of formula (I), or stereoisomers, tautomers, or deuterated analogs thereof, or pharmaceutically acceptable salts of any of the foregoing, and at least one epidermal growth factor receptor (EGFR) inhibitor. In some embodiments, the inhibitor of the RAS/MAPK pathway is a KRAS inhibitor, a RAF inhibitor, such as a BRAF monomer or RAF dimer inhibitor, a MEK inhibitor, an ERK inhibitor, an EGFR inhibitor, or a MAPK inhibitor, or any combination thereof. In certain embodiments, the inhibitor of the RAS/MAPK pathway is an EGFR inhibitor or a MAPK inhibitor, or a combination thereof. Examples of EGFR inhibitors, MAPK inhibitors, and/or RAS/MAPK pathway inhibitors are disclosed in Moore, A. R., Rosenberg, S. C., McCormick, F. et a. RAS-targeted therapies: is the undruggable drugged?. *Nat Rev Drug Discov* (2020) incorporated herein by reference and include, but are not limited to: sotorasib (AMG 510 from Amgen), MRTX849 (from Mirati Therapeutics), JNJ-74699157/ARS-3248 (from J&J Wellspring Biosciences), LY3499446 (from Eli Lilly), GDCBI 1701963 (from Boehringer Ingelheim), mRNA-5671 (from Modema Therapeutics), G12D inhibitor (from Mirati Therapeutics), RAS(ON) inhibitors (from Revolution Medicines), BBP-454 (from BridgeBio Pharma), SP600125, PLX4032, GW5074, AZD6244, PD98059, simvastatin, alisertib, teriflunomide, NSC95397, PD325901, PD98059, lovastatin, sorafenib (NEXAVAR®, Bayer Labs), vermurafenib (ZELBORAF®, Hoffman La Roche Inc.), dabrafenib (TAFLINAR®, Novartis Pharmaceuticals Corportation), selumetinib (KOSELUGO™, AstraZeneca Pharmaceuticals LP), trametinib (MEKINIST®, Novartis Pharmaceuticals Corporation), ulixertinib, silimarin, sirolimus (RAPAMUNE®, PV Prism CV), lapatinib (TYKERB®/TYVERB®, GlaxoSmithKline), crizotinib (XALKORI®, PF Prism CV), taselisib (Roche), PF-0491502, PF502, enterolactone, PLX4720, PD0325901, PD184352, SC-514, alisterib (MLN8237), SB415286, PLX4720, obtaoclax (GX15-070), pimasterib, venetoclax (ABT-199/VENCLEXTA®/VENCLYXTO®), eprenetapopt (APR-246), gemcitabine (GEMZAR®), birinapant (TL32711), pexmetinib (ARRY-614), afuresertib, ralimetinib (LY2228820, Eli Lilly), cobimetinib (COTELLIC®, Exelixis/Genentech), prexasertib (LY2606368), erlotinib (TARCEVA®, OSI Pharmaceuticals), bevacizumab (AVASTIN®, Genentech), belvarafenib (Hanmi Pharm./Genentech, Inc.), and binimetinib (MEKTOVI®, Array Biopharma Inc.).

Breast Cancer

Compounds of the disclosure can be administered alone or they can be used in a combination therapy for the treatment of breast cancer. For instance, the combination therapy includes administering a compound of the disclosure and administering at least one additional therapeutic agent (e.g. one, two, three, four, five, or six additional therapeutic agents) for the treatment of breast cancer.

Standard of care for breast cancer is determined by both disease (tumor, stage, pace of disease, etc.) and patient characteristics (age, by biomarker expression and intrinsic phenotype). General guidance on treatment options are described in the NCCN Guidelines (e.g., NCCN Clinical Practice Guidelines in Oncology, Breast Cancer, version 2.2016, National Comprehensive Cancer Network, 2016, pp. 1-202), and in the ESMO Guidelines (e.g., Senkus, E., et al. Primary Breast Cancer: ESMO Clinical Practice Guidelines for diagnosis, treatment and follow-up. Annals of Oncology 2015; 26(Suppl. 5): v8-v30; and Cardoso F., et al. Locally recurrent or metastatic breast cancer: ESMO Clinical Practice Guidelines for diagnosis, treatment and follow-up. Annals of Oncology 2012; 23 (Suppl. 7):vii11-vii19.).

In some aspects, the compounds are for use in a combination therapy for the treatment of breast cancer in combination with one or more other therapeutic agents. In a further aspect, the compounds are for use in a combination therapy for the treatment of early breast cancer or locally advanced breast cancer. In a further aspect, the compounds are for use in a combination therapy for the treatment of advanced breast cancer or metastatic breast cancer.

In particular, compounds of the disclosure can be used either alone or in combination with standard of care treatment options for breast cancer, which in general include surgery, systemic chemotherapy (either pre- or post-operatively) and/or radiation therapy. Depending on tumor and patient characteristics, systemic chemotherapy may be administered as adjuvant (post-operative) therapy or as neoadjuvant (pre-operative) therapy.

Thus, in one embodiment, the combination therapy comprises administering a compound of the present disclosure and administering at least one additional therapeutic agent such as doxorubicin, epirubicin, cyclophosphamide, docetaxel, paclitaxel, methotrexate, and/or 5-fluorouracil.

In one embodiment, the combination therapy comprises administering a compound of the present disclosure and administering doxorubicin and cyclophosphamide (AC chemotherapy). In one embodiment, the combination therapy comprises administering a compound of the present disclosure and administering docetaxel, doxorubicin and cyclophosphamide (TAC chemotherapy). In one embodiment, the combination therapy comprises administering a compound of the present disclosure and administering cyclophosphamide, methotrexate and 5-fluorouracil (CMF chemotherapy). In one embodiment, the combination therapy comprises administering a compound of the present disclosure and administering epirubicin and cyclophosphamide (EC chemotherapy). In one embodiment, the combination therapy comprises administering a compound of the present disclosure and administering 5-fluorouracil, epirubicin and cyclophosphamide (FEC chemotherapy). In one embodiment, the combination therapy comprises administering a compound of the present disclosure and administering 5-fluorouracil, doxorubicin and cyclophosphamide (FAC chemotherapy). In one embodiment, the combination therapy comprises administering a compound of the present disclosure and administering taxane, in particular docetaxel or paclitaxel.

In one embodiment, when the compounds of the disclosure are for use in the treatment of metastatic breast cancer, the combination therapy comprises administering a compound of the present disclosure and administering at least one additional therapeutic agent such as doxorubicin, pegylated liposomal doxorubicin, epirubicin, cyclophosphamide, carboplatin, cisplatin, docetaxel, paclitaxel, albumin-bound paclitaxel, capecitabine, gemcitabine, vinorelbine, eribulin, Ixabepilone, methotrexate, and/or 5-fluorouracil (5-FU). In one embodiment, the combination therapy comprises administering a compound of the present disclosure and administering docetaxel and capecitabine for use in the treatment of metastatic breast cancer. In one embodiment, the combination therapy comprises administering a compound of the present disclosure and administering gemcitabine and paclitaxel for use in the treatment of metastatic breast cancer.

Breast Cancer—Hormone Receptor Positive (ER+ and or PR+)

In a further aspect, the disclosure provides a method for treating hormone receptor positive (HR+) breast cancer (also called estrogen receptor positive (ER+) breast cancer or estrogen receptor positive and/or progesterone receptor positive (PR+) breast cancer), by administering an effective amount of a compound of the present disclosure. In a further aspect of the embodiment, the breast cancer is early or locally advanced hormone receptor positive (HR+) breast cancer, also named early or locally advanced ER+ breast cancer. In a further aspect, the breast cancer is advanced hormone receptor positive (HR+) breast cancer or metastatic hormone receptor positive (HR+) breast cancer, also named advanced ER+ breast cancer or metastatic ER+ breast cancer.

In some aspects, the compounds are for use in a combination therapy for the treatment of hormone receptor positive (HR+) breast cancer or estrogen receptor positive (ER+) breast cancer. In a further aspect, the compounds are for use in a combination therapy for the treatment of early or locally advanced hormone receptor positive (HR+) breast cancer, also named early or locally advanced ER+ breast cancer. In a further aspect of the embodiment, the compounds are for use in a combination therapy for the treatment of advanced hormone receptor positive (HR+) breast cancer or metastatic hormone receptor positive (HR+) breast cancer, also named advanced ER+ breast cancer or metastatic ER+ breast cancer. In one embodiment, the method comprises administering to an individual having hormone receptor positive (HR+) breast cancer or estrogen receptor positive (ER+) breast cancer an effective amount of a compound of the present disclosure in combination with one or more other therapeutic agents.

In particular, compounds of the disclosure can be used either alone or in combination with standard of care treatment options for hormone receptor positive (HR+) breast cancer or estrogen receptor positive (ER+) breast cancer, which in general include surgery, systemic chemotherapy (either pre- or post-operatively) and/or radiation therapy. Depending on tumor and patient characteristics, systemic chemotherapy may be administered as adjuvant (post-operative) therapy or as neoadjuvant (pre-operative) therapy.

In one embodiment, compounds of the disclosure are for use in the treatment of hormone receptor positive (HR+) breast cancer or estrogen receptor positive (ER+) breast cancer in combination with endocrine therapy. In one embodiment, the combination therapy comprises administering a compound of the present disclosure and administering tamoxifen. In one embodiment, the combination therapy comprises administering an a compound of the present disclosure and administering an aromatase inhibitor, such as anastrozole, letrozole or exemestane for use in the treatment of hormone receptor positive (HR+) breast cancer or estrogen receptor positive (ER+) breast cancer. In one embodiment, the combination therapy comprises administering an a compound of the present disclosure and administering at least one additional therapeutic agent such as anastrozole, letrozole, exemestane and everolimus, palbociclib and letrozole, palbociclib and letrozole, fulvestrant, tamoxifen, toremifene, megestrol acetate, fluoxemesterone, and/or ethinyl estradiol for use in the treatment of hormone receptor positive (HR+) breast cancer or estrogen receptor positive (ER+) breast cancer.

In one embodiment, compounds of the disclosure are for use in the treatment of hormone receptor positive (HR+) breast cancer or estrogen receptor positive (ER+) breast cancer in combination with one or more chemotherapeutic agents. In one embodiment, the combination therapy comprises administering a compound of the present disclosure and administering at least one additional therapeutic agent such as doxorubicin, epirubicin, cyclophosphamide, docetaxel, paclitaxel, methotrexate, and/or 5-fluorouracil for use in the treatment of hormone receptor positive (HR+) breast cancer or estrogen receptor positive (ER+) breast cancer.

In one aspect, compounds of the disclosure are for use in combination with doxorubicin and cyclophosphamide (AC chemotherapy). In one embodiment, the combination therapy comprises administering a compound of the present disclosure and administering docetaxel, doxorubicin and cyclophosphamide (TAC chemotherapy). In one embodiment, the combination therapy comprises administering a compound of the present disclosure and administering cyclophosphamide, methotrexate and 5-fluorouracil (CMF chemotherapy). In one embodiment, the combination therapy comprises administering a compound of the present disclosure and administering epirubicin and cyclophosphamide (EC chemotherapy). In one embodiment, the combination therapy comprises administering a compound of the present disclosure and administering 5-fluorouracil, epirubicin and cyclophosphamide (FEC chemotherapy). In one embodiment, the combination therapy comprises administering a compound of the present disclosure and administering 5-fluorouracil, doxorubicin and cyclophosphamide (FAC chemotherapy). In one embodiment, the combination therapy comprises administering a compound of the present disclosure and administering a taxane, such as docetaxel or paclitaxel.

In one embodiment, compounds of the disclosure are for use in the treatment of metastatic breast cancer. In one embodiment, the combination therapy comprises administering an a compound of the present disclosure and administering doxorubicin, pegylated liposomal doxorubicin, epirubicin, cyclophosphamide, carboplatin, cisplatin, docetaxel, paclitaxel, albumin-bound paclitaxel, capecitabine, gemcitabine, vinorelbine, eribulin, ixabepilone, methotrexate and 5-fluorouracil (5-FU) for use in the treatment of metastatic breast cancer. In one embodiment, the combination therapy comprises administering a compound of the present disclosure and administering docetaxel and capecitabine for use in the treatment of metastatic breast cancer. In one embodiment, the combination therapy comprises administering a compound of the present disclosure and administering gemcitabine and paclitaxel for use in the treatment of metastatic breast cancer.

Breast Cancer—HER2+

In a further aspect, the disclosure provides a method for treating Her2+ positive breast cancer, by administering an effective amount of a compound of the present disclosure. In a further aspect of the embodiment, the breast cancer is early or locally advanced Her2+ positive breast cancer, also named early or locally advanced Her2+ positive breast cancer. In a further aspect, the breast cancer is advanced breast cancer, also named advanced Her2+ positive breast cancer or metastatic ER+ breast cancer.

In some aspects, the compounds are for use in a combination therapy for treatment of Her2+ positive breast cancer. In a further aspect, the compounds are for use in a combination therapy for treatment of early or locally advanced Her2+ positive breast cancer, also named early or locally advanced Her2+ positive breast cancer. In a further aspect of the embodiment, the compounds are for use in a combination therapy for treatment of advanced Her2+ positive breast cancer, also named advanced Her2+ positive breast cancer or metastatic ER+ breast cancer. In one embodiment, the method comprises administering to an individual having Her2+ positive breast cancer an effective amount of a compound of the present disclosure in combination with one or more other therapeutic agents.

In particular, compounds of the disclosure can be used either alone or in combination with standard of care treatment options for Her2+ positive breast cancer, which in general include surgery, systemic chemotherapy (either pre- or post-operatively) and/or radiation therapy. Depending on tumor and patient characteristics, systemic chemotherapy may be administered as adjuvant (post-operative) therapy or as neoadjuvant (pre-operative) therapy.

In one embodiment, the combination therapy comprises administering a compound of the present disclosure and administering a Her2 antibody to treat Her2+ positive breast cancer. In one aspect, the combination therapy comprises administering a compound of the present disclosure and administering trastuzumab or pertuzumab to treat Her2+ positive breast cancer. In another aspect, the combination therapy comprises administering a compound of the present disclosure and administering a chemotherapy to treat Her2+ positive breast cancer. In one embodiment, the combination therapy comprises administering a compound of the present disclosure and administering doxorubicin and cyclophosphamide followed by trastuzumab to treat Her2+ positive breast cancer. In a further embodiment, compounds of the disclosure are for use in the treatment of Her2+ positive breast cancer in combination with chemotherapy followed by a taxane and trastuzumab to treat Her2+ positive breast cancer. In another aspect, compounds of the disclosure are for use in the treatment of Her2+ positive breast cancer in combination with trastuzumab (Herceptin) and pertuzumab (Perjeta) to treat Her2+ positive breast cancer.

In another aspect, compounds of the disclosure are used in combination with docetaxel, carboplatin and trastuzumab (TCH chemotherapy). In a further aspect, compounds of the disclosure are administered in combination with docetaxel, carboplatin, trastuzumab and pertuzumab. In a further aspect, compounds of the disclosure are administered in combination with 5-fluorouracil, epirubicin and cyclophosphamide (FEC chemotherapy and pertuzumab, trastuzumab and docetaxel or paclitaxel. In another aspect, compounds of the disclosure are used in combination with paclitaxel and trastuzumab. In a further aspect, compounds of the disclosure are administered in combination with Pertuzumab and trastuzumab and paclitaxel or docetaxel.

If the compounds of the disclosure are for use in the treatment of metastatic Her2+ positive breast cancer, they can also be used in combination with one or more chemotherapeutic agents selected from the group consisting of doxorubicin (A) (Adriamycin), pegylated liposomal doxorubicin (Doxil), epirubicin (E) (Ellence), cyclophosphamide (C) (Cytoxan), carboplatin (Platinol), cisplatin (Paraplatin), docetaxel (T) (Taxotere), paclitaxel (Taxol), albumin-bound paclitaxel (Abraxane), capecitabine (Xeloda), gemcitabine (Cynzar), vinorelbine (Navelbine), eribulin (Halaven), and Ixabepilone (Ixempra), In one aspect, the compounds of the disclosure are for use in the treatment of metastatic Her2+ positive breast cancer in combination with ado-trastuzumab emtansine (T-DM1).

In a particular aspect, compounds of the disclosure are for use in the treatment of metastatic Her2+ positive breast cancer in combination with trastuzumab and pertuzumab and a taxane. In one aspect, the taxane is docetaxel. In another aspect, the taxane is paclitaxel.

Breast Cancer—Triple Negative

Compounds of the disclosure can be used either alone or in a combination therapy with standard of care treatment options for triple negative breast cancer (TNBC), which in general include surgery, systemic chemotherapy (either pre- or post-operatively) and/or radiation therapy.

Standard of care for TNBC is determined by both disease (stage, pace of disease, etc.) and patient (age, co-morbidities, symptoms, etc.) characteristics. General guidance on treatment options are described in the NCCN Guidelines (e.g., NCCN Clinical Practice Guidelines in Oncology, Breast Cancer, version 2.2016, National Comprehensive Cancer Network, 2016, pp. 1-202), and in the ESMO Guidelines (e.g., Senkus, E., et al. Primary Breast Cancer: ESMO Clinical Practice Guidelines for diagnosis, treatment and follow-up. Annals of Oncology 2015; 26(Suppl. 5): v8-v30; and Cardoso F., et al. Locally recurrent or metastatic breast cancer: ESMO Clinical Practice Guidelines for diagnosis, treatment and follow-up. Annals of Oncology 2012; 23 (Suppl. 7):vii11-vii19.). See also, Rodler, E, et al. Breast Disease. 2010/2011; 32:99-122.

Metastatic TNBC

Systemic chemotherapy is the standard treatment for patients with metastatic TNBC, although no standard regimen or sequence exists. Single-agent cytotoxic chemotherapeutic agents as shown in Table 1 are generally regarded as the primary option for patients with metastatic TNBC, although combination chemotherapy regimens such as those shown in Table 2 may be used, for instance when there is aggressive disease and visceral involvement. Additional details on chemotherapy combinations that can be utilized are provided below in the section on early and locally advanced treatment options. Treatment may also involve sequential rounds of different single agent treatments. Palliative surgery and radiation may be utilized as appropriate to manage local complications.

The methods provided herein include administering a compound of the present disclosure to a patient with metastatic TNBC in combination with one of the single-agent chemotherapy agents listed in Table 1 or in combination with sequential rounds of different chemotherapy agents listed in Table 1. Such methods may optionally be combined with surgery and/or radiation treatment.

TABLE 1

Single agent chemotherapy regimens

| Class | Typical agents |
|---|---|
| Anthracyclines | Doxorubicin |
| | Pegylated liposomal doxorubicin |
| | Epirubicin |
| Taxanes | Paclitaxel |
| | Docetaxel |
| | Albumin-bound paclitaxel (nab-paclitaxel) |
| Anti-metabolites | Capecitabine |
| | Gemcitabine |
| Non-taxane microtubule inhibitors | Vinorelbine |
| | Eribulin |
| | Ixabepilone |
| Platinum | Carboplatin |
| | Cisplatin |
| Alkylating agent | Cyclophosphamide |

In one embodiment, the combination therapy comprises administering a compound of the present disclosure and administering an anthracycline such as doxorubicin, pegylated liposomal doxorubicin, or epirubicin.

In one embodiment, the combination therapy comprises administering a compound of the present disclosure and administering a taxane such as paclitaxel, docetaxel or albumin-bound paclitaxel (e.g., nab-paclitaxel).

In one embodiment, the combination therapy comprises administering a compound of the present disclosure and administering an anti-metabolite, including, for example, capecitabine or gemcitabine.

In one embodiment, the combination therapy comprises administering a compound of the present disclosure and administering a non-taxane microtubule inhibitor, such as vinorelbine, eribulin or ixabepilone.

In one embodiment, the combination therapy comprises administering a compound of the present disclosure and administering a platinum compound, such as carboplatin or cisplatin.

In one embodiment, the combination therapy comprises administering a compound of the present disclosure and administering an alkylating agent such as cyclophosphamide.

In some embodiments, a compound of the present disclosure is administered with a combination of chemotherapy agents as summarized in Table 2 below.

Additional guidance for treating metastatic TNBC is provided in Jones S E, et al. J Clin Concol. 2006; 24:5381-5387; Heemskerk-Gerritsen BAM, et al. Ann Surg. Oncol. 2007; 14:3335-3344; and Kell M R, et al. MBJ. 2007; 334:437-438.

Early and Locally Advanced TNBC

Patients with early and potentially resectable locally advanced TNBC (i.e. without distant metastatic disease) are managed with locoregional therapy (surgical resection with or without radiation therapy) with or without systemic chemotherapy.

Surgical treatment can be breast-conserving (e.g., a lumpectomy, which focuses on removing the primary tumor with a margin), or can be more extensive (e.g., mastectomy, which aims for complete removal of all of the breast tissue). Radiation therapy is typically administered post-surgery to the breast/chest wall and/or regional lymph nodes, with the goal of killing microscopic cancer cells left post-surgery. In the case of a breast conserving surgery, radiation is administered to the remaining breast tissue and sometimes to the regional lymph nodes (including axillary lymph nodes). In the case of a mastectomy, radiation may still be administered if factors that predict higher risk of local recurrence are present.

In one embodiment, a compound of the present disclosure is administered in combination with surgical treatment, either as a neoadjuvant or adjuvant therapy. In another embodiment, a compound of the present disclosure is administered before or after radiation treatment. In still another embodiment, a compound of the present disclosure is administered in combination with surgical and radiation treatment.

Depending on tumor and patient characteristics, chemotherapy may be administered in the adjuvant (post-operative) or neoadjuvant (pre-operative) setting. Examples of adjuvant/neoadjuvant chemotherapy regimens used to treat TNBC recommended by current guidelines are shown in Table 2. A compound of the present disclosure can be combined with any of the regimens shown in Table 2.

TABLE 2

| Combination chemotherapy regimens | | |
|---|---|---|
| Class | Typical agents | Shorthand |
| Anthracycline and alkylating agent followed by taxane | Doxorubicin + cyclophosphamide followed by a taxane (e.g., docetaxel or paclitaxel) | AC→ T |
| Anthracycline and alkylating agent | Doxorubicin + cyclophosphamide (or liposomal doxorubicin + cyclophosphamide)<br>Epirubicin + cyclophosphamide | AC<br>EC |
| Taxane, anthracycline, and alkylating agent | Docetaxel + doxorubicin + cyclophosphamide | TAC |
| Taxane and alkylating agent | Docetaxel + cyclophosphamide | TC |
| Alkylating agent, methotrexate and anti-metabolite | Cyclophosphamide + methotrexate + fluorouracil | CMF |
| Anti-metabolite, anthracycline, and alkylating agent | Fluorouracil + doxorubicin + cyclophosphamide<br>Fluorouracil + epirubicin + cyclophosphamide | FAC<br>FEC |
| Anti-metabolite, anthracycline, and alkylating agent followed by taxane | Fluorouracil + epirubicin + cyclophosphamide followed by docetaxel or paclitaxel<br>Fluorouracil + doxorubicin + cyclophosphamide followed by paclitaxel | FEC/CEF→T<br>FAC→T |
| Taxane and anti-metabolite | Docetaxel + capecitabine, or Paclitaxel + gemcitabine | GT |
| Anti-metabolite and platinum | Gemcitabine + carboplatin | |

TABLE 2-continued

| Combination chemotherapy regimens | | |
|---|---|---|
| Class | Typical agents | Shorthand |
| Anti-metabolite and non-taxane microtubule inhibitor | Capecitibine + vinorelbine<br>Gemcitabine + vinorelbine | |
| Taxane and VEGF inhibitor (e.g., anti-VEGF antibody) | Paclitaxel + bevacizumab | |

In one embodiment, the combination therapy comprises administering a compound of the present disclosure and administering an anthracycline and an alkylating agent, optionally followed by a taxane. In one such embodiment, the compound of the present disclosure is administered with doxorubicin and cyclophosphamide followed by a taxane (e.g., docetaxel or paclitaxel), which is a chemotherapy regimen designated as AC→T.

In one embodiment, the combination therapy comprises administering a compound of the present disclosure and administering an anthracycline and an alkylating agent. For example, in one embodiment, the combination therapy comprises administering a compound of the present disclosure and administering doxorubicin or liposomal doxorubicin and cyclophosphamide, which is designated as AC. In another embodiment, the combination therapy comprises administering a compound of the present disclosure and administering epirubicin and cyclophosphamide, which is a chemotherapy regimen referred to as EC.

In one embodiment, the combination therapy comprises administering a compound of the present disclosure and administering a taxane, an anthracycline, and an alkylating agent. For instance, in one embodiment, the combination therapy comprises administering a compound of the present disclosure and administering docetaxel, doxorubicin and cyclophosphamide, a chemotherapy regimen which is denoted as TAC.

In another embodiment, the combination therapy comprises administering a compound of the present disclosure and administering taxane and an alkylating agent. In one such embodiment, the combination therapy comprises administering a compound of the present disclosure and administering docetaxel and cyclophosphamide, which is a chemotherapy regimen referred to as TC.

In still another embodiment, the combination therapy comprises administering a compound of the present disclosure and administering taxane and an alkylating agent. For instance, in one embodiment, the combination therapy comprises administering a compound of the present disclosure and administering docetaxel and cyclophosphamide, a chemotherapy regimen designated as TC.

In one embodiment, the combination therapy comprises administering a compound of the present disclosure and administering an alkylating agent, methotrexate, and an anti-metabolite. As an example, in one embodiment, the combination therapy comprises administering a compound of the present disclosure and administering an alkylating agent, methotrexate and an anti-metabolite. In one such embodiment, the combination therapy comprises administering a compound of the present disclosure and administering cyclophosphamide, methotrexate and fluorouracil, a chemotherapy regimen which is referred to as CMF.

In another embodiment, the combination therapy comprises administering a compound of the present disclosure and administering an anti-metabolite, an anthracycline, and an alkylating agent. In one such embodiment, the combination therapy comprises administering a compound of the present disclosure and administering fluorouracil, doxorubicin and cyclophosphamide, which is a chemotherapy regimen denoted as FAC. In another such embodiment, the combination therapy comprises administering a compound of the present disclosure and administering fluorouracil, epirubicin and cyclophosphamide, a chemotherapy regimen designated as FEC.

In still another embodiment, the combination therapy comprises administering a compound of the present disclosure and administering an anti-metabolite, an anthracycline, and an alkylating agent followed by taxane. As an example, in one embodiment, the combination therapy comprises administering a compound of the present disclosure and administering fluorouracil, epirubicin and cyclophosphamide followed by docetaxel or paclitaxel, a chemotherapy regimen referred to as FEC (or CEF)→T. In another embodiment, the combination therapy comprises administering a compound of the present disclosure and administering fluorouracil, doxorubicin and cyclophosphamide followed by paclitaxel, which is a chemotherapy regimen designated as FAC→T.

In yet another embodiment, the combination therapy comprises administering a compound of the present disclosure and administering taxane and an anti-metabolite. As an example, in one embodiment, the combination therapy comprises administering a compound of the present disclosure and administering docetaxel and capecitabine. In another example the combination therapy comprises administering a compound of the present disclosure and administering paclitaxel and gemcitabine, a chemotherapy regimen referred to as GT.

In one embodiment, the combination therapy comprises administering a compound of the present disclosure and administering an anti-metabolite and a platinum compound. For instance, in one embodiment, the combination therapy comprises administering a compound of the present disclosure and administering gemcitabine and carboplatin.

In another embodiment, the combination therapy comprises administering a compound of the present disclosure and administering an anti-metabolite and a non-taxane microtubule inhibitor. In one such embodiment, the combination therapy comprises administering a compound of the present disclosure and administering capecitibine and vinorelbine. In another such embodiment, the combination therapy comprises administering a compound of the present disclosure and administering gemcitabine and vinorelbine.

In still another embodiment, the combination therapy comprises administering a compound of the present disclosure and administering a taxane and a VEGF inhibitor (e.g., anti-VEGF antibody). For instance, in one embodiment, the combination therapy comprises administering a compound of the present disclosure and administering paclitaxel and bevacizumab.

Additional guidance for treating early and locally advanced TNBC is provided in Solin U., Clin Br Cancer. 2009; 9:96-100; Freedman G M, et al. Cancer. 2009; 115: 946-951; Heemskerk-Gerritsen BAM, et al. Ann Surg Oncol. 2007; 14:3335-3344; and Kell M R, et al. MBJ. 2007; 334:437-438.

Non-Small Cell Lung Cancer (NSCLC)

Compounds of the disclosure can be administered alone or they can be used in a combination therapy. For instance, the combination therapy includes administering a compound of the disclosure and administering at least one additional therapeutic agent (e.g. one, two, three, four, five, or six additional therapeutic agents).

In some aspects, the compounds are for use in a combination therapy for the treatment of non-small cell lung cancer NSCLC, such as a squamous cell carcinoma, adenocarcinoma, large cell carcinoma, adenosquamous carcinoma, undifferentiated carcinoma, or a combination thereof.

In one embodiment, the NSCLC is in occult stage, stage 0, I, II, III, or IV.

In one embodiment, the NSLCL is in occult stage, stage 0, IA, IB, IIA, IIB, IIIA, IIIB, or IV.

The present disclosure is directed to use of disclosed compounds for an adjuvant or neo-adjuvant treatment.

The present disclosure is directed to use of disclosed compounds for a first line, second line, or third line treatment.

The present disclosure is directed to use of disclosed compounds for a single agent treatment.

The present disclosure is directed to use of disclosed compounds for a treatment of a stage IV or a recurrent disease.

The present disclosure is directed to use of disclosed compounds for a treatment which is combined with surgery, radiation therapy, or a combination thereof.

In one embodiment, the combination therapy comprises administering a compound of the present disclosure and administering at least one additional therapeutic agent such as cisplatin, carboplatin, paclitaxel, paclitaxel protein bound, docetaxel, gemcitabine, vinorelbine, etoposide, nintedanib, vinblastine, and/or pemetrexed.

In one embodiment, the combination therapy comprises administering a compound of the present disclosure and administering at least one additional therapeutic agent such as afatinib, bevacizumab, cabozantinib, ceritinib, crizotinib, erlotinib hydrochloride, osimertinib, ramucirumab, gefitinib, alectinib, trastuzumab, cetuximab, ipilimumab, trametinib, dabrafenib, vemurafenib, dacomitinib, tivantinib, and/or onartuzumab.

In one embodiment, the combination therapy comprises administering a compound of the present disclosure and administering at least one additional therapeutic agent such as afatinib, crizotinib, erlotinib hydrochloride, and/or gefitinib.

In one embodiment, the combination therapy comprises administering a compound of the present disclosure and administering checkpoint inhibitor agents, such as pembrolizumab, atezolizumab, and/or nivolumab.

In one embodiment, the combination therapy comprises administering a compound of the present disclosure and administering at least one additional therapeutic agent such as cisplatin, carboplatin, paclitaxel, paclitaxel protein bound, docetaxel, gemcitabine, vinorelbine, etoposide, nintedanib, vinblastine, pemetrexed, afatinib, bevacizumab, cabozantinib, ceritinib, crizotinib, erlotinib hydrochloride, osimertinib, ramucirumab, gefitinib, necitumumab, alectinib, trastuzumab, cetuximab, ipilimumab, trametinib, dabrafenib, vemurafenib, dacomitinib, tivantinib, onartuzumab, pembrolizumab, atezolizumab, and/or nivolumab.

Small Cell Lung Cancer (SCLC)

Compounds of the disclosure can be administered alone or they can be used in a combination therapy. For instance, the combination therapy includes administering a compound of the disclosure and administering at least one additional therapeutic agent (e.g. one, two, three, four, five, or six additional therapeutic agents).

In some aspects, the compounds are for use in a combination therapy for the treatment of Small Cell Lung Cancer (SCLC).

In one embodiment, the SCLC is a small cell carcinoma (oat cell cancer), mixed small cell/large cell carcinoma or combined small cell carcinoma.

In one embodiment, the SCLC is in occult stage, stage 0, I, II, III, or IV.

In one embodiment, the SLCL is in occult stage, stage 0, IA, IB, IIA, IIB, IIIA, IIIB, or IV.

In one embodiment, the SLCL is in stage I-III (limited stage).

The present disclosure is directed to use of disclosed compounds for a first line treatment of stage IV (extensive stage).

The present disclosure is directed to use of disclosed compounds for a second line treatment of stage IV (relapsed or refractory disease).

The present disclosure is directed to use of disclosed compounds for a third line treatment of stage IV (relapsed or refractory disease).

In one embodiment, a compound of the present disclosure is administered with one or more additional therapeutic agents selected from Etoposide, a platinum compound, Irinotecan, Topotecan, vinca alkaloids, alkylating agents, Doxorubicin, taxanes, and Gemcitabine. In another embodiment, the platinum compound is Cisplatin or Carboplatin. In another embodiment, the vinca alkaloid is Vinblastine, Vincristine, or Vinorelbine. In another embodiment, the alkylating agent is Cyclophosphamide or Ifosfamide. In another embodiment, the taxane is Docetaxel or Paclitaxel.

Ovarian Cancer

In a further aspect, the disclosure provides a method for treating an ovarian cancer (such as epithelial ovarian cancer (EOC), ovarian germ cell tumors, or ovarian stromal tumors) by administering an effective amount of a compound of the present disclosure. In a further aspect of the embodiment, the ovarian cancer is an epithelial ovarian cancer (EOC). In a further aspect of the embodiment, the ovarian cancer is an ovarian germ cell tumor. In a further aspect of the embodiment, the ovarian cancer is an ovarian stromal cell tumor. In one embodiment, the method comprises administering to an individual having ovarian cancer an effective amount of a compound of the present disclosure.

Compounds of the disclosure can be administered alone or they can be used in a combination therapy to treat ovarian cancer. For instance, the combination therapy includes administering a compound of the disclosure and administering at least one additional therapeutic agent (e.g. one, two, three, four, five, or six additional therapeutic agents).

In some aspects, the compounds are for use in a combination therapy for the treatment of an ovarian cancer (such as epithelial ovarian cancer (EOC), ovarian germ cell tumors, or ovarian stromal tumors). In one embodiment, the combination therapy comprises administering a compound of the present disclosure and administering at least one additional therapeutic agent such as a platinum compound (such as carboplatin, cisplatin, less often oxaliplatin or iproplatin), and/or a taxane (such as paclitaxel or docetaxel, or albumin bound paclitaxel (nab-paclitaxel)). In one embodiment, the combination therapy comprises administering a compound of the present disclosure and administering carboplatin and a taxane (such as paclitaxel or docetaxel or Albumin bound paclitaxel (nab-paclitaxel)).

In one embodiment, the combination therapy comprises administering a compound of the present disclosure and administering at least one additional therapeutic agent such as albumin bound paclitaxel (nab-paclitaxel), altretamine, capecitabine, cyclophosphamide, etoposide, gemcitabine, ifosfamide, irinotecan, liposomal doxorubicin, melphalan, pemetrexed, topotecan, vinorelbine, bevacizumab, a platinum compound (such as carboplatin, cisplatin, oxaliplatin, or iproplatin), and/or a taxane (such as paclitaxel or docetaxel, or albumin bound paclitaxel (nab-paclitaxel)).

In one embodiment, the combination therapy comprises administering a compound of the present disclosure and administering bevacizumab and a taxane (such as paclitaxel or docetaxel, or albumin bound paclitaxel (nab-paclitaxel)).

In one embodiment, the combination therapy comprises administering a compound of the present disclosure and administering at least one additional therapeutic agent such as cisplatin, etoposide, and/or bleomycin.

In one embodiment, the combination therapy comprises administering a compound of the present disclosure and administering cisplatin (Platinol), etoposide, and bleomycin (PEB (or BEP)).

In one embodiment, the combination therapy comprises administering a compound of the present disclosure and administering paclitaxel (Taxol), ifosfamide, and cisplatin (TIP).

In one embodiment, the combination therapy comprises administering a compound of the present disclosure and administering vinblastine, ifosfamide, and cisplatin (VeIP).

In one embodiment, the combination therapy comprises administering a compound of the present disclosure and administering etoposide (VP-16), ifosfamide, and cisplatin (VIP).

V. Methods of Manufacturing

In another embodiment, processes for making the subject compound are provided. The following synthetic reaction schemes detailed in the General Schemes and Examples are merely illustrative of some of the methods by which the compounds of the present disclosure (or an embodiment or aspect thereof) can be synthesized. Various modifications to these synthetic reaction schemes can be made and will be suggested to one skilled in the art having referred to the disclosure contained in this Application.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Intermediates and final compounds were purified by either flash chromatography, and/or by reverse-phase preparative HPLC (high performance liquid chromatography), and/or by supercritical fluid chromatography (SFC).

Liquid chromatography-mass spectrometry (LCMS) was performed using a (1) Agilent technologies 6110/6120/G1946/G1925B Quadrupole in ESI+ mode, or (2) Shimadzu liquid chromatography-mass spectrometry (LCMS) 2010 mass spectrometer in ESI+ mode. Mass spectra data generally only indicates the parent ions unless otherwise stated. (MS or HRMS data is provided for a particular intermediate or compound where indicated.)

Nuclear magnetic resonance spectroscopy (NMR) was performed using a (1) Bruker 400 NMR spectrometer, or (2) Varian 400 NMR spectrometer, and referenced to tetramethylsilane. NMR data is provided for a particular intermediate or compound where indicated.

VI. General Schemes and Examples

General Schemes

The following generalized schemes are used to prepare the disclosed compounds, intermediates, and pharmaceutically acceptable salts thereof. Disclosed compounds and intermediates may be prepared using standard organic synthetic techniques and from commerically available starting materials and reagents. It will be appreciated that synthetic procedures employed in the preparation of disclosed compounds and intermediates will depend on the particular substituents present in the compound or intermediate and that various protection, deprotection, and conversion steps that are standard in organic synthesis may be required, but may not be illustrated in the following general schemes. It is also to be understood that any of the steps shown in any of the following general schemes may be used in any combination and in any order that is chemically feasible to achieve a desired intermediate or disclosed compound. It is further to be understood that, when the stereochemistry of a particular compound or intermediate is not disclosed in any given example, the stereochemistry of said compound or intermediate may be determined by any known means common in the art.

SCHEME 1

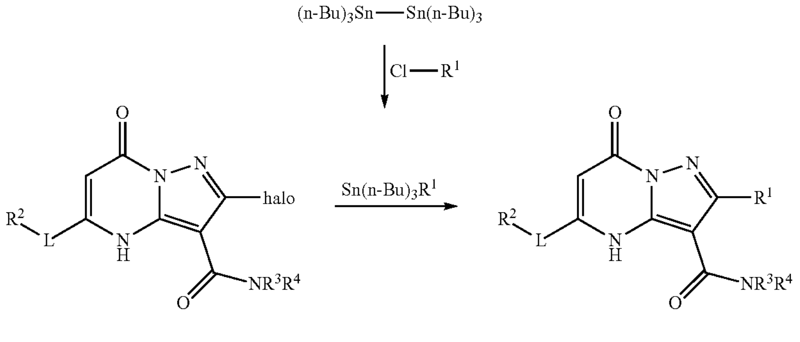

Scheme 1 describes a general synthetic scheme for converting a halo (halogen) moiety to an $R^1$ moiety, as defined above for formula (I), using a tin compound. L, $R^2$, $R^3$, and $R^4$ are as defined above for formula (I). Halo refers to any halogen, including, for example, chlorine, bromine, or iodine.

SCHEME 2

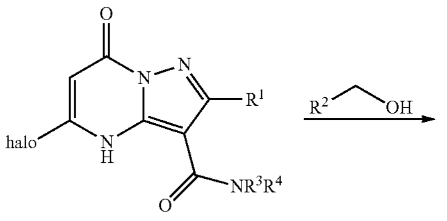

-continued

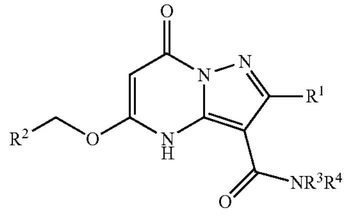

Scheme 2 describes a general synthetic scheme for converting a halo (halogen) moiety to an -L-$R^2$ moiety, as defined above for formula (I), wherein the -L-$R^2$ moiety is —O—$CH_2$—$R^2$. $R^1$, $R^3$, and $R^4$ are as defined above for formula (I). Halo refers to any halogen, including, for example, chlorine, bromine, or iodine.

SCHEME 3

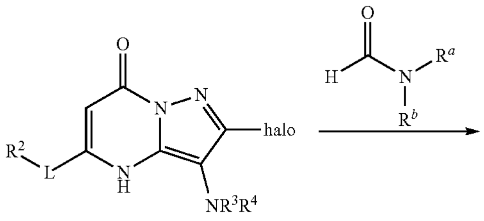

-continued

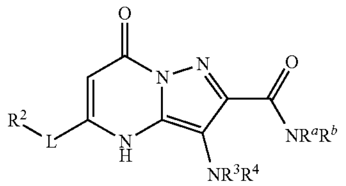

Scheme 3 describes a general synthetic scheme for converting a halo (halogen) moiety to a —C(O)—$NR^aR^b$ moiety at position $R^1$ as defined above for formula (I). $R^2$, $R^3$, $R^4$, $R^a$, and $R^b$ are as defined above for formula (I). Halo refers to any halogen, including, for example, chlorine, bromine, or iodine.

SCHEME 4
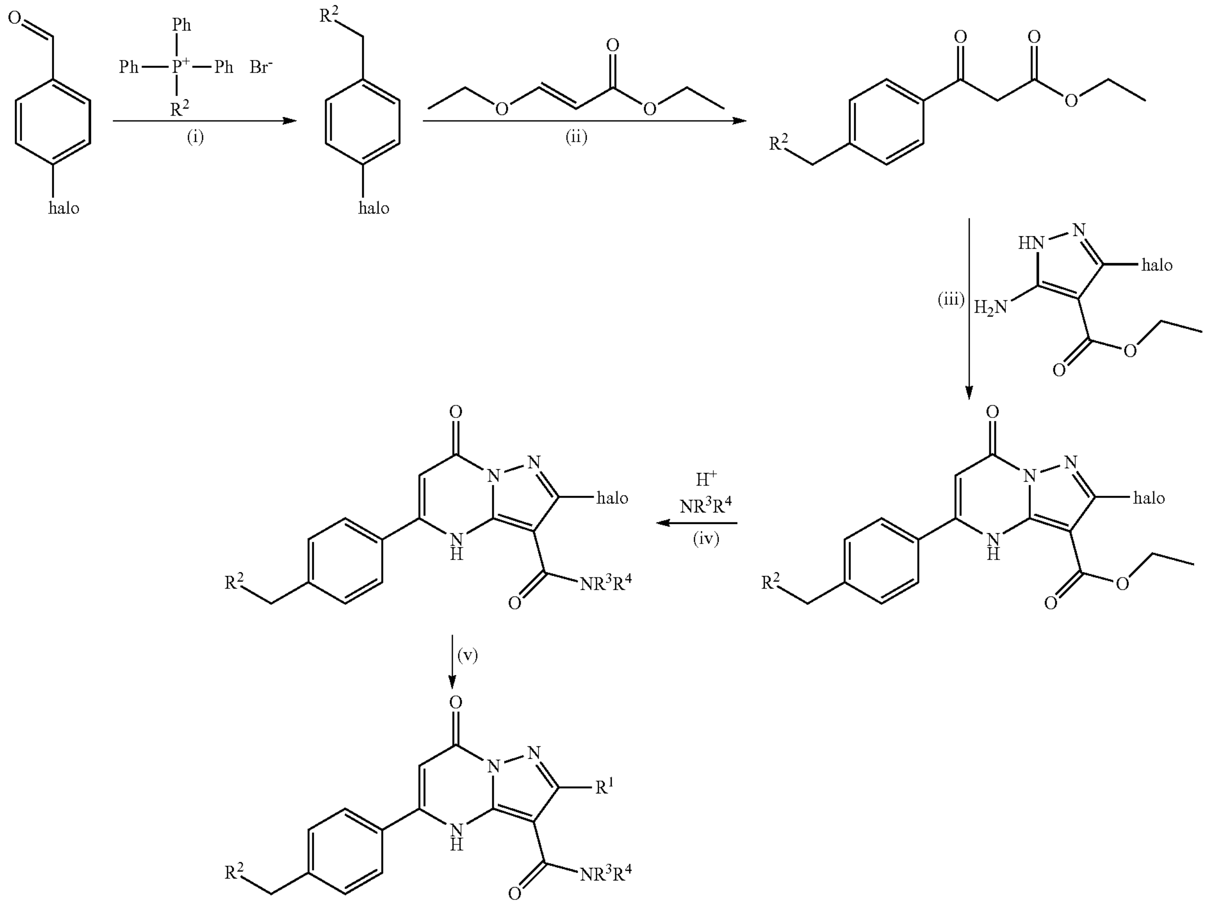
Scheme 4 describes a general synthetic scheme to produce a compound of formula (I). $R^1$, $R^2$, $R^3$, and $R^4$ are as defined above for formula (I). Halo refers to any halogen, including, for example, chlorine, bromine, or iodine.
SCHEME 5
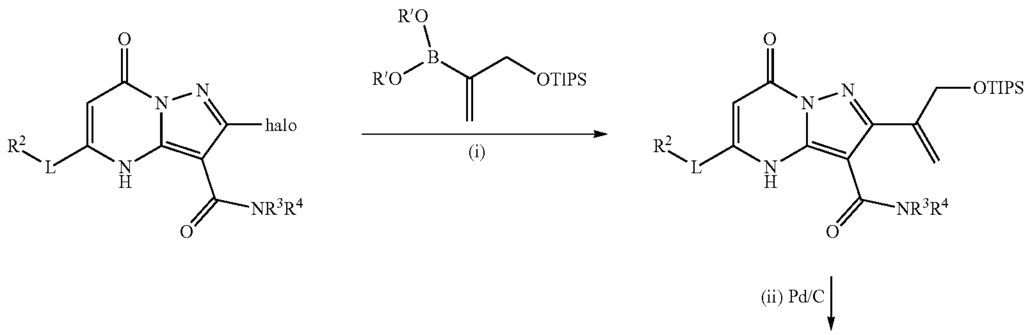

-continued

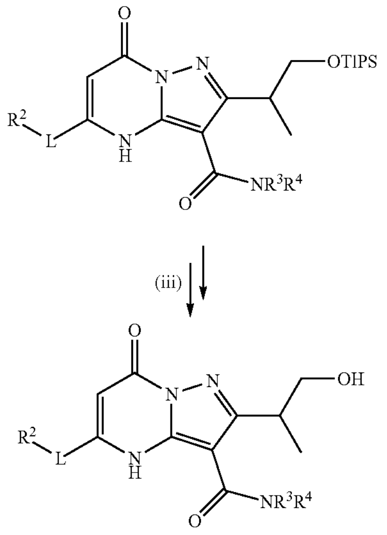

Scheme 5 describes a general synthesis scheme for converting a halogen (halo) moiety into an alkyl moiety at position $R^1$ of the compound of formula (I). $R^2$, $R^3$, $R^4$, and L are as defined above for formula (I). Halo refers to any halogen, including, for example, chlorine, bromine, or iodine. TIPS is triisopropylsilyl. R' may be any suitable atom or group, including, for example, hydrogen. In certain embodiments, the two R' substituents in

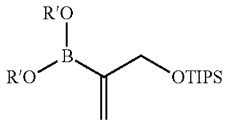

of step (i) may form a ring structure (together with the atoms to which they are attached). In some embodiments, the compound of formula

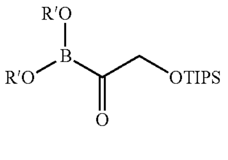 is 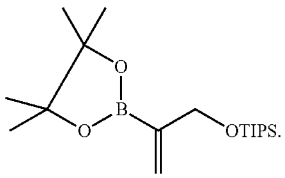

EXAMPLES

The following are examples of methods and compositions of the disclosure. It is understood that various other embodiments may be practiced, given the general description provided above. The disclosure will be more fully understood by reference to the following examples. The claims should not, however, be construed as limited to the scope of the examples.

Intermediate A

Preparation of 2-Bromo-5-(4-cyclohexylphenyl)-3-(3-(fluoromethyl)azetidine-1-carbonyl)pyrazolo[1,5-a]pyrimidin-7(4H)-one The general reaction scheme was as follows:

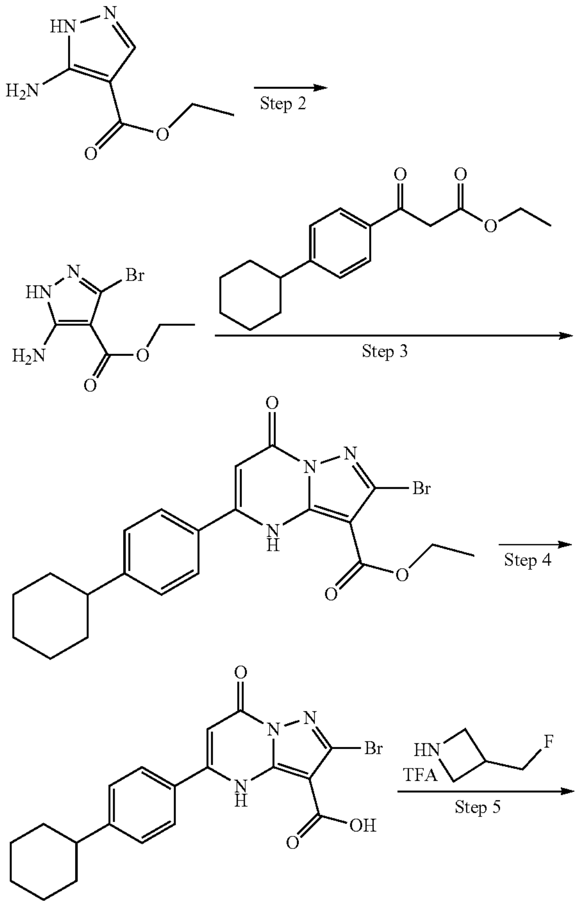

-continued

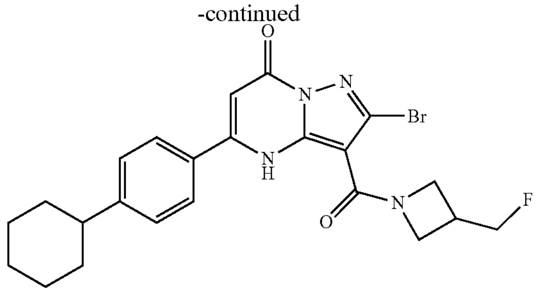

Intermediate A

Step 1: Ethyl 3-(4-cyclohexylphenyl)-3-oxopropanoate

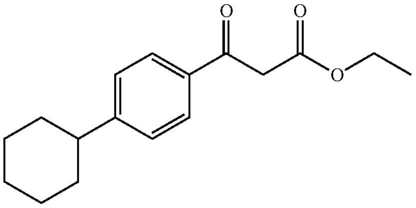 [SMILES: CCOC(=O)CC(=O)c1ccc(C2CCCCC2)cc1]

To a solution of 1-(4-cyclohexylphenyl)ethanone (40 g, 197 mmol) in THF (400 mL) was added NaH (60% in mineral oil, 17.4 g, 435 mmol) slowly at 0° C., then diethyl carbonate (70 g, 593 mmol) was added slowly and stirred for 5 h. The reaction solution was quenched with saturated aqueous $NH_4Cl$ (500 mL) and extracted with EtOAc (500 mL×2). The combined organic layers were washed with brine (500 mL×2) and concentrated in vacuo. The residue was purified by column chromatography on silica gel (0-10% EtOAc in petroleum ether) to afford the title compound (50 g, 92%, ketone/enol=2.4:1) as a yellow oil. $^1H$ NMR (400 MHz, $CDCl_3$): δ 12.58 (s, 1H of enol), 7.86 (d, J=8.4 Hz, 2H of ketone), 7.71 (d, J=8.4 Hz, 2H of enol), 7.32 (d, J=8.4 Hz, 2H of ketone), 7.26 (d, J=8.4 Hz, 2H of enol), 5.64 (s, 1H of enol), 4.25-4.17 (m, 4H), 3.92 (s, 2H of ketone), 2.59-2.51 (m, 2H), 1.80-1.77 (m, 8H), 1.71-1.68 (m, 2H), 1.45-1.41 (m, 8H), 1.34 (t, J=7.2 Hz, 3H of enol), 1.32-1.29 (m, 2H), 1.27 (t, J=7.2 Hz, 3H of ketone).

Step 2: Ethyl 5-amino-3-bromo-1H-pyrazole-4-carboxylate

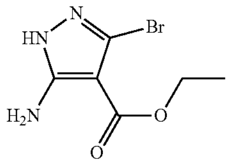

To a solution of ethyl 5-amino-1H-pyrazole-4-carboxylate (50 g, 322 mmol) in acetonitrile (500 mL) was added NBS (60 g, 337 mmol) slowly at 15° C., then stirred for 16 hours. The reaction solution was poured into water (500 mL) and extracted with EtOAc (300 mL×3), then washed with brine (300 mL×2) and concentrated in vacuo to afford the title crude compound (75 g, 79% purity) as a yellow solid which was used directly without further purification. LCMS (ESI): m/z 234.0 $(M+H)^+$.

Step 3: Ethyl 2-bromo-5-(4-cyclohexylphenyl)-7-oxo-4,7-dihydropyrazolo[1,5-a]pyrimidine-3-carboxylate

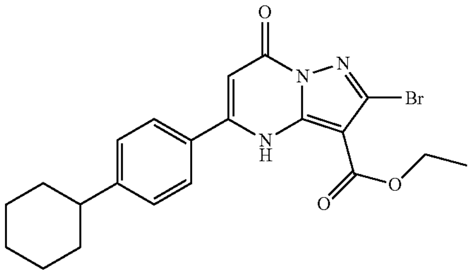 [SMILES: CCOC(=O)c1c(Br)nn2c(=O)cc(-c3ccc(C4CCCCC4)cc3)[nH]c12]

A mixture of the resulting crude ethyl 5-amino-3-bromo-1H-pyrazole-4-carboxylate (50 g) and ethyl 3-(4-cyclohexylphenyl)-3-oxo-propanoate (65 g, 236 mmol), p-TsOH·$H_2O$ (3.6 g, 21 mmol) in n-BuOH (400 mL) was stirred at 130° C. for 5 hours. The reaction solution was filtered and the filter cake was washed with EtOAc (100 mL) to afford the title compound (60 g, 63% over 2 steps) as a yellow solid. $^1H$ NMR (400 MHz, DMSO-$d_6$): δ 11.50 (s, 1H), 7.68 (d, J=8.4 Hz, 2H), 7.44 (d, J=8.4 Hz, 2H), 6.28 (s, 1H), 4.38 (q, J=7.2 Hz, 2H), 2.69-2.51 (m, 1H), 1.80-1.77 (m, 4H), 1.71-1.68 (m, 1H), 1.48-1.19 (m, 8H). LCMS (ESI): m/z 443.9 $(M+H)^+$.

Step 4: 2-Bromo-5-(4-cyclohexylphenyl)-7-oxo-4,7-dihydropyrazolo[1,5-a]pyrimidine-3-carboxylic acid

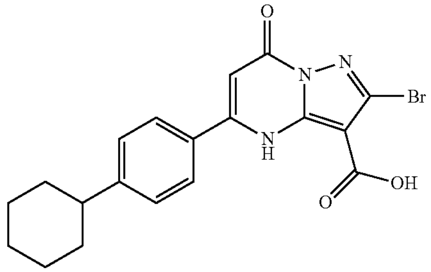 [SMILES: O=C(O)c1c(Br)nn2c(=O)cc(-c3ccc(C4CCCCC4)cc3)[nH]c12]

A mixture of lithium hydroxide monohydrate (9.5 g, 225 mmol) and ethyl 2-bromo-5-(4-cyclohexylphenyl)-7-oxo-4,7-dihydropyrazolo[1,5-a]pyrimidine-3-carboxylate (10 g, 22.5 mmol) in water (150 mL) and ethanol (150 mL) was stirred at 80° C. for 16 hours. The reaction solution was concentrated in vacuo, the residue was dissolved in water (200 mL) and adjusted with aqueous 1 M HCl until pH 3. The solid was filtrated, washed with water (50 mL) and dried in vacuum to afford the title compound (8 g, 90%) as a white solid which was used directly without further purification. LCMS (ESI): m/z 416.1 $(M+H)^+$.

Step 5: 2-Bromo-5-(4-cyclohexylphenyl)-3-(3-(fluoromethyl)azetidine-1-carbonyl) pyrazolo[1,5-a]pyrimidin-7(4H)-one

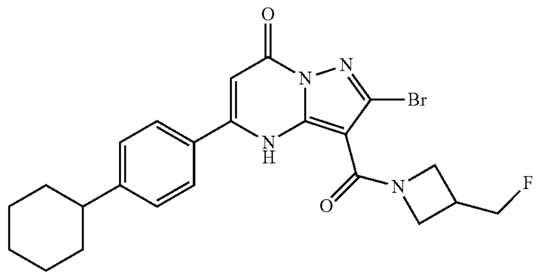 [SMILES: O=C(c1c(Br)nn2c(=O)cc(-c3ccc(C4CCCCC4)cc3)[nH]c12)N1CC(CF)C1]

To a solution of 2-bromo-5-(4-cyclohexylphenyl)-7-oxo-4,7-dihydropyrazolo[1,5-a]pyrimidine-3-carboxylic acid (13 g, 31.2 mmol) and DIPEA (15.5 mL, 93.7 mmol) in DMF (100 mL) was added HATU (18.2 g, 47.9 mmol) which was then stirred for 20 minutes. To the reaction mixture 3-(fluoromethyl) azetidine 2,2,2-trifluoroacetate (16 g, 78.1 mmol) was added and the reaction was stirred for 16 hours at room temperature. The reaction was then poured into brine (500 mL) and the pH was adjusted to 6 with aqueous 2 M HCl. The solid was filtrated and washed with water (50 mL) and EtOAc (200 mL) and dried to afford the title compound (12 g, 79%) as a white solid. $^1$H NMR (400 MHz, DMSO-$d_6$): δ 12.55 (s, 1H), 7.69 (d, J=8.4 Hz, 2H), 7.43 (d, J=8.4 Hz, 2H), 6.13 (s, 1H), 4.63 (dd, J=47.2, 6.0 Hz, 2H), 4.17-4.13 (m, 2H), 3.87-3.83 (m, 2H), 3.11-2.94 (m, 1H), 2.61-2.59 (m, 1H), 1.81-1.78 (m, 4H), 1.71-1.69 (m, 1H), 1.52-1.32 (m, 4H), 1.31-1.17 (m, 1H); LCMS (ESI): m/z 487.0 $(M+H)^+$.

Intermediate B

Preparation of 5-(4-Cyclohexylphenyl)-3-(3-(fluoromethyl)azetidine-1-carbonyl)-7-oxo-4,7-dihydropyrazolo[1,5-a]pyrimidine-2-carboxylic acid The general reaction scheme was as follows:

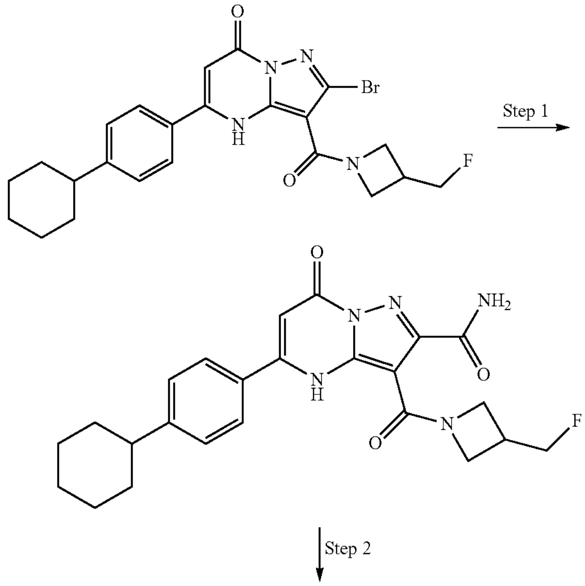

-continued

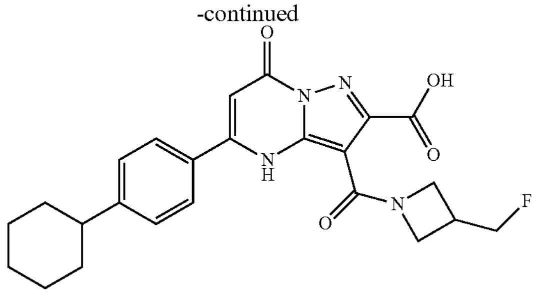

Intermediate B

Step 1: 5-(4-Cyclohexylphenyl)-3-(3-(fluoromethyl) azetidine-1-carbonyl)-7-oxo-4,7-dihydropyrazolo[1,5-a]pyrimidine-2-carboxamide

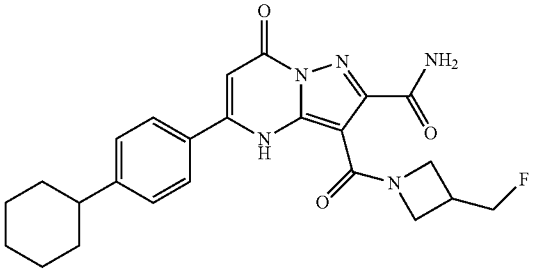 [SMILES: NC(=O)c1nn2c(=O)cc(-c3ccc(C4CCCCC4)cc3)[nH]c2c1C(=O)N1CC(CF)C1]

A mixture of 2-bromo-5-(4-cyclohexylphenyl)-3-(3-(fluoromethyl)azetidine-1-carbonyl) pyrazolo[1,5-a]pyrimidin-7(4H)-one (Intermediate A, 2.5 g, 5.1 mmol), DMAP (1 g, 8.2 mmol) and Pd(dppf)$Cl_2$ (375 mg, 0.51 mmol) in formamide (20 mL) was stirred at 120° C. under a CO atmosphere (15 Psi) for 16 hours. The reaction solution was poured into water (50 mL), extracted with EtOAc (50 mL×2), dried and concentrated in vacuo. The residue was purified by chromatography on silica gel (0-10% MeOH in DCM) to afford the title compound (450 mg, 19%) as a yellow solid. $^1$H NMR (400 MHz, DMSO-$d_6$): δ 12.45 (br s, 1H), 8.11 (br s, 1H), 7.77 (d, J=8.0 Hz, 2H), 7.71 (br s, 1H), 7.41 (d, J=8.0 Hz, 2H), 6.11 (s, 1H), 4.58 (dd, J=47.2, 6.4 Hz, 2H), 4.12-4.06 (m, 2H), 3.80-3.77 (m, 2H), 2.98-2.88 (m, 1H), 2.61-2.56 (m, 1H), 1.80-1.78 (m, 4H), 1.71-1.68 (m, 1H), 1.49-1.34 (m, 4H), 1.30-1.20 (m, 1H); LCMS (ESI): m/z 452.2.

Step 2: 5-(4-Cyclohexylphenyl)-3-(3-(fluoromethyl) azetidine-1-carbonyl)-7-oxo-4,7-dihydropyrazolo[1,5-a]pyrimidine-2-carboxylic acid

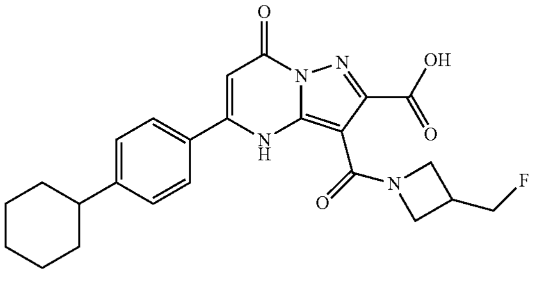 [SMILES: O=C(O)c1nn2c(=O)cc(-c3ccc(C4CCCCC4)cc3)[nH]c2c1C(=O)N1CC(CF)C1]

mixture of 5-(4-cyclohexylphenyl)-3-(3-(fluoromethyl)azetidine-1-carbonyl)-7-oxo-4,7-dihydropyrazolo[1,5-a]pyrimidine-2-carboxamide (360 mg, 0.8 mmol) and KOH (1 g, 17.8 mmol) in ethanol (30 mL) was stirred at 90° C. for 16 hours, then the mixture was concentrated in vacuo. The crude organic residue was then dissolved in water (20 mL) and acidified to pH 5 with aqueous 1M HCl. The aqueous layer was extracted with DCM (30 mL×3). The organic layers were dried over $Na_2SO_4$ and concentrated in vacuo to afford the title compound (220 mg, 61%) as a yellow solid which was used for the next step directly without further purification. $^1$H NMR (400 MHz, DMSO-$d_6$): δ 7.76 (d, J=8.4 Hz, 2H), 7.40 (d, J=7.6 Hz, 2H), 6.15 (s, 1H), 4.61 (dd, J=47.2, 5.6 Hz, 2H), 4.44-3.81 (m, 4H), 3.06-2.92 (m, 1H), 2.63-2.55 (m, 1H), 1.82-1.77 (m, 4H), 1.74-1.67 (m, 1H), 1.47-1.37 (m, 4H), 1.22-1.25 (m, 1H); LCMS (ESI): m/z 453.2 $(M+H)^+$.

Intermediate C

Preparation of 2-Bromo-5-(4-(cyclopentylmethyl)phenyl)-3-(3-(fluoromethyl)azetidine-1-carbonyl)pyrazolo[1,5-a]pyrimidin-7(4H)-one The general reaction scheme was as follows:

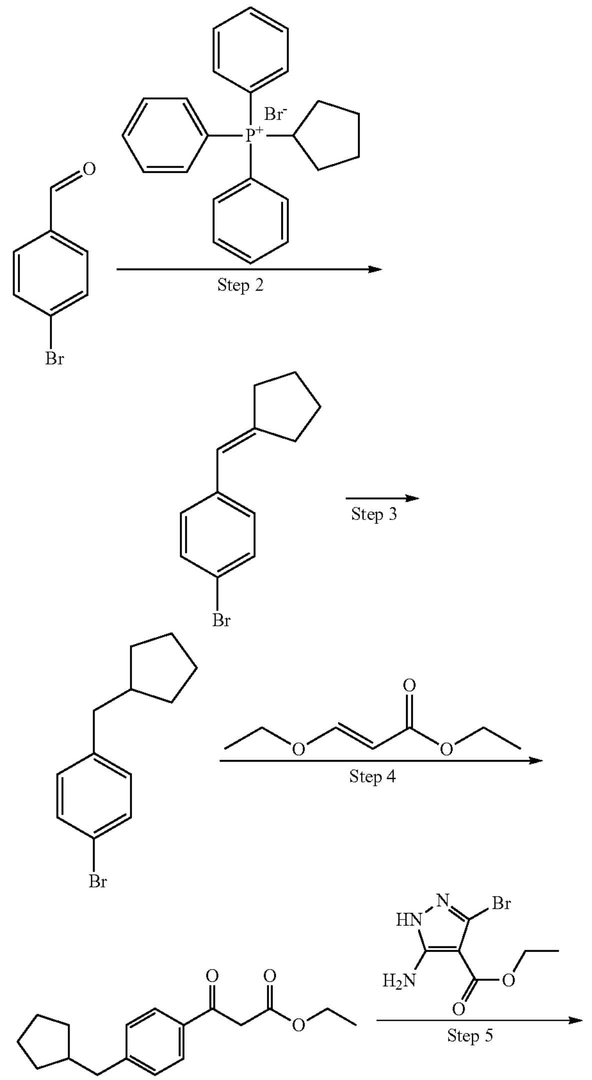

-continued

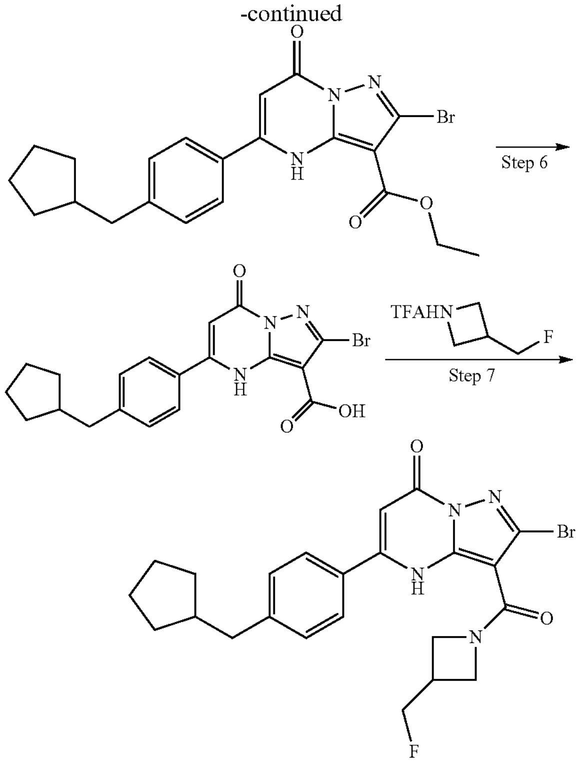

Intermediate C

Step 1: Cyclopentyltriphenylphosphonium bromide

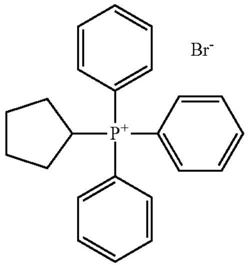 [SMILES: c1ccc([P+](c2ccccc2)(c2ccccc2)C2CCCC2)cc1 ; [Br-]]

A mixture of triphenylphosphine (79.2 g, 301.95 mmol) and bromocyclopentane (50.0 g, 335.5 mmol)) were stirred at 140° C. for 6 hours under nitrogen atmosphere. The suspension was filtered. The resulting filtered cake was washed with toluene and dried to afford the title compound (60.0 g, 48%) as a white solid. $^1$H NMR (400 MHz, $D_2O$): δ 7.78-7.68 (m, 9H), 7.63-7.55 (m, 6H), 4.00-3.87 (m, 1H), 2.35-2.22 (m, 2H), 1.85-1.65 (m, 2H), 1.63-1.49 (m, 2H), 1.36-1.24 (m, 2H).

Step 2: 1-Bromo-4-(cyclopentylidenemethyl)benzene

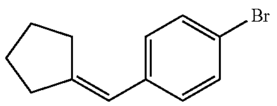 [SMILES: Brc1ccc(C=C2CCCC2)cc1]

To a solution of cyclopentyltriphenylphosphonium bromide (50.0 g, 121.6 mmol) in toluene (150 mL) was added LiHMDS (130.5 mL, 130.5 mmol) at −78° C. under a nitrogen atmosphere and the solution was stirred for 30 minutes. Then 4-bromobenzaldehyde (15.0 g, 81.07 mmol) was added into the mixture and was stirred at 120° C. for 16 hours. The reaction solution was poured into water (100 mL) and extracted with EtOAc (50 mL×3). The combined organic layers were washed with brine (50 mL×2). The organic layer was dried over anhydrous $Na_2SO_4$ and concentrated in vacuo. The residue was purified by flash chromatography on silica gel eluting with petroleum ether to afford the title compound (15.0 g, 78%) as a colorless oil. $^1$H NMR (400 MHz, $CDCl_3$): δ 7.42 (d, J=8.4 Hz, 2H), 7.17 (d, J=8.4 Hz, 2H), 6.30 (s, 1H), 2.55-2.44 (m, 4H), 1.85-1.74 (m, 2H), 1.71-1.64 (m, 2H).

Step 3: 1-Bromo-4-(cyclopentylmethyl)benzene

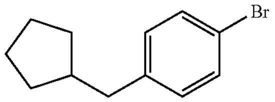 [SMILES: Brc1ccc(CC2CCCC2)cc1]

To a mixture of 1-bromo-4-(cyclopentylidenemethyl)benzene (9.0 g, 37.95 mmol) in ethanol (900 mL) was added $PtO_2$ (431.0 mg, 1.90 mmol). The reaction suspension was stirred at 30° C. under $H_2$ (35 Psi) for 12 min. The suspension was filtered through a pad of celite and the filtered cake was washed with EtOH (500 mL×2). The filtrate was concentrated in vacuo to afford the title compound (9.0 g, 99%) as a colorless oil. $^1$H NMR (400 MHz, $CDCl_3$): δ 7.39 (d, J=8.0 Hz, 2H), 7.05 (d, J=8.0 Hz, 2H), 2.56 (d, J=7.6 Hz, 2H), 2.09-2.0 (m, 1H), 1.74-1.62 (m, 4H), 1.54-1.51 (m, 2H), 1.22-1.12 (m, 2H).

Step 4: Ethyl 3-(4-(cyclopentylmethyl)phenyl)-3-oxopropanoate

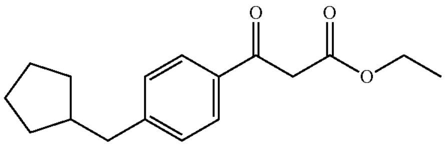 [SMILES: CCOC(=O)CC(=O)c1ccc(CC2CCCC2)cc1]

In a glovebox under a nitrogen atmosphere a mixture of 1-bromo-4-(cyclopentylmethyl)benzene (16.0 g, 66.9 mmol) in dioxane (200 mL) was added ethyl 3-ethoxyacrylate (28.9 g, 200.71 mmol), N-cyclohexyl-N-methylcyclohexanamine (13.1 g, 66.9 mmol) and LiCl (8.5 g, 200.71 mmol) at which point the mixture was stirred at room temperature for 10 minutes. Then $Pd(P^tBu_3)_2$ (2.1 g, 4.01 mmol) was added and the reaction mixture was taken out of the glovebox. The reaction mixture was then stirred at 110° C. for 16 hours. The solution was quenched with brine (300 mL) and extracted with ethyl acetate (200 mL×2). The combined organic layers were dried over $Na_2SO_4$ and concentrated in vacuo. The crude product was dissolved into 1,2-dichloroethane and 6 M HCl (60 mL) was added into the mixture. The mixture was stirred at room temperature for 3 h. The solution was adjusted to pH 8 with saturated aqueous $NaHCO_3$ and extracted with $CH_2Cl_2$ (200 mL×2). The combined organic layers were dried over $Na_2SO_4$ and concentrated in vacuo. The residue was purified by flash chromatography (0-5% EtOAc in petroleum ether) on silica gel to afford the title compound (5.5 g, 30%, ketone/enol=3:1) as a colorless oil. $^1$H NMR (400 MHz, $CDCl_3$): δ 12.59 (s, 1H of enol), 7.87 (d, J=8.4 Hz, 2H of ketone), 7.69 (d, J=8.4 Hz, 2H of enol), 7.28 (d, J=8.4 Hz, 2H of ketone), 7.23 (d, J=8.4 Hz, 2H of enol), 5.64 (s, 1H of enol), 4.30-4.20 (m, 4H), 3.98 (s, 2H of ketone), 2.69-2.64 (m, 4H), 2.15-2.04 (m, 2H), 1.75-1.63 (m, 8H), 1.55-1.48 (m, 4H), 1.34 (t, J=7.2 Hz, 3H of enol), 1.27 (t, J=7.2 Hz, 3H of ketone), 1.23-1.15 (m, 4H).

Step 5: Ethyl 2-bromo-5-(4-(cyclopentylmethyl)phenyl)-7-oxo-4,7-dihydropyrazolo [1,5-a]pyrimidine-3-carboxylate

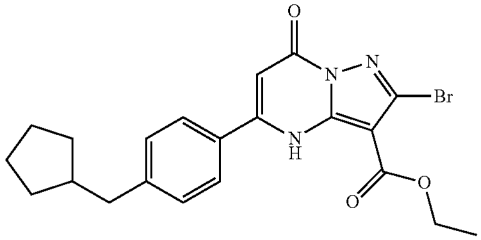 [SMILES: CCOC(=O)c1c(Br)nn2c(=O)cc(-c3ccc(CC4CCCC4)cc3)[nH]c12]

A mixture of ethyl 3-(4-(cyclopentylmethyl)phenyl)-3-oxopropanoate (1.83 g, 6.67 mmol), 4-methyl benzenesulfonic acid monohydrate (104.0 mg, 0.55 mmol) and ethyl 5-amino-3-bromo-1H-pyrazole-4-carboxylate (1.30 g, 5.55 mmol) in n-BuOH (10 mL) was stirred at 120° C. for 16 hours. The reaction mixture was then evaporated to dryness. The residue was purified by flash chromatography (0-50% EtOAc in petroleum ether) on silica gel to afford the title compound (1.20 g, 40%) as a white solid. $^1$H NMR (400 MHz, DMSO-$d_6$): δ 11.50 (s, 1H), 7.70 (d, J=8.0 Hz, 2H), 7.42 (d, J=8.0 Hz, 2H), 6.31 (s, 1H), 4.35 (q, J=7.2 Hz, 2H), 2.67 (d, J=7.2 Hz, 2H), 2.21-2.05 (m, 1H), 1.71-1.57 (m, 4H), 1.55-1.45 (m, 2H), 1.38 (t, J=7.2 Hz, 3H), 1.26-1.18 (m, 2H); LCMS (ESI): m/z 444.1 $(M+H)^+$.

Step 6: 2-Bromo-5-(4-(cyclopentylmethyl)phenyl)-7-oxo-4,7-dihydropyrazolo[1,5-a] pyrimidine-3-carboxylic acid

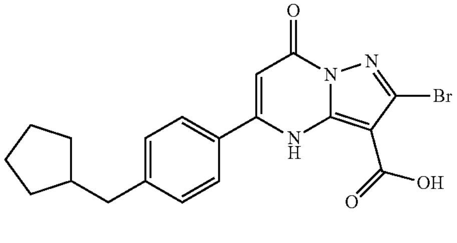 [SMILES: O=C(O)c1c(Br)nn2c(=O)cc(-c3ccc(CC4CCCC4)cc3)[nH]c12]

To a mixture of ethyl 2-bromo-5-(4-(cyclopentylmethyl) phenyl)-7-oxo-4,7-dihydro pyrazolo[1,5-a]pyrimidine-3-carboxylate (1.20 g, 2.7 mmol) in water (15 mL) and EtOH (15 mL) was added lithium hydroxide monohydrate (1.13 g, 27.0 mmol). The mixture was stirred at 90° C. for 16 hours. The solution was adjusted to pH 4 with the addition of 1M aqueous HCl. The resulting mixture was extracted with ethyl acetate (50 mL×2). The combined organic layers were dried over $Na_2SO_4$, filtered and concentrated in vacuo to afford the title compound (950 mg, 85%) as a white solid. $^1H$ NMR (400 MHz, DMSO-$d_6$): δ 11.29 (s, 1H), 7.70 (d, J=8.0 Hz, 2H), 7.40 (d, J=8.0 Hz, 2H), 6.29 (s, 1H), 2.67 (d, J=7.2 Hz, 2H), 2.15-2.07 (m, 1H), 1.70-1.56 (m, 4H), 1.54-1.43 (m, 2H), 1.25-1.15 (m, 2H); LCMS (ESI): m/z 416.1 $(M+H)^+$.

Step 7: 2-Bromo-5-(4-(cyclopentylmethyl)phenyl)-3-(3-(fluoromethyl)azetidine-1-carbonyl)pyrazolo[1,5-a]pyrimidin-7(4H)-one

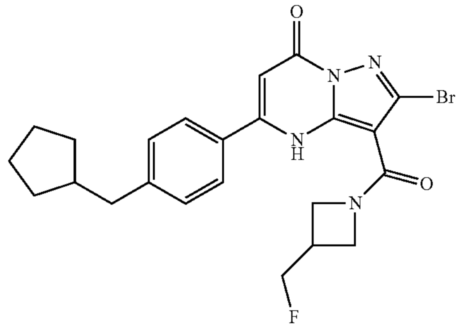 [SMILES: O=C(c1c(Br)nn2c(=O)cc(-c3ccc(CC4CCCC4)cc3)[nH]c12)N1CC(CF)C1]

title compound (900 mg, 75%) was furnished as a yellow solid, which was prepared from 2-bromo-5-(4-(cyclopentylmethyl)phenyl)-7-oxo-4,7-dihydropyrazolo[1,5-a]pyrimidine-3-carboxylic acid (1.0 g, 2.4 mmol) and 3-(fluoromethyl)azetidine trifluoroacetate (1.31 g, 6.01 mmol) following the procedure outlined for Intermediate A, Step 5. $^1H$ NMR (400 MHz, DMSO-$d_6$): δ 7.70 (d, J=8.4 Hz, 2H), 7.40 (d, J=8.4 Hz, 2H), 6.14 (s, 1H), 4.63 (dd, J=47.2, 6.0 Hz, 2H), 4.18-4.13 (m, 2H), 3.88-3.85 (m, 2H), 3.03-2.98 (m, 1H), 2.68-2.66 (m, 2H), 2.15-2.08 (m, 1H), 1.68-1.58 (m, 4H), 1.53-1.45 (m, 2H), 1.23-1.19 (m, 2H); LCMS: m/z 487.1 $(M+H)^+$.

Intermediate D

Preparation of Ethyl 2-bromo-5-chloro-7-oxo-4,7-dihydropyrazolo[1,5-a]pyrimidine-3-carboxylate The general reaction scheme was as follows:

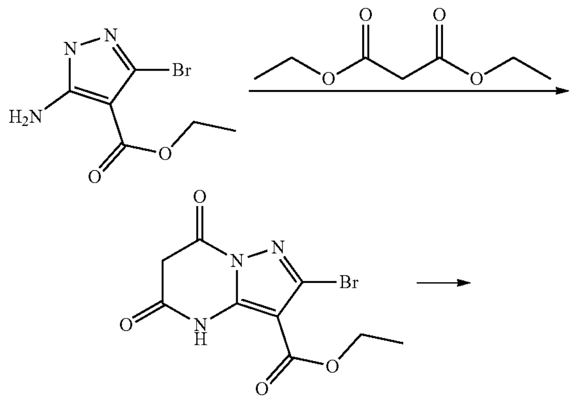

-continued

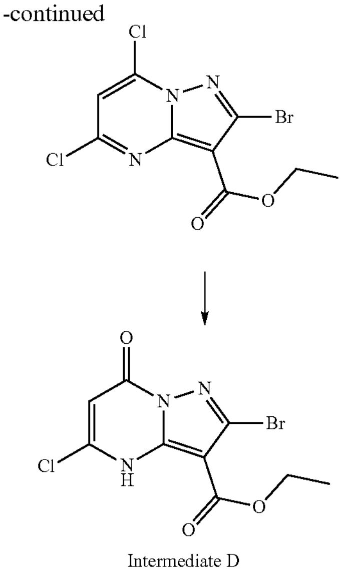

Intermediate D

Step 1: Ethyl 2-bromo-5,7-dioxo-4,5,6,7-tetrahydropyrazolo[1,5-a]pyrimidine-3-carboxylate

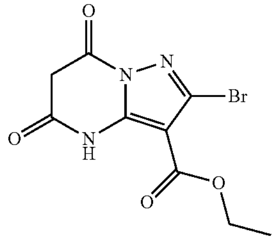 [SMILES: CCOC(=O)c1c(Br)nn2c1NC(=O)CC2=O]

A mixture of ethyl 5-amino-3-bromo-1H-pyrazole-4-carboxylate (22.0 g, 94 mmol), t-BuONa (27.1 g, 281.99 mmol) and diethyl malonate (43.0 mL, 281.99 mmol) in n-BuOH (40.0 mL) was stirred at 120° C. for 3 hours. The reaction mixture was adjusted to pH 4 with addition of 1M aqueous HCl. The mixture was filtered, washed with petroleum ether (100 mL×2), washed with EtOAc (50 mL) and dried with $Na_2SO_4$ to afford the title compound (18 g, 64%) as a yellow solid. $^1H$ NMR (400 MHz, DMSO-$d_6$): 5.10 (s, 1H), 4.31 (q, J=7.2 Hz, 2H), 1.29 (t, J=7.2 Hz, 3H); LCMS (ESI): m/z 302.0 $(M+H)^+$.

Step 2: Ethyl 2-bromo-5,7-dichloropyrazolo[1,5-a]pyrimidine-3-carboxylate

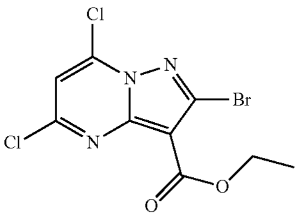 [SMILES: CCOC(=O)c1c(Br)nn2c(Cl)cc(Cl)nc12]

To a three necked flask charged with $POCl_3$ (119.0 mL, 1.28 mol) was added ethyl 2-bromo-5,7-dioxo-4,5,6,7-tetrahydropyrazolo[1,5-a]pyrimidine-3-carboxylate (30.0 g, 99.3 mmol) and N,N-diethylaniline (46.0 mL, 297.9 mmol). The solution was stirred at 100° C. for 16 hours at which point the reaction mixture was concentrated to remove $POCl_3$. The residue was quenched with water (200 mL) and extracted with EtOAc (200 mL×2). The organic phase was washed with brine (100 mL), dried with $Na_2SO_4$ and concentrated in vacuo. The residue was purified by flash column chromatography (eluting with 0-20% EtOAc in petroleum ether) to afford the title compound (10.67 g, 32%) as a light yellow solid. $^1H$ NMR (400 MHz, $CDCl_3$): δ 7.17 (s, 1H), 4.49 (q, J=7.2 Hz, 2H), 1.47 (t, J=7.2 Hz, 3H).

Step 3: Ethyl 2-bromo-5-chloro-7-oxo-4,7-dihydropyrazolo[1,5-a]pyrimidine-3-carboxylate

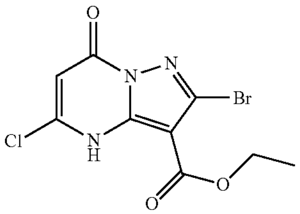 [SMILES: CCOC(=O)c1c(Br)nn2c(=O)cc(Cl)[nH]c12]

To a mixture of ethyl 2-bromo-5,7-dichloropyrazolo[1,5-a]pyrimidine-3-carboxylate (25.0 g, 73.75 mmol) in THF (180 mL) was added 1 M aqueous NaOH (185.0 mL, 0.18 mol) at room temperature. The reaction was stirred at room temperature for 12 hours. The reaction was filtered, concentrated in vacuo and then washed with ethyl acetate (80 mL×2) to afford the title compound (19 g, 80%) as a white solid. $^1H$ NMR ($CD_3OD$): 5.86 (s, 1H), 4.38 (q, J=7.2 Hz, 2H), 1.39 (t, J=7.2 Hz, 3H); LCMS (ESI): m/z 319.7 $(M+H)^+$.

Intermediate E

Preparation of 2-Bromo-5-chloro-3-(3-(fluoromethyl)azetidine-1-carbonyl)pyrazolo[1,5-a]pyrimidin-7(4H)-one The general reaction scheme was as follows:

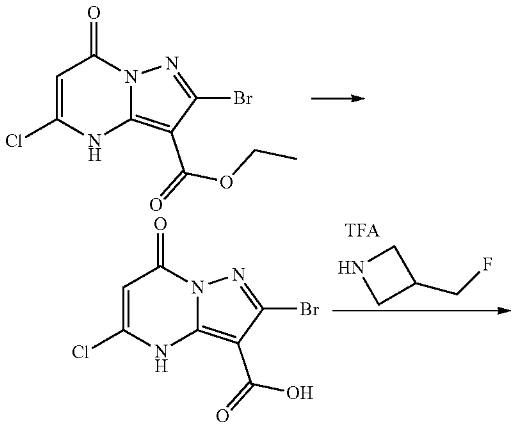

-continued

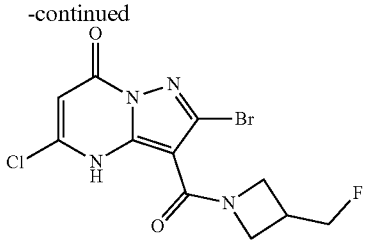

Intermediate E

Step 1: 2-Bromo-5-chloro-7-oxo-4,7-dihydropyrazolo[1,5-a]pyrimidine-3-carboxylic acid

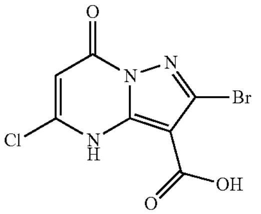 [SMILES: O=C(O)c1c(Br)nn2c(=O)cc(Cl)[nH]c12]

A mixture of ethyl 2-bromo-5-chloro-7-oxo-4,7-dihydropyrazolo[1,5-a]pyrimidine-3-carboxylate (45.0 g, 140.39 mmol) and lithium hydroxide monohydrate (58.90 g, 1.40 mol) was dissolved in 1:1 water/ethanol (420 mL) and stirred at 80° C. for 16 hours. The reaction solution was concentrated and the pH was adjusted to 4 with the addition of aqueous 4 M HCl. The precipitated solid was collected and dried in vacuo to afford the title compound (40 g, 97%) as a white solid. $^1H$ NMR (400 MHz, DMSO-$d_6$): 5.30 (s, 1H); LCMS (ESI): m/z 291.7 $(M+H)^+$.

Step 2: 2-Bromo-5-chloro-3-(3-(fluoromethyl)azetidine-1-carbonyl)pyrazolo[1,5-a]pyrimidin-7(4H)-one

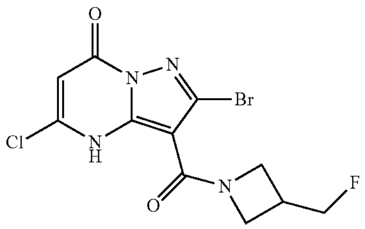 [SMILES: O=C(c1c(Br)nn2c(=O)cc(Cl)[nH]c12)N1CC(CF)C1]

To a solution of 2-bromo-5-chloro-7-oxo-4,7-dihydropyrazolo[1,5-a]pyrimidine-3-carboxylic acid (16.7 g, 57.1 mmol) and HATU (32.6 g, 85.65 mmol) in DMF (70 mL) was added N,N-diisopropylethylamine (30.5 mL, 171.3 mmol). The mixture was stirred for 20 minutes at room temperature and 3-(fluoromethyl)azetidine hydrochloride (10.8 g, 85.65 mmol) was added. The resulting reaction solution was stirred at room temperature for 16 hours. The reaction mixture was poured into water (200 mL) and extracted with DCM (200 mL×3) and washed with brine (200 mL). The organic phase was dried over $Na_2SO_4$, filtered and concentrated to dryness. The crude organics were purified by flash column chromatography (eluting 0-10% methanol in dichloromethane) to afford the title compound (12 g, 58%) as a light yellow solid. $^1$H NMR (400 MHz, DMSO-$d_6$): δ 5.76 (s, 1H), 4.63 (dd, J=47.2, 5.6 Hz, 2H), 4.18-4.12 (m, 2H), 3.86-3.83 (m, 2H), 3.05-2.91 (m, 1H).

Intermediate F

Preparation of 5-Chloro-3-(3-(fluoromethyl)azetidine-1-carbonyl)-2-(3-methylpyrazin-2-yl)pyrazolo[1,5-a]pyrimidin-7(4R)-one

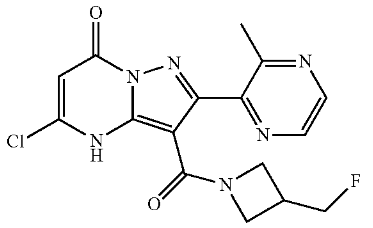 [SMILES: Cc1nccnc1-c1nn2c(=O)cc(Cl)[nH]c2c1C(=O)N1CC(CF)C1]

To a solution of 2-bromo-5-chloro-3-(3-(fluoromethyl)azetidine-1-carbonyl)pyrazolo [1,5-a]pyrimidin-7(4H)-one (3.0 g, 7.43 mmol), 2-methyl-3-(tributyl stannyl)pyrazine (2.85 g, 7.43 mmol) in DMF (60 mL) was added CsF (3.38 g, 22.28 mmol), CuI (110 mg, 1.11 mmol) and Pd(dppf)$Cl_2$ (543 mg, 0.74 mmol). The reaction mixture was stirred at 110° C. for 3 hours under a nitrogen atmosphere. The reaction mixture was concentrated in vacuo and purified by flash chromatography on silica gel eluting with DCM/MeOH (0 to 20%) to afford the title compound (600 mg, 21%) as a black solid. $^1$H NMR (400 MHz, $CD_3OD$): δ 8.61-8.45 (m, 2H), 5.85 (s, 1H), 4.59 (dd, J=47.2, 5.6 Hz, 2H), 4.52-4.35 (m, 1H), 4.25-4.05 (m, 2H), 3.98-4.84 (m, 1H), 3.06-2.94 (m, 1H), 2.64 (s, 3H); LCMS (ESI): m/z 377.1 $(M+H)^+$.

Intermediate G

Preparation of 5-Chloro-3-(3-(fluoromethyl)azetidine-1-carbonyl)-2-(pyrimidin-2-yl)pyrazolo[1,5-a]pyrimidin-7(4H)-one

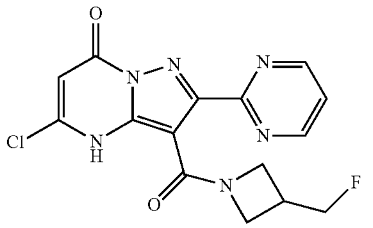 [SMILES: O=C(c1c(-c2ncccn2)nn2c(=O)cc(Cl)[nH]c12)N1CC(CF)C1]

The title compound (800 mg, 47%) was furnished as a white solid, which was prepared from 2-bromo-5-chloro-3-(3-(fluoromethyl)azetidine-1-carbonyl)pyrazolo[1,5-a]pyrimidin-7(4H)-one (Intermediate E, 2.0 g, 4.68 mmol) and 2-(tributylstannyl) pyrimidine (1.73 g, 4.68 mmol) following the procedure outlined for Intermediate F. $^1$H NMR (400 MHz, DMSO-$d_6$): δ 8.88 (d, J=4.8 Hz, 2H), 7.47 (t, J=4.8 Hz, 1H), 5.47 (s, 1H), 4.54 (dd, J=47.2, 6.0 Hz, 2H), 4.09-3.95 (m, 2H), 3.80-3.70 (m, 2H), 2.97-2.84 (m, 1H). LCMS (ESI+) m/z 363.1 $(M+H)^+$.

Intermediate J

Preparation of 5-Chloro-3-(3-(fluoromethyl)azetidine-1-carbonyl)-2-(pyrazin-2-yl)pyrazolo[1,5-a]pyrimidin-7(4H)-one

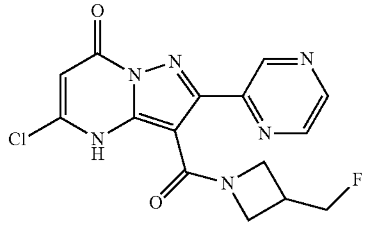 [SMILES: O=C(c1c(-c2cnccn2)nn2c(=O)cc(Cl)[nH]c12)N1CC(CF)C1]

The title compound was prepared from 2-bromo-5-chloro-3-(3-(fluoromethyl)azetidine-1-carbonyl)pyrazolo[1,5-a]pyrimidin-7(4H)-one (Intermediate E, 500 mg, 1.17 mmol) and 2-(tributylstannyl)pyrazine (432 mg, 1.17 mmol) following the procedure outlined for Intermediate F. Purification by reverse phase chromatography (0.225% FA in water/MeCN furnished the desired compounds as a white solid (50 mg, 12%). $^1$H NMR (400 MHz, $CD_3OD$): δ 9.38 (s, 1H), 8.77-8.69 (m, 1H), 8.66 (d, J=2.0, 1H), 6.13 (s, 1H), 4.54 (dd, J=47.2, 5.2 Hz, 2H), 4.38-4.17 (m, 1H), 4.15-3.90 (m, 2H), 3.86-3.66 (m, 1H), 3.07-2.91 (m, 1H); LCMS (ESI): m/z 363.0 $(M+H)^+$.

Intermediate K

Preparation of 2-bromo-3-(3-(fluoromethyl)azetidine-1-carbonyl)-5-((4-isopropylbenzyl)oxy)pyrazolo[1,5-a]pyrimidin-7(4H)-one The general reaction scheme was as follows:

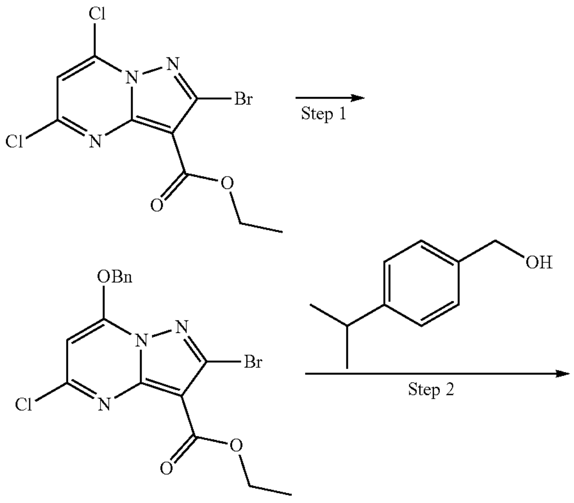

-continued

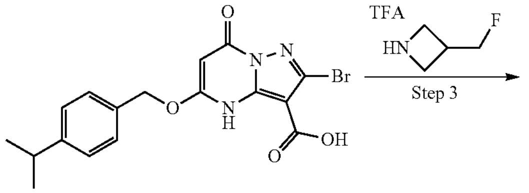

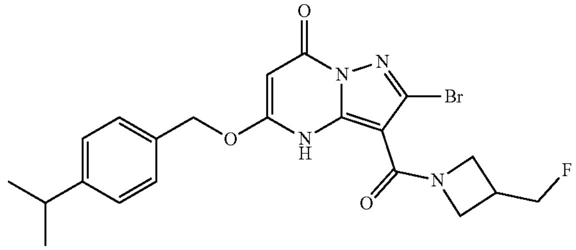

Intermediate K

Step 1: Ethyl 7-(benzyloxy)-2-bromo-5-chloropyrazolo[1,5-a]pyrimidine-3-carboxylate

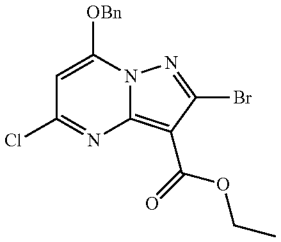 [SMILES: CCOC(=O)c1c(Br)nn2c(OCc3ccccc3)cc(Cl)nc12]

To a mixture of ethyl 2-bromo-5,7-dichloropyrazolo[1,5-a]pyrimidine-3-carboxylate (10.0 g, 29.5 mmol) and benzyl alcohol (3.0 mL, 32.45 mmol) in acetonitrile (200 mL) was added DBU (9.0 g, 59.0 mmol) slowly at 0° C. The solution was then stirred at 0° C. for 1 hour at which point the reaction mixture was filtered. The filter cake was washed with acetonitrile (10 mL×2) and dried to afford the title compound (4.7 g, 38%) as a light yellow solid. $^1H$ NMR (400 MHz, DMSO-$d_6$): δ 7.58-7.56 (m, 2H), 7.55-7.53 (m, 3H), 5.60 (s, 1H), 4.33-4.28 (q, J=7.2 Hz, 2H), 1.33-1.26 (t, J=7.2 Hz, 3H).

Step 2: 2-Bromo-5-((4-isopropylbenzyl)oxy)-7-oxo-4,7-dihydropyrazolo[1,5-a]pyrimidine-3-carboxylic acid

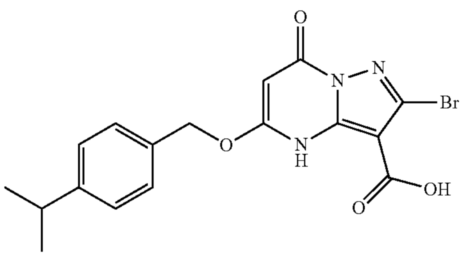 [SMILES: CC(C)c1ccc(COc2cc(=O)n3nc(Br)c(C(=O)O)c3[nH]2)cc1]

A mixture of ethyl 7-(benzyloxy)-2-bromo-5-chloropyrazolo[1,5-a]pyrimidine-3-carboxylate (5.3 g, 12.91 mmol), (4-isopropylphenyl)methanol (5.8 g, 38.72 mmol) and t-BuONa (4.3 g, 45.17 mmol) in 1,4-dioxane (30 mL) was stirred at 90° C. under a nitrogen atmosphere for 16 hours. The reaction mixture was quenched with water (30 mL) and extracted with ethyl acetate (60 mL×2). Then the aqueous layer was adjusted to pH 4 by addition of aqueous 2 M HCl, and then extracted with ethyl acetate (40×2 mL). The organic phase was washed with brine (30 mL) and concentrated to dryness. The crude was triturated with ethyl acetate (5 mL) and filtered to afford the title compound (3.8 g, 72%) as a white solid. LCMS (ESI): m/z 405.8 $(M+H)^+$.

Step 3: 2-Bromo-3-(3-(fluoromethyl)azetidine-1-carbonyl)-5-((4-isopropylbenzyl)oxy) pyrazolo[1,5-a]pyrimidin-7(4H)-one

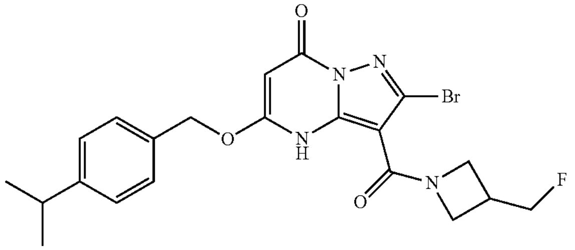 [SMILES: CC(C)c1ccc(COc2cc(=O)n3nc(Br)c(C(=O)N4CC(CF)C4)c3[nH]2)cc1]

The title compound (280 mg, 7%) was obtained as a white solid. It was prepared from 2-bromo-5-((4-isopropylbenzyl)oxy)-7-oxo-4,7-dihydropyrazolo[1,5-a]pyrimidine-3-carboxylic acid (3.30 g, 8.12 mmol) following the procedure outlined for Intermediate A, Step 5. $^1H$ NMR (400 MHz, DMSO-$d_6$): δ 7.33 (d, J=7.6 Hz, 2H), 7.23 (d, J=7.6 Hz, 2H), 5.26-5.24 (m, 2H), 5.11 (br, s, 1H), 4.53 (dd, J=47.2, 5.6 Hz, 2H), 4.19-4.01 (m, 3H), 3.73-3.71 (m, 1H), 2.91-2.84 (m, 2H), 1.19 (d, J=6.8 Hz, 6H); LCMS (ESI): m/z 477.0 $(M+H)^+$.

Intermediate L

Preparation of 5-(4-Cyclohexylphenyl)-2-(dimethylcarbamoyl)-7-oxo-4,7-dihydropyrazolo[1,5-a]pyrimidine-3-carboxylic acid The general reaction scheme was as follows:

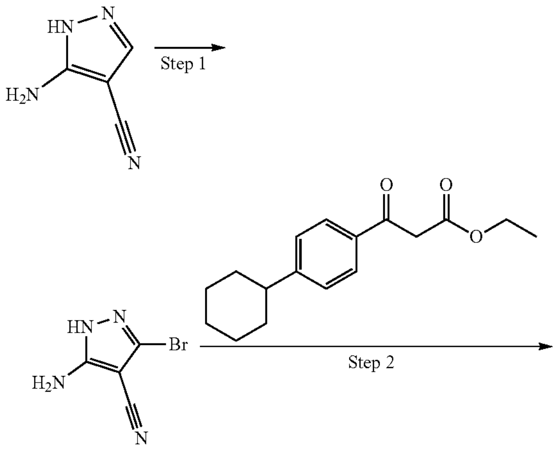

-continued

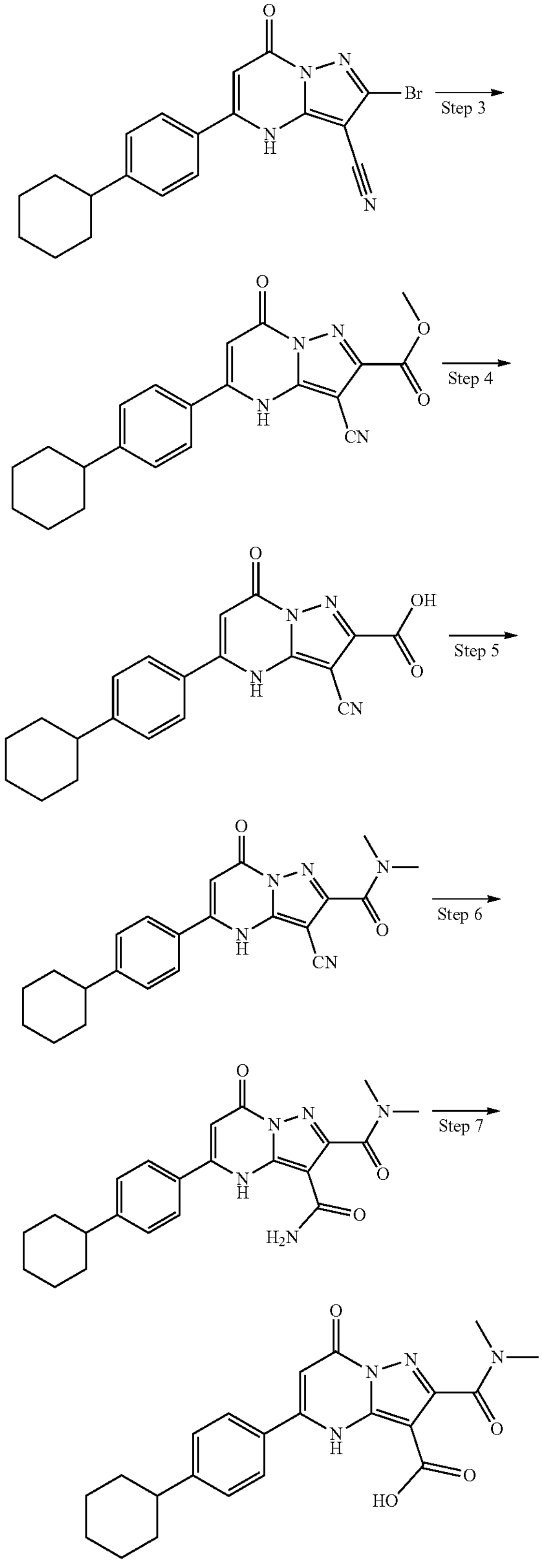

Intermediate L

Step 1: 5-Amino-3-bromo-1H-pyrazole-4-carbonitrile

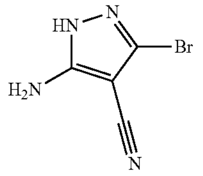

To a solution of 5-amino-1H-pyrazole-4-carbonitrile (20 g, 185 mmol) in MeCN (500 mL) was added NBS (36 g, 203 mmol) slowly at 16° C. and then stirred for 3 hours. The reaction mixture was poured into water (100 mL) and extracted with EtOAc (50 mL×3), washed with brine (50 mL×2) and concentrated to give the crude product. The crude material was purified by silica gel chromatography (0-5% methanol in dichloromethane) to afford the title compound (10 g, 29%). LCMS (ESI): m/z 187.0 $(M+H)^+$.

Step 2: 2-Bromo-5-(4-cyclohexylphenyl)-7-oxo-4,7-dihydropyrazolo[1,5-a]pyrimidine-3-carbonitrile

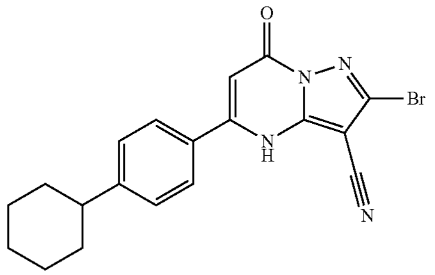 [SMILES: N#Cc1c(Br)nn2c(=O)cc(-c3ccc(C4CCCCC4)cc3)[nH]c12]

To a mixture of 5-amino-3-bromo-1H-pyrazole-4-carbonitrile (7 g, 37 mmol), ethyl 3-(4-cyclohexylphenyl)-3-oxopropanoate (12 g, 45 mmol) and $TsOH \cdot H_2O$ (644 mg, 3.74 mmol) in n-butanol (100 mL) was stirred at 120° C. for 5 hours. The precipitated solid was collected by filtration, washed with EtOH (20 mL) and dried to afford the title compound as a white solid (6 g, 40%). $^1H$ NMR (400 MHz, DMSO-$d_6$): δ 11.10 (s, 1H), 7.75 (d, J=8.4 Hz, 2H), 7.42 (d, J=8.4 Hz, 2H), 6.26 (s, 1H), 2.62-2.50 (m, 1H), 1.82-1.79 (m, 4H), 1.76-1.69 (m, 1H), 1.46-1.40 (m, 4H), 1.39-1.20 (m, 1H); LCMS (ESI): m/z 396.9 $(M+H)^+$.

Step 3: Methyl 3-cyano-5-(4-cyclohexylphenyl)-7-oxo-4,7-dihydropyrazolo[1,5-a]pyrimidine-2-carboxylate

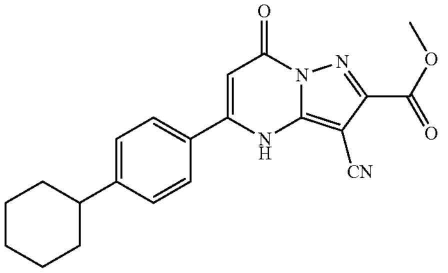 [SMILES: COC(=O)c1nn2c(=O)cc(-c3ccc(C4CCCCC4)cc3)[nH]c2c1C#N]

A mixture of 2-bromo-5-(4-cyclohexylphenyl)-7-oxo-4,7-dihydropyrazolo[1,5-a]pyrimidine-3-carbonitrile (3.0 g, 7.55 mmol), triethylamine (8.4 mL, 60.41 mmol) and $PdCl_2$ (dppf) (828 mg, 1.13 mmol) in 1:1 DMF/methanol (100 mL) was stirred at 80° C. for 48 hours under carbon monoxide atmosphere at 50 psi. The reaction mixture was concentrated to remove methanol, diluted with water (100 mL) and extracted with EtOAc (100 mL×3). The organics where then washed with brine (100 mL×2) and concentrated to dryness. The residue was purified by column chromatography on silica gel (0-2% methanol in dichloromethane) to afford the title compound as a brown solid (1.3 g, 45%). $^1$H NMR (400 MHz, DMSO-$d_6$): δ 7.93 (d, J=8.4 Hz, 2H), 7.31 (d, J=8.4 Hz, 2H), 6.21 (s, 1H), 3.90 (s, 3H), 2.62-2.50 (m, 1H), 1.82-1.79 (m, 4H), 1.76-1.69 (m, 1H), 1.46-1.40 (m, 4H), 1.39-1.20 (m, 1H); LCMS (ESI): m/z 377.0 $(M+H)^+$.

Step 4: 3-Cyano-5-(4-cyclohexylphenyl)-7-oxo-4,7-dihydropyrazolo[1,5-a]pyrimidine-2-carboxylic acid

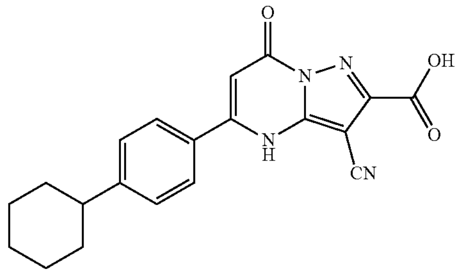 [SMILES: N#Cc1c(C(=O)O)nn2c(=O)cc(-c3ccc(C4CCCCC4)cc3)[nH]c12]

A mixture of methyl 3-cyano-5-(4-cyclohexylphenyl)-7-oxo-4,7-dihydropyrazolo[1,5-a]pyrimidine-2-carboxylate (1 g, 2.66 mmol), NaOH (0.53 g, 13.28 mmol) in 1:1 methanol/water (40 mL) was stirred at room temperature for 5 hours. The reaction mixture was then concentrated to remove methanol and diluted with water (100 mL). The solution was adjusted to pH 3 with aqueous 2M HCl, extracted with dichloromethane (100 mL×3) and concentrated to dryness to afford the title compound as a yellow solid (0.5 g, 52%). LCMS (ESI): m/z 363.0 $(M+H)^+$.

Step 5: 3-Cyano-5-(4-cyclohexylphenyl)-N,N-dimethyl-7-oxo-4,7-dihydropyrazolo [1,5-a]pyrimidine-2-carboxamide

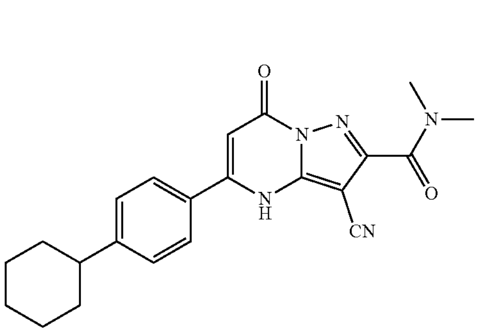 [SMILES: CN(C)C(=O)c1nn2c(=O)cc(-c3ccc(C4CCCCC4)cc3)[nH]c2c1C#N]

A solution of 3-cyano-5-(4-cyclohexylphenyl)-7-oxo-4,7-dihydropyrazolo[1,5-a]pyrimidine-2-carboxylic acid (400 mg, 1.1 mmol), N,N-dimethylamine hydrochloride (270 mg, 3.31 mmol) and N,N-diisopropylethylamine (0.91 mL, 5.52 mmol) in DMF (20 mL) was added HATU (629 mg, 1.66 mmol) which was then stirred at room temperature for 2 hours. The reaction mixture was then poured into water (100 mL), extracted with EtOAc (200 mL×3), washed with brine (200 mL×2) and concentrated to dryness. The residue was purified by column chromatography on silica gel (0-2.5% methanol in dichloromethane) to afford the title compound (400 mg, 93%). LCMS (ESI) m/z 390.1 $(M+H)^+$.

Step 6: 5-(4-Cyclohexylphenyl)-$N^2$,$N^2$-dimethyl-7-oxo-4,7-dihydropyrazolo[1,5-a]pyrimidine-2,3-dicarboxamide

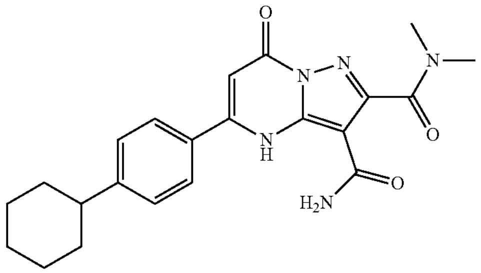 [SMILES: CN(C)C(=O)c1nn2c(=O)cc(-c3ccc(C4CCCCC4)cc3)[nH]c2c1C(N)=O]

A mixture of 3-cyano-5-(4-cyclohexylphenyl)-N,N-dimethyl-7-oxo-4,7-dihydro pyrazolo[1,5-a]pyrimidine-2-carboxamide (300 mg, 0.77 mmol) was added $H_2SO_4$ (10 mL) and then stirred for 16 hours at room temperature. The reaction mixture was poured into water (50 mL), extracted with EtOAc (50 mL×3), and concentrated to afford the title compound as a brown solid (300 mg, 80% purity) which was used directly without further purification. LCMS (ESI): m/z 408.1 $(M+H)^+$.

Step 7: 5-(4-Cyclohexylphenyl)-2-(dimethylcarbamoyl)-7-oxo-4,7-dihydropyrazolo [1,5-a]pyrimidine-3-carboxylic acid

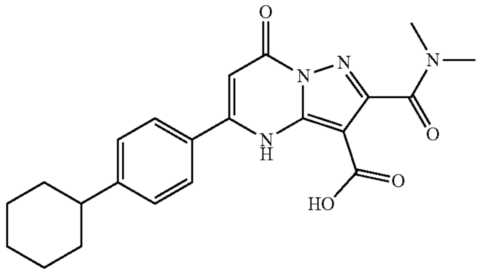 [SMILES: CN(C)C(=O)c1nn2c(=O)cc(-c3ccc(C4CCCCC4)cc3)[nH]c2c1C(=O)O]

To a solution of the resulting crude 5-(4-cyclohexylphenyl)-$N^2$,$N^2$-dimethyl-7-oxo-4,7-dihydropyrazolo[1,5-a]pyrimidine-2,3-dicarboxamide (200 mg) in sulfuric acid (5 mL) was added $NaNO_2$ (135 mg, 1.96 mmol) in water (5 mL) at 0° C. and stirred for 1 hour. The reaction mixture was poured into water (50 mL), extracted with EtOAc (50 mL×3) and concentrated to afford the title compound as a brown solid (170 mg, 81% over 2 steps) which was used without further purification. $^1$H NMR (400 MHz, DMSO-$d_6$): δ 11.44 (s, 1H), 7.70 (d, J=8.4 Hz, 2H), 7.45 (d, J=8.4 Hz, 2H), 6.28 (s, 1H), 3.02 (s, 3H), 2.86 (s, 3H), 2.62-2.50 (m, 1H), 1.82-1.79 (m, 4H), 1.76-1.69 (m, 1H), 1.47-1.40 (m, 4H), 1.39-1.20 (m, 1H); LCMS (ESI): m/z 409.1 $(M+H)^+$.

Intermediate M

Preparation of 2-Bromo-5-(4-cyclohexyl-3-fluoro-phenyl)-3-(3-(fluoromethyl)azetidine-1-carbonyl) pyrazolo[1,5-a]pyrimidin-7(4H)-one The general reaction scheme was as follows:

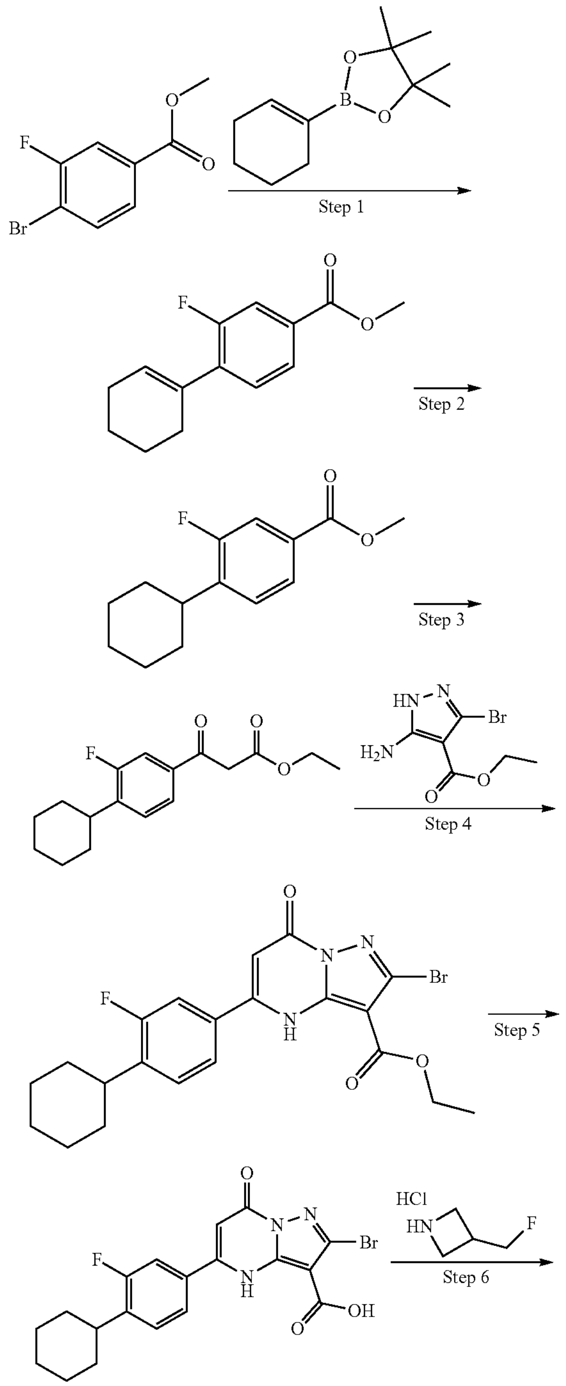

-continued

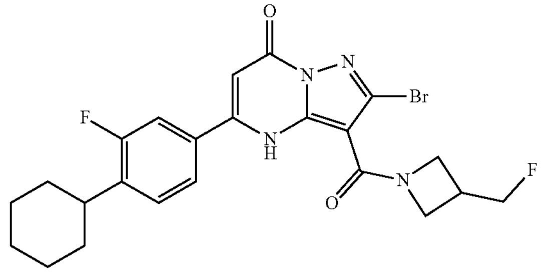

Intermediate M

Step 1: Methyl 2-fluoro-2',3',4',5'-tetrahydro-[1,1'-biphenyl]-4-carboxylate

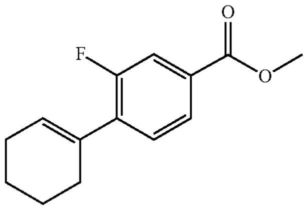 [SMILES: COC(=O)c1ccc(C2=CCCCC2)c(F)c1]

The title compound (7.5 g, 75%) was furnished as a yellow oil, which was prepared from methyl 4-bromo-3-fluorobenzoate (10 g, 42.9 mmol) and (cyclohex-1-en-1-yl)-4,4,5,5-tetramethyl-1,3,2-dioxaborolane (9.9 g, 47.5 mmol) following the procedure outlined for Example 3, Step 2. $^{1}H$ NMR (400 MHz, $CDCl_3$): δ 7.73 (dd, J=8.0, 1.6 Hz, 1H), 7.64 (dd, J=11.2, 1.6 Hz, 1H), 7.31-7.23 (m, 1H), 6.03 (s, 1H), 3.89 (s, 3H), 2.36-2.35 (m, 2H), 2.24-2.16 (m, 2H), 1.79-1.71 (m, 2H), 1.70-1.63 (m, 2H).

Step 2: Methyl 4-cyclohexyl-3-fluorobenzoate

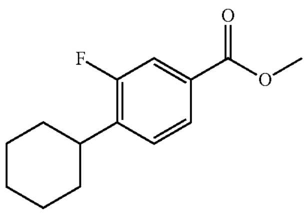 [SMILES: COC(=O)c1ccc(C2CCCCC2)c(F)c1]

The title compound (7.3 g, 97%) was furnished as a colorless oil, which was prepared from methyl 2-fluoro-2',3',4',5'-tetrahydro-[1,1'-biphenyl]-4-carboxylate (7.5 g, 32 mmol) following the procedure outlined for Example 3, Step 3. $^{1}H$ NMR (400 MHz, $CDCl_3$): δ 7.74 (dd, J=8.0, 1.6, 1H), 7.63 (dd, J=10.8, 1.6 Hz, 1H), 7.34-7.17 (m, 1H), 3.88 (s, 3H), 2.92-2.77 (m, 1H), 1.90-1.79 (m, 4H), 1.78-1.71 (m, 1H), 1.46-1.35 (m, 4H), 1.32-1.26 (m, 1H).

Step 3: Ethyl 3-(4-cyclohexyl-3-fluorophenyl)-3-oxopropanoate

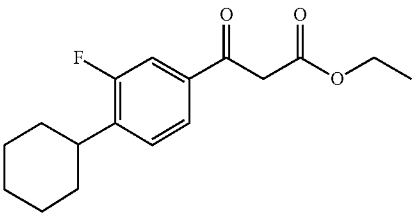 [SMILES: CCOC(=O)CC(=O)c1ccc(C2CCCCC2)c(F)c1]

The title compound (7 g, 78%, ketone/enol=2:1) was furnished as a yellow oil, which was prepared from methyl 4-cyclohexyl-3-fluorobenzoate (7.3 g, 31 mmol) following the procedure outlined for Example 3, Step 4. $^1$H NMR (400 MHz, $CDCl_3$): δ 12.52 (s, 1H of enol), 7.65 (d, J=8.4 Hz, 1H of ketone), 7.56 (dd, J=10.8, 1.2 Hz, 1H of ketone), 7.47 (d, J=8.4 Hz, 1H of enol), 7.40 (dd, J=11.2, 1.2 Hz, 1H of enol), 7.32 (t, J=8.0 Hz, 1H of ketone), 7.27-7.26 (m, 1H of enol), 5.60 (s, 1H of enol), 4.32-4.12 (m, 4H), 3.92 (s, 2H of ketone), 2.92-2.87 (m, 2H), 1.85-1.82 (m, 8H), 1.77-1.74 (m, 2H), 1.47-1.39 (m, 8H), 1.34-1.30 (m, 2H), 1.30-1.22 (m, 6H).

Step 4: Ethyl 2-bromo-5-(4-cyclohexyl-3-fluorophenyl)-7-oxo-4,7-dihydropyrazolo[1,5-a]pyrimidine-3-carboxylate

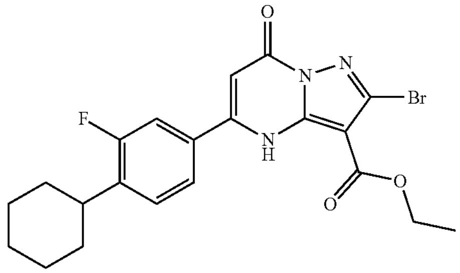 [SMILES: CCOC(=O)c1c(Br)nn2c(=O)cc(-c3ccc(C4CCCCC4)c(F)c3)[nH]c12]

A mixture of ethyl 3-(4-cyclohexyl-3-fluoro-phenyl)-3-oxo-propanoate (12 g, 41 mmol), p-TsOH·$H_2O$ (1.7 g, 8.9 mmol) and ethyl 5-amino-3-bromo-1H-pyrazole-4-carboxylate (10 g, 34 mmol) in 1-butanol (90 mL) was stirred at 130° C. for 5 hours. The reaction solution was filtrated to give the title compound (13 g, 82%) as a yellow solid. $^1$H NMR (400 MHz, DMSO-$d_6$): δ 11.65 (s, 1H), 7.64-7.51 (m, 3H), 6.35 (s, 1H), 4.33 (q, J=7.2 Hz, 2H), 2.91-2.85 (m, 1H), 1.86-1.73 (m, 5H), 1.56-1.39 (m, 4H), 1.37-1.34 (m, 4H).

Step 5: 2-Bromo-5-(4-cyclohexyl-3-fluorophenyl)-7-oxo-4,7-dihydropyrazolo[1,5-a]pyrimidine-3-carboxylic acid

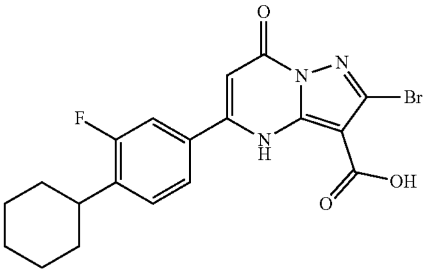 [SMILES: O=C(O)c1c(Br)nn2c(=O)cc(-c3ccc(C4CCCCC4)c(F)c3)[nH]c12]

A mixture of lithium hydroxide monohydrate (11.8 g, 281 mmol) and ethyl 2-bromo-5-(4-cyclohexyl-3-fluoro-phenyl)-7-oxo-4H-pyrazolo[1,5-a]pyrimidine-3-carboxylate (13 g, 28 mmol) in water (50 mL) and ethanol (50 mL) was stirred at 80° C. for 16 hours. The reaction solution was concentrated and pH was adjusted to 6 with 1 N aqueous HCl. The mixture was filtrated and dried to give the title compound (9.5 g, 78%) as a white solid. LCMS (ESI): m/z 433.9 $(M+H)^+$.

Step 6: 2-Bromo-5-(4-cyclohexyl-3-fluorophenyl)-3-(3-(fluoromethyl)azetidine-1-carbonyl)pyrazolo[1,5-a]pyrimidin-7(4H)-one

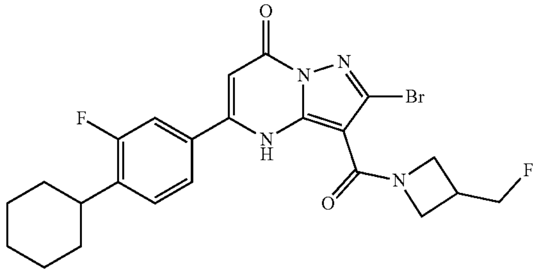 [SMILES: O=C(c1c(Br)nn2c(=O)cc(-c3ccc(C4CCCCC4)c(F)c3)[nH]c12)N1CC(CF)C1]

To a solution of DIPEA (3.81 mL, 23 mmol) and 2-bromo-5-(4-cyclohexyl-3-fluoro-phenyl)-7-oxo-4H-pyrazolo[1,5-a]pyrimidine-3-carboxylic acid (2 g, 4.6 mmol) in DMF (10 mL) was added HATU (2.7 g, 6.91 mmol), then stirred for 20 min. The mixture was added 3-(fluoromethyl)azetidine hydrochloride (1.2 g, 9.6 mmol), and then the reaction was stirred for 2 hours. The reaction mixture was diluted in water (100 mL), extracted with EtOAc (50 mL×2). The combined organic layers were dried over $Na_2SO_4$ and concentrated. The residue was purified by chromatography on silica gel (0-10% MeOH in DCM) to afford the title compound (1 g, 43%) as a white solid. $^1$H NMR (400 MHz, DMSO-$d_6$): δ 7.63-7.39 (m, 3H), 6.17 (s, 1H), 4.59 (dd, J=47.2, 6.0 Hz, 2H), 4.14-4.10 (m, 2H), 3.89-3.78 (m, 2H), 3.04-2.93 (m, 1H), 2.87-2.81 (m, 1H), 1.83-1.64 (m, 5H), 1.54-1.21 (m, 5H). LCMS (ESI): m/z 505.1 $(M+H)^+$.

Intermediate N

Preparation of Cis-3-(fluoromethyl)-2-methylazetidine 2,2,2-trifluoroacetate

The general reaction scheme was as follows:

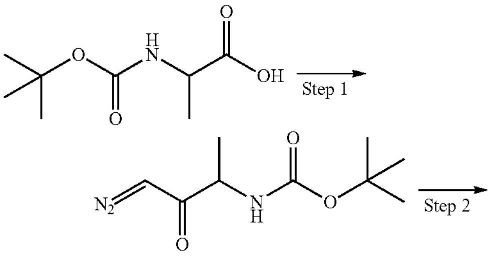

-continued

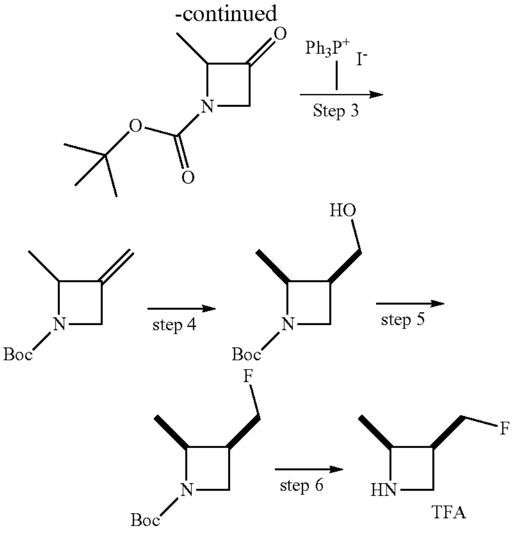

Intermediate N

Step 1: Tert-butyl (4-diazo-3-oxobutan-2-yl)carbamate

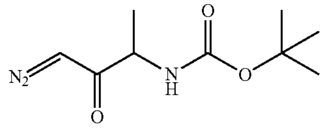

A mixture of 2-(tert-butoxycarbonylamino)propanoic acid (30 g, 159 mmol), DIPEA (47 mL, 270 mmol) and isobutyl chloroformate (33 g, 238 mmol) in THF (300 mL) was stirred at 0° C. for 4 hours. Acetonitrile (200 mL) and (diazomethyl)trimethyl silane (160 mL, 317 mmol) where added, and the reaction mixture was stirred at 0° C. for 3 hours, warmed to room temperature and stirred for an additional 16 hours. The reaction mixture was then diluted with EtOAc (500 mL) and washed with brine (500 mL×2). The organic layer was dried over anhydrous $Na_2SO_4$, filtered and concentrated. The residue was purified by silica gel column chromatography (0-15% EtOAc in petroleum ether) to afford the title compound (15 g, 44%) as a yellow solid. $^1$H NMR (400 MHz, DMSO-$d_6$): δ 7.28 (d, J=7.2 Hz, 1H), 6.02 (s, 1H), 3.99 (q, J=7.6 Hz, 1H), 1.38 (s, 9H), 1.15 (d, J=7.6 Hz, 3H).

Step 2: Tert-butyl 2-methyl-3-oxoazetidine-1-carboxylate

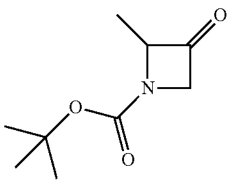

A mixture of rhodium(II) acetate dimer (830 mg, 1.88 mmol), tert-butyl N-(3-diazo-1-methyl-2-oxo-propyl)carbamate (20 g, 93.8 mmol) and TEA (0.12 mL, 0.9 mmol) in DCM (300 mL) was stirred at 0° C. for 16 hours. The reaction mixture was diluted in EtOAc (150 mL) and washed with brine (150 mL×2). The combined organic layer was dried over anhydrous $Na_2SO_4$, filtered and concentrated. The crude residue was purified by silica gel column chromatography (0-10% EtOAc in petroleum ether) to afford the title compound (11.4 g, 66%) as a colorless liquid. $^1$H NMR (400 MHz, $CDCl_3$): δ 4.98-4.88 (m, 1H), 4.77-4.49 (m, 2H), 1.49 (s, 9H), 1.46 (d, J=7.2 Hz, 3H).

Step 3: Tert-butyl 2-methyl-3-methyleneazetidine-1-carboxylate

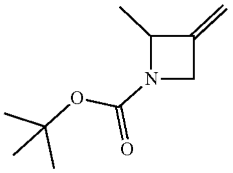

To a solution of methyltriphenylphosphoniumiodide (52 g, 129.58 mmol) in THF (300 mL) was added t-BuOK (15 g, 134.97 mmol) at 0° C. and the reaction was stirred at 0° C. for 30 minutes. At which point tert-butyl 2-methyl-3-oxo-azetidine-1-carboxylate (10 g, 53.99 mmol) was added was stirred for an additional 2 hours. The reaction mixture was diluted in EtOAc (150 mL) and washed with brine (150 mL×2). The organic layer was dried over anhydrous $Na_2SO_4$, filtered and concentrated. The residue was purified by silica gel column chromatography (0-10% EtOAc in petroleum ether) to afford the title compound (6 g, 61%) as a colorless liquid. $^1$H NMR (400 MHz, $CDCl_3$): δ 4.95 (s, 2H), 4.80-4.70 (m, 1H), 4.49-4.35 (m, 2H), 1.46 (s, 9H), 1.42 (d, J=6.4 Hz, 3H).

Step 4: Cis-tert-butyl 3-(hydroxymethyl)-2-methylazetidine-1-carboxylate

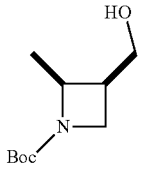

To a solution of tert-butyl 2-methyl-3-methyleneazetidine-1-carboxylate (3.0 g, 16.37 mmol) in THF (30 mL) at 0° C. was added borane (1 M in THF, 24.6 mL, 24.6 mmol). The solution was stirred for 1 hour at which point the reaction was quenched with methanol (10 mL). Then 3 M aqueous NaOH (5 mL) and 30% hydrogen peroxide in water (4.1 mL, 40.9 mmol) was added dropwise at 0° C. The reaction was stirred for 1 hour then diluted with water (50 mL). The mixture was extracted with EtOAc (50 mL×2). The organic phase was washed with brine (30 mL), dried with $Na_2SO_4$, filtered and concentrated in vacuo. The crude was purified by silica gel chromatography (0-18% EtOAc in petroleum ether) to afford the title compound (1.6 g, 49%) as a colorless oil. $^1$H NMR (400 MHz, $CDCl_3$): δ 4.42-4.28

(m, 1H), 3.90-3.78 (m, 2H), 3.74-3.66 (m, 1H), 3.54-3.47 (m, 1H), 2.71-2.62 (m, 1H), 1.40 (s, 9H), 1.35 (d, J=6.8 Hz, 3H).

Step 5: Cis-tert-butyl 3-(fluoromethyl)-2-methylazetidine-1-carboxylate

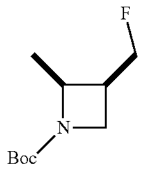

To a solution of 1,1,2,2,3,3,4,4,4-nonafluorobutane-1-sulfonyl fluoride (2.7 g, 8.94 mmol) and cis-tert-butyl 3-(hydroxymethyl)-2-methylazetidine-1-carboxylate (1.2 g, 5.96 mmol) in THF (20 mL) was added BTPP (3.73 g, 11.92 mmol) at room temperature. The solution was stirred for 16 hours and poured into water (50 mL). The solution was extracted with EtOAc (50 mL×2, washed with brine (30 mL), dried with $Na_2SO_4$, filtered and concentrated in vacuo. The crude was purified by silica gel chromatography (0-5% EtOAc in petroleum ether) to afford the title compound (1.0 g, 83%) as a colorless oil. $^1H$ NMR (400 MHz, $CDCl_3$): δ 4.74-4.48 (m, 2H), 4.47-4.40 (m, 1H), 3.98-3.90 (m, 1H), 3.60-3.52 (m, 1H), 2.94-2.78 (m, 1H), 1.44 (s, 9H), 1.37 (d, J=6.8 Hz, 3H).

Step 6: Cis-3-(fluoromethyl)-2-methylazetidine 2,2,2-trifluoroacetate

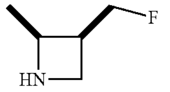

To a mixture of cis-tert-butyl 3-(fluoromethyl)-2-methylazetidine-1-carboxylate (1.0 g, 4.92 mmol) in DCM (5 mL) was added TFA (3.5 mL, 46.97 mmol) at 0° C. The reaction mixture was stirred at room temperature for 2 hours at which point the reaction was concentrated to afford the title compound (1 g, 93%) as a colorless oil. The crude material was used directly in the next step without further purification. $^1H$ NMR (400 MHz, $CDCl_3$): δ 4.89-4.73 (m, 2H), 4.70-4.64 (m, 1H), 4.30-4.18 (m, 1H), 3.99-3.86 (m, 1H), 3.23-3.07 (m, 1H), 1.63-1.58 (m, 3H).

Intermediate O

Preparation of triisopropyl((2-(4,4,5,5-tetramethyl-1,3,2-dioxaborolan-2-yl)allyl)oxy)silane The general reaction scheme was as follows:

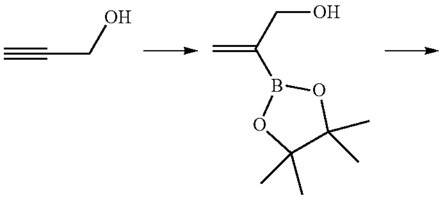

-continued

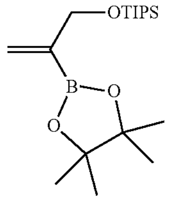

Intermediate O

Step 1: 2-(4,4,5,5-Tetramethyl-1,3,2-dioxaborolan-2-yl)prop-2-en-1-ol

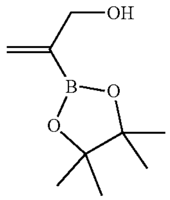

A solution of cuprous chloride (936 mg, 9.45 mmol), t-BuONa (1.34 g, 14.18 mmol), bis(pinacolato)diboron (26.41 g, 104 mmol), and prop-2-yn-1-ol (5.30 g, 94.54 mmol) in toluene (50 mL) was charged in a vial. The vial was purged and backfilled with $nitrogen_2$. Tri-tert-butylphosphine (10% solution in toluene, 26.4 mL, 11.3 mmol) was added to the vial dropwise. Finally, methanol (7.6 mL, 189 mmol) was added to the solution and the resulting mixture was stirred at room temperature for 1 hour. The reaction mixture was quenched with 4 M HCl in EtOAc and filtered. The filter cake was washed with DCM (100 mL) and concentrated to dryness. The residue was purified by silica gel column chromatography (0-17% EtOAc in petroleum ether) to afford the title compound (10 g, 57%) as a colorless oil. $^1H$ NMR (400 MHz, $CDCl_3$): 5.90 (s, 1H), 5.84 (s, 1H), 4.25 (s, 2H), 2.00-1.98 (m, 1H), 1.28 (s, 12H).

Step 2: Triisopropyl((2-(4,4,5,5-tetramethyl-1,3,2-dioxaborolan-2-yl)allyl)oxy)silane

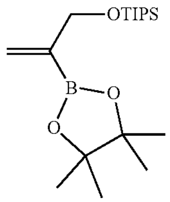

To a solution of 2-(4,4,5,5-tetramethyl-1,3,2-dioxaborolan-2-yl)prop-2-en-1-ol (1 g, 5.43 mmol) in DCM (30 mL) was added chlorotriisopropylsilane (2.1 g, 10.87 mmol) and imidazole (0.74 g, 10.87 mmol). The mixture was stirred at room temperature for 16 hours. The reaction mixture was diluted in EtOAc (50 mL), washed with brine (50 mL×2), dried over anhydrous $Na_2SO_4$, filtered and concentrated in vacuo. The residue was purified by silica gel chromatography to afford the title compound (1.0 g, 54%) as a colorless liquid. $^1H$ NMR (400 MHz, $CDCl_3$): δ 6.06 (s, 1H), 5.92-

5.87 (m, 1H), 4.37 (s, 2H), 1.27 (s, 12H), 1.18-1.10 (m, 3H), 1.09-1.06 (d, J=7.2 Hz, 18H).

Intermediate P

Preparation of Ethyl 5-chloro-2-(3-methylpyrazin-2-yl)-7-oxo-4,7-dihydropyrazolo[1,5-a]pyrimidine-3-carboxylate

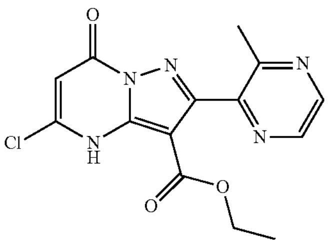 [SMILES: CCOC(=O)c1c(-c2nccnc2C)nn2c(=O)cc(Cl)[nH]c12]

A mixture of ethyl 2-bromo-5-chloro-7-oxo-4,7-dihydropyrazolo[1,5-a]pyrimidine-3-carboxylate (10 g, 31.2 mmol), 2-methyl-3-(tributylstannyl)pyrazine (12 g, 31.2 mmol), CsF (14 g, 93.6 mmol), CuI (463 mg, 4.68 mmol) and Pd(dppf)$Cl_2$ (2.3 g, 3.12 mmol) in DMF (200 mL) was stirred at 100° C. for 16 hours under nitrogen atmosphere. The reaction mixture was concentrated in vacuo and purified by flash chromatography on silica gel eluting with MeOH/DCM (0-40%) to afford the title compound (3.9 g, 29%) as a black solid. $^1$H NMR (400 MHz, DMSO-$d_6$): δ 8.53 (d, J=2.4 Hz, 1H), 8.48 (d, J=2.4 Hz, 1H), 5.67 (s, 1H), 3.91 (q, J=7.2 Hz, 2H), 2.30 (s, 3H), 0.86 (t, J=7.2 Hz, 3H); LCMS (ESI): m/z 333.9 $(M+H)^+$.

Intermediate Q

Preparation of Ethyl 2-(3-methylpyrazin-2-yl)-7-oxo-5-(4-(2,2,2-trifluoro-1-phenylethoxy)phenyl)-4,7-dihydropyrazolo[1,5-a]pyrimidine-3-carboxylate

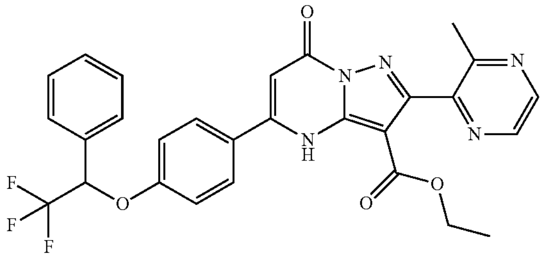 [SMILES: CCOC(=O)c1c(-c2nccnc2C)nn2c(=O)cc(-c3ccc(OC(c4ccccc4)C(F)(F)F)cc3)[nH]c12]

Step 1: 2,2,2-Trifluoro-1-phenylethyl trifluoromethanesulfonate

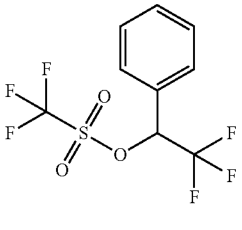 [SMILES: O=S(=O)(OC(c1ccccc1)C(F)(F)F)C(F)(F)F]

To a solution of 2,2,2-trifluoro-1-phenylethanol (4.8 g, 27.25 mmol) in THF (50 mL) was added NaH (60% in mineral oil, 1.2 g, 29.98 mmol) at 0° C., then the mixture was stirred for 15 minutes. Trifluoromethanesulfonyl chloride (5.0 g, 29.98 mmol) was added dropwise at 0° C. After 15 minutes the reaction solution was poured into water (60 mL) and extracted with EtOAc (40 mL×3) and washed with brine (40 mL). The organic layers were dried over anhydrous sodium sulfate, filtered and concentrated under reduced pressure to afford the title compound (8.4 g, 98%) as a brown oil. $^1$H NMR (400 MHz, $CDCl_3$): δ 7.59-7.47 (m, 5H), 5.85 (q, J=6.0 Hz, 1H).

Step 2: 4,4,5,5-Tetramethyl-2-(4-(2,2,2-trifluoro-1-phenylethoxy)phenyl)-1,3,2-dioxaborolane

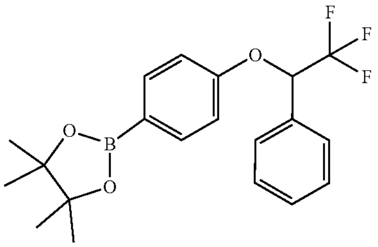 [SMILES: CC1(C)OB(c2ccc(OC(c3ccccc3)C(F)(F)F)cc2)OC1(C)C]

A mixture of 4-(4,4,5,5-tetramethyl-1,3,2-dioxaborolan-2-yl)phenol (4.0 g, 18.18 mmol), $Cs_2CO_3$ (11.8 g, 36.35 mmol) and 2,2,2-trifluoro-1-phenylethyl trifluoromethanesulfonate (8.4 g, 27.26 mmol) in DMF (50 mL) was stirred at room temperature for 2 hours. The reaction solution was diluted with water (150 mL) and extracted with ethyl acetate (50 mL×2). The combined organic layers were washed with brine (50 mL), dried over anhydrous sodium sulfate, filtered and concentrated in vacuo. The residue was purified by flash chromatography on silica gel (0-10% EtOAc in petroleum ether) to afford the title compound (3.4 g, 50%) as a colorless oil. $^1$H NMR (400 MHz, $CDCl_3$): δ 7.69 (d, J=8.4 Hz, 2H), 7.51-7.37 (m, 5H), 6.89 (d, J=8.4 Hz, 2H), 5.47 (q, J=6.4 Hz, 1H), 1.31 (s, 12H). Step 3: Ethyl 2-(3-methylpyrazin-2-yl)-7-oxo-5-(4-(2,2,2-trifluoro-1-phenylethoxy)phenyl)-4,7-dihydropyrazolo[1,5-a]pyrimidine-3-carboxylate

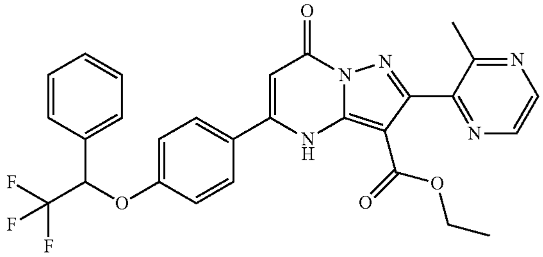 [SMILES: CCOC(=O)c1c(-c2nccnc2C)nn2c(=O)cc(-c3ccc(OC(c4ccccc4)C(F)(F)F)cc3)[nH]c12]

A mixture of ethyl 5-chloro-2-(3-methylpyrazin-2-yl)-7-oxo-4,7-dihydropyrazolo[1,5-a]pyrimidine-3-carboxylate (700 mg, 2.1 mmol), 4,4,5,5-tetramethyl-2-(4-(2,2,2-trifluoro-1-phenylethoxy)phenyl)-1,3,2-dioxaborolane (1.58 g, 4.2 mmol), $Na_2CO_3$ (667 mg, 6.3 mmol), Xphos-Pd-G2 (165 mg, 0.21 mmol) and Xphos (100 mg, 0.21 mmol) in DMSO (20 mL) and water (2 mL) was stirred at 110° C. for 16 hours under a nitrogen atmosphere. The reaction solution was poured into water (100 mL), extracted with EtOAc (50 mL×3), washed with brine (50 mL×2) and concentrated to dryness. The residue was purified by column chromatography on silica gel (0-5% MeOH in DCM) to afford the crude title compound (500 mg, 80% purity) as a brown solid. LCMS (ESI): m/z 550.1 $(M+H)^+$.

Example 1

Preparation of 5-(4-Cyclohexylphenyl)-3-(3-(fluoromethyl)azetidine-1-carbonyl)-N,N-dimethyl-7-oxo-4,7-dihydropyrazolo[1,5-a]pyrimidine-2-carboxamide

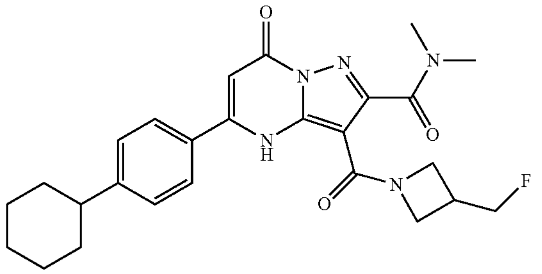 [SMILES: CN(C)C(=O)c1nn2c(=O)cc(-c3ccc(C4CCCCC4)cc3)[nH]c2c1C(=O)N1CC(CF)C1]

To a solution of 5-(4-cyclohexylphenyl)-3-(3-(fluoromethyl)azetidine-1-carbonyl)-7-oxo-4,7-dihydropyrazolo[1,5-a]pyrimidine-2-carboxylic acid (Intermediate B, 40 mg, 0.09 mmol), N,N-dimethylamine hydrochloride (18 mg, 0.22 mmol) and DIPEA (0.12 mL, 0.74 mmol) in DMF (3 mL) was added HATU (50 mg, 0.13 mmol) and the reaction mixture was stirred for 3 hours. The reaction mixture was diluted with EtOAc (40 mL) and washed with water (50 mL×2). The organic layer was dried over $Na_2SO_4$, filtered and concentrated in vacuo. The crude was purified by prep-HPLC (acetonitrile 0-45/0.1% FA in water, Xtimate C18 150*40 mm*10 um) to afford the title compound (8.4 mg, 20%) as a white solid. $^1H$ NMR (400 MHz, DMSO-$d_6$): δ 12.06 (s, 1H), 7.73 (d, J=8.4 Hz, 2H), 7.45 (d, J=8.4 Hz, 2H), 6.22 (s, 1H), 4.59 (dd, J=47.2, 5.6 Hz, 2H), 4.14-4.11 (m, 2H), 3.93-3.73 (m, 2H), 3.01-2.99 (m, 7H), 2.69-2.54 (m, 1H), 1.82-1.79 (m, 4H), 1.73-1.70 (m, 1H), 1.52-1.33 (m, 4H), 1.32-1.17 (m, 1H); LCMS (ESI): m/z 480.2 $(M+H)^+$.

Example 2

Preparation of 5-(4-(Cyclopentylmethyl)phenyl)-3-(3-(fluoromethyl)azetidine-1-carbonyl)-N,N-dimethyl-7-oxo-4,7-dihydropyrazolo[1,5-a]pyrimidine-2-carboxamide The general reaction scheme was as follows:

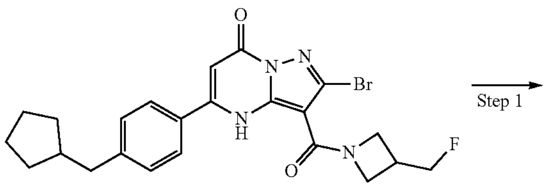

-continued

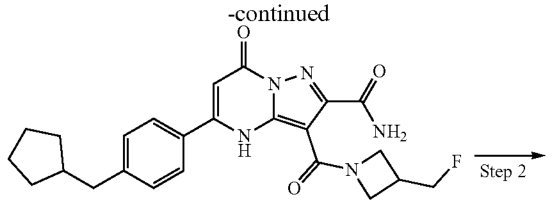

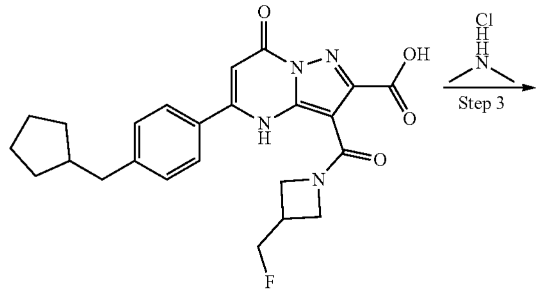

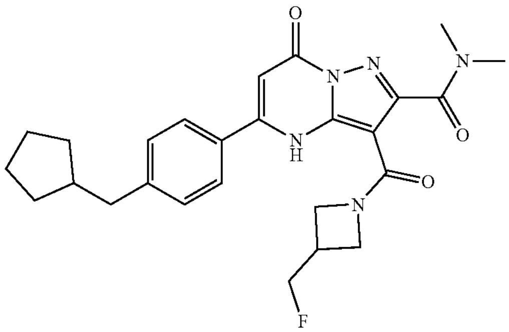

Step 1: 5-(4-(Cyclopentylmethyl)phenyl)-3-(3-(fluoromethyl)azetidine-1-carbonyl)-7-oxo-4,7-dihydropyrazolo[1,5-a]pyrimidine-2-carboxamide

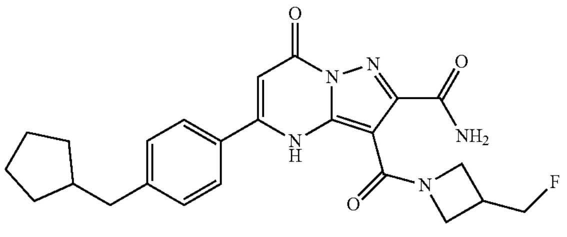 [SMILES: NC(=O)c1nn2c(=O)cc(-c3ccc(CC4CCCC4)cc3)[nH]c2c1C(=O)N1CC(CF)C1]

The title compound (35 mg, 38%) was furnished as a brown solid. It was prepared from 2-bromo-5-(4-(cyclopentylmethyl)phenyl)-3-(3-(fluoromethyl)azetidine-1-carbonyl)pyrazolo[1,5-a]pyrimidin-7(4H)-one (100 mg, 0.21 mmol) following the procedure outlined for Intermediate B, Step 1. LCMS (ESI): m/z 452.2 $(M+H)^+$.

Step 2: 5-(4-(Cyclopentylmethyl)phenyl)-3-(3-(fluoromethyl)azetidine-1-carbonyl)-7-oxo-4,7-dihydropyrazolo[1,5-a]pyrimidine-2-carboxylic acid

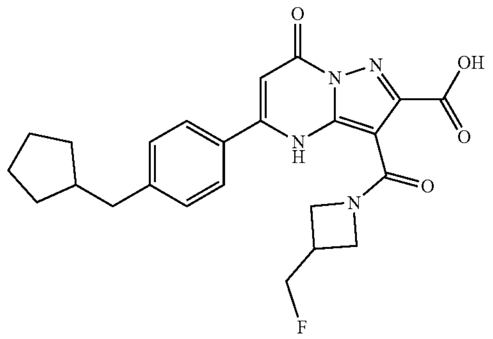 [SMILES: O=C(O)c1nn2c(=O)cc(-c3ccc(CC4CCCC4)cc3)[nH]c2c1C(=O)N1CC(CF)C1]

The title compound (30 mg, 85%) was furnished as a white solid. It was prepared from 5-(4-(cyclopentylmethyl)phenyl)-3-(3-(fluoromethyl)azetidine-1-carbonyl)-7-oxo-4,7-dihydropyrazolo[1,5-a]pyrimidine-2-carboxamide (35 mg, 0.08 mmol) following the procedure outlined for Intermediate B, Step 2. LCMS (ESI): m/z 453.2 $(M+H)^+$.

Step 3: 5-(4-(Cyclopentylmethyl)phenyl)-3-(3-(fluoromethyl)azetidine-1-carbonyl)-N,N-dimethyl-7-oxo-4,7-dihydropyrazolo[1,5-a]pyrimidine-2-carboxamide

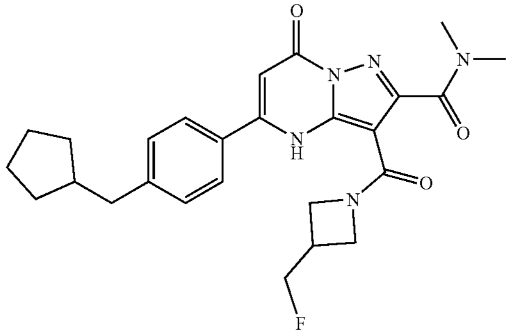 [SMILES: CN(C)C(=O)c1nn2c(=O)cc(-c3ccc(CC4CCCC4)cc3)[nH]c2c1C(=O)N1CC(CF)C1]

The title compound (9.39 mg, 18%) furnished as a white solid. It was prepared from 5-(4-(cyclopentylmethyl)phenyl)-3-(3-(fluoromethyl)azetidine-1-carbonyl)-7-oxo-4,7-dihydropyrazolo[1,5-a]pyrimidine-2-carboxylic acid (40 mg, 0.09 mmol) following the procedure outlined for Example 1. $^1H$ NMR (400 MHz, DMSO-$d_6$): δ 7.95 (d, J=8.0 Hz, 2H), 7.26 (d, J=8.0 Hz, 2H), 6.10 (s, 1H), 4.60 (dd, J=47.2, 5.2 Hz, 2H), 4.33-4.02 (m, 4H), 2.95 (s, 3H), 2.80 (s, 3H), 2.62-2.60 (m, 2H), 2.18-2.04 (m, 1H), 2.00-1.96 (m, 1H), 1.66-1.62 (m, 4H), 1.51-1.46 (m, 2H), 1.21-1.13 (m, 2H); LCMS (ESI): m/z 480.3 $(M+H)^+$.

Example 3

Preparation of 5-(4-Cyclohexyl-3,5-difluorophenyl)-3-(3-(fluoromethyl)azetidine-1-carbonyl)-N,N-dimethyl-7-oxo-4,7-dihydropyrazolo[1,5-a]pyrimidine-2-carboxamide The general reaction scheme was as follows:

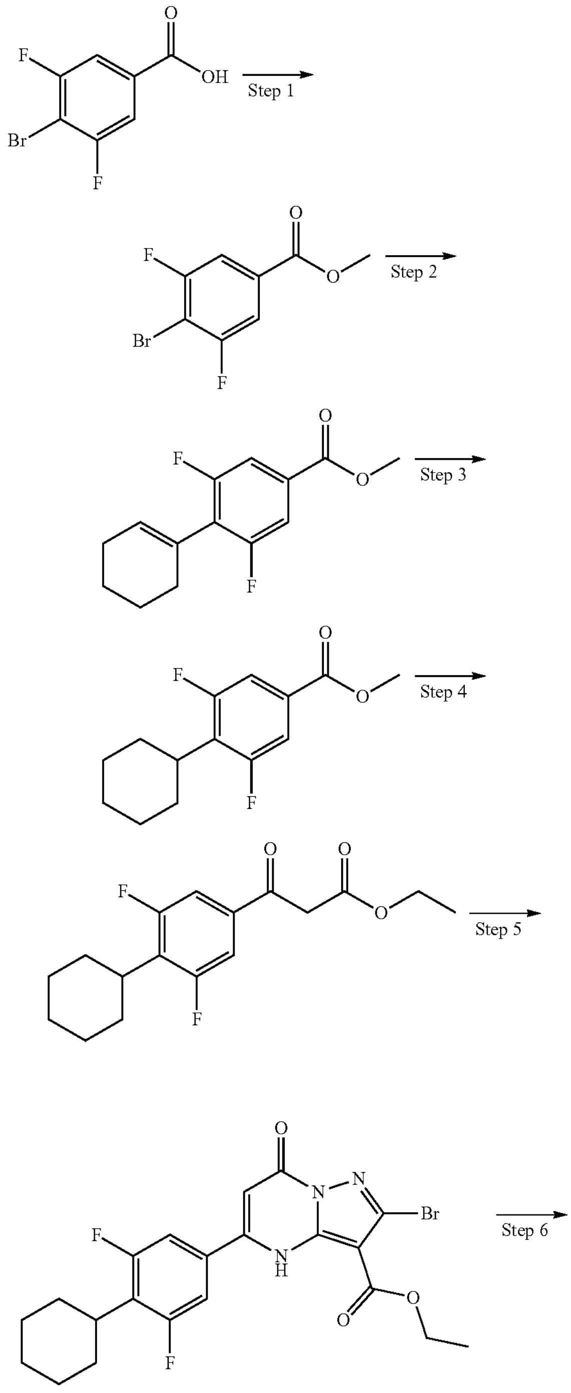

-continued

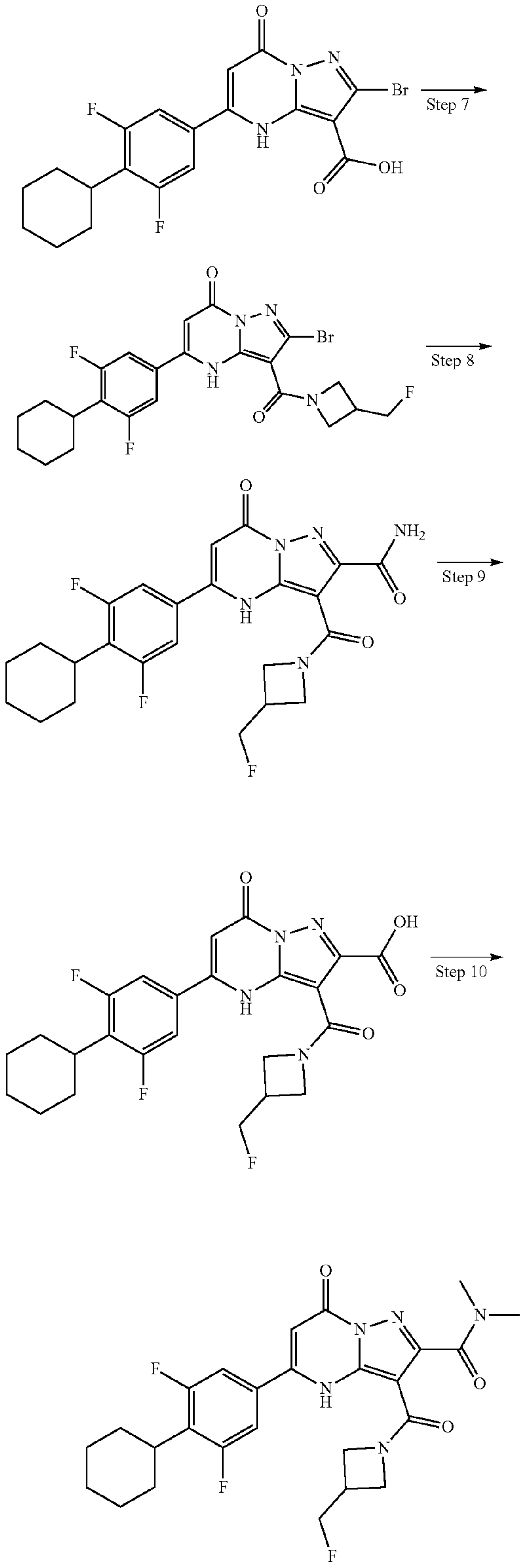

Step 1: Methyl 4-bromo-3,5-difluorobenzoate

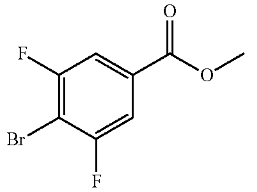

A solution of 4-bromo-3,5-difluoro-benzoic acid (25.0 g, 105.5 mmol) in MeOH (50 mL) was stirred at 0° C. for 15 minutes, and then $SOCl_2$ (25.1 g, 210.95 mmol) was added. The mixture was stirred at 60° C. for 16 hours. Then the reaction mixture was diluted with saturated aqueous $NH_4Cl$ (500 mL) and extracted with ethyl acetate (500×2 mL). The organic layer was washed with brine (100 mL×2), dried over anhydrous sodium sulfate, filtered and concentrated in vacuo to afford the title compound (24.4 g, 92%) as a yellow solid. $^1H$ NMR (400 MHz, $CDCl_3$): δ 7.62-7.58 (m, 2H), 3.92 (s, 3H).

Step 2: Methyl 2,6-difluoro-2',3',4',5'-tetrahydro-[1,1'-biphenyl]-4-carboxylate

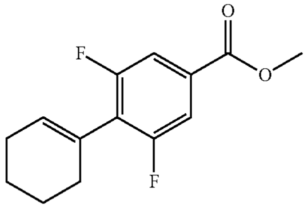 [SMILES: COC(=O)c1cc(F)c(C2=CCCCC2)c(F)c1]

A mixture of methyl 4-bromo-3,5-difluoro-benzoate (22.5 g, 89.63 mmol), $Na_2CO_3$ (2.92 g, 275.9 mmol), 2-(cyclohex-1-en-1-yl)-4,4,5,5-tetramethyl-1,3,2-dioxaborolane (22.57 g, 108.46 mmol) and $Pd(dppf)Cl_2$ (6.59 g, 8.96 mmol) in 1,4-dioxane (200 mL) was stirred at 100° C. for 16 hours under a nitrogen atmosphere. The reaction mixture was cooled to room temperature and filtered. The filtrate was collected, extracted with EtOAc (200 mL×2), dried over $Na_2SO_4$, filtered and concentrated in vacuo. The residue was purified by column chromatography (0-10% EtOAc in petroleum ether) to give the title compound (21.6 g, 85.8 mmol, 96%) as a yellow oil. $^1H$ NMR (400 MHz, $CDCl_3$): 7.56-7.47 (m, 2H), 5.88 (br s, 1H), 3.92 (s, 3H), 2.31-2.16 (m, 4H), 1.82-1.68 (m, 4H).

Step 3: Methyl 4-cyclohexyl-3,5-difluorobenzoate

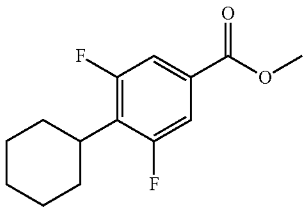 [SMILES: COC(=O)c1cc(F)c(C2CCCCC2)c(F)c1]

To a mixture of methyl 2,6-difluoro-2',3',4',5'-tetrahydro-[1,1'-biphenyl]-4-carboxylate (21.65 g, 85.82 mmol) in MeOH (150 mL) was added 10% Pd/C (1.83 g, 1.72 mmol). The mixture was stirred at 80° C. under a hydrogen atmosphere (1 atm) for 16 hours. The reaction mixture was filtered and concentrated in vacuo to afford the title compound (18.82 g, 86%) as a white solid which was used without further purification. $^1$H NMR (400 MHz, $CDCl_3$): δ 7.45 (d, J=8.8 Hz, 2H), 3.90 (s, 3H), 3.07-2.92 (m, 1H), 1.84-1.80 (m, 4H), 1.53-1.52 (m, 1H), 1.41-1.27 (m, 4H), 1.29-1.23 (m, 1H).

Step 4: Ethyl 3-(4-cyclohexyl-3,5-difluorophenyl)-3-oxopropanoate

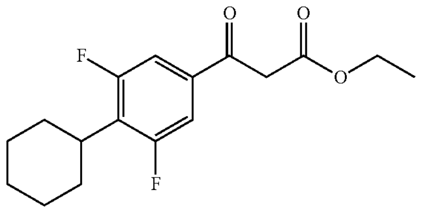 [SMILES: CCOC(=O)CC(=O)c1cc(F)c(C2CCCCC2)c(F)c1]

To a solution of ethyl acetate (10.85 mL, 111.02 mmol) in THF (100 mL) was added LiHMDS (111 mL, 111 mmol) dropwise at −40° C. Then methyl 4-cyclohexyl-3,5-difluorobenzoate (18.82 g, 74.02 mmol) in THF (50 mL) was added to the reaction mixture at −40° C. dropwise. The resulting solution was stirred for 2 hours, at which point the reaction was quenched with saturate aqueous $NH_4Cl$. The resulting solution was extracted with EtOAc (100 mL×2). The organic layers were combined, dried over anhydrous sodium sulfate, filtered and concentrated in vacuo to afford the title compound (18.9 g, 82%, ketone/enol=3:2) as a yellow oil, which was used directly without further purification. $^1$H NMR (400 MHz, $CDCl_3$): δ 12.51 (s, 1H of enol), 7.40 (d, J=8.8 Hz, 2H), 7.23 (d, J=10.0 Hz, 2H), 5.56 (s, 1H of enol), 4.32-4.19 (m, 4H), 3.91 (s, 2H of ketone), 3.12-2.93 (m, 2H), 1.89-1.80 (m, 8H), 1.79-1.64 (m, 8H), 1.61-1.57 (m, 2H), 1.45-1.38 (m, 2H), 1.34-1.32 (m, 6H).

Step 5: Ethyl 2-bromo-5-(4-cyclohexyl-3,5-difluorophenyl)-7-oxo-4,7-dihydropyrazolo [1,5-a]pyrimidine-3-carboxylate

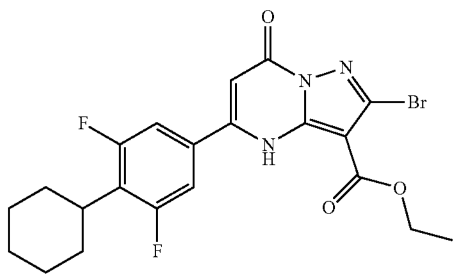 [SMILES: CCOC(=O)c1c(Br)nn2c(=O)cc(-c3cc(F)c(C4CCCCC4)c(F)c3)[nH]c12]

A mixture of ethyl 3-(4-cyclohexyl-3,5-difluorophenyl)-3-oxopropanoate (5.0 g, 16.11 mmol), p-TsOH·$H_2O$ (833 mg, 4.83 mmol) and ethyl 5-amino-3-bromo-1H-pyrazole-4-carboxylate (4.71 g, 16.11 mmol) in acetonitrile (50 mL) was stirred at 100° C. for 16 hours. The reaction was then concentrated and water (50 mL) was added. The resulting solution was extracted with ethyl acetate (100 mL×2). The combined organic layers were dried over anhydrous sodium sulfate, filtered and concentrated in vacuo. The residue was purified by flash chromatography (0-5% MeOH in DCM) to afford the title compound (3.14 g, 41%) as a white solid. $^1$H NMR (400 MHz, DMSO-$d_6$): δ 7.48 (d, J=9.6 Hz, 2H), 6.36 (s, 1H), 4.30 (q, J=7.2 Hz, 2H), 3.04-2.97 (m, 1H), 1.84-1.69 (m, 7H), 1.39-1.29 (m, 6H).

Step 6: 2-Bromo-5-(4-cyclohexyl-3,5-difluorophenyl)-7-oxo-4,7-dihydropyrazolo[1,5-a]pyrimidine-3-carboxylic acid

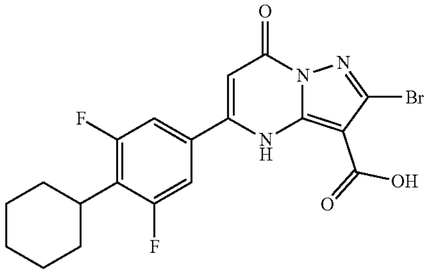 [SMILES: O=C(O)c1c(Br)nn2c(=O)cc(-c3cc(F)c(C4CCCCC4)c(F)c3)[nH]c12]

A mixture of lithium hydroxide monohydrate (310 mg, 7.39 mmol) and ethyl 2-bromo-5-(4-cyclohexyl-3,5-difluorophenyl)-7-oxo-4,7-dihydropyrazolo[1,5-a]pyrimidine-3-carboxylate (355 mg, 0.74 mmol) in water (3 mL) and ethanol (3 mL) was stirred at 80° C. for 16 hours. The reaction solution was concentrated and adjusted to pH 4 with addition of aqueous 4 M HCl solution. The mixture was extracted with EtOAc (60 mL×2). The combined organics were dried over $Na_2SO_4$ and concentrated to afford the title compound (320 mg, 96%) as a white solid. $^1$H NMR (400 MHz, DMSO-$d_6$): δ 7.47 (d, J=9.6 Hz, 2H), 6.31 (s, 1H), 3.05-2.91 (m, 1H), 1.82-1.66 (m, 8H), 1.35-1.32 (m, 2H).

Step 7: 2-Bromo-5-(4-cyclohexyl-3,5-difluorophenyl)-3-(3-(fluoromethyl)azetidine-1-carbonyl)pyrazolo[1,5-a]pyrimidin-7(4H)-one

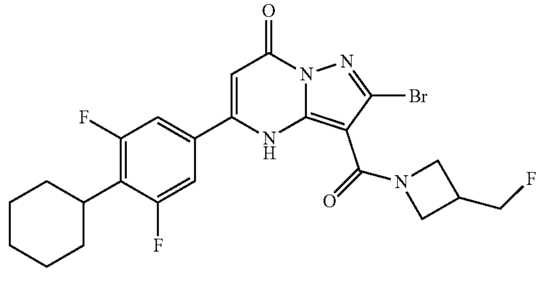 [SMILES: O=C(c1c(Br)nn2c(=O)cc(-c3cc(F)c(C4CCCCC4)c(F)c3)[nH]c12)N1CC(CF)C1]

To a solution of 2-bromo-5-(4-cyclohexyl-3,5-difluorophenyl)-7-oxo-4,7-dihydro pyrazolo[1,5-a]pyrimidine-3-carboxylic acid (2.0 g, 4.42 mmol) and DIPEA (3.65 mL, 22.11 mmol) in DMF (15 mL) was added HATU (2.52 g, 6.63 mmol). The solution was stirred for 20 minutes then 3-(fluoromethyl) azetidine 2,2,2-trifluoroacetate (1.16 g, 9.17 mmol) was added. The reaction solution was stirred for 2 hours and was quenched with water (50 mL). The mixture was extracted with EtOAc (50 mL×3, dried over $Na_2SO_4$, filtered and concentrated in vacuo. The residue was purified by flash silica gel chromatography (0-10% MeOH in DCM) to afford the title compound (1.22 g, 53%) as a white solid. $^1$H NMR (400 MHz, DMSO-$d_6$): δ 7.70 (d, J=10.8 Hz, 2H), 6.16 (s, 1H), 4.62 (dd, J=47.2, 5.6 Hz, 2H), 4.35-4.17 (m, 2H), 4.14-4.09 (m, 1H), 3.79-3.76 (m, 1H), 2.97-2.94 (m, 2H), 1.84-1.69 (m, 7H), 1.44-1.22 (m, 3H); LCMS (ESI): m/z 523.1 $(M+H)^+$.

Step 8: 5-(4-Cyclohexyl-3,5-difluorophenyl)-3-(3-(fluoromethyl)azetidine-1-carbonyl)-7-oxo-4,7-dihydropyrazolo[1,5-a]pyrimidine-2-carboxamide

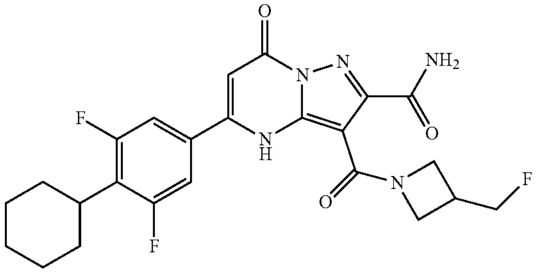 [SMILES: NC(=O)c1nn2c(=O)cc(-c3cc(F)c(C4CCCCC4)c(F)c3)[nH]c2c1C(=O)N1CC(CF)C1]

A mixture of 2-bromo-5-(4-cyclohexyl-3,5-difluorophenyl)-3-(3-(fluoromethyl) azetidine-1-carbonyl)pyrazolo[1,5-a]pyrimidin-7(4H)-one (600.0 mg, 1.15 mmol), 1,1'-bis(diphenyl phosphino)ferrocene palladium dichloride (83.9 mg, 0.11 mmol) and 4-dimethylaminopyridine (223.5 mg, 1.83 mmol) in formamide (1.03 g, 23 mmol) was stirred at 120° C. under CO (15 psi) for 16 hours. The reaction mixture was diluted in water (10 mL) and extracted with EtOAc (50 mL×2). The combined organics were dried over $Na_2SO_4$ and concentrated to dryness. The residue was purified by flash chromatography on silica gel eluting with $CH_2Cl_2$/MeOH (10:1) to afford the title compound (188 mg, 34% yield) as a white solid. LCMS (ESI): m/z 488.2 $(M+H)^+$.

Step 9: 5-(4-Cyclohexyl-3,5-difluorophenyl)-3-(3-(fluoromethyl)azetidine-1-carbonyl)-7-oxo-4,7-dihydropyrazolo[1,5-a]pyrimidine-2-carboxylic acid

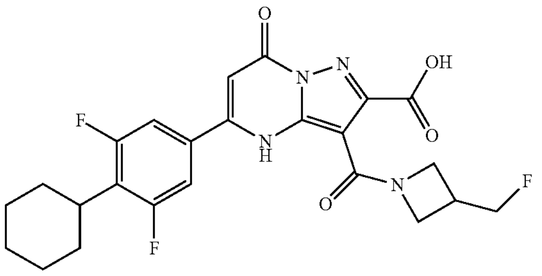 [SMILES: O=C(O)c1nn2c(=O)cc(-c3cc(F)c(C4CCCCC4)c(F)c3)[nH]c2c1C(=O)N1CC(CF)C1]

The title compound (80 mg, 43%) was furnished as a yellow solid, which was prepared from 5-(4-cyclohexyl-3,5-difluorophenyl)-3-(3-(fluoromethyl)azetidine-1-carbonyl)-7-oxo-4,7-dihydropyrazolo[1,5-a]pyrimidine-2-carboxamide (188 mg, 0.39 mmol) following the procedure outlined for Intermediate B, Step 2. LCMS (ESI): m/z 489.2 $(M+H)^+$.

Step 10: 5-(4-Cyclohexyl-3,5-difluorophenyl)-3-(3-(fluoromethyl)azetidine-1-carbonyl)-N,N-dimethyl-7-oxo-4,7-dihydropyrazolo[1,5-a]pyrimidine-2-carboxamide

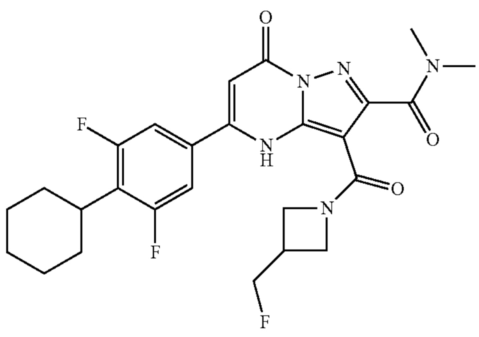 [SMILES: CN(C)C(=O)c1nn2c(=O)cc(-c3cc(F)c(C4CCCCC4)c(F)c3)[nH]c2c1C(=O)N1CC(CF)C1]

The title compound (10.9 mg, 13%) was furnished as a white solid, which was prepared from 5-(4-cyclohexyl-3,5-difluorophenyl)-3-(3-(fluoromethyl)azetidine-1-carbonyl)-7-oxo-4,7-dihydropyrazolo[1,5-a]pyrimidine-2-carboxylic acid (80 mg, 0.16 mmol) following the procedure outlined for Example 1. $^1$H NMR (400 MHz, DMSO-$d_6$): δ 7.69 (d, J=10.8 Hz, 2H), 6.16 (s, 1H), 4.60 (dd, J=47.6, 5.6 Hz, 2H), 4.42-3.61 (m, 4H), 3.00-2.90 (m, 5H), 2.79 (s, 3H), 1.84-1.76 (m, 4H), 1.75-1.70 (m, 1H), 1.39-1.20 (m, 5H); LCMS (ESI): m/z 516.2 $(M+H)^+$.

Example 4

Preparation of 5-(4-Cyclohexyl-3-fluorophenyl)-3-(3-(fluoromethyl)azetidine-1-carbonyl)-N,N-dimethyl-7-oxo-4,7-dihydropyrazolo[1,5-a]pyrimidine-2-carboxamide The general reaction scheme was as follows:

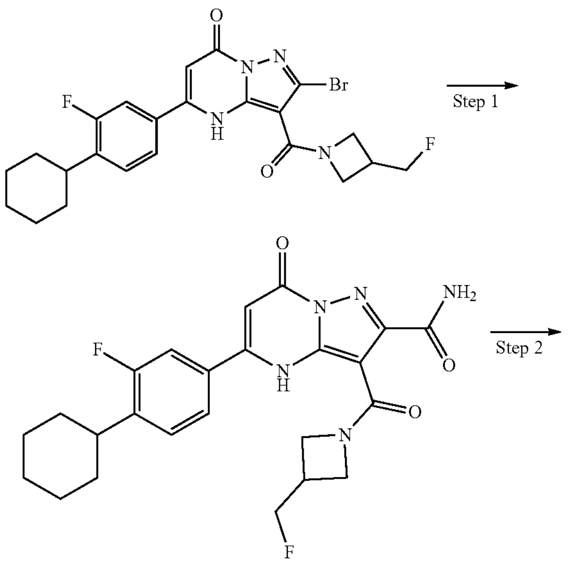

-continued

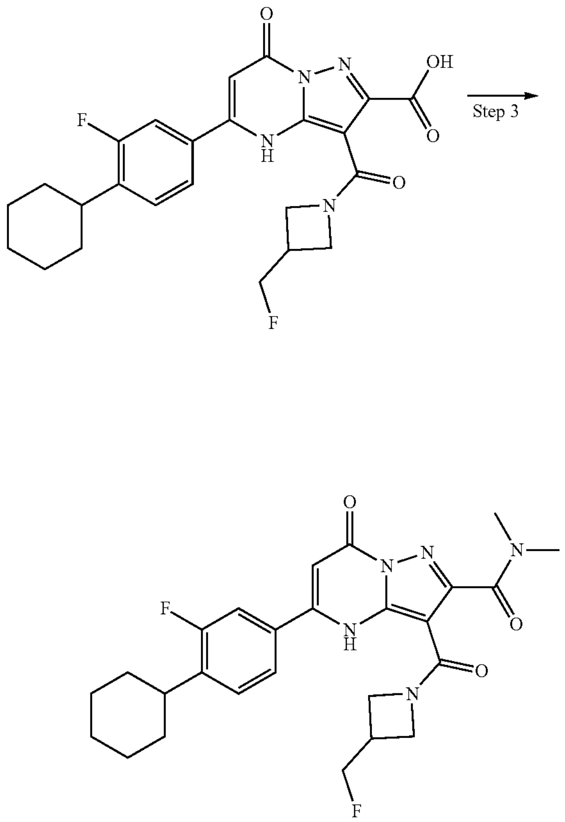

Step 1: 5-(4-Cyclohexyl-3-fluorophenyl)-3-(3-(fluoromethyl)azetidine-1-carbonyl)-7-oxo-4,7-dihydropyrazolo[1,5-a]pyrimidine-2-carboxamide

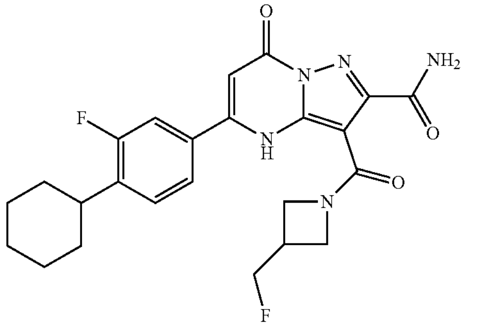 [SMILES: NC(=O)c1nn2c(=O)cc(-c3ccc(C4CCCCC4)c(F)c3)[nH]c2c1C(=O)N1CC(CF)C1]

The title compound (200 mg, 43%) was furnished as a yellow brown solid, which was prepared from 2-bromo-5-(4-cyclohexyl-3-fluorophenyl)-3-(3-(fluoromethyl)azetidine-1-carbonyl)pyrazolo[1,5-a]pyrimidin-7(4H)-one (500 mg, 0.99 mmol) following the procedure outlined for Intermediate B, Step 1. LCMS (ESI) m/z 470.2 $(M+H)^+$.

Step 2: 5-(4-Cyclohexyl-3-fluorophenyl)-3-(3-(fluoromethyl)azetidine-1-carbonyl)-7-oxo-4,7-dihydropyrazolo[1,5-a]pyrimidine-2-carboxylic acid

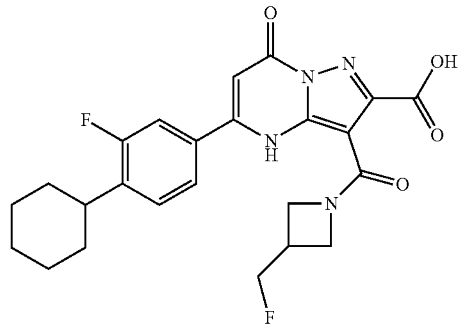 [SMILES: O=C(O)c1nn2c(=O)cc(-c3ccc(C4CCCCC4)c(F)c3)[nH]c2c1C(=O)N1CC(CF)C1]

The title compound (70 mg, 35%) was furnished as a brown solid, which was prepared from 5-(4-cyclohexyl-3-fluorophenyl)-3-(3-(fluoromethyl)azetidine-1-carbonyl)-7-oxo-4,7-dihydropyrazolo[1,5-a]pyrimidine-2-carboxamide (200 mg, 0.43 mmol) following the procedure outlined for Intermediate B, Step 2. LCMS (ESI) m/z 471.2 $(M+H)^+$.

Step 3: 5-(4-Cyclohexyl-3-fluorophenyl)-3-(3-(fluoromethyl)azetidine-1-carbonyl)-N,N-dimethyl-7-oxo-4,7-dihydropyrazolo[1,5-a]pyrimidine-2-carboxamide

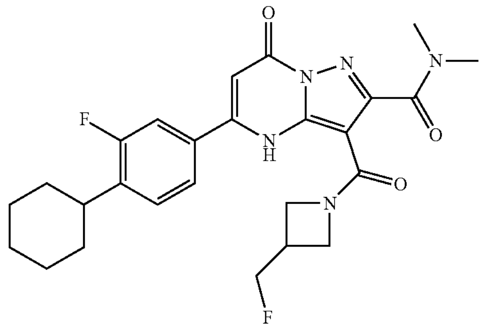 [SMILES: CN(C)C(=O)c1nn2c(=O)cc(-c3ccc(C4CCCCC4)c(F)c3)[nH]c2c1C(=O)N1CC(CF)C1]

The title compound (29.3 mg, 40%) was furnished as a white solid, which was prepared from 5-(4-cyclohexyl-3-fluorophenyl)-3-(3-(fluoromethyl)azetidine-1-carbonyl)-7-oxo-4,7-dihydropyrazolo[1,5-a]pyrimidine-2-carboxylic acid (70 mg, 0.15 mmol) following the procedure outlined for Example 1. $^1H$ NMR (400 MHz, $CD_3OD$): δ 7.80-7.72 (m, 2H), 7.40-7.36 (m, 1H), 6.40 (s, 1H), 4.63 (dd, J=47.2, 6.4 Hz, 2H), 4.60-4.42 (m, 2H), 4.28-4.25 (m, 1H), 4.01-3.98 (m, 1H), 3.08 (s, 6H), 2.95-2.92 (m, 2H), 1.90-1.81 (m, 4H), 1.78-1.76 (m, 1H), 1.58-1.46 (m, 4H), 1.34-1.27 (m, 1H); LCMS (ESI) m/z 498.3 $(M+H)^+$.

Example 5

Preparation of 5-(4-Cyclohexylphenyl)-3-((2S,3S)-3-(fluoromethyl)-2-methylazetidine-1-carbonyl)-N,N-dimethyl-7-oxo-4,7-dihydropyrazolo[1,5-a]pyrimidine-2-carboxamide

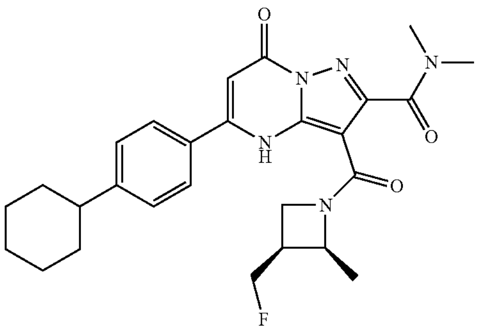 [SMILES: C[C@H]1[C@@H](CF)CN1C(=O)c1c(C(=O)N(C)C)nn2c(=O)cc(-c3ccc(C4CCCCC4)cc3)[nH]c12]

To a solution of 5-(4-cyclohexylphenyl)-2-(dimethylcarbamoyl)-7-oxo-4,7-dihydro pyrazolo[1,5-a]pyrimidine-3-carboxylic acid (Intermediate K, 70 mg, 0.17 mmol) and DIPEA (0.3 mL, 1.71 mmol) in DMF (5 mL) was added HATU (97 mg, 0.26 mmol). The reaction mixture was stirred at room temperature for 10 min and (2R,3R)-3-(fluoromethyl)-2-methyl-azetidine 2,2,2-trifluoroacetic acid (116 mg, 0.54 mmol) was added. The reaction mixture was stirred at room temperature for 2 hours at which point it was poured into water (50 mL), extracted with EtOAc (50 mL×2), washed with brine (50 mL) and concentrated in vacuo. The residue was purified by preparative TLC (5% methanol in dichloromethane) to afford the title compound (27.0 mg, 32%) as a gray solid. $^1$H NMR (400 MHz, DMSO-$d_6$): δ 7.97-7.85 (m, 2H), 7.35-7.29 (m, 2H), 6.13 (s, 1H), 4.85-4.60 (m, 3H), 3.95-3.90 (m, 2H), 2.93-2.71 (m, 6H), 2.53-2.50 (m, 2H), 1.85-1.80 (m, 4H), 1.73-1.70 (m, 1H), 1.46-1.19 (m, 8H); LCMS (ESI): m/z 494.1 $(M+H)^+$.

Example 6

Preparation of 5-(4-Cyclohexylphenyl)-3-((2R,3R)-3-(fluoromethyl)-2-methylazetidine-1-carbonyl)-N,N-dimethyl-7-oxo-4,7-dihydropyrazolo[1,5-a]pyrimidine-2-carboxamide

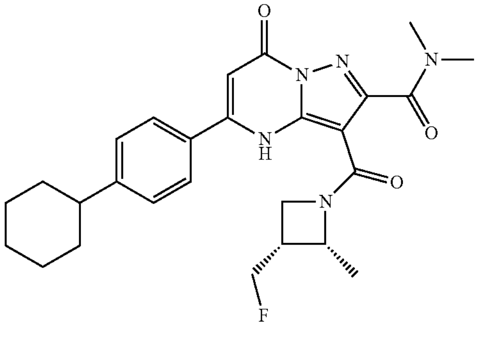 [SMILES: C[C@@H]1[C@H](CF)CN1C(=O)c1c(C(=O)N(C)C)nn2c(=O)cc(-c3ccc(C4CCCCC4)cc3)[nH]c12]

The title compound (11.5 mg, 14%) was prepared from 5-(4-cyclohexylphenyl)-2-(dimethylcarbamoyl)-7-oxo-4,7-dihydropyrazolo[1,5-a]pyrimidine-3-carboxylic acid (70 mg, 0.17 mmol) and (2S,3S)-3-(fluoromethyl)-2-methylazetidine 2,2,2-trifluoroacetic acid salt (120 mg, 0.54 mmol) following the procedure outlined for Example 5. $^1$H NMR (400 MHz, DMSO-$d_6$): δ 7.97-7.75 (m, 2H), 7.31-7.29 (m, 2H), 6.12 (s, 1H), 4.82-4.63 (m, 3H), 3.98-3.92 (m, 2H), 2.93-2.71 (m, 6H), 2.53-2.50 (m, 2H), 1.85-1.80 (m, 4H), 1.73-1.70 (m, 1H), 1.46-1.19 (m, 8H); LCMS (ESI) m/z 494.1 $(M+H)^+$.

Example 7

Preparation of 5-(4-Cyclohexylphenyl)-3-(3-(fluoromethyl)azetidine-1-carbonyl)-2-(3-(trifluoromethyl)pyrazin-2-yl)pyrazolo[1,5-a]pyrimidin-7(4H)-one

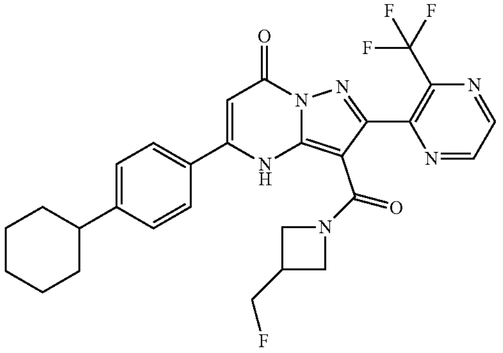 [SMILES: O=C(c1c(-c2nccnc2C(F)(F)F)nn2c(=O)cc(-c3ccc(C4CCCCC4)cc3)[nH]c12)N1CC(CF)C1]

Step 1: 2-(Tributylstannyl)-3-(trifluoromethyl)pyrazine

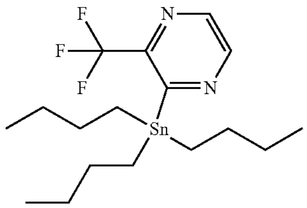 [SMILES: CCC[CH2][Sn]([CH2]CCC)([CH2]CCC)[c]1nccnc1C(F)(F)F]

To a solution of n-$Bu_6Sn_2$ (1.27 g, 2.12 mmol) and 2-chloro-3-(trifluoromethyl)pyrazine (0.2 g, 1.1 mmol) in 1,4-dioxane (10 mL) was added (A-$^{ta}$Phos)$_2$PdCl$_2$ (116 mg, 0.16 mmol). The mixture was stirred at 150° C. in microwave for 30 min under $N_2$. The resulting solution was extracted with EtOAc (30 mL×2) and the organic layers were combined. The organic layer was dried over anhydrous sodium sulfate and concentrated in vacuo. The residue was purified by preparative TLC (5% EtOAc in petroleum ether) to afford the title compound (50 mg, 10%) as a colorless liquid. $^1$H NMR (400 MHz, $CDCl_3$): δ 8.88 (d, J=2.0 Hz, 1H), 8.48 (d, J=2.0 Hz, 1H), 1.55-1.46 (m, 6H), 1.41-1.28 (m, 12H), 0.86-0.91 (m, 9H).

Step 2: 5-(4-Cyclohexylphenyl)-3-(3-(fluoromethyl)azetidine-1-carbonyl)-2-(3-(trifluoromethyl)pyrazin-2-yl)pyrazolo[1,5-a]pyrimidin-7(4H)-one

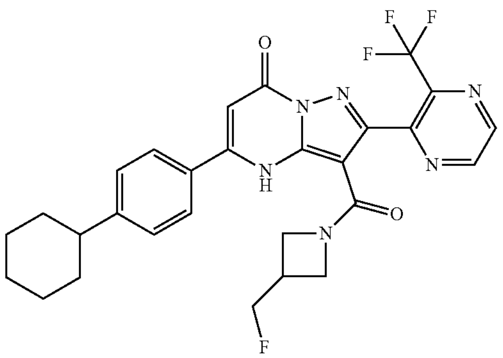 [SMILES: O=C(c1c(-c2nccnc2C(F)(F)F)nn2c(=O)cc(-c3ccc(C4CCCCC4)cc3)[nH]c12)N1CC(CF)C1]

A mixture of 2-(tributylstannyl)-3-(trifluoromethyl)pyrazine (45 mg, 0.10 mmol), 2-bromo-5-(4-cyclohexylphenyl)-3-(3-(fluoromethyl)azetidine-1-carbonyl)pyrazolo[1,5-a]pyrimidin-7(4H)-one (25 mg, 0.05 mmol), CuCl (0.76 mg, 0.01 mmol), CsF (23 mg, 0.15 mmol) and $Pd(dppf)Cl_2$ (4 mg, 0.01 mmol) in DMAc (2 mL) was stirred at 140° C. in the microwave for 3 hours. The reaction mixture was diluted in EtOAc (50 mL) and washed with brine (50 mL×2). The organic layer was purified by preparative TLC (5% MeOH in DCM) to afford the title compound (1.36 mg, 5%) as a white solid. $^1H$ NMR (400 MHz, $CD_3OD$): δ 9.00-8.85 (m, 1H), 8.84-8.78 (m, 1H), 7.96 (d, J=7.2 Hz, 2H), 7.34 (d, J=7.2 Hz, 2H), 6.33 (s, 1H), 4.70-4.50 (m, 2H), 4.52-3.85 (m, 4H), 3.10-2.95 (m, 1H), 2.65-2.55 (m, 1H), 1.95-1.85 (m, 4H), 1.83-1.75 (m, 1H), 1.58-1.42 (m, 4H), 1.35-1.30 (m, 1H); LCMS (ESI): m/z 555.1 $(M+H)^+$.

Example 8

Preparation of 3-(5-(4-Cyclohexylphenyl)-3-(3-(fluoromethyl)azetidine-1-carbonyl)-7-oxo-4,7-dihydropyrazolo[1,5-a]pyrimidin-2-yl)pyrazine-2-carbonitrile

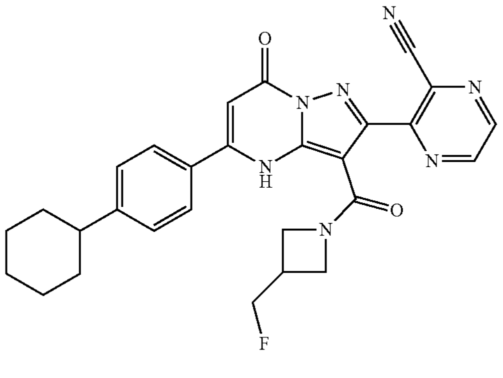 [SMILES: N#Cc1nccnc1-c1nn2c(=O)cc(-c3ccc(C4CCCCC4)cc3)[nH]c2c1C(=O)N1CC(CF)C1]

Step 1: 3-(Tributylstannyl)pyrazine-2-carbonitrile

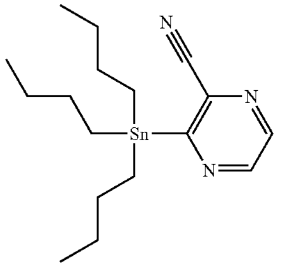 [SMILES: CCC[CH2][Sn]([CH2]CCC)([CH2]CCC)[c]1nccnc1C#N]

The title compound (1.68 g, 40%) was prepared from 3-chloropyrazine-2-carbonitrile (1.5 g, 10.75 mmol) following the procedure outlined for Example 7, Step 1. $^1H$ NMR (400 MHz, $CDCl_3$): δ 8.85-8.82 (m, 1H), 8.50-8.46 (m, 1H), 1.70-1.58 (m, 6H), 1.36-1.31 (m, 12H), 0.93-0.89 (m, 9H).

Step 2: 3-(5-(4-Cyclohexylphenyl)-3-(3-(fluoromethyl)azetidine-1-carbonyl)-7-oxo-4,7-dihydropyrazolo[1,5-a]pyrimidin-2-yl)pyrazine-2-carbonitrile

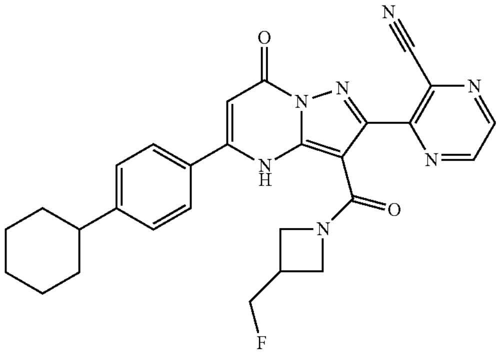 [SMILES: N#Cc1nccnc1-c1nn2c(=O)cc(-c3ccc(C4CCCCC4)cc3)[nH]c2c1C(=O)N1CC(CF)C1]

The title compound (8.2 mg, 1%) was prepared from 3-(tributylstannyl)pyrazine-2-carbonitrile (1.68 g, 4.25 mmol) and 2-bromo-5-(4-cyclohexylphenyl)-3-(3-(fluoromethyl)azetidine-1-carbonyl)pyrazolo[1,5-a]pyrimidin-7(4H)-one (600 mg, 1.23 mmol) following the procedure outlined for Example 7, Step 2. $^1H$ NMR (400 MHz, $CD_3OD$): δ 9.00-8.70 (m, 2H), 8.00-7.90 (m, 2H), 7.50-7.30 (m, 2H), 6.29 (s, 1H), 4.70-4.55 (m, 2H), 4.49-3.83 (m, 4H), 3.10-2.95 (m, 1H), 2.70-2.55 (m, 1H), 1.95-1.85 (m, 4H), 1.85-1.75 (m, 1H), 1.57-1.45 (m, 4H), 1.39-1.32 (m, 1H); LCMS (ESI): m/z 512.1 $(M+H)^+$.

The following compounds were prepared from 2-bromo-5-(4-cyclohexylphenyl)-3-(3-(fluoromethyl)azetidine-1-carbonyl)pyrazolo[1,5-a]pyrimidin-7(4H)-one (Intermediate A) and the corresponding stannane reagents following the procedure outlined for Example 7, Step 2. The corresponding stannane reagents were prepared from aryl chlorides and $(A\text{-}taPhos)_2PdCl_2$ following the procedure outlined for Example 7, Step 1.

| Ex. | Structure | Name | LCMS $[M + H]^+$ | $^1H$ NMR |
|---|---|---|---|---|
| 9 | 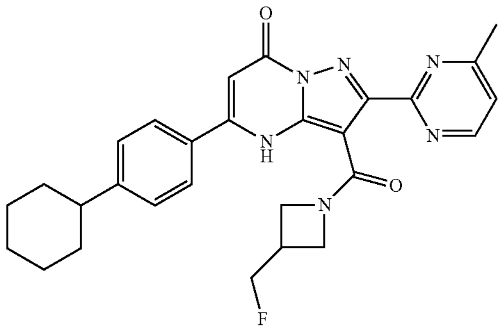 [SMILES: Cc1ccnc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(4-methylpyrimidin-2-yl)pyrazolo[1,5-a]pyrimidin-7(4H)-one | 501.2 | $^1H$ NMR (400 MHz, DMSO-$d_6$): δ 12.53 (s, 1H), 8.85 (s, 1H), 7.80-7.70 (m, 2H), 7.50-7.40 (m, 3H), 6.11 (s, 1H), 4.52 (dd, J = 46.8, 5.6 Hz, 2H), 4.19-3.52 (m, 4H), 3.00-2.80 (m, 1H), 2.65-2.55 (m, 4H), 1.85-1.75 (m, 4H), 1.73-1.65 (m, 1H), 1.51-1.26 (m, 4H), 1.25-1.20 (m, 1H) |
| 10 | 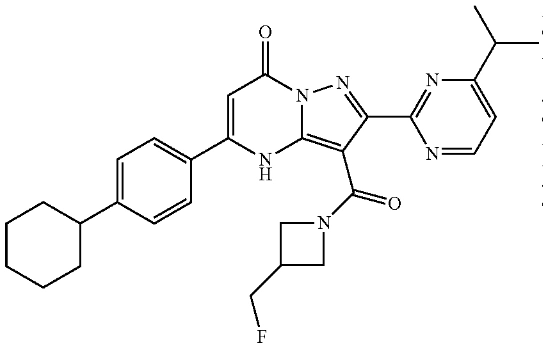 [SMILES: CC(C)c1ccnc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(4-isopropylpyrimidin-2-yl)pyrazolo[1,5-a]pyrimidin-7(4H)-one | 529.2 | $^1H$ NMR (400 MHz, DMSO-$d_6$): δ 12.49 (s, 1H), 8.84 (s, 1H), 7.72 (d, J = 7.6 Hz, 2H), 7.50-7.40 (m, 3H), 6.11 (s, 1H), 4.53 (dd, J = 47.6, 6.0 Hz, 2H), 4.16-3.43 (m, 4H), 3.10-3.00 (m, 1H), 2.95-2.85 (m, 1H), 2.65-2.55 (m, 1H), 1.85-1.78 (m, 4H), 1.75-1.70 (m, 1H), 1.51-1.37 (m, 4H), 1.34-1.25 (m, 7H) |
| 11 | 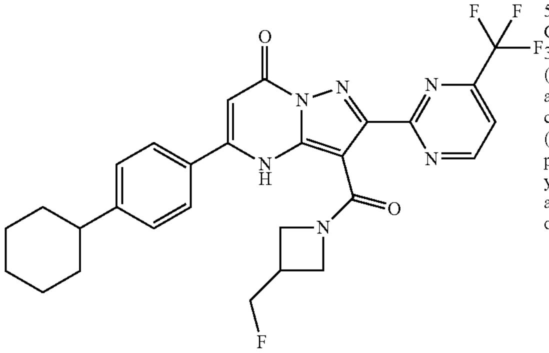 | 5-(4-Cyclohexylphenyl)-3-(3-(fluoromethyl)azetidine-1-carbonyl)-2-(4-(trifluoromethyl)pyrimidin-2-yl)pyrazolo[1,5-a]pyrimidin-7(4H)-one | 555.3 | $^1H$ NMR (400 MHz, $CDCl_3$): δ 10.44 (s, 1H), 9.24 (d, J = 4.8 Hz, 1H), 7.75 (d, J = 4.8 Hz, 1H), 7.65 (d, J =8.4 Hz, 2H), 7.40 (d, J = 8.0 Hz, 2H), 6.29 (s, 1H), 4.42 (dd, J = 46.8, 5.2 Hz, 2H), 3.80-3.79 (m, 4H), 2.91-2.89 (m, 1H), 2.62-2.60 (m, 1H), 1.91-1.89 (m, 4H), 1.81-1.78 (m, 1H), 1.46-1.44 (m, 4H), 1.35-1.34 (m, 1H) |
| 12 | 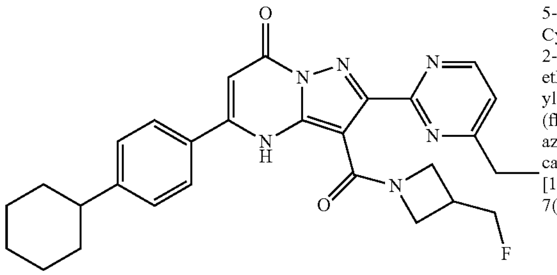 | 5-(4-Cyclohexylphenyl)-2-(4-ethylpyrimidin-2-yl)-3-(3-(fluoromethyl)azetidine-1-carbonyl)pyrazolo[1,5-a]pyrimidin-7(4H)-one | 515.3 | 1H NMR (400 MHz, DMSO-$d_6$): δ 8.79 (s, 1H), 7.80-7.76 (m, 2H), 7.43-7.38 (m, 3H), 6.08 (s, 1H), 4.54 (dd, J = 47.6, 5.6 Hz, 2H), 4.21-3.67 (m, 4H), 2.93-2.89 (m, 2H), 2.84 (q, J = 7.2 Hz, 2H), 1.83-1.79 (m, 4H), 1.73-1.70 (m, 1H), 1.48-1.37 (m, 4H), 1.31-1.27 (m, 4H) |

-continued

| Ex. | Structure | Name | LCMS [M + H]+ | 1H NMR |
|---|---|---|---|---|
| 13 | 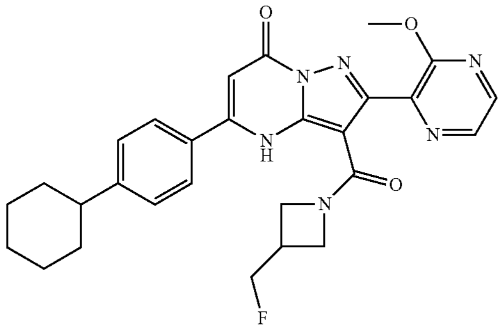 [SMILES: COc1nccnc1-c1nn2c(=O)cc(-c3ccc(C4CCCCC4)cc3)[nH]c2c1C(=O)N1CC(CF)C1] | 5-(4-Cyclohexylphenyl)-3-(3-(fluoromethyl)azetidine-1-carbonyl)-2-(3-methoxypyrazin-2-yl)pyrazolo[1,5-a]pyrimidin-7(4H)-one | 517.3 | $^1H$ NMR (400 MHz, DMSO-$d_6$): δ 8.24-8.20 (m, 2H), 8.00 (d, J = 8.0 Hz, 2H), 7.30 (d, J = 8.0 Hz, 2H), 6.08 (s, 1H), 4.62 (dd, J = 47.6, 5.6 Hz, 2H), 4.54-4.14 (m, 2H), 4.06-4.03 (m, 1H), 3.86 (s, 3H), 3.75-3.72 (m, 1H), 2.99-2.95 (m, 1H), 2.62-2.57 (m, 1H), 1.84-1.80 (m, 4H), 1.74-1.70 (m, 1H), 1.51-1.37 (m, 4H), 1.31-1.27 (m, 1H) |
| 14 | 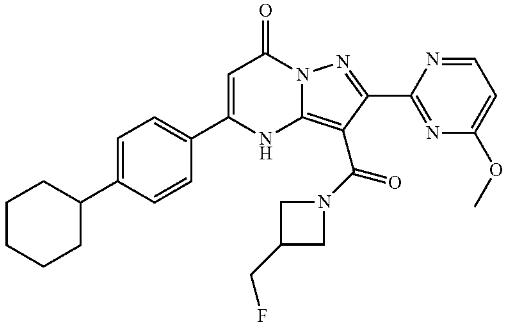 [SMILES: COc1ccnc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(4-methoxypyrimidin-2-yl)pyrazolo[1,5-a]pyrimidin-7(4H)-one | 517.3 | $^1H$ NMR (400 MHz, $CD_3OD$): δ 8.30 (s, 1H), 7.95 (d, J = 7.2 Hz, 2H), 7.35 (d, J = 7.2 Hz, 2H), 6.80 (s, 1H), 6.43 (s, 1H), 4.64-4.52 (m, 2H), 4.33-4.30 (m, 2H), 4.16-3.95 (m, 5H), 3.08-3.06 (m, 1H), 2.62-2.58 (m, 1H), 1.90-1.80 (m, 4H), 1.79-1.76 (m, 1H), 1.59-1.43 (m, 4H), 1.29-1.26 (m, 1H) |

Example 15

Preparation of 5-(4-Cyclohexylphenyl)-3-(3-(fluoromethyl)azetidine-1-carbonyl)-2-(pyrimidin-2-yl)pyrazolo[1,5-a]pyrimidin-7(4H)-one

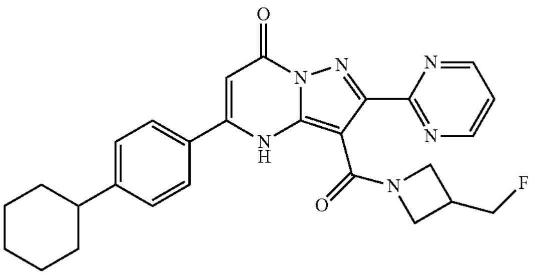 [SMILES: O=C(c1c(-c2ncccn2)nn2c(=O)cc(-c3ccc(C4CCCCC4)cc3)[nH]c12)N1CC(CF)C1]

The title compound (8.72 mg, 4%) was prepared from 2-bromo-5-(4-cyclohexylphenyl)-3-(3-(fluoromethyl)azetidine-1-carbonyl)pyrazolo[1,5-a]pyrimidin-7(4H)-one (200.0 mg, 0.41 mmol)) and 2-(tributylstannyl)pyrimidine (303 mg, 0.82 mmol) following the procedure outlined for Example 7, Step 2. $^1H$ NMR (400 MHz, $CD_3OD$): δ 8.90-8.88 (m, 2H), 7.90 (d, J=8.0 Hz, 2H), 7.50-7.48 (m, 1H), 7.35 (d, J=8.0 Hz, 2H), 6.29 (s, 1H), 4.62 (dd, J=47.6, 6.0 Hz, 2H), 4.33-4.30 (m, 2H), 4.13-4.11 (m, 1H), 4.05-4.03 (m, 1H), 3.01-2.98 (m, 1H), 2.61-2.59 (m, 1H), 1.92-1.88 (m, 4H), 1.80-1.78 (m, 1H), 1.57-1.43 (m, 4H), 1.37-1.28 (m, 1H); LCMS (ESI): m/z 487.2 $(M+H)^+$.

The following title compounds were prepared from 2-bromo-5-(4-cyclohexylphenyl)-3-(3-(fluoromethyl)azetidine-1-carbonyl)pyrazolo[1,5-a]pyrimidin-7(4H)-one and aryl stannanes following the procedure outlined for Example 7, Step 2. The corresponding stannane reagents are commercially available.

| Ex. | Structure | Name | LCMS $[M + H]^+$ | $^1H$ NMR |
|---|---|---|---|---|
| 16 | 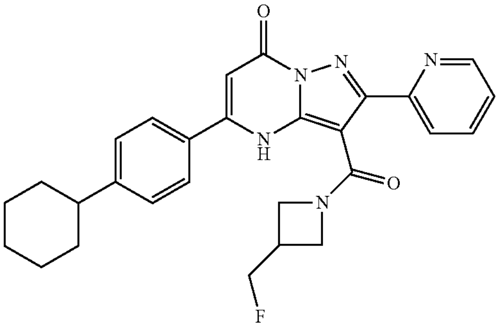 [SMILES: O=C(c1c(-c2ccccn2)nn2c(=O)cc(-c3ccc(C4CCCCC4)cc3)[nH]c12)N1CC(CF)C1] | 5-(4-Cyclohexylphenyl)-3-(3-(fluoromethyl) azetidine-1-carbonyl)-2-(pyridin-2-yl)pyrazolo[1,5-a]pyrimidin-7(4H)-one | 486.1 | $^1H$ NMR (400 MHz, DMSO-$d_6$): δ 8.55 (s, 1H), 7.98-7.93 (m, 4H), 7.32-7.28 (m, 3H), 6.16 (s, 1H), 4.64 (dd, J = 47.2, 6.4 Hz, 2H), 4.15-4.11 (m, 2H), 3.84-3.80 (m, 2H), 2.97-2.94 (m, 1H), 2.62-2.57 (m, 1H), 1.82-1.80 (m, 4H), 1.73-1.70 (m, 1H), 1.46-1.35 (m, 4H), 1.32-1.25 (m, 1H) |
| 17 | 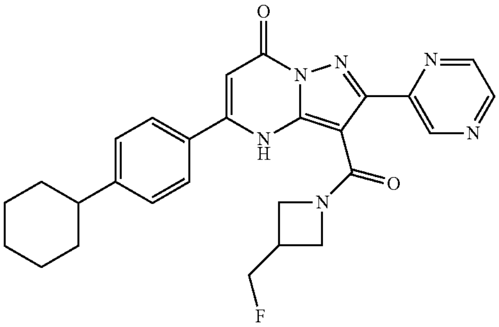 | 5-(4-Cyclohexylphenyl)-3-(3-(fluoromethyl) azetidine-1-carbonyl)-2-(pyrazin-2-yl)pyrazolo[1,5-a]pyrimidin-7(4H)-one | 487.3 | $^1H$ NMR (400 MHz, DMSO-d): δ 12.57 (br s, 1H), 9.11 (s, 1H), 8.79-8.58 (m, 2H), 7.89 (d, J = 7.2 Hz, 2H), 7.34 (d, J = 7.2 Hz, 2H), 6.10 (s, 1H), 4.60 (dd, J = 47.2, 6.4 Hz, 2H), 4.31-3.67 (m, 4H), 2.98-2.95 (m, 1H), 2.58-2.56 (m, 1H), 1.82-1.80 (m, 4H), 1.74-1.70 (m, 1H), 1.50-1.34 (m, 4H), 1.31-1.23 (m, 1H) |
| 18 | 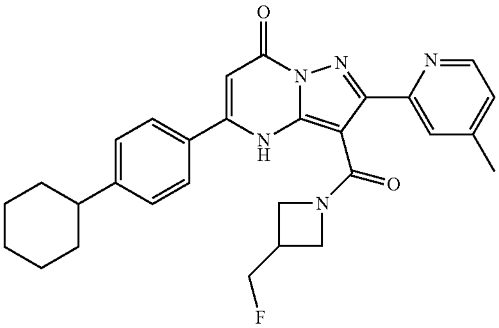 [SMILES: Cc1ccnc(-c2nn3c(=O)cc(-c4ccc(C5CCCCC5)cc4)[nH]c3c2C(=O)N2CC(CF)C2)c1] | 5-(4-Cyclohexylphenyl)-3-(3-(fluoromethyl) azetidine-1-carbonyl)-2-(4-methylpyridin-2-yl)pyrazolo[1,5-a]pyrimidin-7(4H)-one | 500.2 | $^1H$ NMR (400 MHz, DMSO-$d_6$): δ 12.60 (br s, 1H), 8.54 (s, 1H), 7.91-7.68 (m, 3H), 7.40-7.31 (m, 3H), 6.09 (s, 1H), 4.60 (dd, J = 47.2, 6.4 Hz, 2H), 4.16-3.75 (m, 2H), 3.61-3.49 (m, 2H), 2.93-2.85 (m, 1H), 2.61-2.57 (m, 1H), 2.42 (s, 3H), 1.89-1.76 (m, 4H), 1.75-1.69 (m, 1H), 1.43-1.27 (m, 5H) |

Example 19

Preparation of 5-(4-Cyclohexylphenyl)-3-(3-(fluoromethyl)azetidine-1-carbonyl)-2-(oxazol-2-yl)pyrazolo[1,5-a]pyrimidin-7(4H)-one

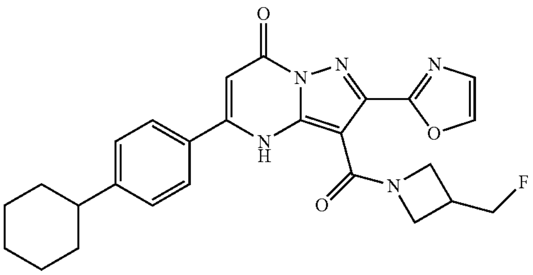 [SMILES: O=C(c1c(-c2ncco2)nn2c(=O)cc(-c3ccc(C4CCCCC4)cc3)[nH]c12)N1CC(CF)C1]

Step 1: 2-(Tributylstannyl)oxazole

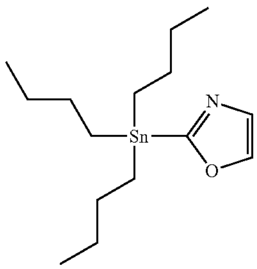 [SMILES: CCC[CH2][Sn]([CH2]CCC)([CH2]CCC)[c]1ncco1]

To a solution of oxazole (4 g, 57.92 mmol) in THF (40 mL) −78° C. under a nitrogen atmosphere was added dropwise n-BuLi (26 mL, 63.71 mmol). The reaction mixture was stirred for 15 min, then $n\text{-}Bu_3SnCl$ (20 g, 61.81 mmol) was added slowly. The reaction mixture was stirred for 1 hour and then concentrated in vacuo to afford the title compound (20.7 g, 99%) as a deep pink oil which was used directly without further purification. $^1$H NMR (400 MHz, $CDCl_3$): δ 7.85 (s, 1H), 7.19 (s, 1H), 1.62-1.59 (m, 6H), 1.37-1.32 (m, 12H), 0.93-0.90 (m, 9H).

Step 2: 5-(4-Cyclohexylphenyl)-3-(3-(fluoromethyl) azetidine-1-carbonyl)-2-(oxazol-2-yl)pyrazolo[1,5-a] pyrimidin-7(4H)-one

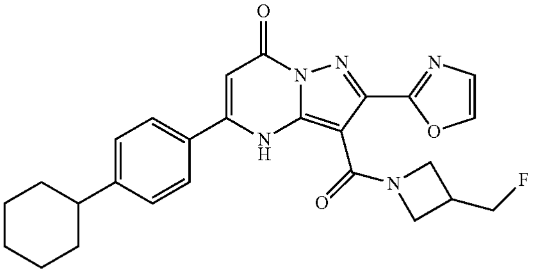 [SMILES: O=C(c1c(-c2ncco2)nn2c(=O)cc(-c3ccc(C4CCCCC4)cc3)[nH]c12)N1CC(CF)C1]

The title compound (19.8 mg, 10%) was prepared from 2-(tributylstannyl)oxazole (294 mg, 0.82 mmol) and 2-bromo-5-(4-cyclohexylphenyl)-3-(3-(fluoromethyl)azetidine-1-carbonyl)pyrazolo[1,5-a]pyrimidin-7(4H)-one (0.2 g, 0.41 mmol) following the procedure outlined for Example 7, Step 2. $^1$H NMR (400 MHz, $CD_3OD$): δ 8.11 (s, 1H) 7.87-7.85 (m, 2H) 7.50-7.36 (m, 3H), 6.28 (s, 1H), 4.62-4.48 (m, 2H), 4.39-4.14 (m, 2H), 4.08-3.98 (m, 2H), 3.01-2.95 (m, 1H), 2.63-2.60 (m, 1H), 1.90-1.87 (m, 4H), 1.79-1.75 (m, 1H), 1.53-1.46 (m, 4H), 1.34-1.30 (m, 1H); LCMS (ESI): m/z 476.2 $(M+H)^+$.

Example 20

Preparation of 5-(4-Cyclohexylphenyl)-N,N-dimethyl-2-(3-methylpyrazin-2-yl)-7-oxo-4,7-dihydropyrazolo[1,5-a]pyrimidine-3-carboxamide

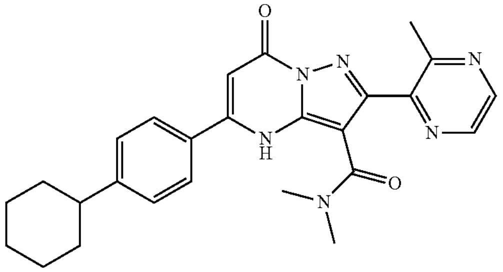 [SMILES: Cc1nccnc1-c1nn2c(=O)cc(-c3ccc(C4CCCCC4)cc3)[nH]c2c1C(=O)N(C)C]

Step 1: 2-Bromo-5-(4-cyclohexylphenyl)-N,N-dimethyl-7-oxo-4,7-dihydropyrazolo[1,5-a]pyrimidine-3-carboxamide

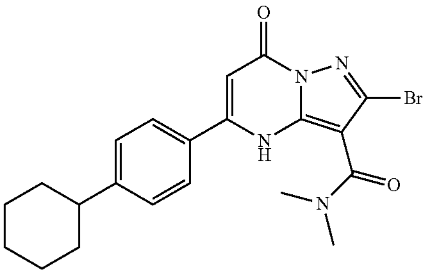 [SMILES: CN(C)C(=O)c1c(Br)nn2c(=O)cc(-c3ccc(C4CCCCC4)cc3)[nH]c12]

The title compound (3.8 g, 71%) was prepared from 2-bromo-5-(4-cyclohexylphenyl)-7-oxo-4,7-dihydropyrazolo[1,5-a]pyrimidine-3-carboxylic acid (5.0 g, 12.01 mmol) and dimethylamine hydrochloride (1.9 g, 24.02 mmol) following the procedure outlined for Intermediate A, Step 5. LCMS (ESI): m/z 443.1 $(M+H)^+$.

Step 2: 5-(4-Cyclohexylphenyl)-N,N-dimethyl-2-(3-methylpyrazin-2-yl)-7-oxo-4,7-dihydropyrazolo[1,5-a]pyrimidine-3-carboxamide

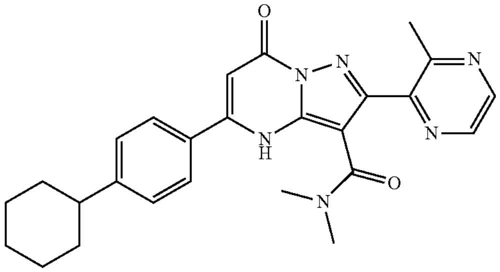 [SMILES: Cc1nccnc1-c1nn2c(=O)cc(-c3ccc(C4CCCCC4)cc3)[nH]c2c1C(=O)N(C)C]

The title compound (12 mg, 8%) was prepared from 2-bromo-5-(4-cyclohexylphenyl)-N,N-dimethyl-7-oxo-4,7-dihydropyrazolo[1,5-a]pyrimidine-3-carboxamide (150 mg, 0.34 mmol) and 2-methyl-3-(tributylstannyl)pyrazine (194 mg, 0.51 mmol) following the procedure outlined for Example 7, Step 2. $^1$H NMR (400 MHz, DMSO-$d_6$): δ 12.57 (s, 1H), 8.58-8.53 (m, 2H), 7.70 (d, J=8.0 Hz, 2H), 7.44 (d, J=8.0 Hz, 2H), 6.11 (s, 1H), 2.87 (s, 6H), 2.74 (s, 3H), 2.63-2.60 (m, 1H), 1.83-1.80 (m, 4H), 1.74-1.70 (m, 1H), 1.51-1.37 (m, 4H), 1.32-1.24 (m, 1H); LCMS (ESI): m/z 457.2 $(M+H)^+$.

Example 21

Preparation of 5-(4-cyclohexyl-3-fluorophenyl)-3-(3-(fluoromethyl)azetidine-1-carbonyl)-2-(3-methylpyrazin-2-yl)pyrazolo[1,5-a]pyrimidin-7(4H)-one

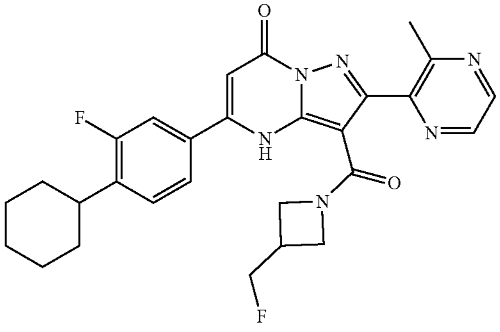 [SMILES: Cc1nccnc1-c1nn2c(=O)cc(-c3ccc(C4CCCCC4)c(F)c3)[nH]c2c1C(=O)N1CC(CF)C1]

The title compound (26 mg, 17%) was prepared from 2-bromo-5-(4-cyclohexyl-3-fluorophenyl)-3-(3-(fluoromethyl)azetidine-1-carbonyl)pyrazolo[1,5-a]pyrimidin-7(4H)-one (150 mg, 0.30 mmol) and 2-methyl-3-(tributylstannyl)pyrazine (170 mg, 0.45 mmol) following the procedure outlined for Example 7, Step 2. $^1$H NMR (400 MHz, DMSO-$d_6$): δ 12.54 (s, 1H), 8.64-8.59 (m, 2H), 7.67-7.60 (m, 2H), 7.58-7.53 (m, 1H), 6.25 (s, 1H), 4.49 (dd, J=47.2, 5.6 Hz, 2H), 4.21-3.40 (m, 4H), 2.92-2.86 (m, 2H), 2.67 (s, 3H), 1.84-1.81 (m, 4H), 1.78-1.72 (m, 1H), 1.56-1.32 (m, 5H); LCMS (ESI): m/z 519.3 $(M+H)^+$.

Example 22

Preparation of 5-(4-Cyclohexyl-3-fluorophenyl)-3-(3-(fluoromethyl)azetidine-1-carbonyl)-2-(pyrimidin-2-yl)pyrazolo[1,5-a]pyrimidin-7(4H)-one

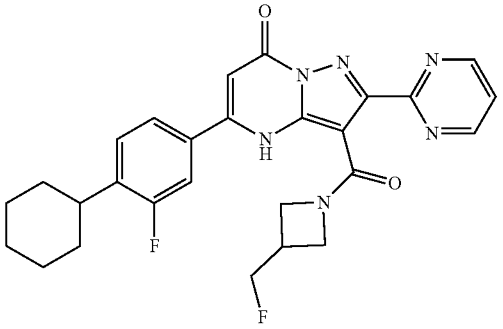 [SMILES: O=C(c1c(-c2ncccn2)nn2c(=O)cc(-c3ccc(C4CCCCC4)c(F)c3)[nH]c12)N1CC(CF)C1]

The title compound (18.1 mg, 18%) was prepared from 2-bromo-5-(4-cyclohexyl-3-fluorophenyl)-3-(3-(fluoromethyl)azetidine-1-carbonyl)pyrazolo[1,5-a]pyrimidin-7(4H)-one (100 mg, 0.20 mmol) and 2-(tributylstannyl)pyrimidine (109 mg, 0.30 mmol) following the procedure outlined for Example 7, Step 2. $^1$H NMR (400 MHz, DMSO-$d_6$): δ 9.00-8.90 (m, 2H), 7.80-7.60 (m, 2H), 7.60-7.40 (m, 2H), 6.13 (s, 1H), 4.70-4.46 (m, 2H), 4.20-3.95 (m, 2H), 3.90-3.65 (m, 2H), 3.00-2.80 (m, 2H), 1.85-1.75 (m, 4H), 1.75-1.70 (m, 1H), 1.57-1.40 (m, 4H), 1.32-1.25 (m, 1H); LCMS (ESI): m/z 505.1 $(M+H)^+$.

Example 23

Preparation of 5-(4-Cyclohexyl-3-fluorophenyl)-3-(3-(fluoromethyl)azetidine-1-carbonyl)-2-(pyrazin-2-yl)pyrazolo[1,5-a]pyrimidin-7(4H)-one

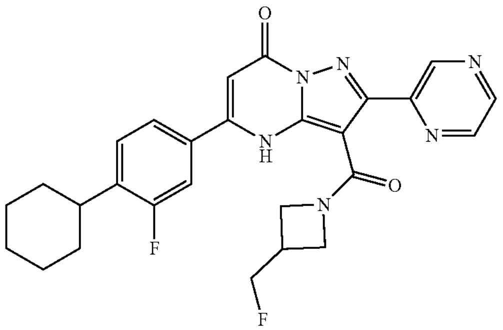 [SMILES: O=C(c1c(-c2cnccn2)nn2c(=O)cc(-c3ccc(C4CCCCC4)c(F)c3)[nH]c12)N1CC(CF)C1]

The title compound (17 mg, 11%) was prepared from 2-bromo-5-(4-cyclohexyl-3-fluorophenyl)-3-(3-(fluoromethyl)azetidine-1-carbonyl)pyrazolo[1,5-a]pyrimidin-7(4H)-one (150 mg, 0.31 mmol) and 2-(tributylstannyl)pyrazine (170 mg, 0.46 mmol) following the procedure outlined for Example 7, Step 2. $^1$H NMR (400 MHz, DMSO-$d_6$): δ 9.08 (s, 1H), 8.74-8.58 (m, 2H), 7.80-7.70 (m, 2H), 7.45-7.37 (m, 1H), 6.13 (s, 1H), 4.61 (dd, J=47.2, 6.0 Hz, 2H), 4.24-3.67 (m, 4H), 3.00-2.90 (m, 1H), 2.90-2.80 (m, 1H), 1.85-1.75 (m, 4H), 1.75-1.65 (m, 1H), 1.54-1.38 (m, 4H), 1.34-1.25 (m, 1H); LCMS (ESI): m/z 505.2 $(M+H)^+$.

Example 24

Preparation of 5-(4-(Cyclopentylmethyl)phenyl)-3-(3-(fluoromethyl)azetidine-1-carbonyl)-2-(pyrimidin-2-yl) pyrazolo[1,5-a]pyrimidin-7(4H)-one

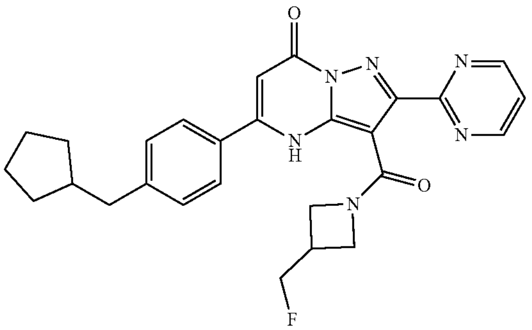

The title compound (14.80 mg, 30%) was prepared from 2-bromo-5-(4-(cyclopentylmethyl)phenyl)-3-(3-(fluoromethyl)azetidine-1-carbonyl)pyrazolo[1,5-a]pyrimidin-7(4H)-one (50.0 mg, 0.10 mmol) and 2-(tributylstannyl)pyrimidine (75.70 mg, 0.21 mmol) following the procedure outlined for Example 7, Step 2. $^1$H NMR (400 MHz, DMSO-$d_6$): δ 12.55 (s, 1H), 8.97 (d, J=4.8 Hz, 2H), 7.72 (d, J=8.4 Hz, 2H), 7.58 (t, J=4.8 Hz, 1H), 7.41 (d, J=8.4 Hz, 2H), 6.13 (s, 1H), 4.53 (dd, J=47.2, 6.0 Hz, 2H), 4.16-3.74 (m, 2H), 3.55-3.40 (m, 2H), 2.98-2.86 (m, 1H), 2.68 (d, J=7.2 Hz, 2H), 2.18-2.07 (m, 1H), 1.69-1.57 (m, 4H), 1.55-1.43 (m, 2H), 1.25-1.18 (m, 2H). LCMS (ESI): m/z 487.1 $(M+H)^+$.

Example 25

Preparation of 5-(4-(Cyclopentylmethyl)phenyl)-3-(3-(fluoromethyl)azetidine-1-carbonyl)-2-(pyrazin-2-yl)pyrazolo[1,5-a]pyrimidin-7(4H)-one

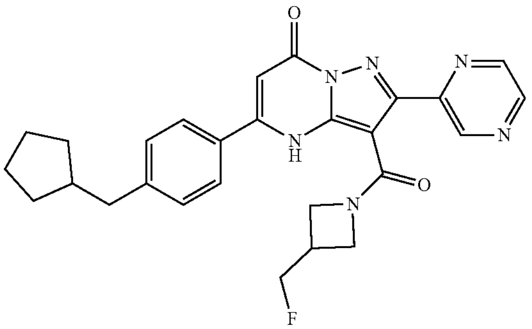 [SMILES: O=C(c1c(-c2cnccn2)nn2c(=O)cc(-c3ccc(CC4CCCC4)cc3)[nH]c12)N1CC(CF)C1]

The title compound (22.8 mg, 45%) was prepared from 2-bromo-5-(4-(cyclopentylmethyl)phenyl)-3-(3-(fluoromethyl)azetidine-1-carbonyl)pyrazolo[1,5-a]pyrimidin-7(4H)-one (50.0 mg, 0.10 mmol) and 2-(tributylstannyl)pyrazine (75.0 mg, 0.21 mmol) following the procedure outlined for Example 7, Step 2. $^1$H NMR (400 MHz, DMSO-$d_6$): δ 12.62 (s, 1H), 9.18 (s, 1H), 8.75-8.70 (m, 2H), 7.85-7.69 (m, 2H), 7.38 (d, J=6.8 Hz, 2H), 6.15 (s, 1H), 4.57 (dd, J=47.2, 6.0 Hz, 2H), 4.15-3.50 (m, 4H), 2.94-2.86 (m, 1H), 2.68 (d, J=7.2 Hz, 2H), 2.16-2.07 (m, 1H), 1.69-1.57 (m, 4H), 1.53-1.45 (m, 2H), 1.23-1.16 (m, 2H). LCMS (ESI): m/z 487.2 $(M+H)^+$.

Example 26

Preparation of 5-(4-Cyclohexylphenyl)-3-(3-(fluoromethyl) azetidine-1-carbonyl)-2-(5-methylpyrazin-2-yl) pyrazolo [1,5-a]pyrimidin-7(4H)-one

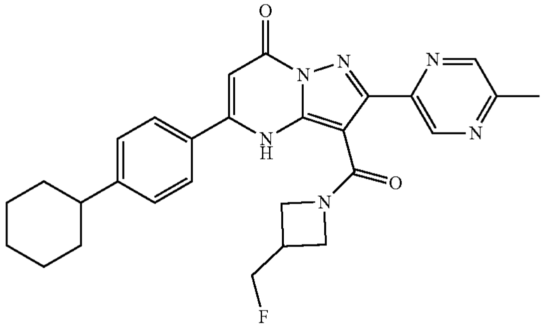 [SMILES: Cc1cnc(-c2nn3c(=O)cc(-c4ccc(C5CCCCC5)cc4)[nH]c3c2C(=O)N2CC(CF)C2)cn1]

Step 1: 2-Methyl-5-(tributylstannyl)pyrazine

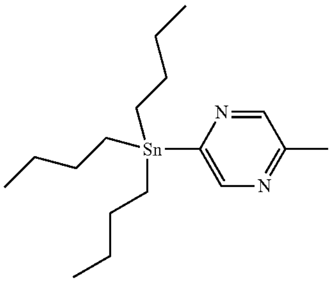 [SMILES: CCC[CH2][Sn]([CH2]CCC)([CH2]CCC)[c]1cnc(C)cn1]

To a solution of 2-bromo-5-methyl-pyrazine (1 g, 5.78 mmol) and tributylchlorostannane (3.16 g, 9.71 mmol) in THF (15 mL) was added n-BuLi (2.8 mL, 7.0 mmol) dropwise at −78° C. and stirred for a further 2 hours at this temperature. The reaction was quenched with water (50 mL) and extracted with hexanes (50 mL×2). The combined organics were dried over $Na_2SO_4$, filtered and concentrated. The crude was purified by column chromatography (0-10% ethyl acetate in petroleum ether) to afford the title compound (600 mg, 27%) as a colorless oil. $^1H$ NMR (400 MHz, $CDCl_3$): δ 8.62 (s, 1H), 8.42 (s, 1H), 2.51 (s, 3H), 1.59-1.49 (m, 6H), 1.36-1.30 (m, 6H), 1.15 (t, J=8.0 Hz, 6H), 0.88 (t, J=7.2 Hz, 9H).

Step 2: 5-(4-Cyclohexylphenyl)-3-(3-(fluoromethyl) azetidine-1-carbonyl)-2-(5-methyl pyrazin-2-yl) pyrazolo[1,5-a]pyrimidin-7(4H)-one

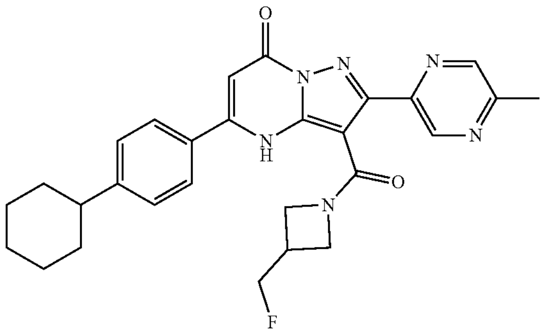 [SMILES: Cc1cnc(-c2nn3c(=O)cc(-c4ccc(C5CCCCC5)cc4)[nH]c3c2C(=O)N2CC(CF)C2)cn1]

The title compound (34 mg, 17%) was prepared from 2-bromo-5-(4-cyclohexylphenyl)-3-(3-(fluoromethyl)azetidine-1-carbonyl)pyrazolo[1,5-a]pyrimidin-7(4H)-one (200 mg, 0.41 mmol) and 2-methyl-5-(tributylstannyl)pyrazine (314 mg, 0.82 mmol) following the procedure outlined for Example 7, Step 2. $^1H$ NMR (400 MHz, $CDCl_3$): δ 10.57 (s, 1H), 9.27 (s, 1H), 8.61 (s, 1H), 7.66 (d, J=8.0 Hz, 2H), 7.40 (d, J=8.0 Hz, 2H), 6.31 (s, 1H), 4.42 (dd, J=46.8, 4.8 Hz, 2H), 4.25-3.68 (m, 4H), 2.82-2.79 (m, 1H), 2.70 (s, 3H), 2.63-2.58 (m, 1H), 1.93-1.89 (m, 4H), 1.83-1.79 (m, 1H), 1.47-1.44 (m, 4H), 1.36-1.27 (m, 1H). LCMS (ESI) m/z 501.3 $(M+H)^+$.

The following compounds were prepared from 2-bromo-5-(4-cyclohexylphenyl)-3-(3-(fluoromethyl)azetidine-1-carbonyl)pyrazolo[1,5-a]pyrimidin-7(4H)-one and stannane reagents following the procedure outlined for Example 26, Step 2. The corresponding stannane reagents are prepared from aryl bromide and n-BuLi following the procedure outlined for Example 26, Step 1.

| Ex. | Structure | Name | LCMS $[M + H]^+$ | $^1H$ NMR |
|---|---|---|---|---|
| 27 | 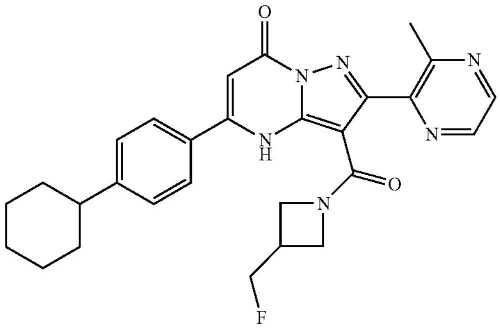 [SMILES: Cc1nccnc1-c1nn2c(=O)cc(-c3ccc(C4CCCCC4)cc3)[nH]c2c1C(=O)N1CC(CF)C1] | 5-(4-Cyclohexylphenyl)-3-(3-(fluoromethyl) azetidine-1-carbonyl)-2-(3-methylpyrazin-2-yl)pyrazolo[1,5-a]pyrimidin-7(4H)-one | 501.2 | $^1H$ NMR (400 MHz, $CDCl_3$): δ 10.84 (s, 1H), 8.67-8.54 (m, 2H), 7.67 (d, J = 8.4 Hz, 2H), 7.41 (J = 8.4 Hz, 2H), 6.33 (s, 1H), 4.46-4.18 (m, 6H), 2.82-2.71 (m, 4H), 2.64-2.60 (m, 1H), 1.93-1.87 (m, 4H), 1.83-1.79 (m, 1H), 1.53-1.39 (m, 4H), 1.32-1.29 (m, 1H) |

-continued

| Ex. | Structure | Name | LCMS $[M + H]^+$ | $^1H$ NMR |
|---|---|---|---|---|
| 28 | 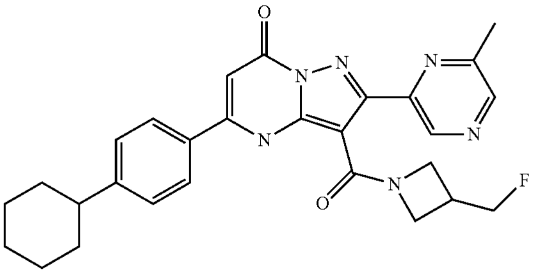 [SMILES: Cc1cncc(-c2nn3c(=O)cc(-c4ccc(C5CCCCC5)cc4)[nH]c3c2C(=O)N2CC(CF)C2)n1] | 5-(4-Cyclohexylphenyl)-3-(3-(fluoromethyl)azetidine-1-carbonyl)-2-(6-methylpyrazin-2-yl)pyrazolo[1,5-a]pyrimidin-7(4H)-one | 501.2 | $^1H$ NMR (400 MHz, $CD_3OD$): δ 9.08 (s, 1H), 8.47 (s, 1H), 7.87-7.85 (m, 2H), 7.40-7.38 (m, 2H), 6.24 (s, 1H), 4.65-4.51 (m, 2H), 4.35-4.12 (m, 2H), 4.05-4.03 (m, 2H), 3.06-2.96 (m, 1H), 2.65-2.52 (m, 4H), 1.90-1.87 (m, 4H), 1.82-1.75 (m, 1H), 1.53-1.45 (m, 4H), 1.40- 1.32 (m, 1H) |
| 29 | 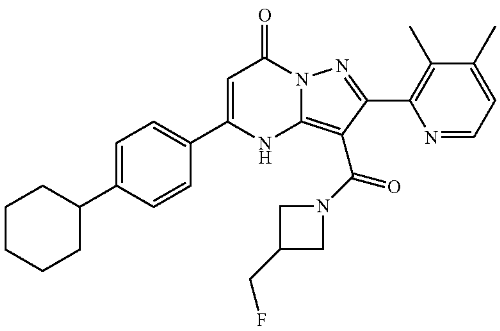 [SMILES: Cc1ccnc(-c2nn3c(=O)cc(-c4ccc(C5CCCCC5)cc4)[nH]c3c2C(=O)N2CC(CF)C2)c1C] | 5-(4-Cyclohexylphenyl)-2-(3,4-dimethylpyridin-2-yl)-3-(3-(fluoromethyl)azetidine-1-carbonyl)pyrazolo[1,5-a]pyrimidin-7(4H)-one | 514.1 | $^1H$ NMR (400 MHz, DMSO-$d_6$): δ 12.05 (s, 1H), 8.37 (d, J = 3.2 Hz, 1H), 7.77 (d, J = 7.6 Hz, 2H), 7.44 (d, J = 7.6 Hz, 2H), 7.32 (d, J = 3.2 Hz, 1H), 6.18 (s, 1H), 4.55-4.34 (m, 2H), 4.13-3.39 (m, 4H), 2.90-2.75 (m, 1H), 2.65-2.59 (m, 1H), 2.37 (s, 3H), 2.28 ( s, 3H), 1.86- 1.79 (m, 4H), 1.75-1.69 (m, 1H), 1.52-1.36 (m, 4H), 1.33-1.22 (m, 1H) |

Example 30

Preparation of 5-(4-Cyclohexylphenyl)-2-(1,5-dimethyl-1H-imidazol-4-yl)-3-(3-(fluoromethyl)azetidine-1-carbonyl)pyrazolo[1,5-a]pyrimidin-7(4H)-one

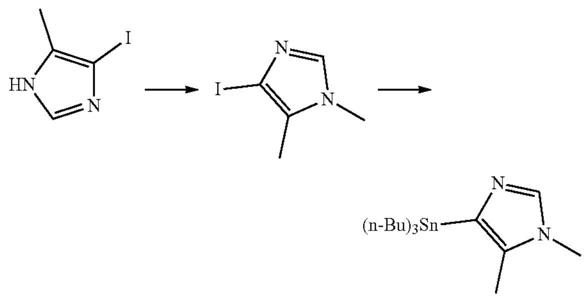

-continued

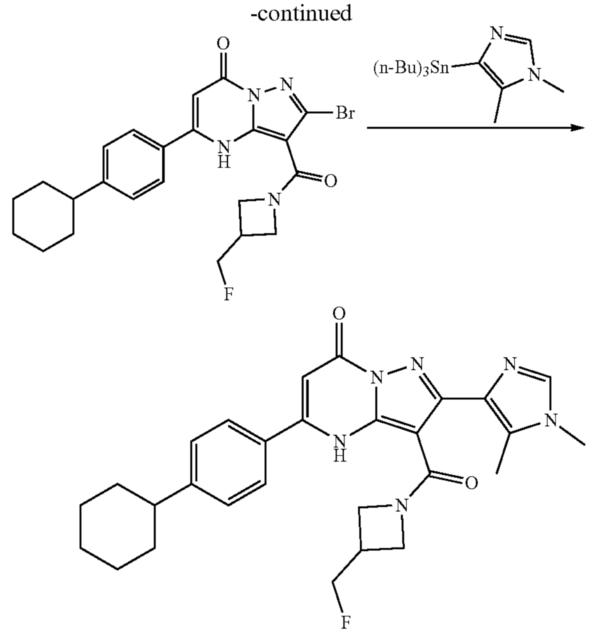

Step 1: 4-Iodo-1,5-dimethyl-1H-imidazole

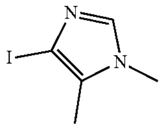

To a solution of 4-iodo-5-methyl-1H-imidazole (2.5 g, 12 mmol) in THF (25 mL) was added NaH (0.53 g, 13.2 mmol, 60 wt % in mineral oil) at 0° C. which was stirred for 30 minutes. Methyl iodide (3.4 mL, 55 mmol) was added and the reaction mixture temperature was raised to room temperature and stirred for 4 hours. The reaction mixture was quenched with water (50 mL) and extracted with ethyl acetate (100 mL×2). The combined organics were washed with brine, dried over $Na_2SO_4$, filtered and concentrated in vacuo. The residue was purified by chromatography on silica gel (50% ethyl acetate in petroleum ether) to give the title compound (1.1 g, 41%) as a pale yellow solid. $^1$H NMR (400 MHz, $CDCl_3$) δ 7.41 (s, 1H), 3.60 (s, 3H), 2.21 (s, 3H).

Step 2: 1,5-Dimethyl-4-(tributylstannyl)-1H-imidazole

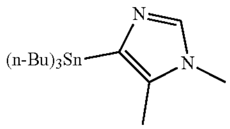

To a solution of 4-iodo-1,5-dimethyl-1H-imidazole (500 mg, 2.2 mmol) in THF (5 mL) was added isopropylmagnesium chloride (2M in THF, 1.2 mL, 2.3 mmol) dropwise at 0° C. The reaction mixture was warmed to room temperature and stirred for 1.5 hours. Tributyl chlorostannane (1.48 g, 4.55 mmol) was added and the reaction mixture was stirred for 1 hour. The reaction mixture was quenched with saturated aqueous $NH_4Cl$ (50 mL×2) solution and extracted with ethyl acetate (50 mL×2). The combined organics were washed with brine, dried over $Na_2SO_4$, filtered and concentrated to give the title compound (0.85 g, 98%) as colorless oil. LCMS (ESI) m/z 387.0 $(M+H)^+$.

Step 3: 5-(4-Cyclohexylphenyl)-2-(1,5-dimethyl-1H-imidazol-4-yl)-3-(3-(fluoromethyl) azetidine-1-carbonyl)pyrazolo[1,5-a]pyrimidin-7(4H)-one

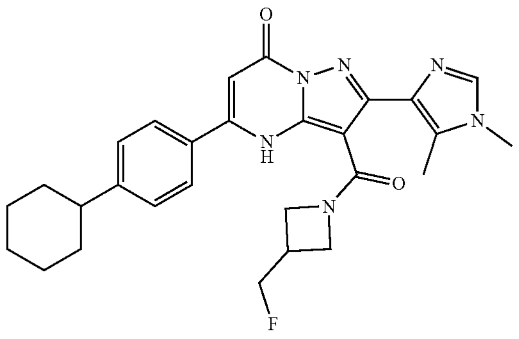 [SMILES: Cc1c(-c2nn3c(=O)cc(-c4ccc(C5CCCCC5)cc4)[nH]c3c2C(=O)N2CC(CF)C2)ncn1C]

A suspension of $Pd(t-Bu_3P)_2$ (15 mg, 0.03 mmol), CsF (160 mg, 1.0 mmol), 2-bromo-5-(4-cyclohexylphenyl)-3-(3-(fluoromethyl)azetidine-1-carbonyl)pyrazolo[1,5-a]pyrimidin-7(4H)-one (100 mg, 0.21 mmol) and 1,5-dimethyl-4-(tributylstannyl)-1H-imidazole (316 mg, 0.82 mmol) in DMA (4 mL) was stirred at 120° C. for 16 h. The mixture was diluted in water (50 mL), extracted with ethyl acetate (10 mL×5). The combined organic layers were washed with brine (50 mL×3), dried over anhydrous $Na_2SO_4$, filtered and concentrated in vacuo. The crude was further purified by reverse-phase preparative HPLC (0.2% FA/$H_2$O-MeCN over a gradient of 27%-57%, Xtimate C18 150*40 mm*10 um) to afford the title compound (27 mg, 27%) as a white solid. $^1$H NMR (400 MHz, DMSO-$d_6$): δ 7.93-7.89 (br s, 2H), 7.30-7.25 (m, 3H), 6.12 (s, 1H), 4.59 (d, J=47.6, 5.6 Hz, 2H), 4.36-3.81 (m, 4H), 3.74 (s, 3H), 2.96-2.88 (m, 1H), 2.62-2.57 (m, 1H), 2.54 (s, 3H), 1.82-1.80 (m, 4H), 1.73-1.70 (m, 1H), 1.47-1.40 (m, 4H), 1.30-1.24 (m, 1H); LCMS (ESI): m/z 503.3 $(M+H)^+$.

Example 31

Preparation of 5-(4-Cyclohexylphenyl)-2-(1-ethyl-1H-imidazol-4-yl)-3-(3-(fluoromethyl)azetidine-1-carbonyl)pyrazolo[1,5-a]pyrimidin-7(4H)-one

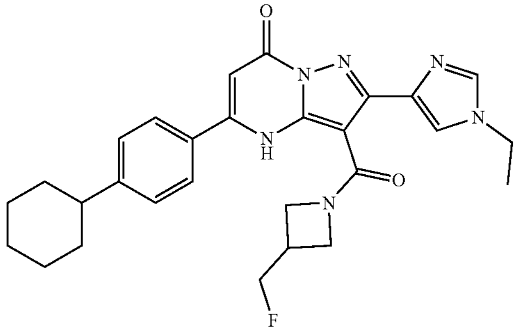 [SMILES: CCn1cnc(-c2nn3c(=O)cc(-c4ccc(C5CCCCC5)cc4)[nH]c3c2C(=O)N2CC(CF)C2)c1]

The title compound (70.3 mg, 34%) was prepared from 2-bromo-5-(4-cyclohexylphenyl)-3-(3-(fluoromethyl)azetidine-1-carbonyl)pyrazolo[1,5-a]pyrimidin-7(4H)-one and 4-iodo-1H-imidazole following the similar procedure outlined for Example 30, Steps 1-3. $^1$H NMR (400 MHz, DMSO-$d_6$): δ 8.00-7.84 (m, 4H), 7.23-7.18 (m, 2H), 6.10 (s, 1H), 4.60 (d, J=47.2, 5.2 Hz, 2H), 4.10-4.10 (m, 4H), 3.89-3.80 (m, 2H), 2.98-2.92 (m, 1H), 2.59-2.56 (m, 1H), 1.83-1.80 (m, 4H), 1.73-1.70 (m, 1H), 1.31-1.53 (m, 7H), 1.29-1.26 (m, 1H); LCMS (ESI) m/z 503.3 $(M+H)^+$.

Example 32

Preparation of 5-(4-Cyclohexylphenyl)-3-(3-(fluoromethyl)azetidine-1-carbonyl)-2-(1-methyl-1H-imidazol-4-yl)pyrazolo[1,5-a]pyrimidin-7(4H)-one

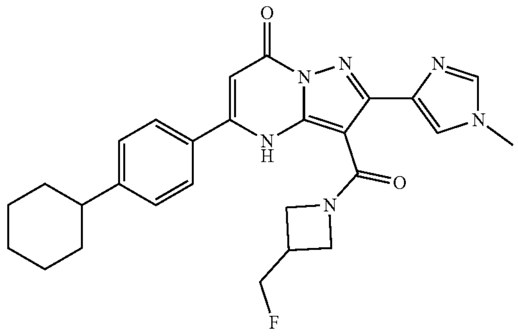 [SMILES: Cn1cnc(-c2nn3c(=O)cc(-c4ccc(C5CCCCC5)cc4)[nH]c3c2C(=O)N2CC(CF)C2)c1]

The title compound (40.7 mg, 10%) was prepared from 2-bromo-5-(4-cyclohexylphenyl)-3-(3-(fluoromethyl)azetidine-1-carbonyl)pyrazolo[1,5-a]pyrimidin-7(4H)-one and 4-iodo-1-methyl-1H-imidazole following the procedure outlined for Example 30, Step 2-3. $^{1}$H NMR (400 MHz, DMSO-$d_6$): δ 12.40 (br s, 1H), 7.89-7.62 (m, 4H), 7.39-7.35 (m, 2H), 6.11 (s, 1H), 4.61 (d, J=47.6, 5.6 Hz, 2H), 4.15 (s, 2H), 3.88-3.83 (m, 5H), 3.01-2.90 (m, 1H), 2.97-2.92 (m, 1H), 1.89-1.75 (m, 4H), 1.77-1.69 (m, 1H), 1.45-1.37 (m, 4H), 1.32-1.22 (m, 1H); LCMS (ESI): m/z 489.1 $(M+H)^+$.

Example 33

Preparation of (S)-5-(4-cyclohexylphenyl)-3-(3-(fluoromethyl)azetidine-1-carbonyl)-2-(2-methylazetidine-1-carbonyl)pyrazolo[1,5-a]pyrimidin-7(4H)-one and (R)-5-(4-cyclohexylphenyl)-3-(3-(fluoromethyl)azetidine-1-carbonyl)-2-(2-methylazetidine-1-carbonyl)pyrazolo[1,5-a]pyrimidin-7(4H)-one

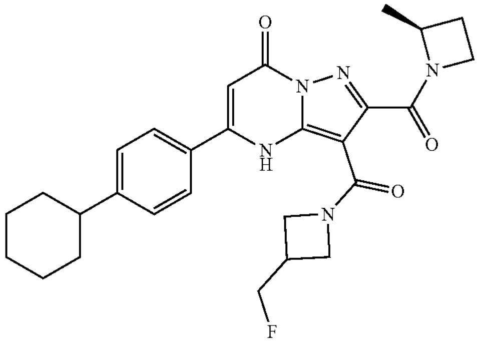

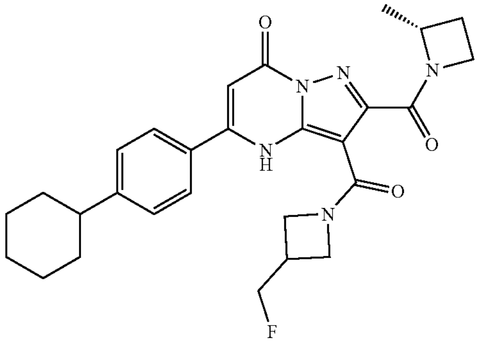

Step 1: 5-(4-Cyclohexylphenyl)-3-(3-(fluoromethyl)azetidine-1-carbonyl)-2-(2-methyl azetidine-1-carbonyl)pyrazolo[1,5-a]pyrimidin-7(4H)-one

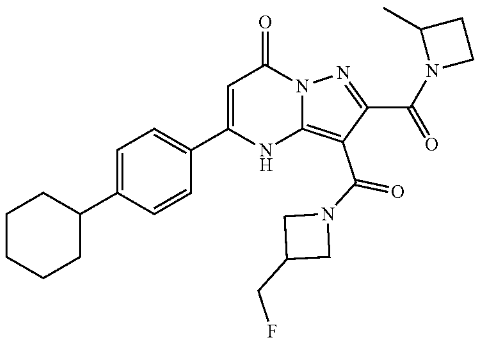 [SMILES: CC1CCN1C(=O)c1nn2c(=O)cc(-c3ccc(C4CCCCC4)cc3)[nH]c2c1C(=O)N1CC(CF)C1]

To a solution of 5-(4-cyclohexylphenyl)-3-(3-(fluoromethyl)azetidine-1-carbonyl)-7-oxo-4,7-dihydropyrazolo[1,5-a]pyrimidine-2-carboxylic acid (Intermediate B, 300 mg, 0.66 mmol) in DMF (5 mL) was added 2-methylazetidine hydrochloride (210 mg, 2.0 mmol) and DIPEA (0.32 mL, 1.95 mmol). To this reaction mixture PyBOP (520 mg, 0.99 mmol) was added. The solution was stirred at room temperature for 2 hours. The reaction mixture was diluted with water (25 mL) and the solution was adjusted to pH 6 with the additions of 1 M aqueous HCl, extracted with ethyl acetate (50 mL×3), dried over $Na_2SO_4$, filtered and concentrated in vacuo. The residue was purified by preparative TLC (10% MeOH in DCM) to afford the title compound (300 mg, 42%) as a yellow solid. LCMS (ESI): m/z 506.3 $(M+H)^+$.

Step 2: (S)-5-(4-cyclohexylphenyl)-3-(3-(fluoromethyl)azetidine-1-carbonyl)-2-(2-methylazetidine-1-carbonyl)pyrazolo[1,5-a]pyrimidin-7(4H)-one and (R)-5-(4-cyclohexylphenyl)-3-(3-(fluoromethyl)azetidine-1-carbonyl)-2-(2-methylazetidine-1-carbonyl) pyrazolo[1,5-a]pyrimidin-7(4H)-one

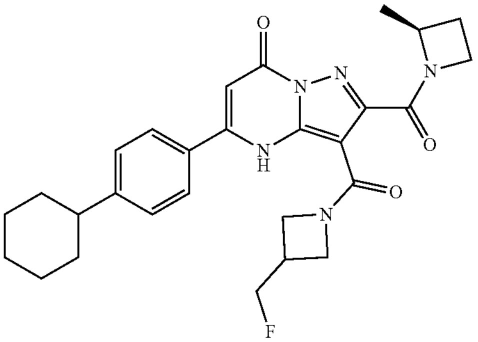

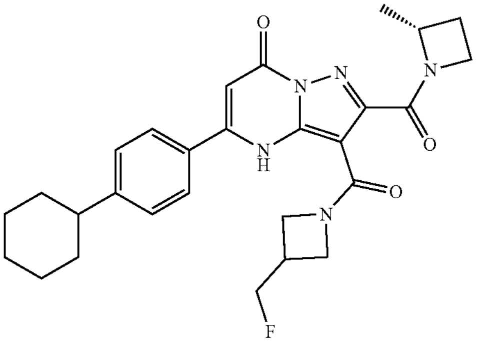

5-(4-Cyclohexylphenyl)-3-(3-(fluoromethyl)azetidine-1-carbonyl)-2-(2-methylazetidine-1-carbonyl)pyrazolo[1,5-a]pyrimidin-7(4H)-one (150 mg, 0.3 mmol) was separated by SFC (Chiralpak AD, isocratic 25% MeOH w/0.1% $NH_4OH$) to give Enantiomer A (first peak on SFC, 19.3 mg, 13%) and Enantiomer B (second peak on SFC, 21.3 mg, 14%) both as white solid.

Enantiomer A: $^{1}$H NMR (400 MHz, $CD_3OD$): δ 7.93-7.91 (m, 2H), 7.32 (d, J=8.0 Hz, 2H), 6.31 (s, 1H), 4.48-4.50 (m, 4H), 4.49-3.83 (m, 5H), 3.07-3.03 (m, 1H), 2.58-2.56 (m, 2H), 1.99-1.73 (m, 6H), 1.59-1.26 (m, 8H); LCMS (ESI): m/z 506.3 $(M+H)^+$.

Enantiomer B: $^{1}$H NMR (400 MHz, $CD_3OD$): δ 7.86-7.83 (m, 2H), 7.39 (d, J=7.2 Hz, 2H), 6.32 (s, 1H), 4.64-4.54 (m, 4H), 4.45-3.96 (m, 5H), 3.03-2.98 (m, 1H), 2.61-2.58 (m, 2H), 1.92-1.77 (m, 6H), 1.59-1.26 (m, 8H); LCMS (ESI): m/z 506.2 $(M+H)^+$.

Example 34

Preparation of 5-(4-Cyclohexylphenyl)-N-ethyl-3-(3-(fluoromethyl)azetidine-1-carbonyl)-N-methyl-7-oxo-4,7-dihydropyrazolo[1,5-a]pyrimidine-2-carboxamide

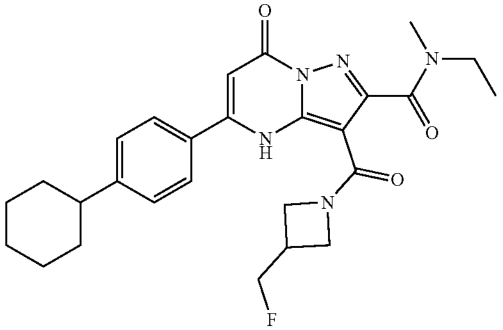 [SMILES: CCN(C)C(=O)c1nn2c(=O)cc(-c3ccc(C4CCCCC4)cc3)[nH]c2c1C(=O)N1CC(CF)C1]

The title compound (32.6 mg, 30%) was prepared from 5-(4-cyclo hexylphenyl)-3-(3-(fluoromethyl)azetidine-1-carbonyl)-7-oxo-4,7-dihydropyrazolo[1,5-a]pyrimidine-2-carboxylic acid (Intermediate B, 100 mg, 0.22 mmol) and N-ethyl-methylamine (39.2 mg, 0.66 mmol) following the procedure outlined for Example 33, Step 1. $^1$H NMR (400 MHz, DMSO-$d_6$): δ 7.92-7.82 (m, 2H), 7.38-7.26 (m, 2H), 6.05 (s, 1H), 4.60 (d, J=47.6, 5.6 Hz, 2H), 4.06-3.82 (m, 2H), 3.80-3.72 (m, 2H), 3.46-3.40 (m, 1H), 3.18-3.13 (m, 1H), 2.93 (s, 3H), 2.80-2.77 (m, 1H), 2.59-2.51 (m, 1H), 1.83-1.80 (m, 4H), 1.70-1.66 (m, 1H), 1.47-1.29 (m, 4H), 1.24-1.18 (m, 1H), 1.14-0.98 (m, 3H). LCMS (ESI): m/z 494.3 $(M+H)^+$.

Example 35

Preparation of 5-(4-Cyclohexylphenyl)-3-(3-(fluoromethyl)azetidine-1-carbonyl)-2-(pyrrolidine-1-carbonyl)pyrazolo[1,5-a]pyrimidin-7(4H)-one

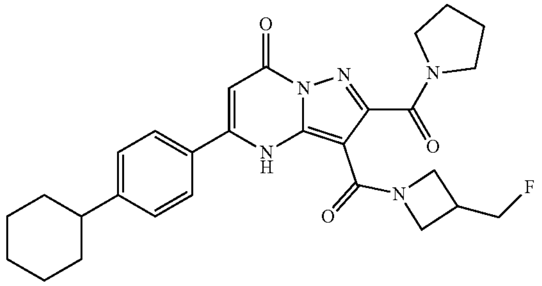 [SMILES: O=C(c1nn2c(=O)cc(-c3ccc(C4CCCCC4)cc3)[nH]c2c1C(=O)N1CC(CF)C1)N1CCCC1]

The title compound (40.01 mg, 35%) was prepared from 5-(4-cyclo hexylphenyl)-3-(3-(fluoromethyl)azetidine-1-carbonyl)-7-oxo-4,7-dihydropyrazolo[1,5-a]pyrimidine-2-carboxylic acid (Intermediate B, 100 mg, 0.22 mmol) and pyrrolidine (47 mg, 0.66 mmol) following the procedure outlined for Example 33, Step 1. $^1$H NMR (400 MHz, DMSO-$d_6$): δ 7.95-7.85 (m, 2H), 7.32 (d, J=5.6 Hz, 2H), 6.09 (s, 1H), 4.59 (dd, J=47.2, 5.6 Hz, 2H), 4.49-3.49 (m, 4H), 3.47-3.42 (m, 4H), 3.05-2.85 (m, 1H), 2.59-2.55 (m, 1H), 1.87-1.76 (m, 8H), 1.75-1.67 (m, 1H), 1.46-1.34 (m, 4H), 1.30-1.23 (m, 1H); LCMS (ESI): m/z 506.3 $(M+H)^+$.

Example 36

Preparation of 5-(4-Cyclohexylphenyl)-3-(3-(fluoromethyl)azetidine-1-carbonyl)-2-(pyridin-3-yl)pyrazolo[1,5-a]pyrimidin-7(4H)-one

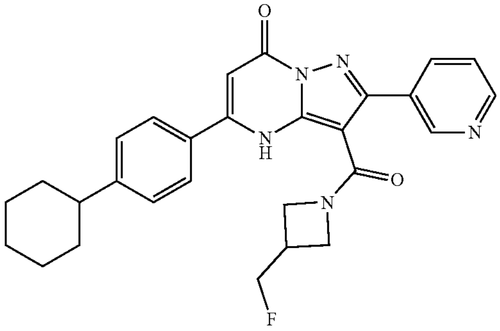

To a solution of pyridin-3-ylboronic acid (101 mg, 0.82 mmol) in DMSO (4 mL) and water (0.4 mL) was added Xphos Pd $G_3$ (34.7 mg, 0.04 mmol), Xphos (19.6 mg, 0.04 mmol), $Cs_2CO_3$ (402 mg, 1.23 mmol) and 2-bromo-5-(4-cyclohexylphenyl)-3-(3-(fluoromethyl) azetidine-1-carbonyl)pyrazolo[1,5-a]pyrimidin-7(4R)-one (200 mg, 0.41 mmol). Then the reaction mixture was stirred at 120° C. for 2 hours under a nitrogen atmosphere in a microwave. To the reaction mixture was added water (10 mL) and adjusted to pH 5 by the addition of 2 M aqueous HCl, extracted with ethyl acetate (10 mL×3), dried with $Na_2SO_4$, filtered and concentrated in vacuo. The crude was purified by preparative TLC (10% methanol in DCM) to afford the title compound (78.1 mg, 39%) as a white solid. $^1$H NMR (400 MHz, DMSO-$d_6$): δ 12.80-12.21 (m, 1H), 8.97 (s, 1H), 8.63 (s, 1H), 8.19 (d, J=8.0 Hz, 1H), 7.81-7.75 (m, 2H), 7.52-7.50 (m, 1H), 7.41 (d, J=6.8 Hz, 2H), 6.13 (s, 1H), 4.59 (dd, J=46.8, 6.0 Hz, 2H), 4.10-4.02 (m, 2H), 3.85-3.79 (m, 2H), 2.96-2.92 (m, 1H), 2.62-2.58 (m, 1H), 1.84-1.80 (m, 4H), 1.74-1.71 (m, 1H), 1.52-1.34 (m, 4H), 1.31-1.22 (m, 1H); LCMS (ESI): m/z 486.3 $(M+H)^+$.

Example 37

Preparation of 5-(4-Cyclohexylphenyl)-3-(3-(fluoromethyl)azetidine-1-carbonyl)-2-phenylpyrazolo[1,5-a]pyrimidin-7(4H)-one

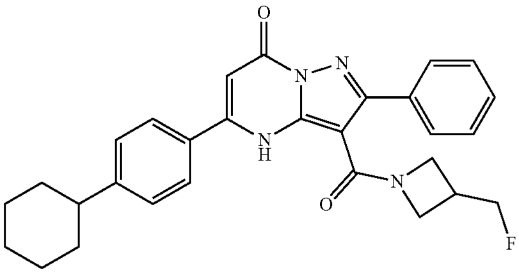 [SMILES: O=C(c1c(-c2ccccc2)nn2c(=O)cc(-c3ccc(C4CCCCC4)cc3)[nH]c12)N1CC(CF)C1]

The title compound (18.2 mg, 9.0%) was prepared from 2-bromo-5-(4-cyclohexylphenyl)-3-(3-(fluoromethyl)azetidine-1-carbonyl)pyrazolo[1,5-a]pyrimidin-7(4H)-one (200.0 mg, 0.40 mmol) and phenyl boronic acid (100 mg, 0.8 mmol) following the procedure outlined for Example 36. $^1$H NMR (400 MHz, DMSO-$d_6$): δ 12.33 (s, 1H), 7.79 (d, J=6.4 Hz, 2H), 7.73 (d, J=8.0 Hz, 2H), 7.51-7.41 (m, 5H), 6.13 (s, 1H), 4.51 (dd, J=46.8, 6.0 Hz, 2H), 4.17-3.37 (m, 4H), 2.92-2.83 (m, 1H), 2.70-2.60 (m, 1H), 1.83-1.80 (m, 4H), 1.74-1.71 (m, 1H), 1.52-1.36 (m, 4H), 1.32-1.24 (m, 1H); LCMS (ESI): m/z 485.1 $(M+H)^+$.

Example 38

Preparation of 5-(4-Cyclohexylphenyl)-3-(3-(fluoromethyl)azetidine-1-carbonyl)-2-(oxazol-5-yl)pyrazolo[1,5-a]pyrimidin-7(4H)-one

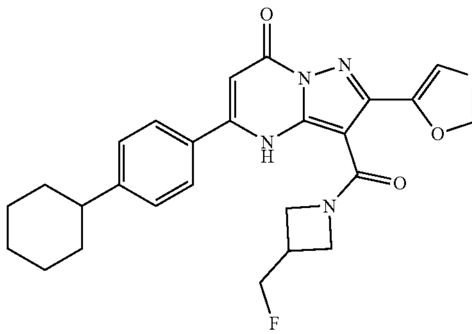

The title compound (43.0 mg, 22%) was prepared from 2-bromo-5-(4-cyclohexylphenyl)-3-(3-(fluoromethyl)azetidine-1-carbonyl)pyrazolo[1,5-a]pyrimidin-7(4H)-one (200 mg, 0.41 mmol) and 5-(4,4,5,5-tetramethyl-1,3,2-dioxaborolan-2-yl)oxazole (161 mg, 0.82 mmol) following the procedure outlined for Example 36. $^1$H NMR (400 MHz, DMSO-$d_6$): δ 8.46 (s, 1H), 7.96-7.93 (m, 2H), 7.79 (s, 1H), 7.31 (d, J=7.6 Hz, 2H), 6.09 (s, 1H), 4.62 (dd, J=47.2, 5.6 Hz, 2H), 4.37-4.03 (m, 3H), 3.84-3.82 (m, 1H), 2.97-2.94 (m, 1H), 2.58-2.55 (m, 1H), 1.82-1.80 (m, 4H), 1.73-1.70 (m, 1H), 1.48-1.34 (m, 4H), 1.30-1.21 (m, 1H); LCMS (ESI): m/z 476.2 $(M+H)^+$.

Example 39

Preparation of 5-(4-Cyclohexylphenyl)-3-((2S,3S)-3-(fluoromethyl)-2-methylazetidine-1-carbonyl)-2-(pyrazin-2-yl)pyrazolo[1,5-a]pyrimidin-7(4H)-one and 5-(4-Cyclohexylphenyl)-3-((2R,3R)-3-(fluoromethyl)-2-methylazetidine-1-carbonyl)-2-(pyrazin-2-yl)pyrazolo[1,5-a]pyrimidin-7(4H)-one The general reaction scheme was as follows:

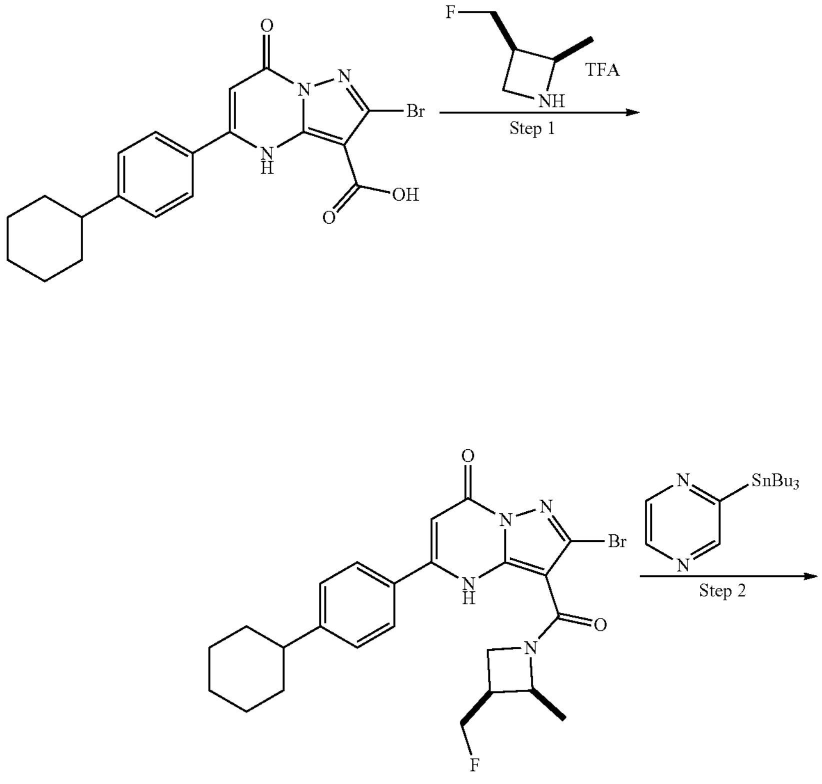

-continued

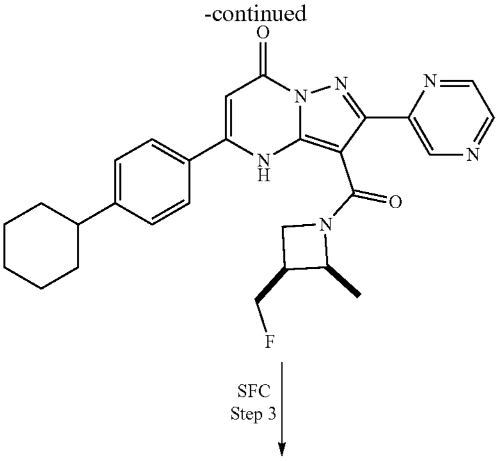

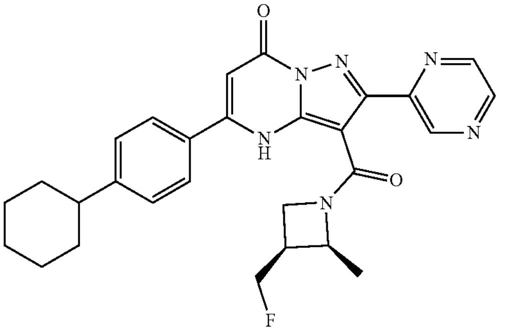

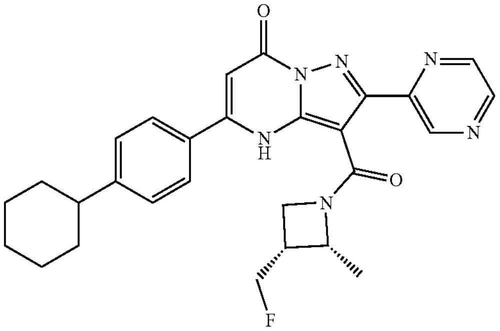

Step 1: Cis-2-bromo-5-(4-cyclohexylphenyl)-3-(3-(fluoromethyl)-2-methylazetidine-1-carbonyl)pyrazolo[1,5-a]pyrimidin-7(4H)-one

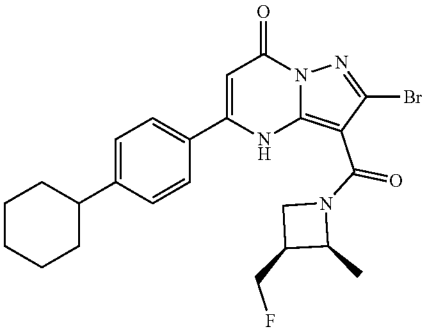 [SMILES: C[C@H]1[C@@H](CF)CN1C(=O)c1c(Br)nn2c(=O)cc(-c3ccc(C4CCCCC4)cc3)[nH]c12]

The title compound (700 mg, 64%) was prepared from 2-bromo-5-(4-cyclohexylphenyl)-7-oxo-4,7-dihydropyrazolo[1,5-a]pyrimidine-3-carboxylic acid (900 mg, 2.16 mmol) and cis-3-(fluoromethyl)-2-methylazetidine 2,2,2-trifluoroacetate (939 mg, 4.32 mmol) following the procedure outlined for Intermediate A, Step 5. $^1$H NMR (400 MHz, DMSO-$d_6$): δ 12.65 (br s, 1H), 7.69 (d, J=8.4 Hz, 2H), 7.44 (d, J=8.4 Hz, 2H), 6.13 (m, 1H), 4.82-4.57 (m, 3H), 4.05-3.97 (m, 1H), 3.88-3.79 (m, 1H), 3.03-2.98 (m, 1H), 2.63-2.60 (m, 1H), 1.82-1.79 (m, 4H), 1.73-1.70 (m, 1H), 1.51-1.20 (m, 8H). LCMS (ESI): m/z 501.2 $(M+H)^+$.

Step 2: Cis-5-(4-cyclohexylphenyl)-3-(3-(fluoromethyl)-2-methylazetidine-1-carbonyl)-2-(pyrazin-2-yl)pyrazolo[1,5-a]pyrimidin-7(4R)-one

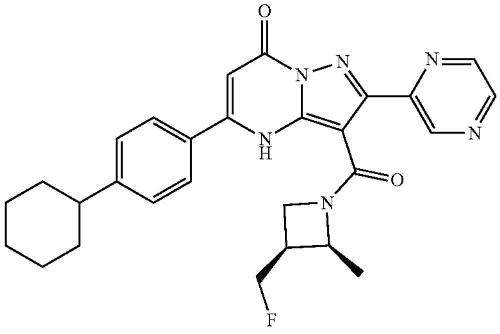 [SMILES: C[C@H]1[C@@H](CF)CN1C(=O)c1c(-c2cnccn2)nn2c(=O)cc(-c3ccc(C4CCCCC4)cc3)[nH]c12]

The title compound (100 mg, 66%) was prepared from cis-2-bromo-5-(4-cyclohexylphenyl)-3-(3-(fluoromethyl)-2-methylazetidine-1-carbonyl)pyrazolo[1,5-a]pyrimidin-7(4H)-one (150 mg, 0.30 mmol) and 2-(tributylstannyl)pyrazine (220 mg, 0.60 mmol) following the procedure outlined for Example 7, Step 2.

Step 3: 5-(4-cyclohexylphenyl)-3-((2S,3S)-3-(fluoromethyl)-2-methylazetidine-1-carbonyl)-2-(pyrazin-2-yl)pyrazolo[1,5-a]pyrimidin-7(4H)-one and 5-(4-cyclohexyl phenyl)-3-((2R,3R)-3-(fluoromethyl)-2-methylazetidine-1-carbonyl)-2-(pyrazin-2-yl) pyrazolo[1,5-a]pyrimidin-7(4H)-one

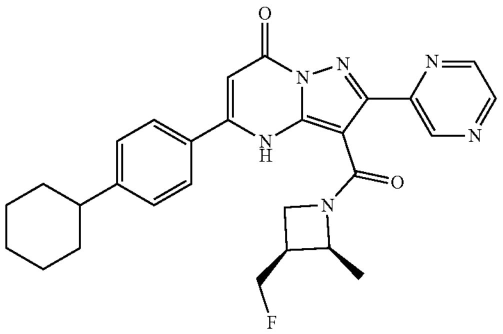

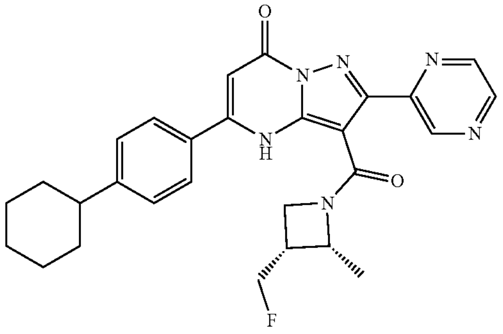

Cis-5-(4-Cyclohexylphenyl)-3-(3-(fluoromethyl)-2-methylazetidine-1-carbonyl)-2-(pyrazin-2-yl)pyrazolo[1,5-a]pyrimidin-7(4H)-one was separated by preparative SFC (condition: DAICEL CHIRALPAK AD-H (250 mm*30 mm, 5 um), 0.1% $NH_3H_2O$ EtOH) to afford Isomer A (5-(4-cyclohexylphenyl)-3-[(2S,3S)-3-(fluoromethyl)-2-methyl-azetidine-1-carbonyl]-2-pyrazin-2-yl-4H-pyrazolo[1,5-a] pyrimidin-7-one; 19 mg, 14%) and Isomer B (5-(4-cyclohexyl phenyl)-3-((2R,3R)-3-(fluoromethyl)-2-methylazetidine-1-carbonyl)-2-(pyrazin-2-yl)pyrazolo[1,5-a]pyrimidin-7(4H)-one; 19 mg, 14%).

Isomer A, second peak on SFC; $^1$H NMR (400 MHz, DMSO-$d_6$): δ 12.73 (br s, 1H), 9.20-9.19 (m 1H), 8.77-8.68 (m, 2H), 7.77-7.74 (m, 2H), 7.41 (br d, J=7.2 Hz, 2H), 6.12 (s, 1H), 4.75-4.48 (m, 3H), 4.20-3.62 (m, 2H), 2.98-2.94 (m, 1H), 2.62-2.60 (m, 1H), 1.83-1.80 (m, 4H), 1.74-1.70 (m, 1H), 1.47-1.24 (m, 8H); LCMS (ESI): m/z 501.2 $(M+H)^+$.

Isomer B, fourth peak on SFC; $^1$H NMR (400 MHz, DMSO-$d_6$): δ 12.73 (br s, 1H), 9.20-9.18 (m, 1H), 8.76-8.69 (m, 2H), 7.78-7.76 (m, 2H), 7.41 (d, J=7.6 Hz, 2H), 6.12 (s, 1H), 4.72-4.54 (m, 3H), 4.19-3.56 (m, 2H), 2.97-2.93 (m, 1H), 2.62-2.60 (m, 1H), 1.83-1.80 (m, 4H), 1.74-1.70 (m, 1H), 1.48-1.30 (m, 8H); LCMS (ESI): m/z 501.2 $(M+H)^+$.

Example 40

Preparation of 5-(4-Cyclohexylphenyl)-3-((2S,3S)-3-(fluoromethyl)-2-methylazetidine-1-carbonyl)-2-(pyrimidin-2-yl)pyrazolo[1,5-a]pyrimidin-7(4H)-one and 5-(4-cyclohexylphenyl)-3-((2R,3R)-3-(fluoromethyl)-2-methylazetidine-1-carbonyl)-2-(pyrimidin-2-yl)pyrazolo[1,5-a]pyrimidin-7(4H)-one

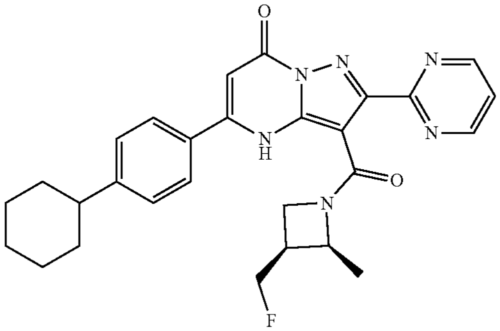

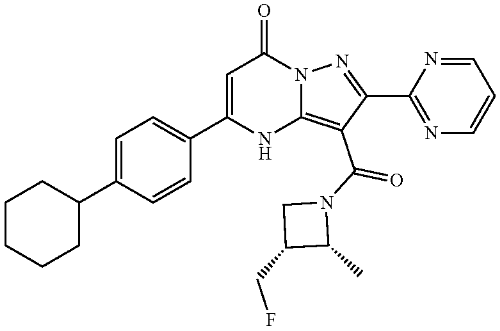

Step 1: Cis-5-(4-cyclohexylphenyl)-3-(3-(fluoromethyl)-2-methylazetidine-1-carbonyl)-2-(pyrimidin-2-yl)pyrazolo[1,5-a]pyrimidin-7(4H)-one

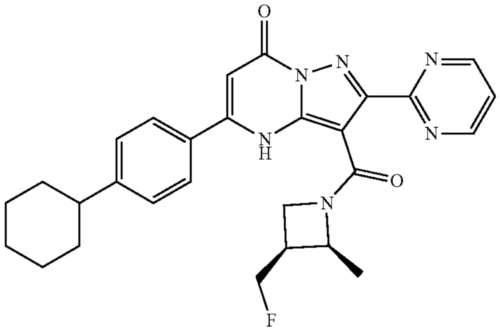 [SMILES: C[C@H]1[C@@H](CF)CN1C(=O)c1c(-c2ncccn2)nn2c(=O)cc(-c3ccc(C4CCCCC4)cc3)[nH]c12]

The title compound (30 mg, 20%) was prepared from cis-2-bromo-5-(4-cyclohexylphenyl)-3-(3-(fluoromethyl)-2-methylazetidine-1-carbonyl)pyrazolo[1,5-a]pyrimidin-7 (4H)-one (from Example 39, 150 mg, 0.30 mmol) and 2-(tributylstannyl) pyrimidine (220 mg, 0.60 mmol) following the procedure outlined for Example 7, Step 2. LCMS (ESI): m/z 501.2 $(M+H)^+$.

Step 2: 5-(4-Cyclohexylphenyl)-3-((2S,3S)-3-(fluoromethyl)-2-methylazetidine-1-carbonyl)-2-(pyrimidin-2-yl)pyrazolo[1,5-a]pyrimidin-7(4H)-one and 5-(4-cyclohexyl phenyl)-3-((2R,3R)-3-(fluoromethyl)-2-methylazetidine-1-carbonyl)-2-(pyrimidin-2-yl)pyrazolo[1,5-a]pyrimidin-7(4H)-one

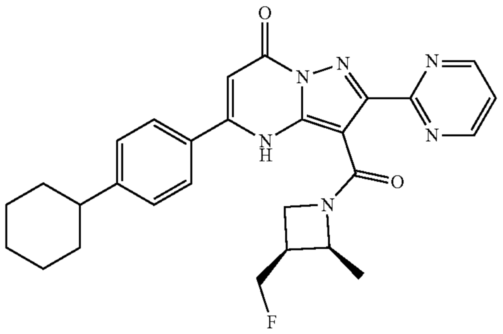

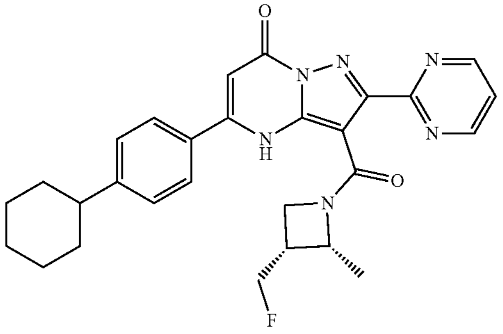

Cis-5-(4-cyclohexylphenyl)-3-(3-(fluoromethyl)-2-methylazetidine-1-carbonyl)-2-(pyrimidin-2-yl)pyrazolo[1,5-a]pyrimidin-7(4H)-one was separated by SFC (condition: DAICEL CHIRALCEL OJ-H (250 mm*30 mm, 5 um), 0.1% $NH_3H_2O$ MeOH) to afford Isomer A (5-(4-cyclohexylphenyl)-3-((2R,3R)-3-(fluoromethyl)-2-methylazetidine-1-carbonyl)-2-(pyrimidin-2-yl)pyrazolo[1,5-a]pyrimidin-7(4H)-one; fourth peak on SFC, 4.6 mg, 11%) as a white solid and a crude second peak which was further purified by SFC ((Column: Phenomenex-Amylose-1 (250 mm*30 mm, 5 um); Condition: 0.1% $NH_3H_2O$/MeOH)) to afford Isomer B (5-(4-cyclohexyl phenyl)-3-((2S,3S)-3-(fluoromethyl)-2-methylazetidine-1-carbonyl)-2-(pyrimidin-2-yl)pyrazolo[1,5-a]pyrimidin-7(4H)-one; 8.2 mg, 20%) as a white solid.

Isomer A, fourth peak on SFC; $^1H$ NMR (400 MHz, DMSO-$d_6$): δ 8.86-8.83 (m, 2H), 7.97-7.95 (m, 2H), 7.44-7.42 (m, 1H), 7.30 (d, J=7.6 Hz, 2H), 6.06 (s, 1H), 4.79-4.56 (m, 3H), 4.22-3.95 (m, 2H), 2.99-2.96 (m, 1H), 2.52-2.50 (m 1H), 1.84-1.80 (m, 4H), 1.74-1.70 (m, 1H), 1.50-1.35 (m, 8H). LCMS (ESI): m/z 501.2 $(M+H)^+$.

Isomer B, second peak on SFC; $^1H$ NMR (400 MHz, DMSO-$d_6$): δ 8.87-8.85 (in, 2H), 7.97-7.96 (m, 2H), 7.48-7.46 (m, 1H), 7.33 (d, J=7.2 Hz, 2H), 6.15 (s, 1H), 4.79-4.58 (m, 3H), 4.34-3.65 (m, 2H), 3.01-2.98 (m, 1H), 2.62-2.56 (m, 1H), 1.85-1.82 (m, 4H), 1.74-1.70 (m, 1H), 1.52-1.30 (m, 7H), 1.29-1.27 (m, 1H). LCMS (ESI); m/z 501.3 $(M+H)^+$.

Example 41

Preparation of 5-(4-Cyclohexylphenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one and 5-(4-cyclohexylphenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one

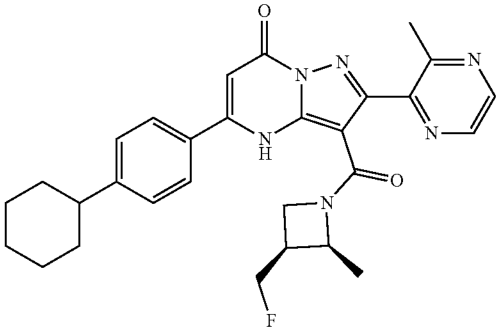 [SMILES: Cc1nccnc1-c1nn2c(=O)cc(-c3ccc(C4CCCCC4)cc3)[nH]c2c1C(=O)N1C[C@H](CF)[C@@H]1C]

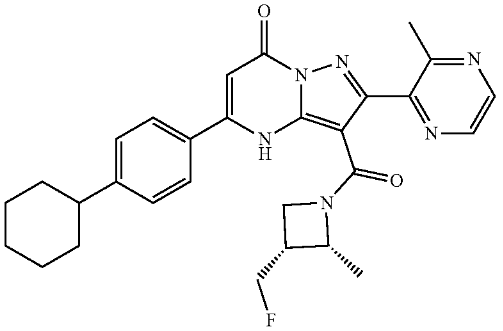

Step 1: Cis-5-(4-cyclohexylphenyl)-3-(3-(fluoromethyl)-2-methylazetidine-1-carbonyl)-2-(3-methylpyrazin-2-yl)pyrazolo[1,5-a]pyrimidin-7(4H)-one

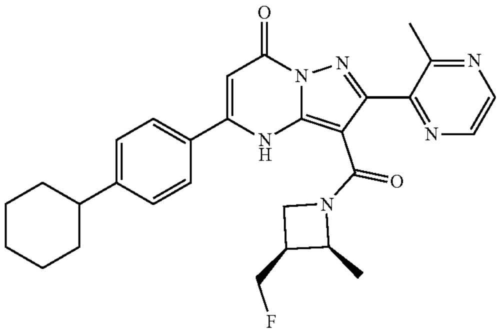

The title compound (140 mg, 54%) was prepared from cis-5-(4-cyclohexylphenyl)-3-(3-(fluoromethyl)-2-methylazetidine-1-carbonyl)-2-(pyrazin-2-yl)pyrazolo[1,5-a]pyrimidin-7(4H)-one (250 mg, 0.50 mmol) and 2-methyl-3-(tributylstannyl) pyrazine (286 mg, 0.75 mmol) following the procedure outlined for Example 7, Step 2. LCMS (ESI): m/z 515.2 $(M+H)^+$.

Step 2: 5-(4-Cyclohexylphenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one and 5-(4-cyclo hexylphenyl)-3-((2R,3R)-3-(fluoromethyl)-2-methylazetidine-1-carbonyl)-2-(3-methyl pyrazin-2-yl)pyrazolo[1,5-a]pyrimidin-7(4H)-one

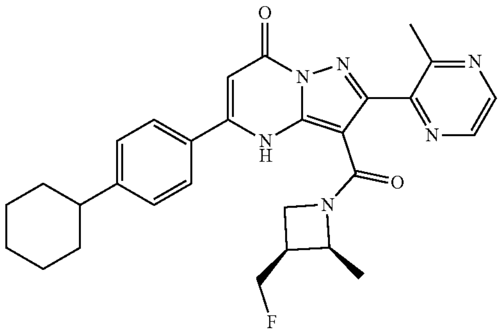

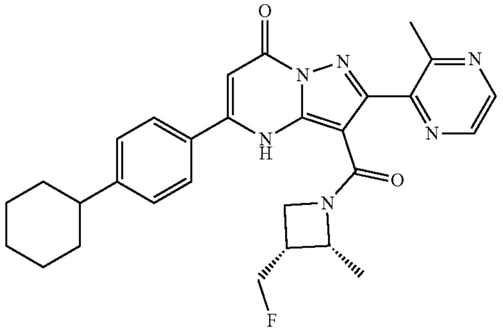

Cis-5-(4-cyclohexylphenyl)-3-(3-(fluoromethyl)-2-methylazetidine-1-carbonyl)-2-(3-methylpyrazin-2-yl)pyrazolo[1,5-a]pyrimidin-7(4H)-one was separated by SFC (column: DAICEL CHIRALPAK IG (250 mm*30 mm, 10 um); Condition: 0.1% $NH_3H_2O$ ETOH to afford Isomer A (5-(4-cyclohexylphenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one; fourth peak on SFC, 23.7 mg, 24%) as a white solid and a crude second peak which was separated by further SFC (DAICEL CHIRALPAK AD (250 mm*30 mm, 10 um), 0.1% $NH_3H_2O$ ETOH, 40%) to afford Isomer B (5-(4-cyclohexylphenyl)-3-((2S,3S)-3-(fluoromethyl)-2-methylazetidine-1-carbonyl)-2-(3-methyl pyrazin-2-yl)pyrazolo[1,5-a]pyrimidin-7(4H)-one; 19.0 mg, 19%) as a white solid.

Isomer A, fourth peak on SFC; 1H NMR (400 MHz, DMSO-$d_6$): δ 8.48-8.45 (m, 2H), 7.96-7.64 (m, 2H), 7.33-7.28 (m, 2H), 6.11 (s, 1H), 4.89-4.39 (m, 3H), 3.90-3.86 (m, 2H), 2.97-2.58 (m, 2H), 2.53 (s, 3H), 1.80-1.76 (m, 4H), 1.71-1.68 (m, 1H), 1.49-1.11 (m, 8H). LCMS (ESI): m/z 515.3 $(M+H)^+$.

Isomer B, second peak on SFC; $^1H$ NMR (400 MHz, DMSO-$d_6$): δ 12.40 (br s, 1H), 8.54-8.50 (m 2H), 7.79-7.77 (m, 2H), 7.38-7.36 (m, 2H), 6.10 (s, 1H), 4.75-4.27 (m, 3H), 3.86-3.84 (m, 2H), 2.87-2.86 (m, 2H), 2.58-2.56 (m, 3H), 1.80-1.76 (m, 4H), 1.70-1.68 (m, 1H), 1.48-1.21 (m, 8H); LCMS (ESI): m/z 515.3 $(M+H)^+$.

Example 42

Preparation of 5-(4-(Cyclopentylmethyl)phenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one and 5-(4-(cyclo pentylmethyl) phenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one

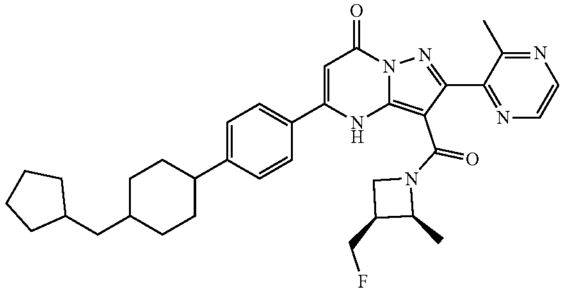 [SMILES: Cc1nccnc1-c1nn2c(=O)cc(-c3ccc(C4CCC(CC5CCCC5)CC4)cc3)[nH]c2c1C(=O)N1C[C@H](CF)[C@@H]1C]

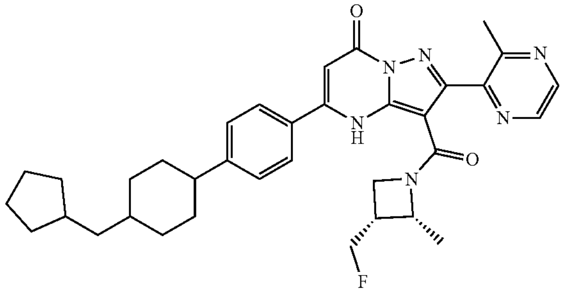

Step 1: Cis-5-(4-(cyclopentylmethyl)phenyl)-3-(3-(fluoromethyl)-2-methylazetidine-1-carbonyl)-2-(3-methylpyrazin-2-yl)pyrazolo[1,5-a]pyrimidin-7(4H)-one

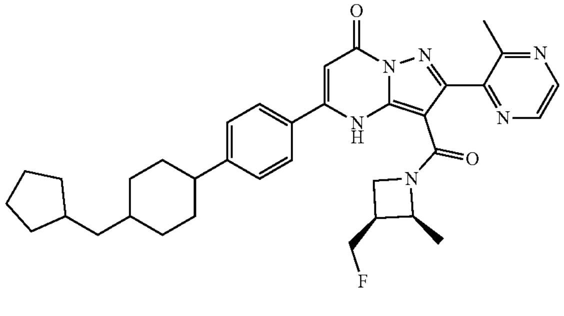

The title compound (250 mg, 70%) was prepared from cis-2-bromo-5-(4-(cyclopentylmethyl)phenyl)-3-(3-(fluoromethyl)-2-methylazetidine-1-carbonyl)pyrazolo[1,5-a]pyrimidin-7(4H)-one (350.0 mg, 0.70 mmol) and 2-methyl-3-(tributylstannyl) pyrazine (401.0 mg, 1.05 mmol) following the procedure outlined for Example 7, Step 2.

Step 2: 5-(4-(Cyclopentylmethyl)phenyl)-3-((2S,3S)-3-(fluoromethyl)-2-methyl azetidine-1-carbonyl)-2-(3-methylpyrazin-2-yl)pyrazolo[1,5-a]pyrimidin-7(4H)-one and 5-(4-(cyclopentylmethyl)phenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one

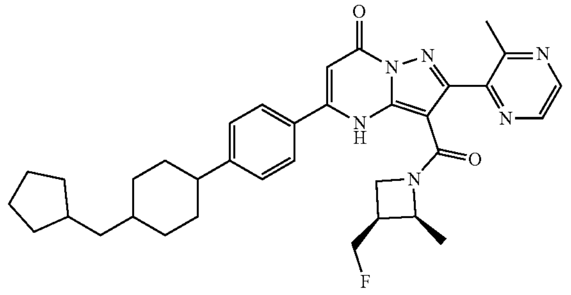

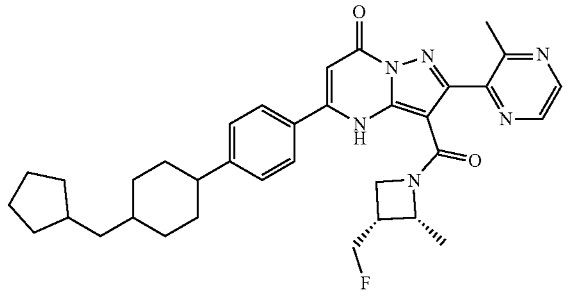

Cis-5-(4-(cyclopentylmethyl)phenyl)-3-(3-(fluoromethyl)-2-methylazetidine-1-carbonyl)-2-(3-methylpyrazin-2-yl)pyrazolo[1,5-a]pyrimidin-7(4H)-one was separated by SFC (condition: Phenomenex-Amylose-1 (250 mm*30 mm, 5 um), Supercritical DAICEL CHIRALPAK IG (250 mm*30 mm, 10 um) 0.1% $NH_3H_2O$ EtOH) to afford Isomer A (5-(4-(cyclopentylmethyl)phenyl)-3-((2R,3R)-3-(fluoromethyl)-2-methylazetidine-1-carbonyl)-2-(3-methylpyrazin-2-yl)pyrazolo[1,5-a]pyrimidin-7(4H)-one; fourth peak on SFC, 23.6 mg, 11%) and a crude second peak which was further purified by SFC (condition: Phenomenex-Amylose-1 (250 mm*30 mm, 5 um), Supercritical 0.1% $NH_3H_2O$, EtOH) to afford Isomer B (5-(4-(cyclopentylmethyl)phenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one; 20.6 mg, 9%) as white solids.

Isomer A, $^1H$ NMR (400 MHz, DMSO-$d_6$): δ 12.41 (s, 1H), 8.66-8.48 (m, 2H), 7.90-7.70 (m, 2H), 7.45-7.31 (m, 2H), 6.17 (s, 1H), 4.74-4.49 (m, 4H), 3.91-3.83 (m, 1H), 2.98-2.86 (m, 1H), 2.73-2.62 (m, 5H), 2.17-2.12 (m, 1H), 1.73-1.59 (m, 4H), 1.55-1.46 (m, 2H), 1.33-1.13 (m, 5H); LCMS (ESI): m/z 515.2 $(M+H)^+$.

Isomer B, $^1H$ NMR (400 MHz, DMSO-$d_6$): δ 12.48 (s, 1H), 8.65-8.54 (m, 2H), 7.80-7.70 (m, 2H), 7.39 (d, J=7.6 Hz, 2H), 6.17 (s, 1H), 4.70-4.35 (m, 4H), 3.89-3.83 (m, 1H), 2.95-2.86 (m, 1H), 2.76-2.60 (m, 5H), 2.14-2.09 (m, 1H), 1.71-1.57 (m, 4H), 1.54-1.44 (m, 2H), 1.33-1.17 (m, 5H); LCMS (ESI): m/z 515.1 $(M+H)^+$.

Example 43

Preparation of 5-(4-(Cyclopentylmethyl)phenyl)-3-((2S,3S)-3-(fluoromethyl)-2-methylazetidine-1-carbonyl)-2-(pyrimidin-2-yl)pyrazolo[1,5-a]pyrimidin-7(4H)-one and 5-(4-(Cyclopentylmethyl)phenyl)-3-((2R,3R)-3-(fluoromethyl)-2-methylazetidine-1-carbonyl)-2-(pyrimidin-2-yl)pyrazolo[1,5-a]pyrimidin-7(4H)-one

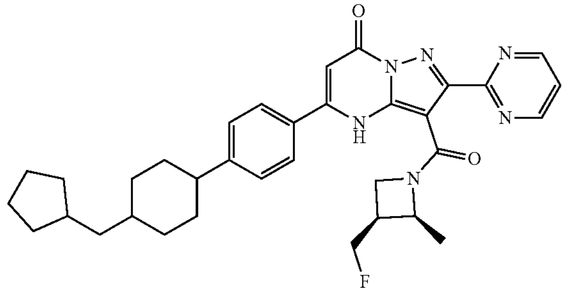 [SMILES: C[C@H]1[C@@H](CF)CN1C(=O)c1c(-c2ncccn2)nn2c(=O)cc(-c3ccc(C4CCC(CC5CCCC5)CC4)cc3)[nH]c12]

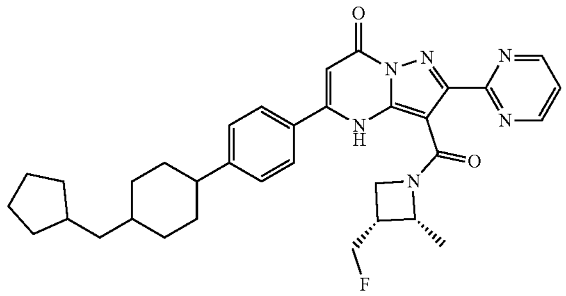

Step 1: Cis-5-(4-(cyclopentylmethyl)phenyl)-3-(3-(fluoromethyl)-2-methylazetidine-1-carbonyl)-2-(pyrimidin-2-yl)pyrazolo[1,5-a]pyrimidin-7(4H)-one

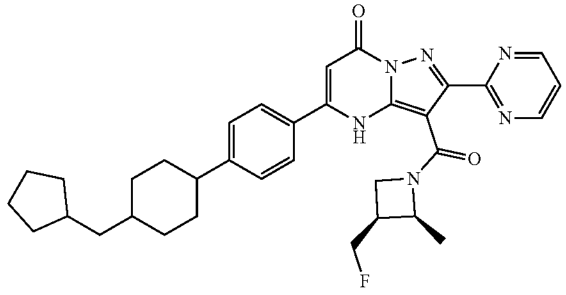

The title compound (160 mg, 64%) was prepared from cis-2-bromo-5-(4-(cyclopentylmethyl)phenyl)-3-(3-(fluoromethyl)-2-methylazetidine-1-carbonyl)pyrazolo [1,5-a]pyrimidin-7(4H)-one (250 mg, 0.50 mmol) and 2-(tributylstannyl)pyrimidine (369 mg, 1.0 mmol) following the procedure outlined for Example 7, Step 2.

Step 2: 5-(4-(Cyclopentylmethyl)phenyl)-3-((2S,3S)-3-(fluoromethyl)-2-methyl azetidine-1-carbonyl)-2-(pyrimidin-2-yl)pyrazolo[1,5-a]pyrimidin-7(4H)-one and 5-(4-(cyclopentylmethyl)phenyl)-3-((2R,3R)-3-(fluoromethyl)-2-methylazetidine-1-carbonyl)-2-(pyrimidin-2-yl)pyrazolo[1,5-a]pyrimidin-7(4H)-one

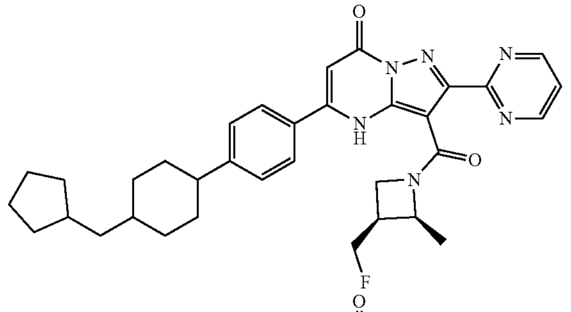

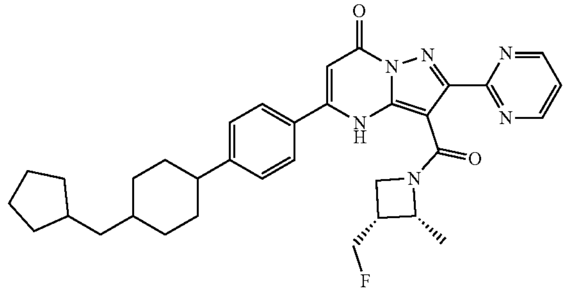

Cis-5-(4-(cyclopentylmethyl)phenyl)-3-(3-(fluoromethyl)-2-methylazetidine-1-carbonyl)-2-(pyrimidin-2-yl)pyrazolo[1,5-a]pyrimidin-7(4H)-one was purified to remove minor trans azetidine isomers (30 mg) by SFC (condition: DAICEL CHIRALCEL OJ-H (250 mm*30 mm, 5 um), Supercritical 0.1% $NH_3H_2O$, MeOH). The resulting cis racemate compound (90 mg) was further resolved by preparative SFC (Phenomenex-Amylose-1 (250 mm*30 mm, 5 um), Supercritical 0.1% $NH_3H_2O$/MeOH) to afford Isomer A (5-(4-(cyclopentylmethyl)phenyl)-3-((2S,3S)-3-(fluoromethyl)-2-methyl azetidine-1-carbonyl)-2-(pyrimidin-2-yl)pyrazolo[1,5-a]pyrimidin-7(4H)-one; first peak on SFC, 12.8 mg, 14%) and Isomer B (5-(4-(cyclopentylmethyl)phenyl)-3-((2R,3R)-3-(fluoromethyl)-2-methyl-azetidine-1-carbonyl)-2-(pyrimidin-2-yl)pyrazolo[1,5-a]pyrimidin-7(4H)-one; second peak on SFC, 8.6 mg, 10%) as both white solid.

Isomer A, $^1H$ NMR (400 MHz, DMSO-$d_6$): δ 12.69 (s, 1H), 8.95 (d, J=4.8 Hz, 2H), 7.80-7.64 (m, 2H), 7.58-7.50 (m, 1H), 7.38 (d, J=7.6 Hz, 2H), 6.10 (s, 1H), 4.72-4.24 (m, 3H), 4.10-3.52 (m, 2H), 2.98-2.85 (m, 1H), 2.67 (d, J=7.6 Hz, 2H), 2.18-2.06 (m, 1H), 1.71-1.57 (m, 4H), 1.56-1.43 (m, 3H), 1.27-1.13 (m, 3H), 1.09-0.91 (m, 1H); LCMS (ESI): m/z 501.3 $(M+H)^+$.

Isomer B, $^1H$ NMR (400 MHz, DMSO-$d_6$): δ 12.70 (s, 1H), 8.97-8.82 (m, 2H), 7.98-7.81 (m, 2H), 7.52-7.43 (m, 1H), 7.36-7.24 (m, 2H), 6.08 (s, 1H), 4.89-4.57 (m, 3H), 4.10-3.83 (m, 2H), 2.99-2.86 (m, 1H), 2.64 (d, J=7.2 Hz, 2H), 2.12-2.06 (m, 1H), 1.64-1.57 (m, 4H), 1.52-1.45 (m, 3H), 1.23-1.16 (m, 3H), 1.06-0.94 (m, 1H); LCMS (ESI): m/z 501.2 $(M+H)^+$.

Example 44

Preparation of 5-(4-(Cyclopentylmethyl)phenyl)-3-((2S,3S)-3-(fluoromethyl)-2-methylazetidine-1-carbonyl)-2-(pyrazin-2-yl)pyrazolo[1,5-a]pyrimidin-7(4H)-one and 5-(4-(cyclopentyl methyl)phenyl)-3-((2R,3R)-3-(fluoromethyl)-2-methylazetidine-1-carbonyl)-2-(pyrazin-2-yl)pyrazolo[1,5-a]pyrimidin-7(4H)-one

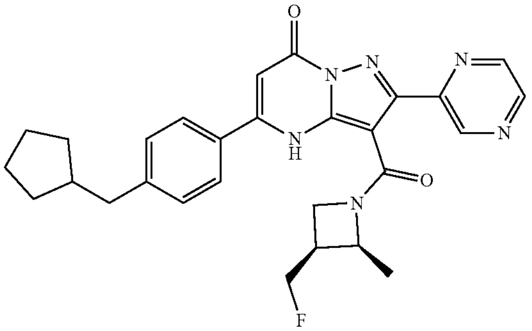

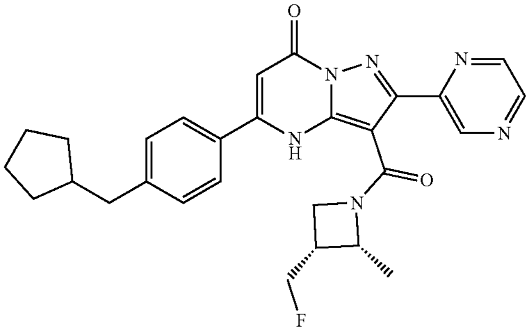

Step 1: Cis-5-(4-(cyclopentylmethyl)phenyl)-3-(3-(fluoromethyl)-2-methylazetidine-1-carbonyl)-2-(pyrazin-2-yl)pyrazolo[1,5-a]pyrimidin-7(4R)-one

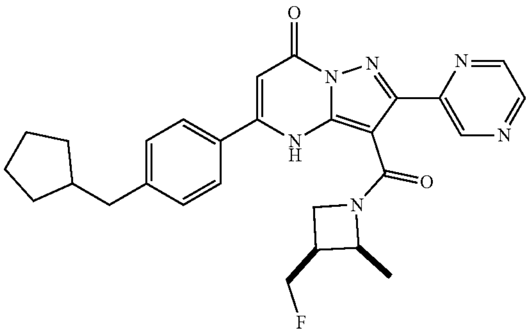 [SMILES: C[C@H]1[C@@H](CF)CN1C(=O)c1c(-c2cnccn2)nn2c(=O)cc(-c3ccc(CC4CCCC4)cc3)[nH]c12]

The title compound (100 mg, 50%) as a white solid was prepared from cis-2-bromo-5-(4-(cyclopentylmethyl)phenyl)-3-(3-(fluoromethyl)-2-methylazetidine-1-carbonyl) pyrazolo [1,5-a]pyrimidin-7(4H)-one (200 mg, 0.40 mmol) and 2-(tributylstannyl) pyrazine (295 mg, 0.80 mmol) following the procedure outlined for Example 7, Step 2.

Step 2: 5-(4-(Cyclopentylmethyl)phenyl)-3-((2S, 3S)-3-(fluoromethyl)-2-methyl azetidine-1-carbonyl)-2-(pyrazin-2-yl)pyrazolo[1,5-a]pyrimidin-7(4H)-one and 5-(4-(cyclopentylmethyl)phenyl)-3-((2R,3R)-3-(fluoromethyl)-2-methylazetidine-1-carbonyl)-2-(pyrazin-2-yl)pyrazolo[1,5-a]pyrimidin-7(4H)-one

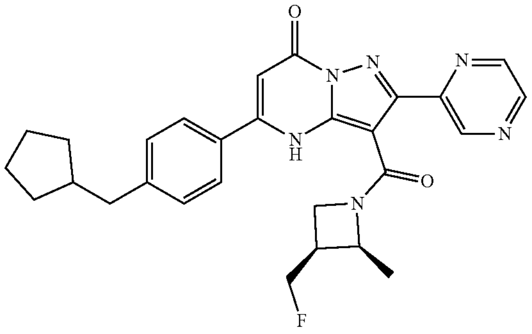

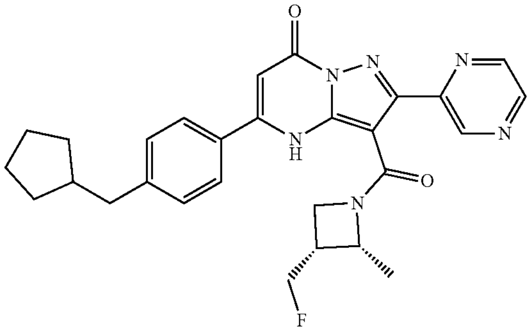

Cis-5-(4-(cyclopentylmethyl)phenyl)-3-(3-(fluoromethyl)-2-methylazetidine-1-carbonyl)-2-(pyrazin-2-yl)pyrazolo[1,5-a]pyrimidin-7(4H)-one was separated by preparative SFC (DAICEL CHIRALCEL OJ-H (250 mm*30 mm, 5 um), Supercritical 0.1% $NH_3H_2O$ MeOH) to afford Isomer A (fourth peak on SFC, 24.7 mg, 25%) as a white solid and crude of the second peak which was further purified by SFC (Phenomenex-Amylose-1 (250 mm*30 mm, 5 um), 0.1% $NH_3H_2O$ EtOH) to afford Isomer B (second peak on SFC, 25.2 mg, 25%) as a white solid.

Isomer A, fourth peak on SFC (OJ). $^1$H NMR (400 MHz, DMSO-$d_6$): δ 12.78 (s, 1H), 9.22 (s, 1H), 8.86-8.64 (m, 2H), 7.73 (d, J=7.2 Hz, 2H), 7.40 (d, J=7.6 Hz, 2H), 6.14 (s, 1H), 4.72-4.28 (m, 3H), 4.10-3.64 (m, 2H), 3.02-2.87 (m, 1H), 2.67 (d, J=7.6 Hz, 2H), 2.21-2.06 (m, 1H), 1.71-1.56 (m, 4H), 1.56-1.41 (m, 3H), 1.26-1.15 (m, 3H), 1.05-1.85 (m, 1H). LCMS (ESI): m/z 501.3 $(M+H)^+$.

Isomer B, second peak on SFC (OJ). $^1$H NMR (400 MHz, DMSO-$d_6$): δ 12.74 (s, 1H), 9.22 (s, 1H), 8.87-8.63 (m, 2H), 7.73 (d, J=7.6 Hz, 2H), 7.40 (d, J=7.6 Hz, 2H), 6.13 (s, 1H), 4.72-4.52 (m, 3H), 4.10-3.50 (m, 2H), 2.98-2.89 (m, 1H), 2.67 (d, J=7.6 Hz, 2H), 2.18-2.07 (m, 1H), 1.70-1.58 (m, 4H), 1.54-1.43 (m, 3H), 1.24-1.17 (m, 2H), 1.08-0.84 (m, 1H). LCMS (ESI): m/z 501.2 $(M+H)^+$.

Example 45

Preparation of 3-(3-(Fluoromethyl)azetidine-1-carbonyl)-5-((4-isopropylbenzyl)oxy)-2-(pyrazin-2-yl)pyrazolo[1,5-a]pyrimidin-7(4H)-one

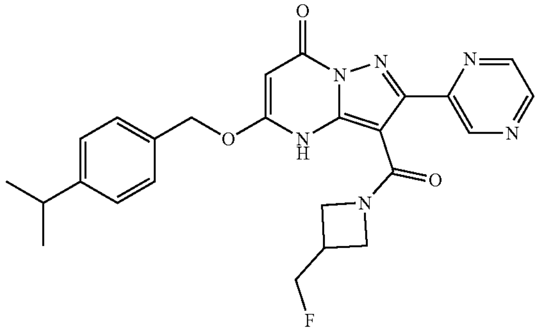 [SMILES: CC(C)c1ccc(COc2cc(=O)n3nc(-c4cnccn4)c(C(=O)N4CC(CF)C4)c3[nH]2)cc1]

The title compound (3 mg, 2%) was prepared from 2-bromo-3-(3-(fluoromethyl)azetidine-1-carbonyl)-5-((4-isopropylbenzyl)oxy)pyrazolo[1,5-a]pyrimidin-7(4H)-one (100 mg, 0.21 mmol) and 2-(tributylstannyl)pyrazine (154 mg, 0.42 mmol) following the procedure outlined for Example 7, Step 2. $^1$H NMR (400 MHz, $CD_3OD$): δ 9.19 (s, 1H), 8.64-8.62 (m, 1H), 8.55-8.53 (m, 1H), 7.36 (d, J=8.0 Hz, 2H), 7.23 (d, J=8.0 Hz, 2H), 5.45-5.30 (m, 3H), 4.62-4.49 (m, 2H), 4.30-4.25 (m, 2H), 4.21-4.12 (m, 1H), 3.99-3.97 (m, 1H), 3.03-2.83 (m, 2H), 1.24 (d, J=7.2 Hz, 6H); LCMS (ESI): m/z 477.2 $(M+H)^+$.

Example 46

Preparation of 5-((4-(Tert-butyl)benzyl)oxy)-3-(3-(fluoromethyl)azetidine-1-carbonyl)-2-(pyrazin-2-yl)pyrazolo[1,5-a]pyrimidin-7(4H)-one

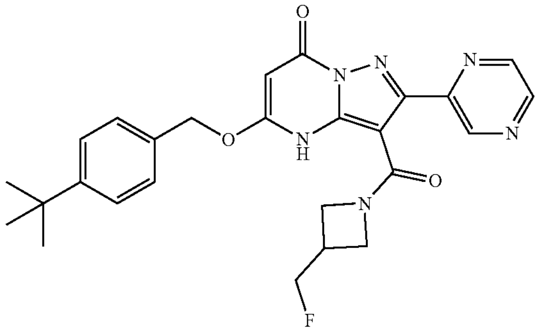 [SMILES: CC(C)(C)c1ccc(COc2cc(=O)n3nc(-c4cnccn4)c(C(=O)N4CC(CF)C4)c3[nH]2)cc1]

Step 1: 2-Bromo-5-((4-(tert-butyl)benzyl)oxy)-3-(3-(fluoromethyl)azetidine-1-carbonyl) pyrazolo[1,5-a] pyrimidin-7(4H)-one

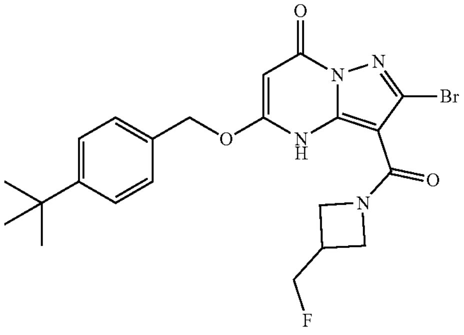 [SMILES: CC(C)(C)c1ccc(COc2cc(=O)n3nc(Br)c(C(=O)N4CC(CF)C4)c3[nH]2)cc1]

The title compound (100 mg, 21%) was prepared from ethyl 7-(benzyloxy)-2-bromo-5-chloropyrazolo[1,5-a]pyrimidine-3-carboxylate (350 mg, 0.96 mmol) and (4-(tert-butyl)phenyl)methanol (240 mg, 1.44 mmol) following the procedure outlined for Intermediate J, Step 2-3. LCMS (ESI): m/z 490.9 $(M+H)^+$.

Step 2: 5-((4-(Tert-butyl)benzyl)oxy)-3-(3-(fluoromethyl)azetidine-1-carbonyl)-2-(pyrazin-2-yl)pyrazolo [1,5-a]pyrimidin-7(4H)-one

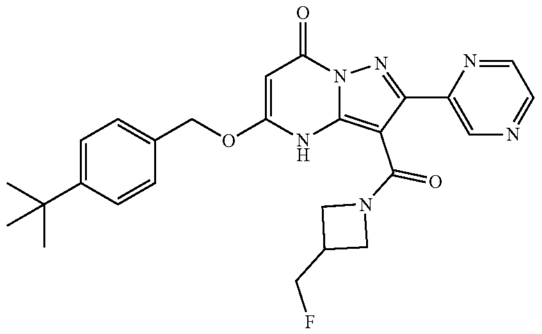 [SMILES: CC(C)(C)c1ccc(COc2cc(=O)n3nc(-c4cnccn4)c(C(=O)N4CC(CF)C4)c3[nH]2)cc1]

The title compound (20 mg, 16%) was prepared from 2-bromo-5-((4-(tert-butyl)benzyl)oxy)-3-(3-(fluoromethyl) azetidine-1-carbonyl)pyrazolo[1,5-a]pyrimidin-7(4H)-one (120 mg, 0.24 mmol) and 2-(tributylstannyl)pyrazine (180 mg, 0.49 mmol) following the procedure outlined for Example 7, Step 2. $^1$H NMR (400 MHz, DMSO-$d_6$): δ 9.12 (s, 1H), 8.72-8.70 (m, 1H), 8.67 (d, J=2.4 Hz, 1H), 7.45-7.43 (m, 4H), 5.47 (br s, 1H), 5.29 (s, 2H), 4.52 (dd, J=47.2, 5.6 Hz, 2H), 4.11-3.57 (m, 4H), 2.91-2.89 (m, 1H), 1.28 (s, 9H); LCMS (ESI): m/z 491.1 $(M+H)^+$.

Example 47

Preparation of 5-((4-(Tert-butyl)benzyl)oxy)-3-(3-(fluoromethyl)azetidine-1-carbonyl)-2-(pyrimidin-2-yl)pyrazolo[1,5-a]pyrimidin-7(4H)-one

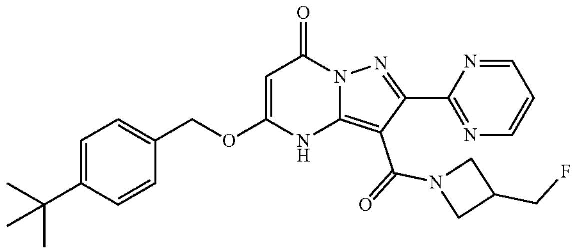 [SMILES: CC(C)(C)c1ccc(COc2cc(=O)n3nc(-c4ncccn4)c(C(=O)N4CC(CF)C4)c3[nH]2)cc1]

To a mixture of 5-chloro-3-(3-(fluoromethyl)azetidine-1-carbonyl)-2-(pyrimidin-2-yl) pyrazolo[1,5-a]pyrimidin-7 (4H)-one (70 mg, 0.19 mmol) in 1,4-dioxane (7 mL) was added NaH (15 mg, 0.38 mmol, 60% in mineral oil). The mixture was stirred at room temperature for 15 min then (4-(tert-butyl)phenyl)methanol (48 mg, 0.29 mmol) and t-BuONa (37 mg, 0.39 mmol). The mixture was stirred at 100° C. for 20 hours and then poured into water (50 mL). The mixture was adjusted to pH 6 with the addition of 1 M aqueous HCl. The aqueous phase was freeze-dried and the mixture was purified by reverse phase HPLC (isocratic, water modified with 0.04% $NH_3H_2O$ and 10 mM $NH_4HCO_3$— MeCN, Xtimate C18 10μ 250 mm*50 mm column) to afford the title compound (5.6 mg, 6%) as a white solid. $^1$H NMR (400 MHz, $CD_3OD$): δ 8.85-8.83 (m, 2H), 7.45-7.39 (m, 5H), 5.38-5.33 (m, 3H), 4.54 (dd, J=47.2, 5.6 Hz, 2H), 4.30-4.09 (m, 2H), 4.01-3.95 (m, 2H), 3.03-2.88 (m, 1H), 1.33 (s, 9H). LCMS (ESI): m/z 491.3 $(M+H)^+$.

Example 48

Preparation of 5-(4-(4,4-Difluorocyclohexyl)phenyl)-3-(3-(fluoromethyl)azetidine-1-carbonyl)-2-(3-methylpyrazin-2-yl)pyrazolo[1,5-a]pyrimidin-7(4R)-one

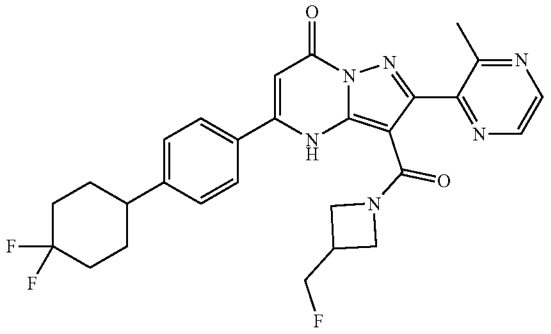 [SMILES: Cc1nccnc1-c1nn2c(=O)cc(-c3ccc(C4CCC(F)(F)CC4)cc3)[nH]c2c1C(=O)N1CC(CF)C1]

Step 1: 4'-Chloro-4,4-difluoro-2,3,4,5-tetrahydro-1,1'-biphenyl

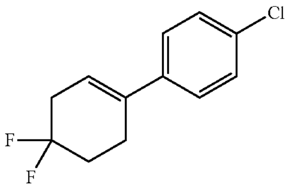 [SMILES: FC1(F)CC=C(c2ccc(Cl)cc2)CC1]

A mixture of 2-(4,4-difluorocyclohexen-1-yl)-4,4,5,5-tetramethyl-1,3,2-dioxaborolane (702 mg, 2.87 mmol), 1-bromo-4-chlorobenzene (500 mg, 2.61 mmol), $Na_2CO_3$ (831 mg, 7.83 mmol) and Pd(dppf)$Cl_2$ (191 mg, 0.26 mmol) in 1,4-dioxane (6 mL) was stirred at 100° C. for 16 hours under a nitrogen atmosphere. Then the reaction mixture was diluted with water (30 mL) and the resulting solution was extracted with EtOAc (30 mL×2). The organic layer was dried over $Na_2SO_4$, filtered and concentrated in vacuo. The residue was purified by flash chromatography on silica gel eluting with petroleum ether to afford the title compound (550 mg, 92%) as a white solid. $^1$H NMR (400 MHz, $CDCl_3$): δ 7.31-7.29 (m, 4H), 5.92-5.90 (m, 1H), 2.78-2.65 (m, 4H), 2.25-2.14 (m, 2H).

Step 2: 2-(4',4'-Difluoro-2',3',4',5'-tetrahydro-[1,1'-biphenyl]-4-yl)-4,4,5,5-tetramethyl-1,3,2-dioxaborolane

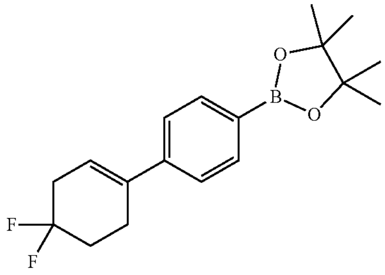 [SMILES: CC1(C)OB(c2ccc(C3=CCC(F)(F)CC3)cc2)OC1(C)C]

A mixture of 4'-chloro-4,4-difluoro-2,3,4,5-tetrahydro-1,1'-biphenyl (550 mg, 2.41 mmol), Xphos Pd G3 (203 mg, 0.24 mmol) and Xphos (115 mg, 0.24 mmol) and $B_2Pin_2$ (1.07 g, 4.2 mmol), KOAc (709 mg, 7.23 mmol) in 1,4-dioxane was stirred at 100° C. for 16 hours. The resulting solution quenched with water (30 mL), extracted with EtOAc (30 mL×2), dried over $Na_2SO_4$, filtered and concentrated in vacuo. The residue was purified by flash chromatography on silica gel eluting with petroleum ether/EtOAc (100:3) to afford the title compound (500 mg, 65%) as a yellow solid. $^1$H NMR (400 MHz, $CDCl_3$): δ 7.78 (d, J=8.0 Hz, 2H), 7.38 (d, J=8.4 Hz, 2H), 5.97 (s, 1H), 2.76-2.71 (m, 4H), 2.24-2.12 (m, 2H), 1.35 (s, 12H).

Step 3: 2-(4-(4,4-Difluorocyclohexyl)phenyl)-4,4,5,5-tetramethyl-1,3,2-dioxaborolane

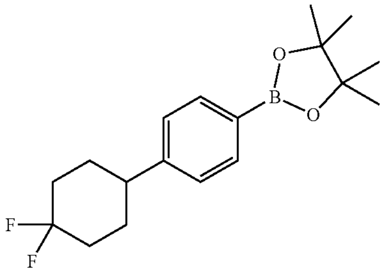 [SMILES: CC1(C)OB(c2ccc(C3CCC(F)(F)CC3)cc2)OC1(C)C]

To a mixture of 2-(4',4'-difluoro-2',3',4',5'-tetrahydro-[1,1'-biphenyl]-4-yl)-4,4,5,5-tetramethyl-1,3,2-dioxaborolane (500 mg, 1.56 mmol) in methanol (10 mL), was added 10% Pd on carbon (333 mg, 0.31 mmol) and the mixture was stirred at 20° C. under a hydrogen atmosphere (1 atm) for 16 hours. The reaction mixture was filtered and concentrated to afford the title compound (440 mg, 87%) as a white solid. $^1$H NMR (400 MHz, $CDCl_3$): δ 7.77 (d, J=8.0 Hz, 2H), 7.24 (d, J=8.0 Hz, 2H), 2.65-2.53 (m, 1H), 2.28-2.16 (m, 2H), 1.97-1.79 (m, 6H), 1.34 (s, 12H).

Step 4: 5-(4-(4,4-Difluorocyclohexyl)phenyl)-3-(3-(fluoromethyl)azetidine-1-carbonyl)-2-(3-methylpyrazin-2-yl)pyrazolo[1,5-a]pyrimidin-7(4H)-one

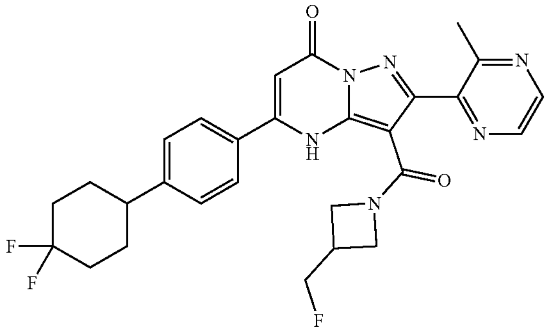 [SMILES: Cc1nccnc1-c1nn2c(=O)cc(-c3ccc(C4CCC(F)(F)CC4)cc3)[nH]c2c1C(=O)N1CC(CF)C1]

To a mixture of 5-chloro-3-(3-(fluoromethyl)azetidine-1-carbonyl)-2-(3-methylpyrazin-2-yl)pyrazolo[1,5-a]pyrimidin-7(4H)-one (100 mg, 0.28 mmol) in DMSO (5 mL) and water (0.5 mL) was added Xphos Pd $G_3$ (24 mg, 0.03 mmol), Xphos (14 mg, 0.03 mmol), 2-[4-(1-cyclopentylcyclopropyl)phenyl]-4,4,5,5-tetramethyl-1,3,2-dioxaborolane (130 mg, 0.41 mmol), $Na_2CO_3$ (89 mg, 0.83 mmol) which was stirred at 100° C. for 16 hours. The reaction mixture was cooled to room temperature and then adjusted to pH 4 with 1 M aqueous HCl. The solution was extracted with EtOAc (20 mL×3) and washed with water (30 mL×2). The organic layer was dried over $Na_2SO_4$, filtered and concentrated. The residue was purified by preparative TLC (5% MeOH in DCM) to afford the title compound (8.6 mg, 6%) as a white solid. $^1$H NMR (400 MHz, DMSO-$d_6$): δ 12.35 (s, 1H), 8.58 (d, J=7.2 Hz, 2H), 7.74 (d, J=8.0 Hz, 2H), 7.45 (d, J=8.0 Hz, 2H), 6.16 (s, 1H), 4.46 (dd, J=46.8, 5.6 Hz, 2H), 4.00-3.59 (m, 4H), 2.82-2.78 (m, 2H), 2.63 (s, 3H), 2.11-1.91 (m, 6H), 1.74-1.68 (m, 2H); LCMS (ESI): m/z 537.1 $(M+H)^+$.

Example 49

Preparation of 5-(4-(Cyclopentyldifluoromethyl)phenyl)-3-(3-(fluoromethyl)azetidine-1-carbonyl)-2-(3-methylpyrazin-2-yl)pyrazolo[1,5-a]pyrimidin-7(4H)-one The general reaction scheme was as follows:

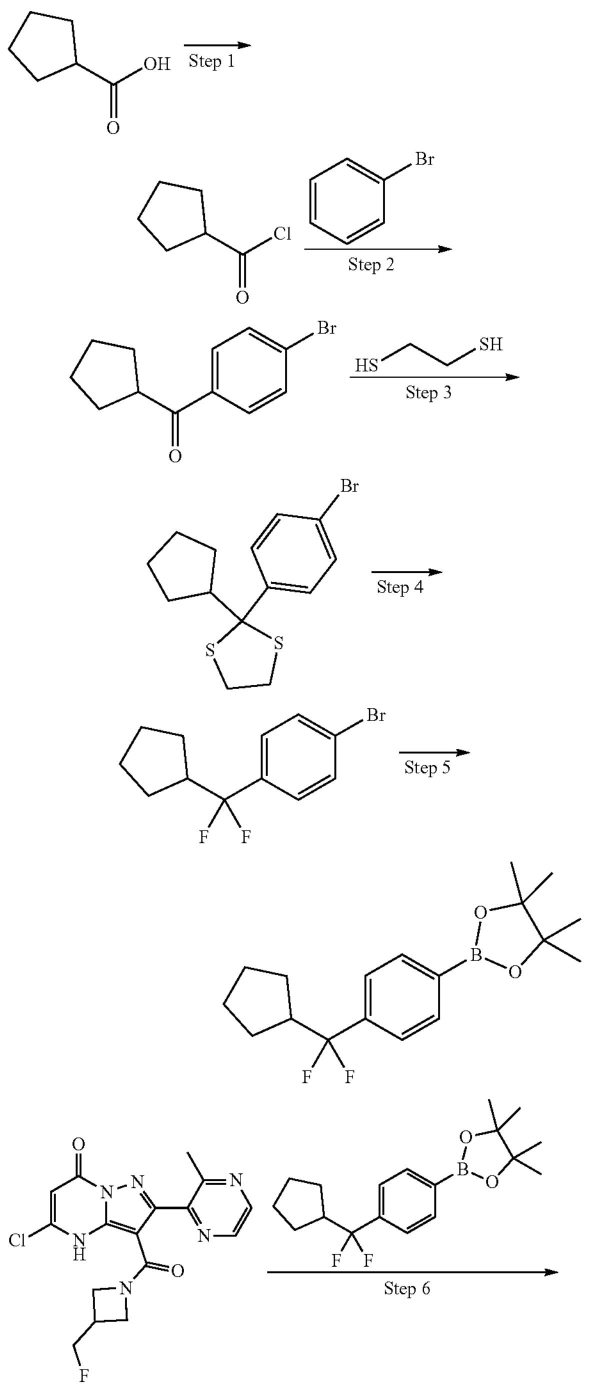

-continued

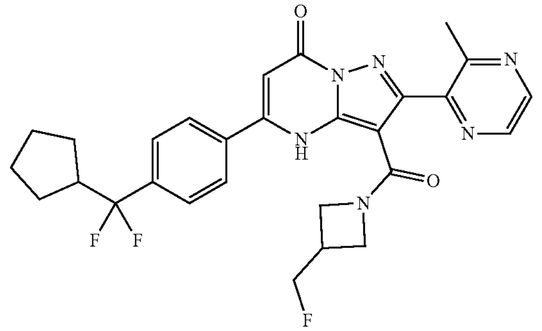 [SMILES: Cc1nccnc1-c1nn2c(=O)cc(-c3ccc(C(F)(F)C4CCCC4)cc3)[nH]c2c1C(=O)N1CC(CF)C1]

Step 1: Cyclopentanecarbonyl Chloride

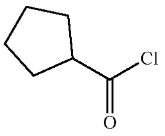

To a stirred solution of cyclopentanecarboxylic acid (10.0 g, 87.6 mmol) in DCM (100 mL) was added $SOCl_2$ (14.8 mL, 175.22 mmol). The mixture was stirred at 0° C. for 15 hours under nitrogen atmosphere. The reaction was concentrated to afford the title compound (10 g, 86%) as a yellow oil which was used without further purification.

Step 2: (4-Bromophenyl)(cyclopentyl)methanone

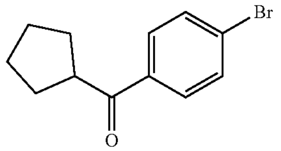 [SMILES: O=C(c1ccc(Br)cc1)C1CCCC1]

To a solution of $AlCl_3$ (10.0 g, 75.4 mmol) and bromobenzene (17.76 g, 113.13 mmol) was added cyclopentanecarbonyl chloride (10.0 g, 75.42 mmol). The mixture was stirred at room temperature for 15 hours under a nitrogen atmosphere. The reaction mixture was concentrated and purified by silica gel column chromatography (0-5% EtOAc in petroleum ether) to afford the title compound (9.5 g, 73%) as a colorless oil. $^1H$ NMR (400 MHz, $CDCl_3$): δ 7.83 (d, J=8.8 Hz, 2H), 7.58 (d, J=8.8 Hz, 2H), 3.68-3.60 (m, 1H), 1.91-1.88 (m, 4H), 1.70-1.64 (m, 4H).

Step 3: 2-(4-Bromophenyl)-2-cyclopentyl-1,3-dithiolane

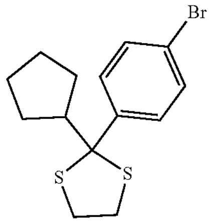 [SMILES: Brc1ccc(C2(C3CCCC3)SCCS2)cc1]

To a stirred solution of (4-bromophenyl)(cyclopentyl) methanone (1.0 g, 3.95 mmol) in DCM (15 mL) was added $BF_3 \cdot Et_2O$ (1.4 mL, 11.1 mmol) and ethane-1,2-dithiol (655 mg, 6.95 mmol) and stirred 20° C. for 16 hours. The mixture was diluted with DCM (50 mL). The organic phase was then washed with 10% aqueous NaOH (40 mL) followed by water and brine. The organic phase was dried over $Na_2SO_4$, filtered and concentrated. The residue was purified by silica gel column chromatography (eluted with 0-5% EtOAc in petroleum ether) to afford the title compound (1.1 g, 85%) as a colorless oil. $^1H$ NMR (400 MHz, $CDCl_3$): δ 7.69 (d, J=8.4 Hz, 2H), 7.42 (d, J=8.4 Hz, 2H), 3.35-3.26 (m, 2H), 3.16-3.04 (m, 2H), 2.75-2.65 (m, 1H), 1.73-1.56 (m, 4H), 1.53-1.38 (m, 4H).

Step 4: 1-Bromo-4-(cyclopentyldifluoromethyl)benzene

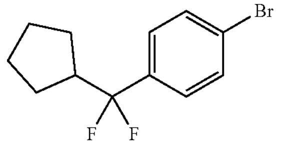 [SMILES: FC(F)(c1ccc(Br)cc1)C1CCCC1]

To a mixture of 2-(4-bromophenyl)-2-cyclopentyl-1,3-dithiolane (100 mg, 0.30 mmol) and NIS (137 mg, 0.61 mmol) in DCM (5 mL) at −70° C. was added 70% pyridine hydrofluoride in pyridine (0.11 mL, 1.21 mmol). After stirring at −70° C. for 15 minutes, the reaction mixture was filtered through $Al_2O_3$ and washed with hexanes. The filtrate was concentrated and purified by silica gel column chromatography (petroleum ether) to afford the title compound (30 mg, 36%) as a colorless oil. $^1H$ NMR (400 MHz, $CDCl_3$): δ 7.47 (d, J=8.4 Hz, 2H), 7.26 (d, J=8.4 Hz, 2H), 2.53-2.50 (m, 1H), 1.63-1.47 (m, 8H).

Step 5: 2-(4-(Cyclopentyldifluoromethyl)phenyl)-4,4,5,5-tetramethyl-1,3,2-dioxaborolane

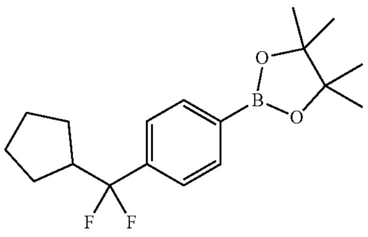 [SMILES: CC1(C)OB(c2ccc(C(F)(F)C3CCCC3)cc2)OC1(C)C]

The title compound (100 mg, 50%) was prepared from 1-bromo-4-(cyclopentyldifluoromethyl)benzene (170 mg, 0.62 mmol) following the procedure outlined for Example 48, Step 2. $^1H$ NMR (400 MHz, $CDCl_3$): δ 7.85 (d, J=8.4 Hz, 2H), 7.47 (d, J=8.4 Hz, 2H), 2.63-2.60 (m, 1H), 1.68-1.53 (m, 8H), 1.36 (s, 12H).

Step 6: 5-(4-(Cyclopentyldifluoromethyl)phenyl)-3-(3-(fluoromethyl)azetidine-1-carbonyl)-2-(3-methylpyrazin-2-yl)pyrazolo[1,5-a]pyrimidin-7(4H)-one

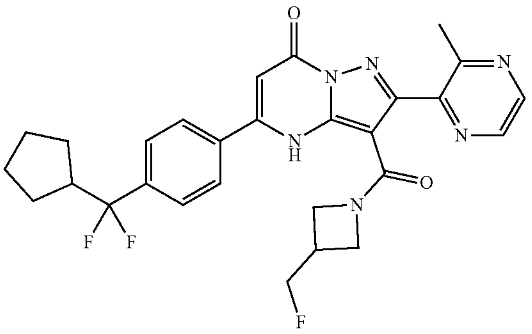 [SMILES: Cc1nccnc1-c1nn2c(=O)cc(-c3ccc(C(F)(F)C4CCCC4)cc3)[nH]c2c1C(=O)N1CC(CF)C1]

The title compound (17 mg, 24%) was prepared from 2-(4-(cyclopentyl difluoromethyl)phenyl)-4,4,5,5-tetramethyl-1,3,2-dioxaborolane (43 mg, 0.13 mmol) and 5-chloro-3-(3-(fluoromethyl)azetidine-1-carbonyl)-2-(3-methylpyrazin-2-yl)pyrazolo[1,5-a]pyrimidin-7(4H)-one (50 mg, 0.13 mmol) following the procedure outlined for Example 48, Step 4. $^1H$ NMR (400 MHz, DMSO-$d_6$): δ 8.50-8.48 (m, 2H), 8.18 (d, J=8.0 Hz, 2H), 7.58 (d, J=8.0 Hz, 2H), 6.19 (s, 1H), 4.66 (dd, J=47.2, 5.2 Hz, 2H), 4.49-4.14 (m, 2H), 4.12-3.64 (m, 2H), 3.03-2.75 (m, 2H), 2.42 (s, 3H), 1.73-1.52 (m, 8H); LCMS (ESI): m/z 537.2 $(M+H)^+$.

Example 50

Preparation of 5-(4-(1-Cyclopentylcyclopropyl)phenyl)-3-(3-(fluoromethyl)azetidine-1-carbonyl)-2-(pyrimidin-2-yl)pyrazolo[1,5-a]pyrimidin-7(4H)-one

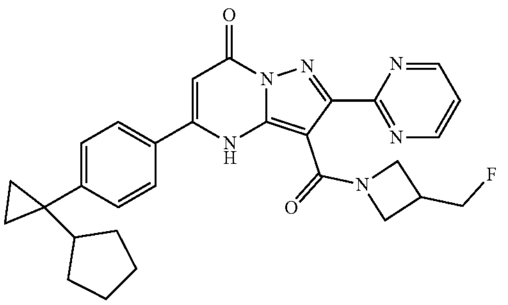 [SMILES: O=C(c1c(-c2ncccn2)nn2c(=O)cc(-c3ccc(C4(C5CCCC5)CC4)cc3)[nH]c12)N1CC(CF)C1]

The title compound (8.62 mg, 6%) was prepared from 5-chloro-3-(3-(fluoromethyl)azetidine-1-carbonyl)-2-(pyrimidin-2-yl)pyrazolo[1,5-a]pyrimidin-7(4H)-one (100 mg, 0.28 mmol) and 2-(4-(1-cyclopentylcyclopropyl)phenyl)-4,4,5,5-tetramethyl-1,3,2-dioxaborolane (129 mg, 0.41 mmol) following the procedure outlined for Example 48 Step 4. $^1H$ NMR (400 MHz, DMSO-$d_6$): δ 8.90-8.80 (m, 2H), 8.00-

7.80 (m, 2H), 7.50-7.40 (m, 1H), 7.36 (d, J=7.6 Hz, 2H), 6.05 (s, 1H), 4.67 (dd, J=47.2, 5.2 Hz, 2H), 4.22-3.59 (m, 4H), 3.00-2.80 (m, 2H), 1.95-1.80 (m, 1H), 1.70-1.55 (m, 2H), 1.50-1.35 (m, 4H), 1.21-1.09 (m, 2H), 0.73-0.71 (in, 2H), 0.67-0.65 (in, 2H); LCMS (ESI): m/z 513.2 $(M+H)^+$.

Example 51

Preparation of 5-(4-Butylphenyl)-3-(3-(fluoromethyl)azetidine-1-carbonyl)-2-(3-methylpyrazin-2-yl)pyrazolo[1,5-a]pyrimidin-7(4H)-one

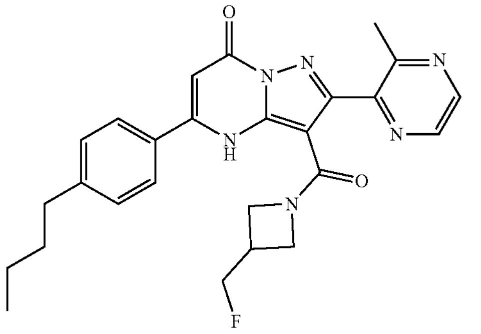 [SMILES: CCCCc1ccc(-c2cc(=O)n3nc(-c4nccnc4C)c(C(=O)N4CC(CF)C4)c3[nH]2)cc1]

The title compound (3.68 mg, 6%) was prepared from 1-bromo-4-butylbenzene and 5-chloro-3-(3-(fluoromethyl)azetidine-1-carbonyl)-2-(3-methylpyrazin-2-yl)pyrazolo[1,5-a]pyrimidin-7(4H)-one following the procedure outlined for Example 48, Steps 2 and 4. $^1$H NMR (400 MHz, DMSO-$d_6$): δ 12.30 (s, 1H), 8.60-8.55 (m, 2H), 7.88-7.78 (m, 2H), 7.39-7.33 (m, 2H), 6.16 (s, 1H), 4.59-4.47 (m, 2H), 3.99-3.72 (m, 4H), 2.92-2.91 (m, 2H), 2.66 (s, 3H), 2.52-2.48 (m, 1H), 1.62-1.58 (m, 2H), 1.36-1.15 (m, 2H), 0.93 (t, J=7.2 Hz, 3H); LCMS (ESI): m/z 475.2 $(M+H)^+$.

Example 52

Preparation of 5-(4-(1-Fluorocyclohexyl)phenyl)-3-(3-(fluoromethyl)azetidine-1-carbonyl)-2-(3-methylpyrazin-2-yl)pyrazolo[1,5-a]pyrimidin-7(4H)-one The general reaction scheme was as follows:

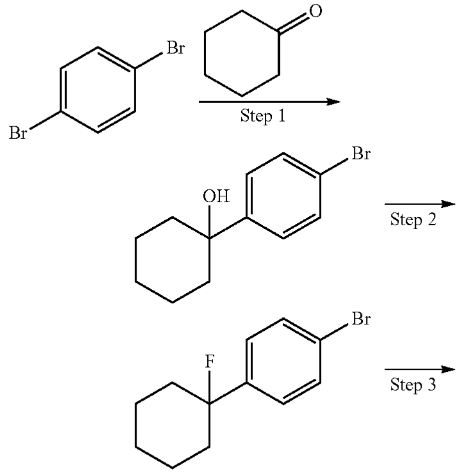

-continued

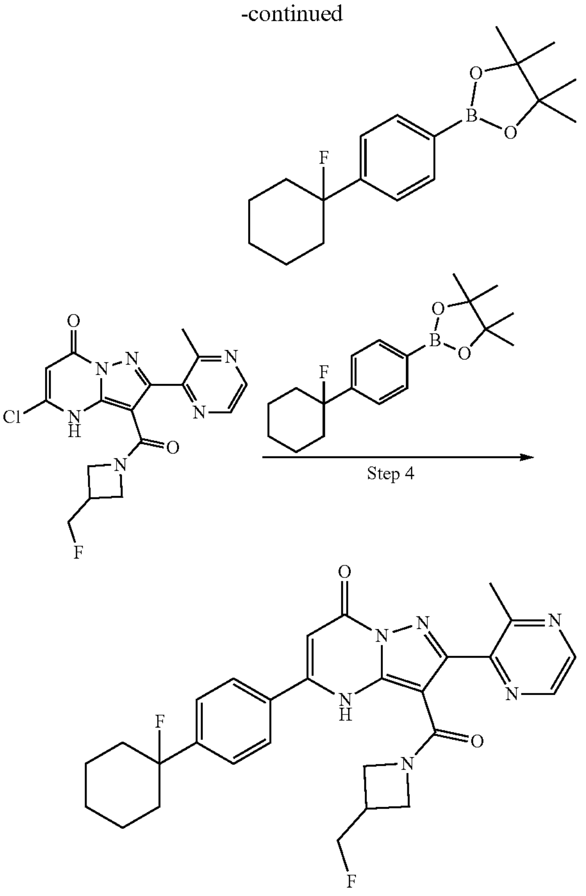

Step 1: 1-(4-Bromophenyl)cyclohexanol

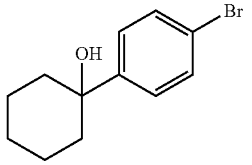 [SMILES: OC1(c2ccc(Br)cc2)CCCCC1]

A mixture of 1,4-dibromobenzene (5.00 g, 21.2 mmol) in THF (50 mL) was cooled to −78° C. and then n-BuLi (9.33 mL, 23.31 mmol) was added under a nitrogen atmosphere. The reaction mixture was stirred at −78° C. for 1 hour, at which point cyclohexanone (2.29 g, 23.31 mmol) was added into the mixture. The reaction was then slowly warmed to 0° C. and stirred for an additional hour. The reaction mixture was then quenched by water (10 mL). The resulting solution was extracted with ethyl acetate (50×2 mL), dried over $Na_2SO_4$, filtered and concentrated in vacuo. The residue was purified by flash chromatography on silica gel to afford the title compound (1 g, 18%) as a colorless solid. $^1$H NMR (400 MHz, $CDCl_3$): δ 7.47 (d, J=8.4 Hz, 2H), 7.40 (d, J=8.4 Hz, 2H), 1.82-1.64 (m, 9H), 1.37-1.23 (m, 1H).

Step 2: 1-Bromo-4-(1-fluorocyclohexyl)benzene

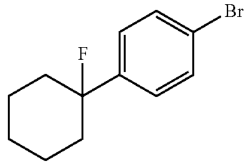 [SMILES: FC1(c2ccc(Br)cc2)CCCCC1]

To a mixture of 1-(4-bromophenyl)cyclohexanol (2.00 g, 7.84 mmol) in dichloromethane (20 mL) was added DAST (3.79 g, 23.52 mmol) at −78° C. The mixture was stirred at −78° C. for 4 hours. The reaction was quenched by the addition of water (5 mL). The resulting solution was extracted with dichloromethane (50 mL), dried over $Na_2SO_4$, filtered and concentrated in vacuo to afford the title crude compound (2 g) as a colorless oil which was used directly without further purification.

Step 3: 2-(4-(1-Fluorocyclohexyl)phenyl)-4,4,5,5-tetramethyl-1,3,2-dioxaborolane

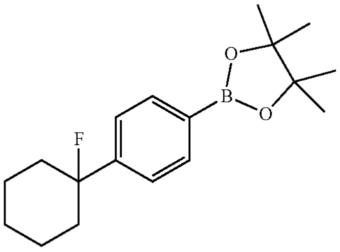 [SMILES: CC1(C)OB(c2ccc(C3(F)CCCCC3)cc2)OC1(C)C]

A mixture of 1-bromo-4-(1-fluorocyclohexyl)benzene (200.0 mg, 0.78 mmol), Pd(dppf)$Cl_2$ and KOAc (229.0 mg, 2.33 mmol), 4,4,4',4',5,5,5',5'-octamethyl-2,2'-bi(1,3,2-dioxaborolane) (395.0 mg, 1.56 mmol) in 1,4-dioxane (4 mL) was stirred at 100° C. under a nitrogen atmosphere for 16 hours. The resulting solution was extracted with EtOAc (30 mL×2), dried over anhydrous sodium sulfate, filtered and concentrated in vacuo. The residue was purified by flash chromatography on silica gel eluting with petroleum ether/ethyl acetate (30:1) to afford the title compound (140.0 mg, 59% over 2 steps) as a white solid.

Step 4: 5-(4-(1-Fluorocyclohexyl)phenyl)-3-(3-(fluoromethyl)azetidine-1-carbonyl)-2-(3-methylpyrazin-2-yl)pyrazolo[1,5-a]pyrimidin-7(4H)-one

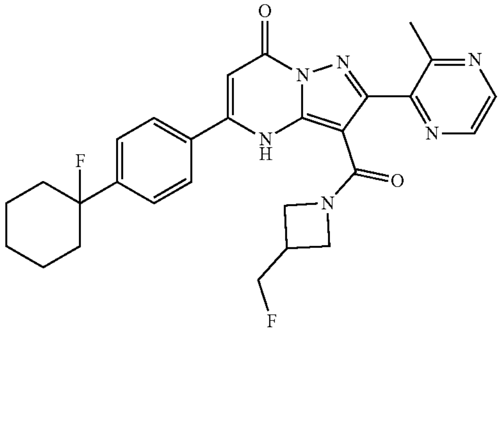 [SMILES: Cc1nccnc1-c1nn2c(=O)cc(-c3ccc(C4(F)CCCCC4)cc3)[nH]c2c1C(=O)N1CC(CF)C1]

The title compound (11.89 mg, 14%) was prepared from 5-chloro-3-(3-(fluoromethyl)azetidine-1-carbonyl)-2-(3-methylpyrazin-2-yl)pyrazolo[1,5-a]pyrimidin-7(4H)-one (100 mg, 0.16 mmol) and 2-(4-(1-fluorocyclohexyl)phenyl)-4,4,5,5-tetramethyl-1,3,2-dioxaborolane (122 mg, 0.24 mmol) following the procedure outlined for Example 48, Step 4. $^1$H NMR (400 MHz, DMSO-$d_6$): δ 8.60-8.40 (m, 2H), 8.14-7.85 (m, 2H), 7.58-7.45 (m, 2H), 6.16 (s, 1H), 4.74-3.60 (m, 6H), 2.98-2.83 (m, 1H), 2.53 (s, 3H), 2.03-1.82 (m, 4H), 1.75-1.63 (m, 5H), 1.43-1.32 (s, 1H); LCMS (ESI): m/z 519.3 $(M+H)^+$.

Example 53

Preparation of 5-([1,1'-Biphenyl]-4-yl)-3-(3-(fluoromethyl)azetidine-1-carbonyl)-2-(3-methylpyrazin-2-yl)pyrazolo[1,5-a]pyrimidin-7(4H)-one

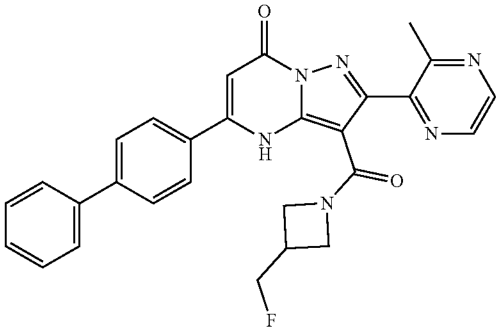 [SMILES: Cc1nccnc1-c1nn2c(=O)cc(-c3ccc(-c4ccccc4)cc3)[nH]c2c1C(=O)N1CC(CF)C1]

Step 1: 5-(4-Chlorophenyl)-3-(3-(fluoromethyl)azetidine-1-carbonyl)-2-(3-methyl pyrazin-2-yl)pyrazolo[1,5-a]pyrimidin-7(4H)-one

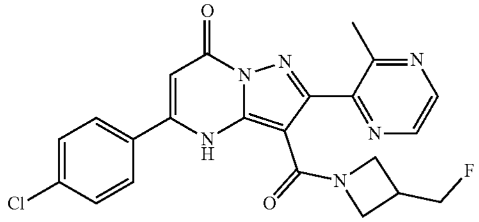 [SMILES: Cc1nccnc1-c1nn2c(=O)cc(-c3ccc(Cl)cc3)[nH]c2c1C(=O)N1CC(CF)C1]

The title compound (3.10 g, 30%) was prepared from 2-bromo-5-(4-chlorophenyl)-3-(3-(fluoromethyl)azetidine-1-carbonyl)pyrazolo[1,5-a]pyrimidin-7(4H)-one (10.0 g, 22.74 mmol) and 2-methyl-3-(tributylstannyl)pyrazine (10.46 g, 27.29 mmol) following the procedure outlined for Intermediate F. $^1$H NMR (400 MHz, DMSO-$d_6$): δ 8.71-8.51 (m, 2H), 7.96-7.77 (m, 2H), 7.67 (d, J=6.8 Hz, 2H), 6.22 (s, 1H), 4.48 (dd, J=46.8, 5.2 Hz, 2H), 4.05-3.79 (m, 2H), 3.73-3.48 (m, 2H), 2.96-2.79 (m, 1H), 2.77-2.57 (m, 3H); LCMS (ESI): m/z 453.1 $(M+H)^+$.

Step 2: 5-([1,1'-Biphenyl]-4-yl)-3-(3-(fluoromethyl) azetidine-1-carbonyl)-2-(3-methyl pyrazin-2-yl) pyrazolo[1,5-a]pyrimidin-7(4H)-one

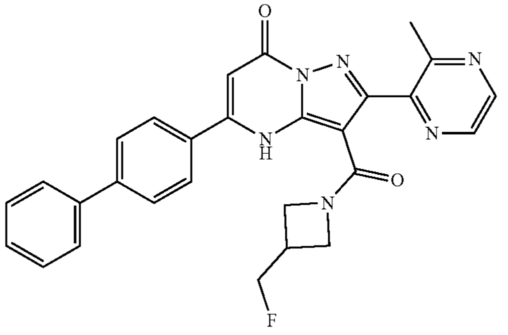 [SMILES: Cc1nccnc1-c1nn2c(=O)cc(-c3ccc(-c4ccccc4)cc3)[nH]c2c1C(=O)N1CC(CF)C1]

The title compound (98 mg, 89%) was prepared from 5-(4-chlorophenyl)-3-[3-(fluoromethyl)azetidine-1-carbonyl]-2-(3-methylpyrazin-2-yl)-4H-pyrazolo[1,5-a]pyrimidin-7-one (100 mg, 0.22 mmol) and 4,4,5,5-tetramethyl-2-phenyl-1,3,2-dioxaborolane (67 mg, 0.33 mmol) following the procedure outlined for Example 48, Step 4. $^{1}$H NMR (400 MHz, DMSO-$d_6$): δ 12.5 (br s, 1H), 8.71-7.96 (m, 4H), 7.85 (d, J=7.2 Hz, 2H), 7.78 (d, J=7.2 Hz, 2H), 7.55-7.48 (m, 2H), 7.45-7.40 (m, 1H), 6.27 (s, 1H), 4.66-4.49 (m, 2H), 4.02-3.97 (m, 2H), 3.87-3.58 (m, 2H), 2.96-2.89 (m, 1H), 2.61-2.58 (m, 3H); LCMS (ESI): m/z 495.2 $(M+H)^+$.

Example 54

Preparation of (R)-1-(5-(4-cyclohexylphenyl)-2-((S)-1-hydroxypropan-2-yl)-7-oxo-4,7-dihydropyrazolo[1,5-a]pyrimidine-3-carbonyl)pyrrolidine-3-carbonitrile and (R)-1-(5-(4-cyclohexylphenyl)-2-((R)-1-hydroxypropan-2-yl)-7-oxo-4,7-dihydropyrazolo[1,5-a]pyrimidine-3-carbonyl) pyrrolidine-3-carbonitrile The general reaction scheme was as follows:

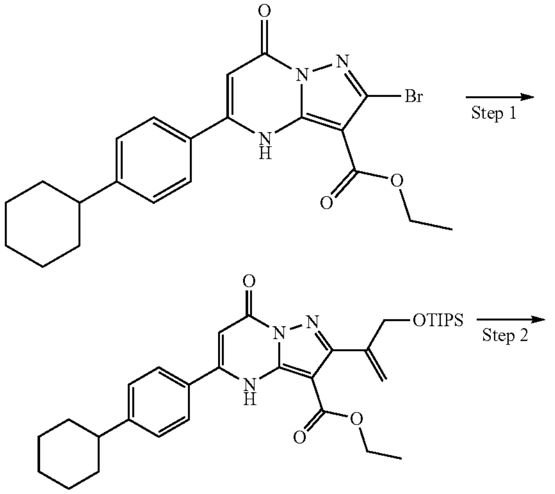

-continued

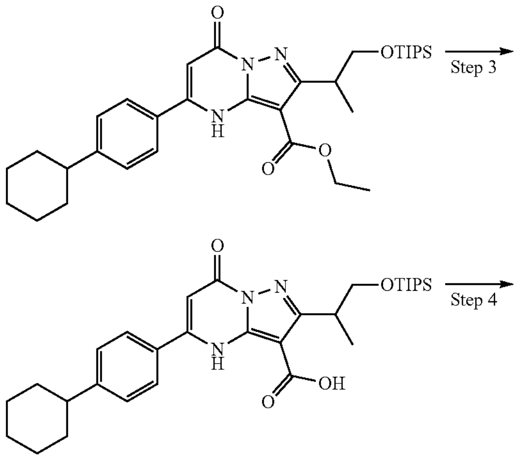

7

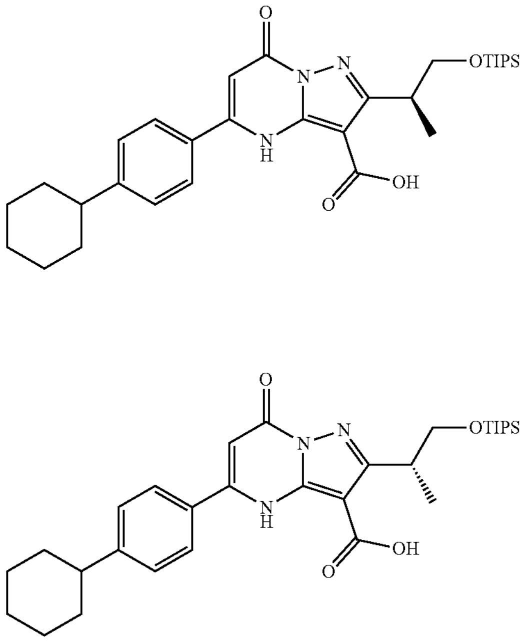

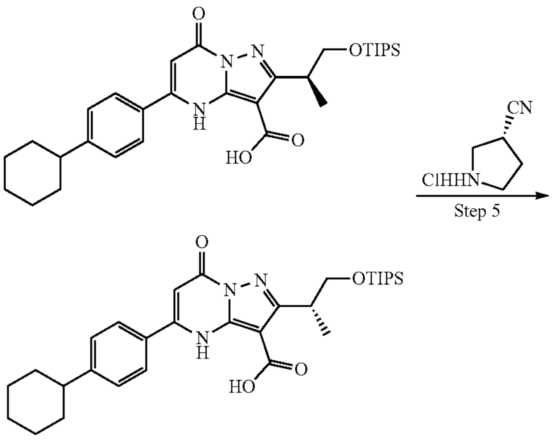

-continued

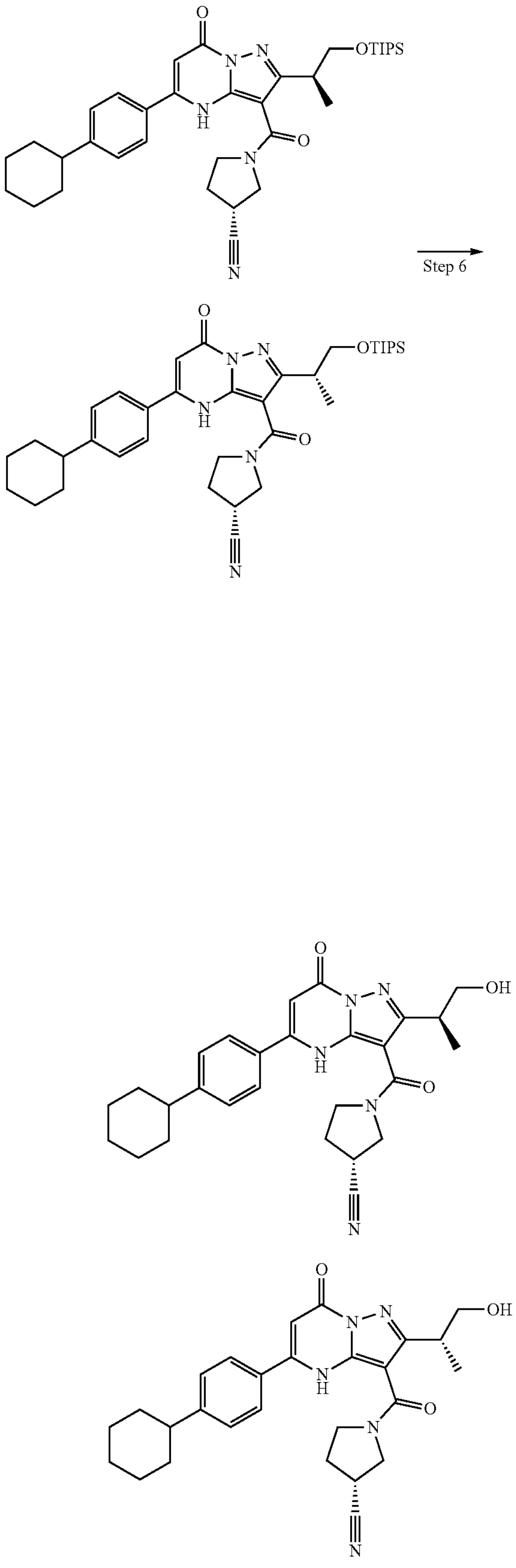

Step 1: Ethyl 5-(4-cyclohexylphenyl)-7-oxo-2-(3-((triisopropylsilyl)oxy)prop-1-en-2-yl)-4,7-dihydropyrazolo[1,5-a]pyrimidine-3-carboxylate

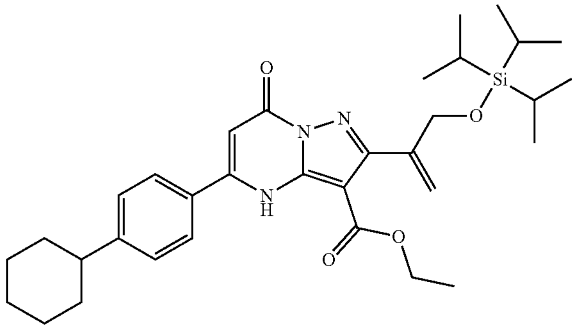 [SMILES: C=C(CO[Si](C(C)C)(C(C)C)C(C)C)c1nn2c(=O)cc(-c3ccc(C4CCCCC4)cc3)[nH]c2c1C(=O)OCC]

A solution of ethyl 2-bromo-5-(4-cyclohexylphenyl)-7-oxo-4,7-dihydropyrazolo[1,5-a]pyrimidine-3-carboxylate (500 mg, 1.13 mmol), triisopropyl-[2-(4,4,5,5-tetramethyl-1,3,2-dioxaborolan-2-yl)allyloxy]silane (575 mg, 1.69 mmol), Xphos (54 mg, 0.11 mmol), $Na_2CO_3$ (358 mg, 3.38 mmol) and Xphos Pd $G_3$ (96 mg, 0.11 mmol) in DMSO (10 mL) and water (2 mL) in a microwave vial was stirred at 120° C. for 2 hours. The reaction mixture was adjusted to pH 6 with the addition of 2 M aqueous HCl and diluted in EtOAc (50 mL). The organic layer was washed with brine (50 mL×2), dried over anhydrous $Na_2SO_4$, filtered and concentrated in vacuo. The residue was purified by silica gel column to afford the title compound (220 mg, 34%) as a colorless oil. $^1H$ NMR (400 MHz, DMSO-$d_6$): δ 11.25 (s, 1H), 7.72 (d, J=8.4 Hz, 2H), 7.46 (d, J=8.4 Hz, 2H), 6.29 (s, 1H), 5.80 (d, J=2.0, 1H), 5.76 (s, 1H), 4.62 (s, 2H), 4.28 (q, J=7.2 Hz, 2H), 2.65-2.57 (m, 1H), 1.86-1.68 (m, 5H), 1.52-1.24 (m, 8H), 1.19-1.11 (m, 3H), 1.08-1.02 (d, J=7.2 Hz, 18H).

Step 2: Ethyl 5-(4-cyclohexylphenyl)-7-oxo-2-(1-((triisopropylsilyl)oxy)propan-2-yl)-4,7-dihydropyrazolo[1,5-a]pyrimidine-3-carboxylate

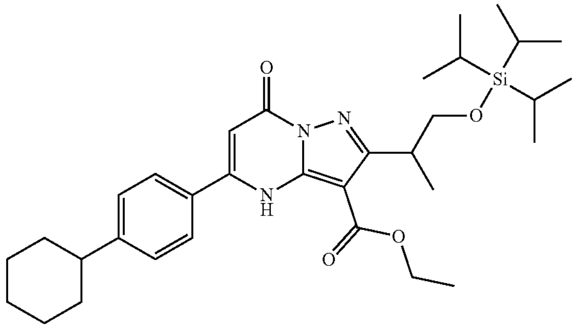 [SMILES: CCOC(=O)c1c(C(C)CO[Si](C(C)C)(C(C)C)C(C)C)nn2c(=O)cc(-c3ccc(C4CCCCC4)cc3)[nH]c12]

A solution of ethyl 5-(4-cyclohexylphenyl)-7-oxo-2-(3-((triisopropylsilyl)oxy)prop-1-en-2-yl)-4,7-dihydropyrazolo[1,5-a]pyrimidine-3-carboxylate (480 mg, 0.83 mmol) and 10% Pd/C (9 mg, 0.08 mmol) in ethanol (10 mL) was stirred at room temperature under a hydrogen atmosphere (1 atm) for 1 hour. The reaction mixture was filtered and concentrated to afford the title compound (0.40 g, 83%) as a colorless oil. LCMS (ESI): m/z 580.4 (M+H)$^+$.

Step 3: 5-(4-Cyclohexylphenyl)-7-oxo-2-(1-((triisopropylsilyl)oxy)propan-2-yl)-4,7-dihydropyrazolo[1,5-a]pyrimidine-3-carboxylic acid

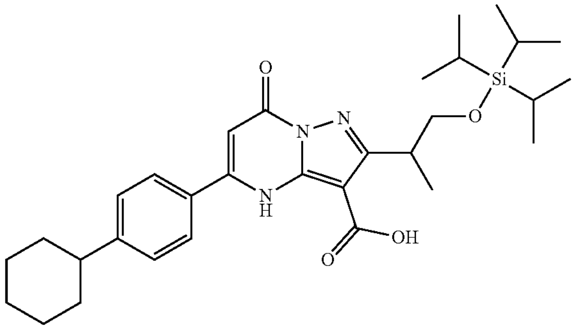 [SMILES: CC(CO[Si](C(C)C)(C(C)C)C(C)C)c1nn2c(=O)cc(-c3ccc(C4CCCCC4)cc3)[nH]c2c1C(=O)O]

A mixture of ethyl 5-(4-cyclohexylphenyl)-7-oxo-2-(1-((triisopropylsilyl)oxy)propan-2-yl)-4,7-dihydropyrazolo[1,5-a]pyrimidine-3-carboxylate (650 mg, 1.12 mmol) and lithium hydroxide monohydrate (470 mg, 11.21 mmol) in water (10 mL) and EtOH (50 mL) was stirred at 80° C. for 16 hours. The reaction mixture was adjusted to pH 5 with 2M aqueous HCl, diluted in EtOAc (50 mL), washed with brine (50 mL×2), dried over anhydrous $Na_2SO_4$, filtered and concentrated. The residue was purified by silica gel column (5% MeOH in DCM) to afford the title compound (450 mg, 73%) as a white solid. LCMS (ESI): m/z 552.2 $(M+H)^+$.

Step 4: (S)-5-(4-cyclohexylphenyl)-7-oxo-2-(1-((triisopropylsilyl)oxy)propan-2-yl)-4,7-dihydropyrazolo[1,5-a]pyrimidine-3-carboxylic acid and (R)-5-(4-cyclohexylphenyl)-7-oxo-2-(1-((triisopropylsilyl)oxy)propan-2-yl)-4,7-dihydropyrazolo[1,5-a]pyrimidine-3-carboxylic acid

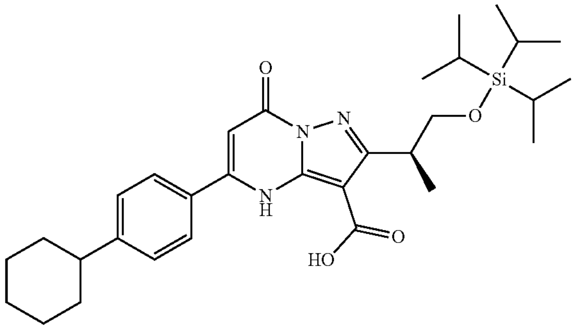

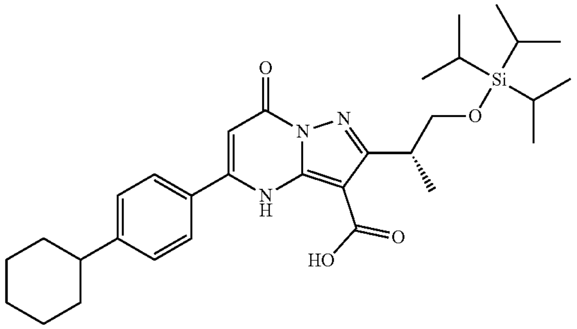

5-(4-Cyclohexylphenyl)-7-oxo-2-(1-((triisopropylsilyl)oxy)propan-2-yl)-4,7-dihydropyrazolo[1,5-a]pyrimidine-3-carboxylic acid (450 mg, 0.82 mmol) was separated by SFC (DAICEL CHIRALCEL OD-H (250 mm*30 mm, 5 um), 0.1% $NH_3H_2O$ EtOH) to afford Enantiomer A (first peak, 200 mg, 44%) as a white solid and Enantiomer B (second peak, 200 mg, 44%) as a white solid.

Step 5: (R)-1-(5-(4-cyclohexylphenyl)-7-oxo-2-(1-((triisopropylsilyl)oxy)propan-2-yl)-4,7-dihydropyrazolo[1,5-a]pyrimidine-3-carbonyl)pyrrolidine-3-carbonitrile To a solution of Enantiomer A (200 mg, 0.36 mmol) and HATU (207 mg, 0.54 mmol) in DMF (5 mL) was added DIPEA (468 mg, 3.62 mmol), then stirred for 20 min. (3R)-Pyrrolidine-3-carbonitrile hydrochloride (72 mg, 0.54 mmol) was added, and then reaction solution was stirred for 2 hours. The reaction mixture was diluted in EtOAc (50 mL) and washed with brine (50 mL×2). The organic layer was purified by preparative TLC (50% ethyl acetate in petroleum ether) to afford the title compound (100 mg, 44%) as a white solid. LCMS (ESI): m/z 630.4 $(M+H)^+$.

Step 6: (R)-1-(5-(4-cyclohexylphenyl)-2-(1-hydroxypropan-2-yl)-7-oxo-4,7-dihydropyrazolo[1,5-a]pyrimidine-3-carbonyl)pyrrolidine-3-carbonitrile To a stirred solution of (R)-1-(5-(4-cyclohexylphenyl)-7-oxo-2-(1-((triisopropylsilyl)oxy)propan-2-yl)-4,7-dihydropyrazolo[1,5-a]pyrimidine-3-carbonyl)pyrrolidine-3-carbonitrile (80 mg, 0.13 mmol; obtained from Enantiomer A) in THF (5 mL) was added TBAF (1 M in THF, 0.25 mL, 0.25 mmol). The mixture was stirred at room temperature for 15 hours. The reaction mixture was then diluted in EtOAc (50 mL) and washed with brine (50 mL×2). The combined organic layer was purified by TLC (10% MeOH in DCM) and HPLC (water modified with 0.04% $NH_3$ in $H_2O$ and 10 mM $NH_4HCO_3$— MeCN, column) to afford the title compound (6.9 mg, 11%) as a white solid.

Final product obtained using Enantiomer A of Step 4: $^1H$ NMR (400 MHz, $CD_3OD$): δ 7.76 (d, J=7.6 Hz, 2H), 7.37 (d, J=7.6 Hz, 2H), 6.16 (s, 1H), 4.00-3.72 (m, 6H), 3.45-3.35 (m, 2H), 2.65-2.55 (m, 1H), 2.44-2.23 (m, 2H), 1.93-1.74 (m, 5H), 1.55-1.43 (m, 4H), 1.40-1.30 (m, 4H); LCMS (ESI): m/z 474.2 $(M+H)^+$.

Steps 5 and 6 were repeated starting from Enantiomer B of Step 4 to afford (R)-1-(5-(4-cyclohexylphenyl)-2-(1-hydroxypropan-2-yl)-7-oxo-4,7-dihydropyrazolo[1,5-a]pyrimidine-3-carbonyl)pyrrolidine-3-carbonitrile (9.67 mg, 13%).

Final product obtained using Enantiomer B of Step 4: $^1H$ NMR (400 MHz, $CD_3OD$): δ 7.84-7.75 (m, 2H), 7.38-7.33 (m, 2H), 6.18 (s, 1H), 4.00-3.90 (m, 2H), 3.85-3.75 (m, 4H), 3.46-3.36 (m, 2H), 2.65-2.55 (m, 1H), 2.46-2.25 (m, 2H), 1.92-1.85 (m, 4H), 1.83-1.75 (m, 1H), 1.55-1.42 (m, 4H), 1.40-1.30 (m, 4H); LCMS (ESI): m/z 474.2 $(M+H)^+$.

Example 55

Preparation of (S)-5-(4-cyclohexylphenyl)-3-(3-(fluoromethyl)azetidine-1-carbonyl)-2-(1-hydroxy-propan-2-yl)pyrazolo[1,5-a]pyrimidin-7(4H)-one and (R)-5-(4-cyclohexylphenyl)-3-(3-(fluoromethyl) azetidine-1-carbonyl)-2-(1-hydroxypropan-2-yl) pyrazolo[1,5-a]pyrimidin-7(4H)-one

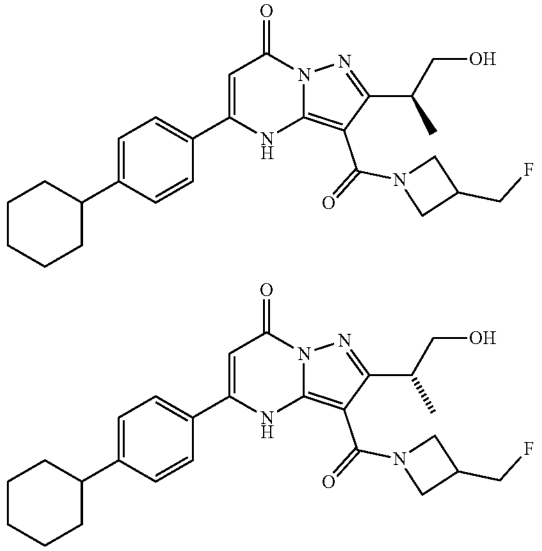

Step 1: 5-(4-Cyclohexylphenyl)-3-(3-(fluoromethyl) azetidine-1-carbonyl)-2-(3-hydroxy prop-1-en-2-yl) pyrazolo[1,5-a]pyrimidin-7(4H)-one

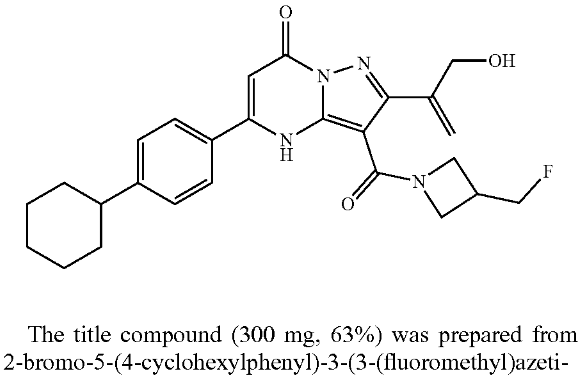

The title compound (300 mg, 63%) was prepared from 2-bromo-5-(4-cyclohexylphenyl)-3-(3-(fluoromethyl)azetidine-1-carbonyl)pyrazolo[1,5-a]pyrimidin-7(4H)-one (500 mg, 1.03 mmol) and 2-(4,4,5,5-tetramethyl-1,3,2-dioxaborolan-2-yl)prop-2-en-1-ol (479 mg, 2.6 mmol) following the procedure outlined for Example 54, Step 1. $^1H$ NMR (400 MHz, DMSO-$d_6$): δ 12.30 (s, 1H), 7.69 (d, J=7.6 Hz, 2H), 7.43 (d, J=7.6 Hz, 2H), 6.06 (s, 1H), 5.68-5.56 (m, 2H), 5.30-5.10 (m, 1H), 4.65 (dd, J=47.2, 5.2 Hz, 2H), 4.37 (s, 2H), 4.20-4.00 (m, 2H), 3.85-3.70 (m, 2H), 3.02-2.86 (m, 2H), 1.85-1.77 (m, 4H), 1.75-1.68 (m, 1H), 1.47-1.36 (m, 4H), 1.30-1.22 (m, 1H); LCMS (ESI): m/z 465.2 $(M+H)^+$.

Step 2: 5-(4-Cyclohexylphenyl)-3-(3-(fluoromethyl) azetidine-1-carbonyl)-2-(1-hydroxy propan-2-yl) pyrazolo[1,5-a]pyrimidin-7(4H)-one

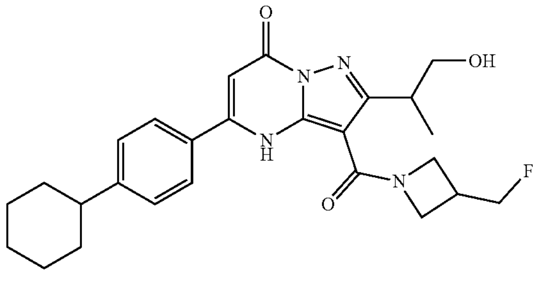

The title compound (100 mg, 33%) was prepared from 5-(4-cyclo hexylphenyl)-3-(3-(fluoromethyl)azetidine-1-carbonyl)-2-(3-hydroxyprop-1-en-2-yl)pyrazolo[1,5-a]pyrimidin-7(4H)-one (300 mg, 0.65 mmol) following the procedure outlined for Example 54, Step 2.

Step 3: (S)-5-(4-cyclohexylphenyl)-3-(3-(fluoromethyl)azetidine-1-carbonyl)-2-(1-hydroxypropan-2-yl)pyrazolo[1,5-a]pyrimidin-7(4H)-one & (R)-5-(4-cyclohexyl phenyl)-3-(3-(fluoromethyl)azetidine-1-carbonyl)-2-(1-hydroxypropan-2-yl)pyrazolo[1,5-a] pyrimidin-7(4H)-one

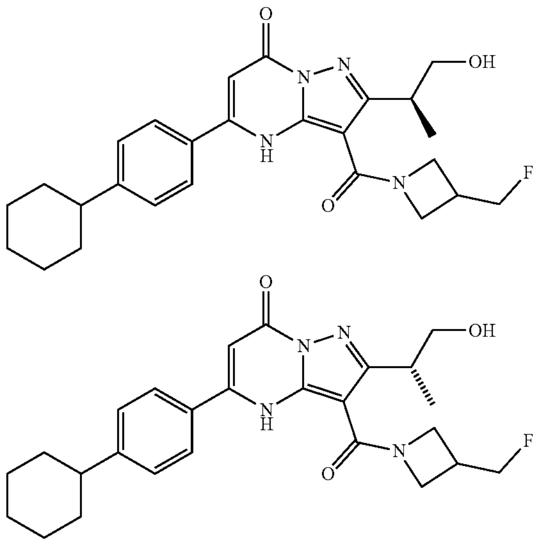

5-(4-Cyclohexylphenyl)-3-(3-(fluoromethyl)azetidine-1-carbonyl)-2-(1-hydroxypropan-2-yl)pyrazolo[1,5-a]pyrimidin-7(4H)-one (100 mg, 0.21 mmol) was separated by SFC (DAICEL CHIRALPAK IG (250 mm*30 mm, 10 um), 0.1% $NH_3H_2O$/MeOH) to afford Enantiomer A ((S)-5-(4-cyclohexylphenyl)-3-(3-(fluoromethyl)azetidine-1-carbonyl)-2-(1-hydroxypropan-2-yl)pyrazolo[1,5-a]pyrimidin-7(4H)-one; the first peak on SFC, 18.5 mg, 18%) and Enantiomer B ((R)-5-(4-cyclohexylphenyl)-3-(3-(fluoromethyl)azetidine-1-carbonyl)-2-(1-hydroxypropan-2-yl)pyrazolo[1,5-a] pyrimidin-7(4H)-one; the second peak on SFC, 16.7 mg, 17%) as both white solids.

Enantiomer A, $^1$H NMR (400 MHz, $CD_3OD$): δ 7.85-7.75 (m, 2H), 7.43-7.35 (m, 2H), 6.19 (s, 1H), 4.68-4.56 (m, 2H), 4.38-4.25 (m, 2H), 4.15-4.00 (m, 2H), 3.92-3.75 (m, 2H), 3.46-3.36 (m, 1H), 3.10-3.00 (m, 1H), 2.65-2.59 (m, 1H), 1.92-1.86 (m, 4H), 1.81-1.76 (m, 1H), 1.55-1.44 (m, 4H), 1.40-1.31 (m, 4H); LCMS (ESI): m/z 467.2 $(M+H)^+$.

Enantiomer B, $^1$H NMR (400 MHz, DMSO-$d_6$): δ 8.00 (d, J=7.6 Hz, 2H), 7.30 (d, J=8.0 Hz, 2H), 6.23 (s, 1H), 5.50-5.35 (m, 1H), 4.67-4.55 (m, 2H), 4.40-4.05 (m, 3H), 3.80-3.75 (m, 1H), 3.60-3.55 (m, 2H), 3.50-3.44 (m, 1H), 3.02-2.89 (m, 1H), 2.60-2.55 (m, 1H), 1.85-1.68 (m, 5H), 1.48-1.33 (m, 4H), 1.30-1.20 (m, 4H); LCMS (ESI): m/z 467.2 $(M+H)^+$.

Example 56

Preparation of 3-((2S,3S)-3-(fluoromethyl)-2-methylazetidine-1-carbonyl)-2-(3-methylpyrazin-2-yl)-5-(4-((S)-2,2,2-trifluoro-1-phenylethoxy)phenyl)pyrazolo[1,5-a]pyrimidin-7(4H)-one and 3-((2S,3S)-3-(fluoromethyl)-2-methylazetidine-1-carbonyl)-2-(3-methylpyrazin-2-yl)-5-(4-((R)-2,2,2-trifluoro-1-phenylethoxy)phenyl)pyrazolo[1,5-a]pyrimidin-7(4H)-one

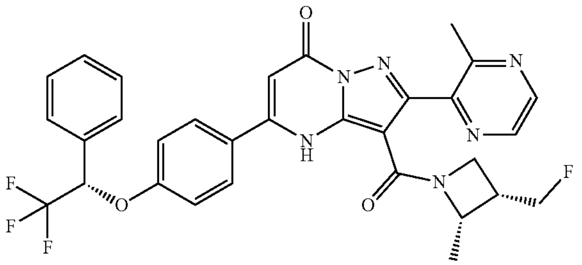 [SMILES: Cc1nccnc1-c1nn2c(=O)cc(-c3ccc(O[C@@H](c4ccccc4)C(F)(F)F)cc3)[nH]c2c1C(=O)N1C[C@H](CF)[C@@H]1C]

Step 1: (S)-ethyl 2-(3-methylpyrazin-2-yl)-7-oxo-5-(4-(2,2,2-trifluoro-1-phenylethoxy) phenyl)-4,7-dihydropyrazolo[1,5-a]pyrimidine-3-carboxylate and (R)-ethyl 2-(3-methylpyrazin-2-yl)-7-oxo-5-(4-(2,2,2-trifluoro-1-phenylethoxy)phenyl)-4,7-dihydropyrazolo[1,5-a]pyrimidine-3-carboxylate

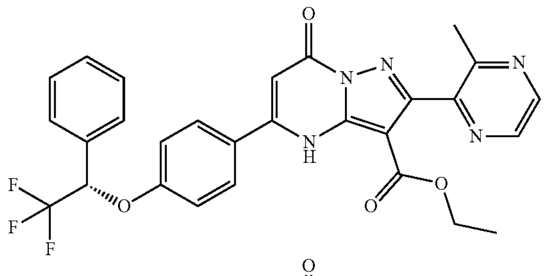

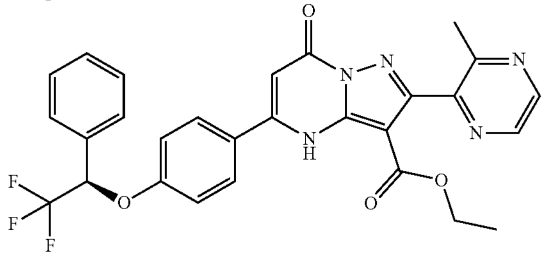

Ethyl 2-(3-methylpyrazin-2-yl)-7-oxo-5-(4-(2,2,2-trifluoro-1-phenylethoxy)phenyl)-4,7-dihydropyrazolo[1,5-a]pyrimidine-3-carboxylate (500 mg, 0.91 mmol) was separated by preparative SFC (condition: DAICEL CHIRALPAK AS-H (250 mm*30 mm, 5 um), 0.1% $NH_3H_2O$ EtOH) to afford Enantiomer A (200 mg, 40%, the first peak on SFC) and Enantiomer B (200 mg, 40%, the second peak on SFC) both as white solid.

Step 2: 2-(3-methylpyrazin-2-yl)-7-oxo-5-(4-(2,2,2-trifluoro-1-phenylethoxy)phenyl)-4,7-dihydropyrazolo[1,5-a]pyrimidine-3-carboxylic acid A mixture of Enantiomer A (200 mg, 0.36 mmol) and lithium hydroxide monohydrate (76 mg, 1.82 mmol) in water (10 mL) and ethanol (10 mL) was stirred at 75° C. for 16 hours. The reaction solution was concentrated and the pH was adjusted to 6 with 1 M aqueous HCl, extracted with EtOAc (50 mL×3), filtered and concentrated in vacuo to afford the title compound (160 mg, 84%) as a brown solid. LCMS (ESI): m/z 522.1 $(M+H)^+$.

Step 3: 3-((2S,3S)-3-(fluoromethyl)-2-methylazetidine-1-carbonyl)-2-(3-methylpyrazin-2-yl)-5-(4-(2,2,2-trifluoro-1-phenylethoxy)phenyl)pyrazolo[1,5-a]pyrimidin-7(4H)-one from Enantiomer A To a solution of 2-(3-methylpyrazin-2-yl)-7-oxo-5-(4-(2,2,2-trifluoro-1-phenyl ethoxy)phenyl)-4,7-dihydropyrazolo[1,5-a]pyrimidine-3-carboxylic acid (60 mg, 0.12 mmol; obtained from Enantiomer A) and DIPEA (148 mg, 1.15 mmol) in DMF (5 mL) was added HATU (66 mg, 0.17 mmol), and the reaction mixture was stirred at 25° C. for 30 minutes. (2S,3S)-3-(Fluoromethyl)-2-methyl-azetidine 2,2,2-trifluoroacetate (50 mg, 0.23 mmol) was added and the solution was stirred for 2 hours. The reaction solution was poured into water (50 mL) and extracted with EtOAc (50 mL×2), washed with brine (50 mL) and concentrated to dryness. The residue was purified by preparative TLC (5% MeOH in DCM) to afford the title compound (15.4 mg, 21%) as a white solid.

Final product obtained using Enantiomer A from Step 1: $^1$H NMR (400 MHz, DMSO-$d_6$): δ 8.47 (s, 2H), 7.99 (d, J=8.4 Hz, 2H), 7.64 (d, J=6.8 Hz, 2H), 7.49-7.42 (m, 3H), 7.10 (d, J=8.4 Hz, 2H), 6.40 (q, J=6.4 Hz, 1H), 6.04 (s, 1H), 4.82-3.86 (m, 5H), 3.11-2.81 (m, 1H), 2.41 (s, 3H), 1.23-1.14 (m, 3H); LCMS (ESI): m/z 607.1 $(M+H)^+$.

Preparation of 3-((2S,3S)-3-(fluoromethyl)-2-methylazetidine-1-carbonyl)-2-(3-methylpyrazin-2-yl)-5-(4-(2,2,2-trifluoro-1-phenylethoxy)phenyl)pyrazolo[1,5-a]pyrimidin-7(4H)-one from Enantiomer B The title compound (14.1 mg, 19%) was furnished as a white solid, which was prepared from Enantiomer B (200 mg, 0.36 mmol) following the procedure outlined for Steps 2 and 3 above.

Final product obtained using Enantiomer B from Step 1: $^1$H NMR (400 MHz, DMSO-$d_6$): δ 8.47 (br s, 2H), 7.99 (d, J=8.4 Hz, 2H), 7.64-7.62 (d, J=7.2 Hz, 2H), 7.49-7.42 (m, 3H), 7.10 (d, J=8.4 Hz, 2H), 6.40 (q, J=6.4 Hz, 1H), 6.04 (s, 1H), 4.82-3.88 (m, 5H), 2.95-2.81 (m, 1H), 2.42 (s, 3H), 1.23-1.14 (m, 3H); LCMS (ESI): m/z 607.1 $(M+H)^+$.

Example 57

Preparation of (S)-3-(3-(Fluoromethyl)azetidine-1-carbonyl)-2-(3-methylpyrazin-2-yl)-5-(4-(2,2,2-trifluoro-1-phenylethoxy)phenyl)pyrazolo[1,5-a]pyrimidin-7(4H)-one and (R)-3-(3-(Fluoromethyl)azetidine-1-carbonyl)-2-(3-methylpyrazin-2-yl)-5-(4-(2,2,2-trifluoro-1-phenylethoxy)phenyl)pyrazolo[1,5-a]pyrimidin-7(4H)-one

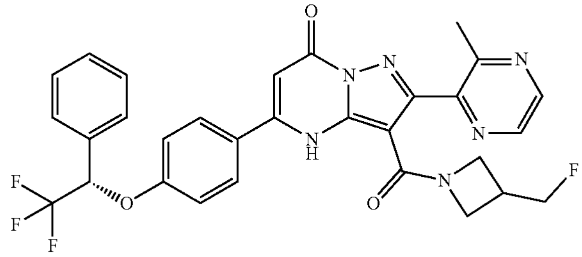 [SMILES: Cc1nccnc1-c1nn2c(=O)cc(-c3ccc(O[C@@H](c4ccccc4)C(F)(F)F)cc3)[nH]c2c1C(=O)N1CC(CF)C1]

To a mixture of (S)-2-(3-methylpyrazin-2-yl)-7-oxo-5-(4-(2,2,2-trifluoro-1-phenylethoxy)phenyl)-4,7-dihydropyrazolo[1,5-a]pyrimidine-3-carboxylic acid (30 mg, 0.06 mmol) and HATU (33 mg, 0.09 mmol) in DMF (1 mL) was added DIPEA (0.05 mL, 0.29 mmol) and the mixture was stirred at 20° C. for 30 minutes. 3-(fluoromethyl)azetidine hydrochloride (11 mg, 0.09 mmol) was added and the reaction was stirred at 20° C. for 2 hours. The resulting solution was diluted with water (60 mL) and extracted with ethyl acetate (20 mL×2). The combined organic layers were dried over anhydrous sodium sulfate, filtered and concentrated in vacuo. The residue was purified by preparative TLC (8% methanol in dichloromethane) to afford the title compound (18.2 mg, 53%) as a white solid. $^1$H NMR (400 MHz, DMSO-$d_6$): δ 8.49 (br s, 2H), 8.03 (d, J=8.4 Hz, 2H), 7.63 (d, J=7.2 Hz, 2H), 7.51-7.41 (m, 3H), 7.13 (d, J=8.4 Hz, 2H), 6.40 (q, J=6.4 Hz, 1H), 6.06 (s, 1H), 4.64 (dd, J=47.2, 6.0 Hz, 2H), 4.44-3.60 (m, 4H), 2.97-2.84 (m, 1H), 2.45 (s, 3H); LCMS (ESI): m/z 593.1 (M+H)$^+$.

Preparation of (R)-3-(3-(Fluoromethyl)azetidine-1-carbonyl)-2-(3-methylpyrazin-2-yl)-5-(4-(2,2,2-trifluoro-1-phenylethoxy)phenyl)pyrazolo[1,5-a]pyrimidin-7(4H)-one

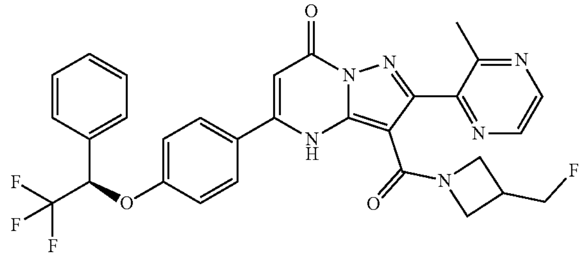 [SMILES: Cc1nccnc1-c1nn2c(=O)cc(-c3ccc(O[C@H](c4ccccc4)C(F)(F)F)cc3)[nH]c2c1C(=O)N1CC(CF)C1]

The title compound (14.1 mg, 19%) was furnished as a white solid, which was prepared from (R)-2-(3-methylpyrazin-2-yl)-7-oxo-5-(4-(2,2,2-trifluoro-1-phenylethoxy)phenyl)-4,7-dihydropyrazolo[1,5-a]pyrimidine-3-carboxylic acid (30 mg, 0.06 mmol) and 3-(fluoro methyl)azetidine hydrochloride (11 mg, 0.09 mmol) following the procedure outlined above. $^1$H NMR (400 MHz, DMSO-$d_6$): δ 8.49 (br s, 2H), 8.01 (d, J=8.0 Hz, 2H), 7.63 (d, J=7.2 Hz, 2H), 7.51-7.42 (m, 3H), 7.12 (d, J=8.0 Hz, 2H), 6.41 (q, J=6.4 Hz, 1H), 6.05 (s, 1H), 4.65 (dd, J=47.2, 6.0 Hz, 2H), 4.45-3.43 (m, 4H), 2.95-2.85 (m, 1H), 2.42 (s, 3H); LCMS (ESI): m/z 593.1 (M+H)$^+$.

Example 58

Preparation of 5-(4-Cyclopentylphenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one

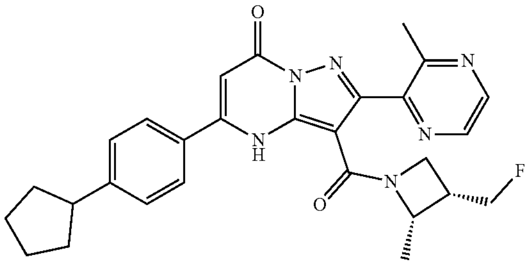 [SMILES: Cc1nccnc1-c1nn2c(=O)cc(-c3ccc(C4CCCC4)cc3)[nH]c2c1C(=O)N1C[C@H](CF)[C@@H]1C]

Step 1: 2-(4-Cyclopentylphenyl)-4,4,5,5-tetramethyl-1,3,2-dioxaborolane

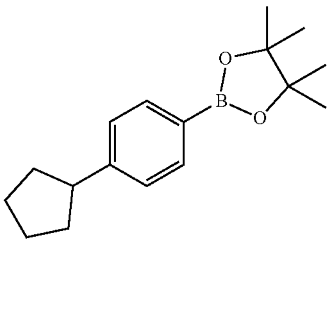 [SMILES: CC1(C)OB(c2ccc(C3CCCC3)cc2)OC1(C)C]

A mixture of bis(pinacolato)diboron (451 mg, 1.78 mmol), Pd(dppf)$Cl_2$ (130 mg, 0.18 mmol), KOAc (523 mg, 5.33 mmol) and 1-bromo-4-cyclopentyl-benzene (0.4 g, 1.78 mmol) in 1,4-dioxane (5 mL) was stirred at 100° C. under a nitrogen atmosphere for 16 hours. The solvent was removed under reduced pressure. The residue was purified by silica gel column chromatography (0-5% EtOAc in petroleum ether) to afford the title compound (300 mg, 62%) as a yellow solid. $^1$H NMR (400 MHz, $CDCl_3$): δ 7.76 (d, J=8.0 Hz, 2H), 7.28 (d, J=8.0 Hz, 2H), 3.08-2.96 (m, 1H), 2.16-2.02 (m, 2H), 1.89-1.77 (m, 2H), 1.76-1.56 (m, 4H), 1.36 (s, 12H).

Step 2: Ethyl5-(4-cyclopentylphenyl)-2-(3-methylpyrazin-2-yl)-7-oxo-4,7-dihydropyrazolo[1,5-a]pyrimidine-3-carboxylate

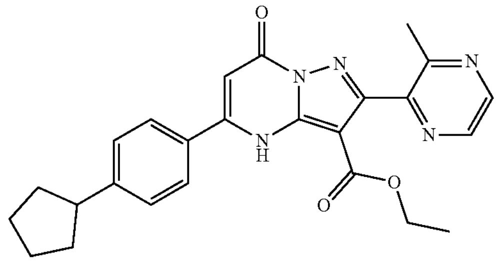 [SMILES: CCOC(=O)c1c(-c2nccnc2C)nn2c(=O)cc(-c3ccc(C4CCCC4)cc3)[nH]c12]

A mixture of ethyl 5-chloro-2-(3-methylpyrazin-2-yl)-7-oxo-4H-pyrazolo[1,5-a]pyrimidine-3-carboxylate (150 mg, 0.45 mmol), Xphos Pd G2 (35 mg, 0.04 mmol), Xphos (21 mg, 0.04 mmol), $Cs_2CO_3$ (439 mg, 1.35 mmol) and 2-(4-cyclopentylphenyl)-4,4,5,5-tetramethyl-1,3,2-dioxaborolane (245 mg, 0.90 mmol) in DMSO (5 mL) and $H_2O$ (1 mL) was stirred at 120° C. for 16 hours under a nitrogen atmosphere. The reaction mixture was diluted with water (10 mL), adjusted to pH 5 by 2 M aqueous HCl solution and extracted with EtOAc (10 mL×2). The combined organic layers were dried over anhydrous sodium sulfate, filtered and concentrated in vacuo. The residue was purified by preparative TLC (5% methanol in dichloromethane) to afford the title compound (110 mg, 55%) as a white solid. $^1H$ NMR (400 MHz, $CD_3OD$): δ 8.63 (d, J=2.4 Hz, 1H), 8.56 (d, J=2.4 Hz, 1H), 7.81 (d, J=8.0 Hz, 2H), 7.49 (d, J=8.0 Hz, 2H), 6.37 (s, 1H), 4.17 (q, J=7.2 Hz, 2H), 3.20-3.05 (m, 1H), 2.51 (s, 3H), 2.19-2.06 (m, 2H), 1.92-1.83 (m, 2H), 1.81-1.73 (m, 2H), 1.72-1.60 (m, 2H), 1.08 (t, J=7.2 Hz, 3H); LCMS (ESI): m/z 444.2 $(M+H)^+$.

Step 3: 5-(4-Cyclopentylphenyl)-2-(3-methylpyrazin-2-yl)-7-oxo-4,7-dihydropyrazolo[1,5-a]pyrimidine-3-carboxylic acid

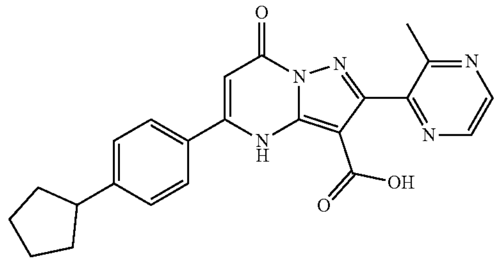 [SMILES: Cc1nccnc1-c1nn2c(=O)cc(-c3ccc(C4CCCC4)cc3)[nH]c2c1C(=O)O]

A mixture of lithium hydroxide monohydrate (104 mg, 2.48 mmol) and ethyl 5-(4-cyclopentylphenyl)-2-(3-methylpyrazin-2-yl)-7-oxo-4H-pyrazolo[1,5-a]pyrimidine-3-carboxylate (110 mg, 0.25 mmol) in water (5 mL) and EtOH (5 mL) was stirred at 80° C. for 16 hours. The reaction solution was concentrated, adjusted to pH 6 with 1 M aqueous HCl solution, and then extracted with EtOAc (10 mL×3). The organic phase was dried over anhydrous sodium sulfate, filtered and concentrated to afford the title compound (100 mg, 97%) as a white solid. LCMS (ESI): m/z 416.2 $(M+H)^+$.

Step 4: 5-(4-Cyclopentylphenyl)-3-((2S,3S)-3-(fluoromethyl)-2-methylazetidine-1-carbonyl)-2-(3-methylpyrazin-2-yl)pyrazolo[1,5-a]pyrimidin-7(4H)-one

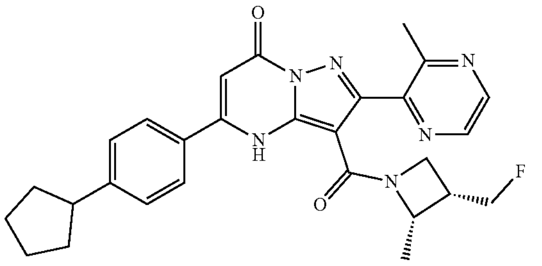 [SMILES: Cc1nccnc1-c1nn2c(=O)cc(-c3ccc(C4CCCC4)cc3)[nH]c2c1C(=O)N1C[C@H](CF)[C@@H]1C]

A solution of 5-(4-cyclopentylphenyl)-2-(3-methylpyrazin-2-yl)-7-oxo-4,7-dihydro pyrazolo[1,5-a]pyrimidine-3-carboxylic acid (100 mg, 0.24 mmol), DIPEA (0.2 mL, 1.2 mmol) and HATU (194 mg, 0.51 mmol) in DMF (8 mL) was stirred at room temperature for 15 min, then (2S,3S)-3-(fluoromethyl)-2-methylazetidine 2,2,2-trifluoroacetate (131 mg, 0.6 mmol, 5% R-isomers) was added, the mixture was stirred at room temperature for 2 hours. The mixture was diluted with water (25 mL) and adjusted to pH 6 with 2 M aqueous HCl solution and extracted with EtOAc (10 mL×3). The combined organic layers were dried over anhydrous sodium sulfate, filtered and concentrated in vacuo. The resulting residue was purified by reverse phase chromatography (MeCN 52%-82%/0.2% FA in water, Xtimate C18 150*40 mm*10 um) followed by preparative SFC (DAICEL CHIRALPAK AD-H (250 mm*30 mm, 5 um), 0.1% $NH_3H_2O$ IPA, 30%-30%) to afford the title compound (30 mg, 25%) as a white solid. $^1H$ NMR (400 MHz, $CD_3OD$): δ 8.60 (d, J=2.4 Hz, 1H), 8.59 (d, J=2.4 Hz, 1H), 7.76 (d, J=8.0 Hz, 2H), 7.49 (d, J=8.0 Hz, 2H), 6.25 (s, 1H), 4.77-3.81 (m, 5H), 3.67-3.37 (m, 1H), 3.20-3.06 (m, 1H), 3.00-2.88 (m, 1H), 2.82 (s, 3H), 2.19-2.08 (m, 2H), 1.93-1.83 (m, 2H), 1.82-1.72 (m, 2H), 1.72-1.60 (m, 2H), 1.50-1.36 (m, 3H). LCMS (ESI): m/z 501.2 $(M+H)^+$.

Example 59

Preparation of 3-((2S,3S)-3-(fluoromethyl)-2-methylazetidine-1-carbonyl)-2-(3-methylpyrazin-2-yl)-5-((E)-non-1-en-1-yl)pyrazolo[1,5-a]pyrimidin-7(4H)-one

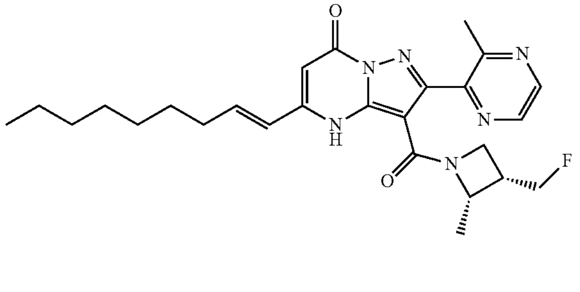 [SMILES: CCCCCCC/C=C/c1cc(=O)n2nc(-c3nccnc3C)c(C(=O)N3C[C@H](CF)[C@@H]3C)c2[nH]1]

Step 1: (E)-4,4,5,5-tetramethyl-2-(non-1-en-1-yl)-1,3,2-dioxaborolane

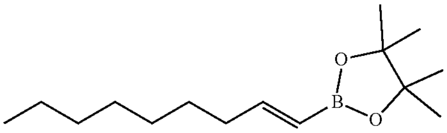 [SMILES: CCCCCCC/C=C/B1OC(C)(C)C(C)(C)O1]

In a glovebox under nitrogen atmosphere, a mixture of $HZrCp_2Cl$ (1.08 g, 4.22 mmol), non-1-yne (2.50 mL, 15.47 mmol) and 4,4,5,5-tetramethyl-1,3,2-dioxaborolane (2.10 mL, 14.06 mmol) was stirred at 60° C. for 16 hours. The residue was purified by silica gel column chromatography (0-5% EtOAc in petroleum ether) to afford the title compound (900 mg, 90% purity) as a colorless oil. $^1H$ NMR (400 MHz, $CDCl_3$): δ 6.64-6.60 (m, 1H), 5.43 (d, J=18.0 Hz, 1H), 2.19-2.11 (m, 2H), 1.66-1.59 (m, 2H), 1.29-1.27 (m, 8H), 1.26 (s, 12H), 0.85-0.83 (m, 3H).

Step 2: (E)-ethyl2-(3-methylpyrazin-2-yl)-5-(non-1-en-1-yl)-7-oxo-4,7-dihydropyrazolo [1,5-a]pyrimidine-3-carboxylate

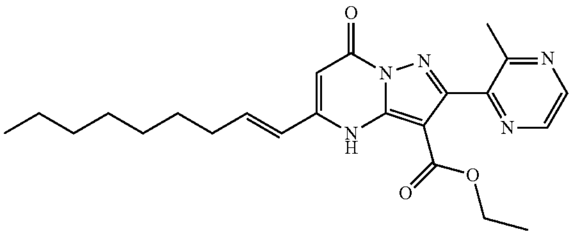 [SMILES: CCCCCCC/C=C/c1cc(=O)n2nc(-c3nccnc3C)c(C(=O)OCC)c2[nH]1]

To a mixture of ethyl 5-chloro-2-(3-methylpyrazin-2-yl)-7-oxo-4,7-dihydropyrazolo [1,5-a]pyrimidine-3-carboxylate (200 mg, 0.60 mmol), (E)-4,4,5,5-tetramethyl-2-(non-1-en-1-yl)-1,3,2-dioxaborolane (378 mg, 1.50 mmol) in DMSO (6 mL) and Water (1.2 mL) were added Xphos-Pd-G2 (47.0 mg, 0.06 mmol), Xphos (28.0 mg, 0.06 mmol) and $Na_2CO_3$ (197 mg, 1.80 mmol), the mixture was stirred at 110° C. under a nitrogen atmosphere for 16 hours. The resulting solution was diluted with water (60 mL) and extracted with ethyl acetate (50×2 mL), the organic layers were combined. The organic layer was dried over anhydrous sodium sulfate, filtered and concentrated in vacuo. The residue was purified by preparative TLC (8% MeOH in DCM) to afford the title compound (100 mg, 39%) as a white solid. $^1H$ NMR (400 MHz, DMSO-$d_6$): δ 11.64 (s, 1H), 8.60 (d, J=2.4 Hz, 1H), 8.53 (d, J=2.4 Hz, 1H), 6.95-6.77 (m, 1H), 6.63 (d, J=16.0 Hz, 1H), 6.20 (s, 1H), 4.02 (q, J=7.2 Hz, 2H), 2.35 (s, 3H), 2.26-2.19 (m, 2H), 1.49-1.39 (m, 2H), 1.33-1.22 (m, 8H), 0.91 (t, J=7.2 Hz, 3H), 0.84 (t, J=6.8 Hz, 3H); LCMS: m/z 424.1 $(M+H)^+$.

Step 3: (E)-2-(3-methylpyrazin-2-yl)-5-(non-1-en-1-yl)-7-oxo-4,7-dihydropyrazolo [1,5-a]pyrimidine-3-carboxylic acid

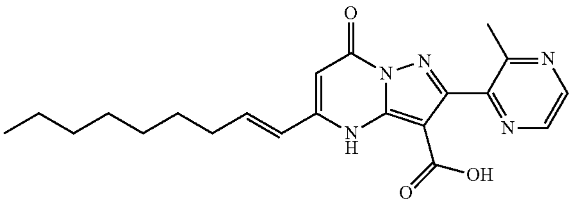 [SMILES: CCCCCCC/C=C/c1cc(=O)n2nc(-c3nccnc3C)c(C(=O)O)c2[nH]1]

A mixture of (E)-ethyl2-(3-methylpyrazin-2-yl)-5-(non-1-en-1-yl)-7-oxo-4,7-dihydropyrazolo[1,5-a]pyrimidine-3-carboxylate (100 mg, 0.24 mmol), lithium hydroxide monohydrate (99 mg, 2.36 mmol) in water (3 mL) and ethanol (3 mL) was stirred at 80° C. for 16 hours. The reaction solution was concentrated in vacuo and the pH was adjusted to 4 with the addition of 4 M aqueous HCl. The resulting solution was extracted with ethyl acetate (40 mL×2) and the organic layers were combined. The organic layer was dried over anhydrous sodium sulfate, filtered and concentrated in vacuo to afford the title compound (90 mg, 96%) as a white solid. $^1H$ NMR (400 MHz, DMSO-$d_6$): δ 12.93 (s, 1H), 11.53 (s, 1H), 8.62 (d, J=2.4 Hz, 1H), 8.57 (d, J=2.4 Hz, 1H), 6.92-6.81 (m, 1H), 6.74 (d, J=16.0 Hz, 1H), 6.25 (s, 1H), 2.41 (s, 3H), 2.29-2.21 (m, 2H), 1.53-1.43 (m, 2H), 1.37-1.22 (m, 8H), 0.87 (t, J=7.2 Hz, 3H); LCMS: m/z 396.0 $(M+H)^+$.

Step 4: 3-((2S,3S)-3-(fluoromethyl)-2-methylazetidine-1-carbonyl)-2-(3-methylpyrazin-2-yl)-5-((E)-non-1-en-1-yl)pyrazolo[1,5-a]pyrimidin-7(4H)-one

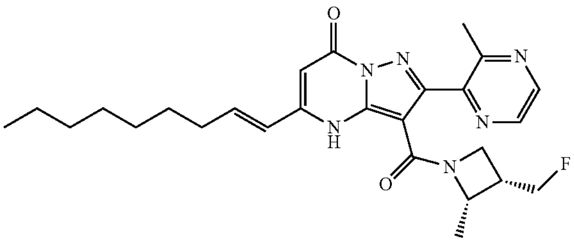 [SMILES: CCCCCCC/C=C/c1cc(=O)n2nc(-c3nccnc3C)c(C(=O)N3C[C@H](CF)[C@@H]3C)c2[nH]1]

To a mixture of (E)-2-(3-methylpyrazin-2-yl)-5-(non-1-en-1-yl)-7-oxo-4,7-dihydropyrazolo [1,5-a]pyrimidine-3-carboxylic acid (90 mg, 0.23 mmol) and HATU (130 mg, 0.34 mmol) in DMF (2 mL) was added DIPEA (147 mg, 1.14 mmol). The mixture was stirred at 20° C. for 30 min. Then (2S,3S)-3-(fluoromethyl)-2-methylazetidine 2,2,2-trifluoroacetate salt (74 mg, 0.34 mmol) was added. The mixture was stirred at 20° C. for 2 hours. The resulting solution was diluted with water (60 mL) and extracted with ethyl acetate (40 mL×2). The organic layer was dried over anhydrous sodium sulfate filtered and concentrated in vacuo, then purified by preparative TLC (8% MeOH in DCM) to afford the title compound (80 mg, 72%) as a white solid. $^1H$ NMR (400 MHz, DMSO-$d_6$): δ 12.10 (s, 1H), 8.60-8.58 (m, 2H), 6.97-6.75 (m, 1H), 6.46 (d, J=13.6 Hz, 1H), 6.06 (s, 1H), 4.74-4.21 (m, 3H), 3.89-3.38 (m, 2H), 2.90-2.78 (m, 1H), 2.70-2.58 (m, 3H), 2.28-2.20 (m, 2H), 1.52-1.42 (m, 2H), 1.38-1.14 (m, 11H), 0.86 (t, J=6.8 Hz, 3H); LCMS (ESI): m/z 481.2 $(M+H)^+$.

Example 60

Preparation of 3-((2S,3S)-3-(fluoromethyl)-2-methylazetidine-1-carbonyl)-2-(3-methylpyrazin-2-yl)-5-nonylpyrazolo[1,5-a]pyrimidin-7(4H)-one

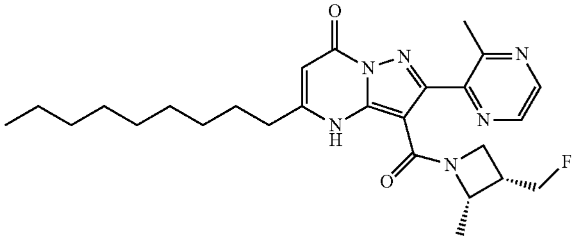 [SMILES: CCCCCCCCCc1cc(=O)n2nc(-c3nccnc3C)c(C(=O)N3C[C@H](CF)[C@@H]3C)c2[nH]1]

To a mixture of 3-((2S,3S)-3-(fluoromethyl)-2-methylazetidine-1-carbonyl)-2-(3-methylpyrazin-2-yl)-5-((E)-non-1-en-1-yl)pyrazolo[1,5-a]pyrimidin-7(4H)-one (40 mg, 0.08 mmol) in methanol (2 mL) was added 10% Pd on carbon (9 mg, 0.01 mmol) at 15° C. a hydrogen atmosphere (15 psi). The mixture was stirred for 1 hour and filtered through Celite®. The filtrate was concentrated in vacuo and purified by preparative TLC (8% MeOH in DCM) to afford the title compound (27.2 mg, 67%) as a white solid. $^1H$ NMR (400 MHz, DMSO-$d_6$): δ 12.21 (s, 1H), 8.62 (d, J=2.4 Hz, 1H), 8.60 (d, J=2.4 Hz, 1H), 5.78 (s, 1H), 4.67-4.20 (m, 3H), 3.88-3.38 (m, 2H), 2.88-2.77 (m, 1H), 2.67 (s, 3H), 2.66-2.61 (m, 2H), 1.73-1.55 (m, 2H), 1.39-1.14 (m, 15H), 0.85 (t, J=6.8 Hz, 3H); LCMS (ESI): m/z 483.2 $(M+H)^+$.

Example 61

Preparation of 3-[(2S,3S)-3-(fluoromethyl)-2-methyl-azetidine-1-carbonyl]-2-(3-methylpyrazin-2-yl)-5-[4-(1,2,2,3,3,4,4,5,5,6,6-undecadeuteriocyclohexyl)phenyl]-4H-pyrazolo[1,5-a]pyrimidin-7-one

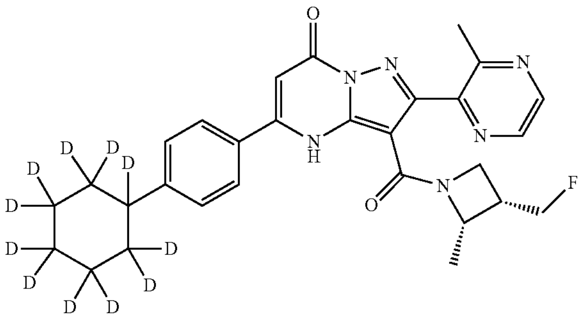 [SMILES: [2H]C1([2H])C([2H])([2H])C([2H])([2H])C([2H])(c2ccc(-c3cc(=O)n4nc(-c5nccnc5C)c(C(=O)N5C[C@H](CF)[C@@H]5C)c4[nH]3)cc2)C([2H])([2H])C1([2H])[2H]]

Step 1: 1-(4-Chlorophenyl)-1,2,2,3,3,4,4,5,5,6,6-undecadeuterio-cyclohexane

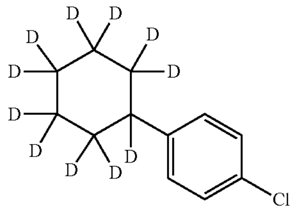 [SMILES: [2H]C1([2H])C([2H])([2H])C([2H])([2H])C([2H])(c2ccc(Cl)cc2)C([2H])([2H])C1([2H])[2H]]

In a glovebox, a vial was charged with 1-bromo-4-chlorobenzene (200 mg, 1.04 mmol), $(Ir[dF(CF_3)ppy]_2(dtbpy))PF_6$ (12 mg, 0.01 mmol), dry molecular sieves (100 mg) and $Na_2CO_3$ (221 mg, 2.09 mmol). A solution of bromocyclohexane-du (0.19 mL, 1.57 mmol) in anhydrous 1,2-dimethoxyethane (2 mL) was then added, followed by tris(trimethylsilyl)silane (390 mg, 1.57 mmol). Meanwhile, a second vial was charged with nickel chloride dimethoxyethane adduct (3 mg, 0.01 mmol) and 4,4'-di-tert-butyl-2,2'-dipyridyl (3 mg, 0.01 mmol). 1,2-dimethoxyethane (2 mL) was then added. This resulted in the formation of a green active Ni catalyst solution. The solution was syringed out and transferred to the first vial. The reaction mixture was sealed up and taken out from the glove box. The reaction mixture was then stirred at room temperature and irradiated with a 34 W blue LED and a cooling fan for 16 hours. The reaction was then concentrated in vacuo and purified by preparative TLC (petroleum ether) to afford the title compound (50 mg, 23%) as a colorless oil. $^1H$ NMR (400 MHz, $CDCl_3$) 7.26 (d, J=8.4 Hz, 2H), 7.14 (d, J=8.4 Hz, 2H).

Step 2: 4,4,5,5-Tetramethyl-2-[4-(1,2,2,3,3,4,4,5,5,6,6 undecadeuteriocyclohexyl)phenyl]-1,3,2-dioxaborolane

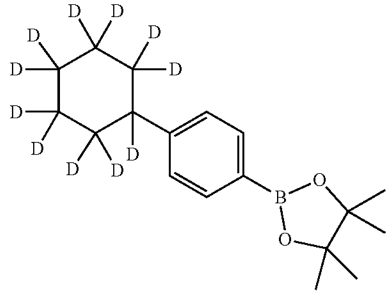 [SMILES: [2H]C1([2H])C([2H])([2H])C([2H])([2H])C([2H])(c2ccc(B3OC(C)(C)C(C)(C)O3)cc2)C([2H])([2H])C1([2H])[2H]]

To a solution of potassium acetate (86 mg, 0.87 mmol) in 1,4-dioxane (5 mL) were added Xphos Pd G3 (25 mg, 0.03 mmol), Xphos (14 mg, 0.03 mmol), 4,4,4',4',5,5,5',5'-octamethyl-2,2'-bi(1,3,2-dioxaborolane) (111 mg, 0.44 mmol) and 1-(4-chlorophenyl)-1,2,2,3,3,4,4,5,5,6,6-undecadeuterio-cyclohexane (60 mg, 0.29 mmol). Then the reaction mixture was placed under nitrogen atmosphere and stirred at 100° C. for 16 hours. The reaction mixture was concentrated in vacuo and purified by preparative TLC (5% ethyl acetate in petroleum ether) to afford the title compound (40 mg, 46%) as a white solid. $^1H$ NMR (400 MHz, $CDCl_3$): δ 7.48 (d, J=8.0 Hz, 2H), 6.96 (d, J=8.0 Hz, 2H), 1.07 (s, 12H).

Step 3: Ethyl 2-(3-methylpyrazin-2-yl)-7-oxo-5-[4-(1,2,2,3,3,4,4,5,5,6,6-undecadeuterio cyclohexyl) phenyl]-4H-pyrazolo[1,5-a]pyrimidine-3-carboxylate

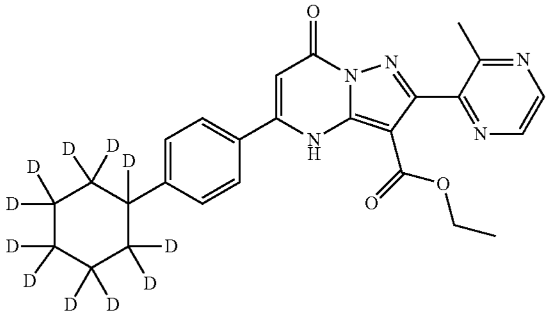 [SMILES: [2H]C1([2H])C([2H])([2H])C([2H])([2H])C([2H])(c2ccc(-c3cc(=O)n4nc(-c5nccnc5C)c(C(=O)OCC)c4[nH]3)cc2)C([2H])([2H])C1([2H])[2H]]

A mixture of Xphos Pd G3 (24 mg, 0.03 mmol), ethyl 5-chloro-2-(3-methylpyrazin-2-yl)-7-oxo-4H-pyrazolo[1,5-a]pyrimidine-3-carboxylate (100 mg, 0.30 mmol), 4,4,5,5-tetramethyl-2-[4-(1,2,2,3,3,4,4,5,5,6,6-undecadeuteriocyclohexyl)phenyl]-1,3,2-dioxaborolane (134 mg, 0.45 mmol), sodium carbonate (95 mg, 0.9 mmol) and Xphos (14 mg, 0.03 mmol) in DMSO (4 mL) and water (0.7 mL) was stirred at 110° C. for 16 hours under a nitrogen atmosphere. The mixture was diluted with $H_2O$ (20 mL), adjusted to pH 6 with aqueous 1 M HCl and extracted by EtOAc (20 mL×3). The combined organic layers were dried over anhydrous sodium sulfate, filtered and concentrated. The residue was purified by pre-TLC (5% MeOH in DCM) to afford the title compound (40 mg, 29%) as a white solid. LCMS (ESI): m/z 469.3 $(M+H)^+$.

Step 4: 2-(3-Methylpyrazin-2-yl)-7-oxo-5-[4-(1,2,2,3,3,4,4,5,5,6,6-undecadeuteriocyclohexyl)phenyl]-4H-pyrazolo[1,5-a]pyrimidine-3-carboxylic acid

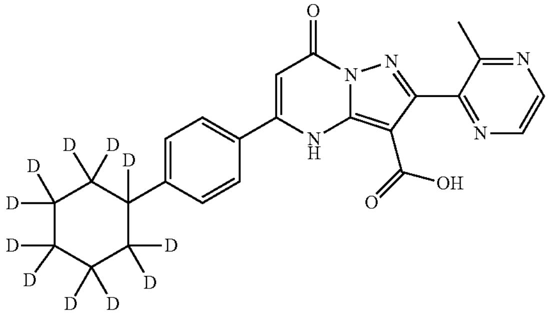 [SMILES: [2H]C1([2H])C([2H])([2H])C([2H])([2H])C([2H])(c2ccc(-c3cc(=O)n4nc(-c5nccnc5C)c(C(=O)O)c4[nH]3)cc2)C([2H])([2H])C1([2H])[2H]]

To a mixture of ethyl 2-(3-methylpyrazin-2-yl)-7-oxo-5-[4-(1,2,2,3,3,4,4,5,5,6,6-undecadeuteriocyclohexyl)phenyl]-4H-pyrazolo[1,5-a]pyrimidine-3-carboxylate (40 mg, 0.09 mmol) in ethanol (1 mL) and water (1 mL) was added lithium hydroxide monohydrate (36 mg, 0.85 mmol), the mixture was stirred at 80° C. for 16 hours. The reaction mixture was adjusted to pH 6 with aqueous 2M HCl and extracted with dichloromethane (50 mL×2). The combined organic layers were dried over anhydrous sodium sulfate, filtered and concentrated in vacuo to afford the title compound (37 mg, 98%) as a yellow solid. LCMS (ESI): m/z 441.3 $(M+H)^+$.

Step 5: 3-[(2S,3S)-3-(fluoromethyl)-2-methyl-azetidine-1-carbonyl]-2-(3-methylpyrazin-2-yl)-5-[4-(1,2,2,3,3,4,4,5,5,6,6-undecadeuteriocyclohexyl)phenyl]-4H-pyrazolo[1,5-a]pyrimidin-7-one

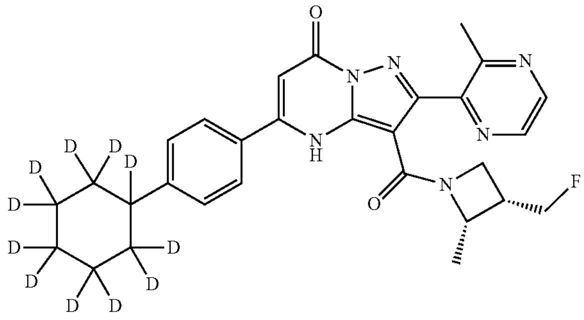 [SMILES: [2H]C1([2H])C([2H])([2H])C([2H])([2H])C([2H])(c2ccc(-c3cc(=O)n4nc(-c5nccnc5C)c(C(=O)N5C[C@H](CF)[C@@H]5C)c4[nH]3)cc2)C([2H])([2H])C1([2H])[2H]]

To a solution of 2-(3-methylpyrazin-2-yl)-7-oxo-5-[4-(1,2,2,3,3,4,4,5,5,6,6-undecadeuteriocyclohexyl)phenyl]-4H-pyrazolo[1,5-a]pyrimidine-3-carboxylic acid (38 mg, 0.09 mmol) and DIPEA (0.07 mL, 0.43 mmol) in DMF (2 mL) was added HATU (49 mg, 0.13 mmol) and the reaction was stirred for 20 min. (2S,3S)-3-(fluoromethyl)-2-methyl-azetidine-2,2,2-trifluoroacetate (37 mg, 0.17 mmol) was then added and the reaction mixture was stirred at 20° C. for 2 hours. The reaction mixture was diluted with 10% aqueous citric acid (10 mL), extracted with EtOAc (20 mL×2). The combined organic layers were dried over anhydrous sodium sulfate, filtered and concentrated in vacuo. The residue was purified by preparative TLC (10% MeOH in DCM) to afford the title compound (28 mg, 62%) as a white solid. $^1H$ NMR (400 MHz, DMSO-$d_6$): δ 8.48 (br s, 2H), 7.99 (d, J=7.6 Hz, 2H), 7.30 (d, J=7.6 Hz, 2H), 6.11 (s, 1H), 4.90-3.85 (m, 5H), 3.01-2.80 (m, 1H), 2.43 (s, 3H), 1.36-1.15 (m, 3H); LCMS (ESI): m/z 526.4 $(M+H)^+$.

Example 62

Preparation of 3-((2S,3S)-3-(fluoromethyl)-2-methylazetidine-1-carbonyl)-2-(3-methylpyrazin-2-yl)-5-(4-neopentylphenyl)pyrazolo[1,5-a]pyrimidin-7(4H)-one

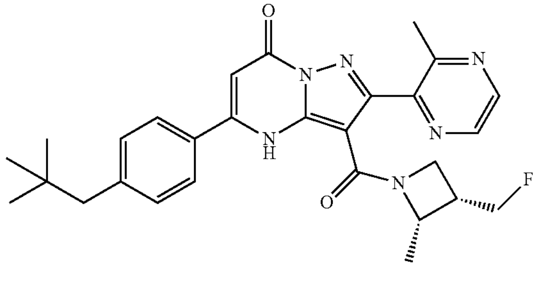 [SMILES: Cc1nccnc1-c1nn2c(=O)cc(-c3ccc(CC(C)(C)C)cc3)[nH]c2c1C(=O)N1C[C@H](CF)[C@@H]1C]

Step 1: 1-Bromo-4-neopentylbenzene

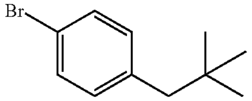

A mixture of neopentylbenzene (6.0 g, 40.47 mmol) and bromine (4.5 mL, 86.62 mmol) in 2,2,2-trifluoroacetic acid (60 mL) was stirred at 20° C. for 16 hours. The reaction was quenched by aqueous $NaHSO_3$ solution (50 mL), extracted with EtOAc (50 mL×2). The organic layer was dried over anhydrous sodium sulfate and concentrated in vacuo. The residue was purified by flash chromatography on silica gel eluting with petroleum ether to afford the title compound (7 g, 76%) as a colorless oil. $^1$H NMR (400 MHz, $CDCl_3$): δ 7.38 (d, J=8.4 Hz, 2H), 6.98 (d, J=8.4 Hz, 2H), 2.43 (s, 2H), 0.88 (s, 9H).

Step 2: 4,4,5,5-Tetramethyl-2-(4-neopentylphenyl)-1,3,2-dioxaborolane

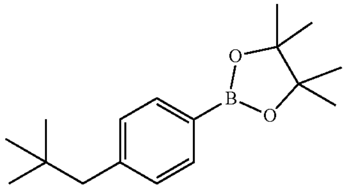 [SMILES: CC(C)(C)Cc1ccc(B2OC(C)(C)C(C)(C)O2)cc1]

A mixture of Pd(dppf)$Cl_2$ (1.95 g, 2.63 mmol), 1-bromo-4-neopentylbenzene (2.0 g, 8.81 mmol), KOAc (2.59 g, 26.42 mmol) and 4,4,4',4',5,5,5',5'-octamethyl-2,2'-bi(1,3,2-dioxaborolane) (3.35 g, 13.21 mmol) in 1,4-dioxane was stirred at 100° C. under a nitrogen atmosphere for 16 hours. The solution was then quenched with water (50 mL), extracted with EtOAc (50 mL×2) and washed with water (50 mL×2). The organic layer was dried over anhydrous sodium sulfate, filtered and concentrated in vacuo. The residue was purified by silica gel column chromatography (0-2% EtOAc in petroleum ether) to afford the title compound (2.2 g, 910%) as a yellow solid. $^1$H NMR (400 MHz, $CDCl_3$): δ 7.72 (d, J=7.6 Hz, 2H), 7.15 (d, J=7.6 Hz, 2H), 2.51 (s, 2H), 1.35 (s, 12H), 0.90 (s, 9H).

Step 3: Ethyl 2-(3-methylpyrazin-2-yl)-5-(4-neopentylphenyl)-7-oxo-4,7-dihydro pyrazolo[1,5-a]pyrimidine-3-carboxylate

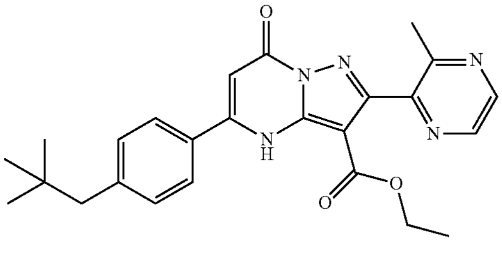 [SMILES: CCOC(=O)c1c(-c2nccnc2C)nn2c(=O)cc(-c3ccc(CC(C)(C)C)cc3)[nH]c12]

A mixture of Xphos Pd $G_2$ (47 mg, 0.06 mmol), ethyl 5-chloro-2-(3-methylpyrazin-2-yl)-7-oxo-4,7-dihydropyrazolo[1,5-a]pyrimidine-3-carboxylate (200 mg, 0.60 mmol), 4,4,5,5-tetramethyl-2-(4-neopentylphenyl)-1,3,2-dioxaborolane (328 mg, 1.2 mmol), $Na_2CO_3$ (190 mg, 1.8 mmol) and Xphos (29 mg, 0.06 mmol) in DMSO (8 mL) and water (1.5 mL) was stirred at 110° C. for 16 hours under a nitrogen atmosphere. The solution was diluted with water (50 mL), extracted with EtOAc (30 mL×2) and washed with water (50 mL×3). The organic layer was dried over anhydrous sodium sulfate, filtered and concentrated in vacuo. The residue was purified by silica gel column chromatography (0-5% MeOH in DCM) to afford the title compound (120 mg, 45%) as a yellow solid. $^1$H NMR (400 MHz, DMSO-$d_6$) δ 11.67 (s, 1H), 8.64 (d, J=2.0 Hz, 1H), 8.60 (d, J=2.0 Hz, 1H), 7.78 (d, J=8.0 Hz, 2H), 7.36 (d, J=8.0 Hz, 2H), 6.35 (s, 1H), 4.11 (q, J=7.2 Hz, 2H), 2.59 (s, 2H), 2.42 (s, 3H), 1.07 (t, J=7.2 Hz, 3H), 0.92 (s, 9H); LCMS (ESI): m/z 446.2 $(M+H)^+$.

Step 4: 2-(3-Methylpyrazin-2-yl)-5-(4-neopentylphenyl)-7-oxo-4,7-dihydropyrazolo[1,5-a]pyrimidine-3-carboxylic acid

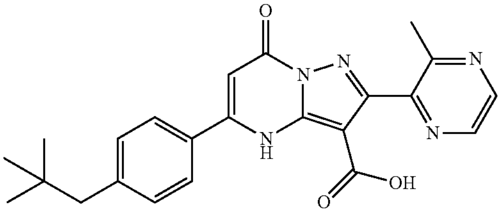 [SMILES: Cc1nccnc1-c1nn2c(=O)cc(-c3ccc(CC(C)(C)C)cc3)[nH]c2c1C(=O)O]

A mixture of lithium hydroxide monohydrate (113 mg, 2.69 mmol) and ethyl 2-(3-methylpyrazin-2-yl)-5-(4-neopentylphenyl)-7-oxo-4,7-dihydropyrazolo[1,5-a]pyrimidine-3-carboxylate (120 mg, 0.27 mmol) in water (4 mL) and ethanol (4 mL) was stirred at 80° C. for 16 hours. The reaction mixture was adjusted pH to 4 with aqueous 1 M HCl. The resulting solution was extracted with EtOAc (30 mL×2) and washed with water (20 mL). Then the organic layer was dried over anhydrous sodium sulfate, filtered and concentrated in vacuo to afford the title compound (100 mg, 89%) as a white solid. LCMS (ESI): m/z 418.2 $(M+H)^+$.

Step 5: 3-((2S,3S)-3-(fluoromethyl)-2-methylazetidine-1-carbonyl)-2-(3-methylpyrazin-2-yl)-5-(4-neopentylphenyl)pyrazolo[1,5-a]pyrimidin-7(4H)-one

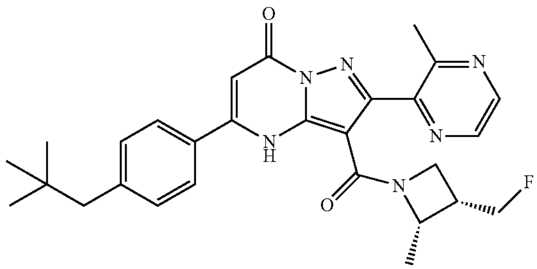 [SMILES: Cc1nccnc1-c1nn2c(=O)cc(-c3ccc(CC(C)(C)C)cc3)[nH]c2c1C(=O)N1C[C@H](CF)[C@@H]1C]

To a solution of 2-(3-methylpyrazin-2-yl)-5-(4-neopentylphenyl)-7-oxo-4,7-dihydro pyrazolo[1,5-a]pyrimidine-3- carboxylic acid (100 mg, 0.24 mmol) and HATU (136 mg, 0.36 mmol) in DMF (3 mL) was added DIPEA (0.1 mL, 0.64 mmol), then stirred for 20 min. (2S,3S)-3-(Fluoromethyl)-2-methyl-azetidine 2,2,2-trifluoroacetate (78 mg, 0.36 mmol) was added and then the reaction solution was stirred for a further 2 hours. The solution was quenched with water (50 mL), extracted with EtOAc (30 mL×2) and washed with water (50 mL×2). The organic layer was dried over anhydrous sodium sulfate, filtered and concentrated in vacuo. The residue was purified by pre-HPLC (water (0.2% FA)-MeCN, 56-86%, Xtimate C18 150*40 mm*10 um) followed by preparative SFC (Phenomenex-Amylose-1 (250 mm*30 mm, 5 um), 0.1% $NH_3H_2O$/EtOH, 30%-30%) to afford the title compound (42.5 mg, 35%) as a white solid. $^1H$ NMR (400 MHz, DMSO-$d_6$): δ 12.49 (s, 1H), 8.64 (d, J=2.4 Hz, 1H), 8.62 (d, J=2.4 Hz, 1H), 7.74 (d, J=8.0 Hz, 2H), 7.36 (d, J=8.0 Hz, 2H), 6.19 (s, 1H), 4.67-3.80 (m, 5H), 3.00-2.80 (m, 1H), 2.71 (s, 3H), 2.58 (s, 2H), 1.22 (br s, 3H), 0.91 (s, 9H); LCMS (ESI): m/z 503.2 $(M+H)^+$.

Example 63

Preparation of (S)-5-(4-cyclohexylphenyl)-3-(3-(fluoromethyl)azetidine-1-carbonyl)-2-(morpholin-2-yl)pyrazolo[1,5-a]pyrimidin-7(4H)-one and (R)-5-(4-cyclohexylphenyl)-3-(3-(fluoromethyl)azetidine-1-carbonyl)-2-(morpholin-2-yl)pyrazolo[1,5-a]pyrimidin-7(4H)-one

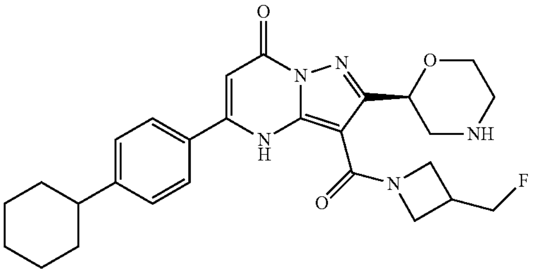

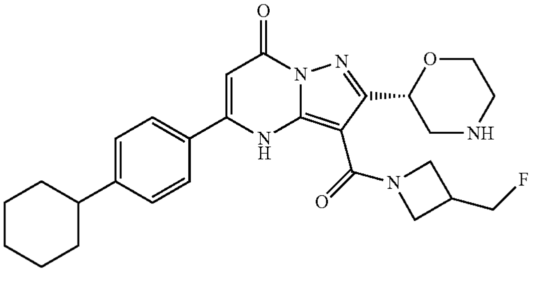

Step 1: Tert-butyl 2-(5-(4-cyclohexylphenyl)-3-(3-(fluoromethyl)azetidine-1-carbonyl)-7-oxo-4,7-dihydropyrazolo[1,5-a]pyrimidin-2-yl)morpholine-4-carboxylate

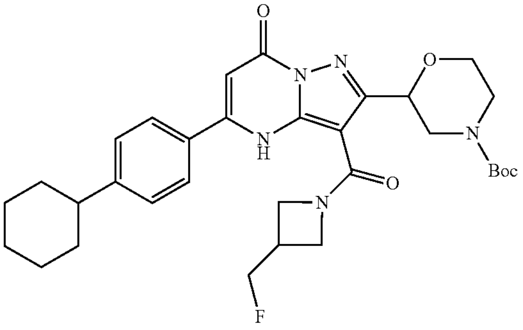 [SMILES: CC(C)(C)OC(=O)N1CCOC(c2nn3c(=O)cc(-c4ccc(C5CCCCC5)cc4)[nH]c3c2C(=O)N2CC(CF)C2)C1]

In a glovebox, a vial was charged with a solution of $(Ir[dF(CF_3)ppy]_2(dtbpy))PF_6$ (11 mg, 0.01 mmol), 2-bromo-5-(4-cyclohexylphenyl)-3-[3-(fluoromethyl)azetidine-1-carbonyl]-4H-pyrazolo[1,5-a]pyrimidin-7-one (500 mg, 1.03 mmol), 4-tert-butoxycarbonyl morpholine-2-carboxylic acid (711 mg, 3.08 mmol), $Cs_2CO_3$ (1 g, 3.08 mmol) and anhydrous DMF (10 mL). Meanwhile, a second vial was charged with nickel chloride dimethoxyethane adduct (22 mg, 0.10 mmol) and 4,4'-di-tert-butyl-2,2'-dipyridyl (41 mg, 0.15 mmol) in DMF (2 mL) was then added. This resulted in the formation of a green active Ni catalyst solution. The nickel solution was syringed out and transferred to the first vial. The reaction vial was sealed and taken out from the glove box. The reaction mixture was then stirred at 25° C. and irradiated with a 34 W blue LED and a cooling fan for 36 hours. The reaction was then filtered, diluted with water (50 mL), extracted EtOAc (50 mL×3) and concentrated in vacuo. The crude organic residue was purified by silica gel chromatography (5% MeOH in dichloromethane) to afford the crude title compound (200 mg, about 20% purity). The crude product was used for next step directly without further purification. LCMS (ESI): m/z 538.2 $(M+H)^+$.

Step 2: 5-(4-Cyclohexylphenyl)-3-(3-(fluoromethyl)azetidine-1-carbonyl)-2-(morpholin-2-yl)pyrazolo[1,5-a]pyrimidin-7(4H)-one

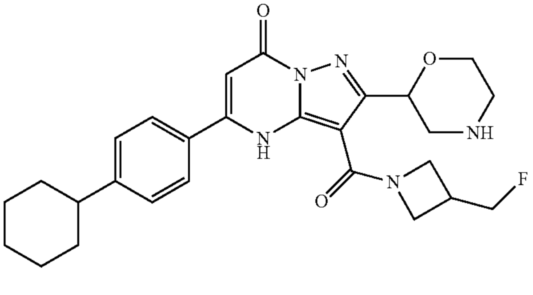

The resulting tert-butyl 2-[5-(4-cyclohexylphenyl)-3-[3-(fluoromethyl)azetidine-1-carbonyl]-7-oxo-4H-pyrazolo[1,5-a]pyrimidin-2-yl]morpholine-4-carboxylate (600 mg) in MeOH (30 mL) was added 4 M hydrochloric acid (30 mL, 120 mmol) in MeOH. The reaction mixture was stirred at 25° C. for 2 hours. The reaction mixture was basified with aqueous 1 M NaOH to pH 8, extracted with EtOAc (30 mL×3). Combined organic layers were dried over anhydrous sodium sulfate, filtered and concentrated. The residue was purified by column (0-30% MeOH in DCM) to afford crude product (500 mg). The crude product was further purified by pre-HPLC (Xtimate C18 150*25 mm*5 um, water (0.225% FA)-ACN, 25%-55%) to afford the title compound (30 mg, 2% over 2 steps) as a yellow solid.

Step 3: (S)-5-(4-cyclohexylphenyl)-3-(3-(fluoromethyl)azetidine-1-carbonyl)-2-(morpholin-2-yl)pyrazolo[1,5-a]pyrimidin-7(4H)-one and (R)-5-(4-cyclohexylphenyl)-3-(3-(fluoromethyl)azetidine-1-carbonyl)-2-(morpholin-2-yl)pyrazolo[1,5-a]pyrimidin-7(4H)-one

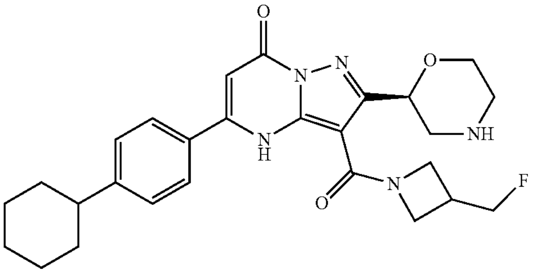

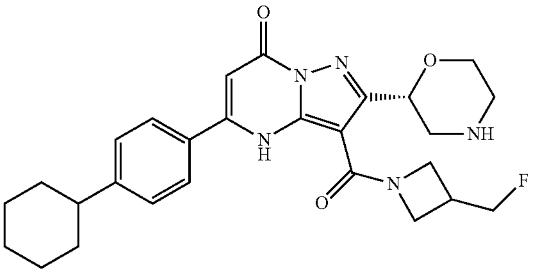 [SMILES: O=C(c1c(C2CNCCO2)nn2c(=O)cc(-c3ccc(C4CCCCC4)cc3)[nH]c12)N1CC(CF)C1]

5-(4-Cyclohexylphenyl)-3-[3-(fluoromethyl)azetidine-1-carbonyl]-2-morpholin-2-yl-4H-pyrazolo[1,5-a]pyrimidin-7-one (30 mg, 0.06 mmol) was separated by SFC (daicel chiralpak ig (250 mm*50 mm, 10 um), 0.1% $NH_3H_2O$ EtOH, 50%) to afford Enantiomer A (8.7 mg, 29%, the first peak on SFC) and Enantiomer B (10.9 mg, 36%, the second peak on SFC) both as white solid.

Enantiomer A: $^1$H NMR (400 MHz, DMSO-$d_6$): δ 7.97 (d, J=6.8 Hz, 2H), 7.28 (d, J=6.8 Hz, 2H), 6.14 (s, 1H), 5.39-5.37 (m, 1H), 4.76-4.44 (m, 6H), 4.20-4.03 (m, 2H), 3.82-3.76 (m, 2H), 3.54-3.43 (m, 2H), 3.13-3.09 (m, 1H), 2.96-2.94 (m, 1H), 1.84-1.79 (m, 4H), 1.73-1.69 (m, 1H), 1.52-1.32 (m, 4H), 1.27-1.24 (m, 1H); LCMS (ESI): m/z 494.3 $(M+H)^+$.

Enantiomer B: $^1$H NMR (400 MHz, DMSO-$d_6$): δ 7.97 (d, J=6.8 Hz, 2H), 7.28 (d, J=6.8 Hz, 2H), 6.12 (s, 1H), 5.40-5.37 (m, 1H), 4.75-4.38 (m, 6H), 4.20-4.02 (m, 2H), 3.80-3.75 (m, 2H), 3.50-3.43 (m, 2H), 3.14-3.09 (m 1H), 2.95-2.94 (m, 1H), 1.84-1.79 (m, 4H), 1.73-1.69 (m, 1H), 1.48-1.32 (m, 4H), 1.31-1.27 (m, 1H); LCMS (ESI): m/z 494.3 $(M+H)^+$.

Abbreviations

AcOH Acetic acid
$Cs_2CO_3$ Cesium carbonate
DCE 1,2-Dichloroethane
DCM Dichloromethane
DIAD Diisopropyl azodicarboxylate
DMF N,N-Dimethylformamide
DMSO Dimethyl sulfoxide
EtOAc Ethyl acetate
EtOH Ethanol
HATU 1-[Bis(dimethylamino)methylene]-1H-1,2,3-triazolo[4,5-b]pyridinium 3-oxid hexafluorophosphate
HCl Hydrochloric acid
$H_2O$ Water
KOAc Potassium acetate
MeOH Methanol
NaH Sodium hydride
$NaHCO_3$ Sodium bicarbonate
$Na_2CO_3$ Sodium carbonate
$Na_2SO_3$ Sodium sulfite
$Na_2SO_4$ Sodium sulfate
NBS N-bromosuccinimide
p-TsOH·$H_2O$ p-Toluenesulfonic acid monohydrate
Pd(dppf)$Cl_2$ 1,1'-Bis(diphenylphosphino)ferrocene palladium(II) dichloride
$PPh_3$ Triphenylphosphine
THF Tetrahydrofuran Example 64

Purified His-tagged TEAD protein (YAP Binding Domain, amino acids 217-447) is pre-incubated with Europium labelled anti-His antibody tracer (Perkin Elmer Cat #AD0110). Small molecule Inhibitors are then incubated with the TEAD-Eu protein complex for 30 minutes to allow for binding to TEAD protein. Biotinylated YAP peptide for TEAD-YAP assays (AA's 50-100) or biotinylated TAZ peptide for TEAD-TAZ assays (AA's 13-57) that has been pre-incubated with streptavidin-xl665 acceptor (CIS-Bio Cat #610SAXAC) or is added to the compound-TEAD mix. The TEAD-YAP-inhibitor mixture is then incubated for 60 minutes at room temperature. All reactions are carried out in a polystyrene plate. After 60 minutes, the plate is read on a plate reader using TR-FRET mode with wavelengths of 665 nm/615 nm. If YAP or TAZ binds to TEAD as expected, a TR-FRET signal results from the proximity of YAP or TAZ and TEAD after binding. If an inhibitor such as peptide 17 (Selleckchem Cat #58164) interferes with YAP-TEAD or TAZ-TEAD binding, the disruption of the YAP or TAZ: TEAD interaction results in a decrease in TR-FRET signal. The potency of compounds as YAP:TEAD or TAZ:TEAD protein-protein interaction (PPi) inhibitors is determined by an $IC_{50}$ or $EC_{50}$ value generated using a non-linear four parameter curve fit. The extent to which representative examples of the disclosed compounds are able to inhibit interaction between TEAD1, TEAD2, TEAD3 or TEAD4 and YAP truncated from amino acids 50-100 or TAZ truncated from amino acids 13-57 as measured by Homogeneous Time Resolved Fluorescence (HTRF) to generate $EC_{50}$ data is provided in Table 3 below.

Biological Data

TABLE 3

| Compound number | TEAD1 YAP50-100 HTRF combined: Max % Inhibition | TEAD2 YAP50-100 HTRF combined: Max % Inhibition | TEAD3 YAP50-100 HTRF combined: Max % Inhibition | TEAD4 YAP50-100 HTRF combined: Max % Inhibition |
|---|---|---|---|---|
| 1 | 70.0 | 74.4 | 75.3 | 55.3 |
| 2 | 62.0 | 68.0 | 60.5 | 51.5 |

TABLE 3-continued

| Compound number | TEAD1 YAP50-100 HTRF combined: Max % Inhibition | TEAD2 YAP50-100 HTRF combined: Max % Inhibition | TEAD3 YAP50-100 HTRF combined: Max % Inhibition | TEAD4 YAP50-100 HTRF combined: Max % Inhibition |
|---|---|---|---|---|
| 3 | 55.0 | 56.5 | 66.5 | 39.5 |
| 4 | 69.0 | 64.0 | 69.0 | 48.5 |
| 5 | 73.0 | 83.0 | 75.5 | 56.0 |
| 6 | 73.0 | 69.5 | 71.5 | 17.0 |
| 7 | 78.0 | 61.0 | 71.0 | 54.0 |
| 8 | 77.0 | 51.0 | 69.5 | 45.5 |
| 9 | 71.0 | 62.0 | 62.0 | 52.0 |
| 10 | 77.0 | 67.0 | 70.5 | 60.5 |
| 11 | 74.0 | 63.5 | 68.5 | 48.0 |
| 12 | 72.0 | 69.0 | 66.0 | 55.0 |
| 13 | 74.0 | 65.0 | 71.5 | 50.0 |
| 14 | 73.0 | 62.5 | 61.0 | 50.0 |
| 15 | 74.0 | 64.8 | 64.0 | 50.5 |
| 16 | 70.0 | 57.5 | 55.0 | 40.5 |
| 17 | 69.0 | 61.6 | 63.3 | 42.0 |
| 18 | 73.0 | 58.5 | 54.5 | 47.0 |
| 19 | 69.0 | 67.5 | 60.0 | 46.0 |
| 20 | 72.0 | 53.5 | 65.5 | 37.0 |
| 21 | 74.0 | 62.5 | 69.5 | 49.5 |
| 22 | 69.0 | 58.0 | 60.0 | 45.5 |
| 23 | 70.0 | 55.5 | 64.0 | 39.5 |
| 24 | 63.0 | 66.0 | 52.0 | 51.0 |
| 25 | 60.0 | 63.5 | 50.0 | 45.5 |
| 26 | 71.0 | 70.0 | 66.0 | 44.5 |
| 27 | 75.0 | 68.6 | 74.6 | 54.1 |
| 28 | 76.0 | 59.5 | 68.0 | 43.5 |
| 29 | 78.0 | 70.0 | 72.5 | 54.0 |
| 30 | 71.0 | 61.5 | 65.0 | 45.0 |
| 31 | 65.0 | 62.0 | 59.0 | 36.0 |
| 32 | 65.0 | 61.5 | 61.0 | 38.5 |
| Enantiomer A, Example 33 | 71.0 | 67.5 | 71.5 | 48.5 |
| Enantiomer B, Example 33 | 72.0 | 72.0 | 69.0 | 49.0 |
| 35 | 72.0 | 71.5 | 68.0 | 52.5 |
| 36 | 70.0 | 73.5 | 71.0 | 48.0 |
| 37 | 66.0 | 54.5 | 64.0 | 27.5 |
| 38 | 64.0 | 61.5 | 65.0 | 41.0 |
| 39 | 65.0 | 62.0 | 61.5 | 34.5 |
| Isomer A, Example 39 | 76.0 | 76.0 | 71.0 | 51.5 |
| Isomer B, Example 39 | 62.0 | 17.5 | 67.0 | 46.0 |
| Isomer A, Example 40 | 75.0 | 76.0 | 68.5 | 53.5 |
| Isomer B, Example 40 | 76.0 | 68.0 | 68.0 | 49.5 |
| Isomer A, Example 41 | 69.0 | 26.0 | 74.0 | 51.0 |
| Isomber B, Example 41 | 80.0 | 77.8 | 80.2 | 57.2 |
| Isomer A, Example 42 | 64.0 | 45.0 | 69.5 | 48.5 |
| Isomer B, Example 42 | 68.0 | 68.0 | 68.0 | 52.5 |
| Isomer A, Example 43 | 64.0 | 71.0 | 58.5 | 52.0 |
| Isomer B, Example 43 | 65.0 | 73.0 | 66.0 | 51.0 |
| Isomer A, Example 44 | 64.0 | 52.0 | 65.5 | 40.0 |
| Isomer B, Example 44 | 69.0 | 70.0 | 61.5 | 50.5 |
| 52 | 70.0 | 68.0 | 57.0 | 66.0 |
| 53 | 72.0 | 64.5 | 58.5 | 65.5 |
| 54 | 71.0 | 59.0 | 56.5 | 60.5 |
| 55 | 72.0 | 56.5 | 62.0 | 44.5 |
| 56 | 57.0 | 61.0 | 49.5 | 33.0 |
| 57 | 56.0 | 51.0 | 53.0 | 35.0 |
| 58 | 71.0 | 63.0 | 64.5 | 59.0 |
| 59 | 68.0 | 61.5 | 65.5 | 40.0 |
| 60 | 80.0 | 66.5 | 78.0 | 60.0 |
| Final product obtained using Enantiomer A from Step 4, Example 54 | 59.0 | 65.0 | 71.5 | 47.5 |
| Final product obtained using Enantiomer B from Step 4, Example 54 | 59.0 | 62.0 | 73.0 | 49.0 |
| Enantiomer A, Example 55 | 62.0 | 61.5 | 69.5 | 42.0 |
| Enantiomer B, Example 55 | 71.0 | 64.0 | 61.5 | 36.5 |
| Final product obtained using Enantiomer A from Step 1, Example 56 | 74.0 | 92.0 | 81.5 | 69.5 |
| Final product obtained using Enantiomer B from Step 1, Example 56 | 66.0 | 83.5 | 71.0 | 59.5 |
| 67 | 69.0 | 92.5 | 79.0 | 72.5 |
| 68 | 65.0 | 84.0 | 67.5 | 64.5 |
| 69 | 79.0 | 76.0 | 80.0 | 62.5 |
| 70 | 58.0 | 67.0 | 64.0 | 58.0 |
| 71 | 53.0 | 64.0 | 61.0 | 48.5 |
| 72 | 77.0 | 73.0 | 76.0 | 54.0 |
| 73 | 74.0 | 67.0 | 69.5 | 58.5 |
| Enantiomer A, Example 63 | 66.0 | 66.0 | 62.0 | 40.0 |
| Enantiomer B, Example 63 | 62.0 | 62.5 | 59.5 | 35.0 |

TABLE 4

| Compound Number | TEAD1 YAP50-100 HTRF combined: $EC_{50}$ (μM) | TEAD2 YAP50-100 HTRF combined: $EC_{50}$ (μM) | TEAD3 YAP50-100 HTRF combined: $EC_{50}$ (μM) | TEAD4 YAP50-100 HTRF combined: $EC_{50}$ (μM) |
|---|---|---|---|---|
| 1 | 0.09 | 0.01 | 0.11 | 0.33 |
| 2 | 0.06 | 0.01 | 0.12 | 0.47 |
| 3 | 0.06 | 0.01 | 0.23 | 0.21 |
| 4 | 0.04 | 0.01 | 0.07 | 0.20 |
| 5 | 0.08 | 0.01 | 0.13 | 0.25 |
| 6 | 0.41 | 0.71 | 4.95 | 19.50 |
| 7 | 0.20 | 0.04 | 0.35 | 0.26 |
| 8 | 0.08 | 0.02 | 0.11 | 0.47 |
| 9 | 0.03 | 0.01 | 0.08 | 0.03 |
| 10 | 0.06 | 0.01 | 0.12 | 0.67 |
| 11 | 0.07 | 0.02 | 0.12 | 1.05 |
| 12 | 0.14 | 0.02 | 0.19 | 0.20 |
| 13 | 0.08 | 0.02 | 0.18 | 0.21 |
| 14 | 0.03 | 0.01 | 0.09 | 0.06 |
| 15 | 0.03 | 0.01 | 0.07 | 0.03 |
| 16 | 0.06 | 0.01 | 0.08 | 0.02 |
| 17 | 0.03 | 0.01 | 0.06 | 0.04 |
| 18 | 0.05 | 0.01 | 0.09 | 0.02 |
| 19 | 0.04 | 0.01 | 0.06 | 0.06 |
| 20 | 0.05 | 0.02 | 0.05 | 0.82 |
| 21 | 0.04 | 0.01 | 0.08 | 0.03 |
| 22 | 0.14 | 0.02 | 0.21 | 0.07 |
| 23 | 0.04 | 0.01 | 0.11 | 0.05 |

TABLE 4-continued

| Compound Number | TEAD1 YAP50-100 HTRF combined: $EC_{50}$ (μM) | TEAD2 YAP50-100 HTRF combined: $EC_{50}$ (μM) | TEAD3 YAP50-100 HTRF combined: $EC_{50}$ (μM) | TEAD4 YAP50-100 HTRF combined: $EC_{50}$ (μM) |
|---|---|---|---|---|
| 24 | 0.02 | 0.00 | 0.02 | 0.01 |
| 25 | 0.03 | 0.01 | 0.04 | 0.02 |
| 26 | 0.06 | 0.03 | 0.14 | 0.34 |
| 27 | 0.03 | 0.01 | 0.10 | 0.03 |
| 28 | 0.04 | 0.02 | 0.10 | 0.13 |
| 29 | 0.06 | 0.02 | 0.18 | 0.03 |
| 30 | 0.07 | 0.01 | 0.09 | 0.18 |
| 31 | 0.08 | 0.02 | 0.17 | 0.78 |
| 32 | 0.05 | 0.01 | 0.06 | 0.38 |
| Enantiomer A, Example 33 | 0.07 | 0.02 | 0.18 | 0.46 |
| Enantiomer B, Example 33 | 0.08 | 0.02 | 0.15 | 0.67 |
| 35 | 0.07 | 0.02 | 0.13 | 0.18 |
| 36 | 0.07 | 0.02 | 0.18 | 1.02 |
| 37 | 0.10 | 0.02 | 0.15 | 0.22 |
| 38 | 0.21 | 0.03 | 0.22 | 0.20 |
| 39 | 0.05 | 0.02 | 0.06 | 0.65 |
| Isomer A, Example 39 | 0.06 | 0.01 | 0.12 | 0.06 |
| Isomer B, Example 39 | 0.17 | 0.17 | 2.45 | 6.45 |
| Isomer A, Example 40 | 0.06 | 0.01 | 0.14 | 0.03 |
| Isomer B, Example 40 | 0.13 | 0.08 | 0.44 | 2.00 |
| Isomer A, Example 41 | 0.15 | 0.06 | 0.53 | 5.50 |
| Isomer B, Example 41 | 0.08 | 0.02 | 0.12 | 0.03 |
| Isomer A, Example 42 | 0.08 | 0.02 | 0.32 | 4.85 |
| Isomer B, Example 42 | 0.04 | 0.01 | 0.08 | 0.02 |
| Isomer A, Example 43 | 0.03 | 0.01 | 0.06 | 0.01 |
| Isomer B, Example 43 | 0.05 | 0.02 | 0.14 | 0.37 |
| Isomer A, Example 44 | 0.06 | 0.04 | 1.05 | 9.35 |
| Isomer B, Example 44 | 0.03 | 0.01 | 0.05 | 0.02 |
| 52 | 0.05 | 0.02 | 0.15 | 0.18 |
| 53 | 0.05 | 0.02 | 0.11 | 0.05 |
| 54 | 0.05 | 0.02 | 0.08 | 0.04 |
| 55 | 0.26 | 0.06 | 0.20 | 0.14 |
| 56 | 0.06 | 0.01 | 0.10 | 0.03 |
| 57 | 0.08 | 0.02 | 0.10 | 0.07 |
| 58 | 0.04 | 0.01 | 0.09 | 0.18 |
| 59 | 0.16 | 0.03 | 0.29 | 0.18 |
| 60 | 0.03 | 0.01 | 0.20 | 0.61 |
| Final product obtained using Enantiomer A from Step 4, Example 54 | 0.13 | 0.04 | 0.25 | 0.55 |
| Final product obtained using Enantiomer B from Step 4, Example 54 | 0.11 | 0.04 | 0.22 | 1.50 |
| Enantiomer A, Example 55 | 0.08 | 0.01 | 0.10 | 0.50 |
| Enantiomer B, Example 55 | 0.08 | 0.01 | 0.08 | 0.20 |
| Final product obtained using Enantiomer A from Step 1, Example 56 | 0.37 | 0.06 | 0.37 | 2.70 |

TABLE 4-continued

| Compound Number | TEAD1 YAP50-100 HTRF combined: $EC_{50}$ (μM) | TEAD2 YAP50-100 HTRF combined: $EC_{50}$ (μM) | TEAD3 YAP50-100 HTRF combined: $EC_{50}$ (μM) | TEAD4 YAP50-100 HTRF combined: $EC_{50}$ (μM) |
|---|---|---|---|---|
| Final product obtained using Enantiomer B from Step 1, Example 56 | 0.43 | 0.08 | 0.83 | 2.85 |
| 67 | 0.19 | 0.05 | 0.18 | 4.25 |
| 68 | 0.19 | 0.06 | 0.51 | 5.55 |
| 69 | 0.04 | 0.01 | 0.11 | 0.17 |
| 70 | 0.01 | 0.00 | 0.04 | 1.30 |
| 71 | 0.05 | 0.01 | 0.06 | 3.45 |
| 72 | 0.07 | 0.02 | 0.16 | 0.03 |
| 73 | 0.12 | 0.02 | 0.15 | 0.10 |
| Enantiomer A, Example 63 | 0.14 | 0.04 | 0.18 | 1.60 |
| Enantiomer B, Example 63 | 0.09 | 0.04 | 0.15 | 1.09 |

TABLE 5

| Compound Number | TEAD1 TAZ HTRF combined: Max % Inhibition | TEAD2 TAZ HTRF combined: Max % Inhibition | TEAD3 TAZ HTRF combined: Max % Inhibition | TEAD4 TAZ HTRF combined: Max % Inhibition |
|---|---|---|---|---|
| 1 | 61.2 | 69.2 | 63.0 | 40.3 |
| 2 | 47.0 | 66.5 | 44.0 | 42.0 |
| 3 | 44.0 | 55.0 | 44.0 | 29.0 |
| 4 | 59.0 | 64.5 | 59.0 | 36.0 |
| 5 | 62.0 | 78.5 | 66.5 | 41.0 |
| 6 | 70.5 | 67.5 | 64.5 | 14.0 |
| 7 | 74.0 | 67.0 | 61.0 | 50.0 |
| 8 | 71.0 | 54.0 | 61.0 | 44.5 |
| 9 | 69.5 | 63.0 | 52.5 | 56.0 |
| 10 | 72.0 | 65.0 | 61.5 | 62.0 |
| 11 | 69.0 | 63.0 | 61.0 | 48.5 |
| 12 | 67.5 | 64.5 | 56.0 | 58.0 |
| 13 | 66.5 | 60.0 | 56.5 | 40.0 |
| 14 | 74.0 | 67.5 | 52.5 | 53.5 |
| 15 | 64.0 | 62.0 | 55.8 | 49.0 |
| 16 | 59.5 | 53.5 | 44.5 | 38.0 |
| 17 | 60.6 | 60.9 | 53.9 | 34.9 |
| 18 | 67.0 | 55.5 | 43.0 | 49.0 |
| 19 | 59.5 | 63.5 | 53.0 | 38.5 |
| 20 | 63.0 | 50.5 | 56.5 | 34.5 |
| 21 | 71.5 | 61.5 | 69.5 | 51.0 |
| 22 | 64.0 | 57.5 | 57.0 | 48.0 |
| 23 | 61.5 | 55.5 | 56.5 | 35.0 |
| 24 | 57.0 | 66.5 | 43.0 | 54.0 |
| 25 | 52.0 | 62.0 | 44.0 | 47.0 |
| 26 | 70.0 | 72.5 | 60.0 | 45.5 |
| 27 | 74.5 | 67.9 | 64.9 | 53.1 |
| 28 | 74.0 | 66.5 | 63.0 | 41.0 |
| 29 | 71.5 | 70.0 | 57.5 | 50.5 |
| 30 | 64.5 | 61.5 | 51.5 | 31.5 |
| 31 | 60.5 | 60.5 | 49.5 | 32.0 |
| 32 | 59.5 | 59.0 | 49.5 | 31.0 |
| Enantiomer A, Example 33 | 61.5 | 63.0 | 58.5 | 41.5 |
| Enantiomer B, Example 33 | 64.0 | 68.0 | 58.5 | 37.5 |
| 35 | 59.0 | 71.5 | 57.0 | 37.0 |
| 36 | 60.5 | 73.5 | 60.0 | 38.0 |
| 37 | 50.0 | 50.0 | 55.0 | 16.5 |
| 38 | 47.5 | 64.0 | 61.0 | 37.5 |
| 39 | 37.5 | 56.5 | 53.5 | 18.0 |
| Isomer A, Example 39 | 69.5 | 77.0 | 69.5 | 58.0 |

TABLE 5-continued

| Compound Number | TEAD1 TAZ HTRF combined: Max % Inhibition | TEAD2 TAZ HTRF combined: Max % Inhibition | TEAD3 TAZ HTRF combined: Max % Inhibition | TEAD4 TAZ HTRF combined: Max % Inhibition |
|---|---|---|---|---|
| Isomer B, Example 39 | 55.0 | 37.0 | 68.0 | 49.5 |
| Isomer A, Example 40 | 64.5 | 70.5 | 63.0 | 53.0 |
| Isomer B, Example 40 | 70.0 | 78.5 | 70.0 | 51.0 |
| Isomer A, Example 41 | 53.5 | 35.0 | 70.0 | 51.5 |
| Isomer B, Example 41 | 71.0 | 74.4 | 73.8 | 57.0 |
| Isomer A, Example 42 | 49.0 | 57.0 | 66.0 | 20.0 |
| Isomer B, Example 42 | 59.0 | 62.0 | 60.0 | 48.5 |
| Isomer A, Example 43 | 54.5 | 63.0 | 52.0 | 52.0 |
| Isomer B, Example 43 | 60.0 | 71.5 | 65.5 | 50.0 |
| Isomer A, Example 44 | 52.0 | 56.5 | 64.0 | 42.0 |
| Isomer B, Example 44 | 59.5 | 67.5 | 56.0 | 52.0 |
| 52 | 62.0 | 69.0 | 48.0 | 58.0 |
| 53 | 62.5 | 67.0 | 46.0 | 51.5 |
| 54 | 63.0 | 59.5 | 45.0 | 56.0 |
| 55 | 67.0 | 60.0 | 55.0 | 39.5 |
| 56 | 57.0 | 60.0 | 43.0 | 35.0 |
| 57 | 46.5 | 53.5 | 50.5 | 54.5 |
| 58 | 70.5 | 66.5 | 58.5 | 68.5 |
| 59 | 65.5 | 61.0 | 59.0 | 42.5 |
| 60 | 78.5 | 66.5 | 74.0 | 64.0 |
| Final product obtained using Enantiomer A from Step 4, Example 54 | 41.5 | 71.0 | 73.0 | 44.5 |
| Final product obtained using Enantiomer B from Step 4, Example 54 | 40.0 | 67.0 | 74.0 | 50.5 |
| Enantiomer A, Example 55 | 44.0 | 51.5 | 59.5 | 32.0 |
| Enantiomer B, Example 55 | 45.5 | 57.0 | 53.5 | 27.0 |
| Final product obtained using Enantiomer A from Step 1, Example 56 | 63.0 | 89.0 | 74.5 | 67.0 |
| Final product obtained using Enantiomer B from Step 1, Example 56 | 60.5 | 77.0 | 68.0 | 53.0 |
| 67 | 65.0 | 89.0 | 71.0 | 71.5 |
| 68 | 63.0 | 75.5 | 64.5 | 61.5 |
| 69 | 73.5 | 75.5 | 75.5 | 65.5 |
| 70 | 54.5 | 66.0 | 52.5 | 63.5 |
| 71 | 52.5 | 64.0 | 49.0 | 56.5 |
| 72 | 74.0 | 75.0 | 71.5 | 56.0 |
| 73 | 65.5 | 68.5 | 59.5 | 56.0 |
| Enantiomer A, Example 63 | 55.5 | 66.0 | 55.5 | 30.5 |
| Enantiomer B, Example 63 | 52.0 | 65.0 | 52.0 | 28.0 |

TABLE 6

| Compound Number | TEAD1 TAZ HTRF combined: $EC_{50}$ (μM) | TEAD2 TAZ HTRF combined: $EC_{50}$ (μM) | TEAD3 TAZ HTRF combined: $EC_{50}$ (μM) | TEAD4 TAZ HTRF combined: $EC_{50}$ (μM) |
|---|---|---|---|---|
| 1 | 0.09 | 0.01 | 0.17 | 0.60 |
| 2 | 0.07 | 0.01 | 0.12 | 0.33 |
| 3 | 0.09 | 0.01 | 0.19 | 0.17 |
| 4 | 0.05 | 0.01 | 0.08 | 0.15 |
| 5 | 0.07 | 0.01 | 0.14 | 0.17 |
| 6 | 0.52 | 0.71 | 6.00 | 35.50 |
| 7 | 0.20 | 0.03 | 0.32 | 0.16 |
| 8 | 0.11 | 0.02 | 0.12 | 0.37 |
| 9 | 0.04 | 0.01 | 0.09 | 0.03 |
| 10 | 0.06 | 0.01 | 0.14 | 0.54 |
| 11 | 0.07 | 0.02 | 0.12 | 0.86 |
| 12 | 0.11 | 0.02 | 0.24 | 0.18 |
| 13 | 0.10 | 0.02 | 0.18 | 0.13 |
| 14 | 0.06 | 0.01 | 0.08 | 0.05 |
| 15 | 0.04 | 0.01 | 0.07 | 0.02 |
| 16 | 0.05 | 0.01 | 0.08 | 0.02 |
| 17 | 0.04 | 0.01 | 0.06 | 0.03 |
| 18 | 0.06 | 0.01 | 0.09 | 0.02 |
| 19 | 0.07 | 0.01 | 0.06 | 0.05 |
| 20 | 0.05 | 0.02 | 0.07 | 0.94 |
| 21 | 0.04 | 0.01 | 0.09 | 0.03 |
| 22 | 0.11 | 0.02 | 0.21 | 0.06 |
| 23 | 0.07 | 0.01 | 0.11 | 0.05 |
| 24 | 0.02 | 0.00 | 0.03 | 0.01 |
| 25 | 0.04 | 0.01 | 0.04 | 0.02 |
| 26 | 0.10 | 0.03 | 0.15 | 0.29 |
| 27 | 0.05 | 0.01 | 0.10 | 0.03 |
| 28 | 0.06 | 0.01 | 0.10 | 0.12 |
| 29 | 0.09 | 0.02 | 0.17 | 0.02 |
| 30 | 0.06 | 0.01 | 0.08 | 0.12 |
| 31 | 0.12 | 0.02 | 0.21 | 0.62 |
| 32 | 0.05 | 0.01 | 0.06 | 0.29 |
| Enantiomer A, Example 33 | 0.10 | 0.02 | 0.21 | 0.41 |
| Enantiomer B, Example 33 | 0.10 | 0.02 | 0.20 | 0.57 |
| 35 | 0.08 | 0.02 | 0.15 | 0.14 |
| 36 | 0.08 | 0.02 | 0.20 | 0.85 |
| 37 | 0.12 | 0.02 | 0.15 | 0.16 |
| 38 | 0.22 | 0.02 | 0.25 | 0.13 |
| 39 | 0.09 | 0.02 | 0.06 | 0.37 |
| Isomer A, Example 39 | 0.07 | 0.01 | 0.13 | 0.06 |
| Isomer B, Example 39 | 0.17 | 0.19 | 2.50 | 6.20 |
| Isomer A, Example 40 | 0.08 | 0.01 | 0.16 | 0.03 |
| Isomer B, Example 40 | 0.14 | 0.12 | 0.53 | 2.10 |
| Isomer A, Example 41 | 0.18 | 0.05 | 0.69 | 4.90 |
| Isomer B, Example 41 | 0.07 | 0.02 | 0.14 | 0.03 |
| Isomer A, Example 42 | 0.08 | 0.02 | 0.34 | 1.10 |
| Isomer B, Example 42 | 0.06 | 0.01 | 0.09 | 0.02 |
| Isomer A, Example 43 | 0.03 | 0.01 | 0.06 | 0.01 |
| Isomer B, Example 43 | 0.05 | 0.02 | 0.15 | 0.27 |
| Isomer A, Example 44 | 0.07 | 0.04 | 1.20 | 9.50 |
| Isomer B, Example 44 | 0.04 | 0.01 | 0.05 | 0.02 |
| 52 | 0.06 | 0.02 | 0.18 | 0.15 |
| 53 | 0.07 | 0.02 | 0.09 | 0.03 |
| 54 | 0.07 | 0.02 | 0.09 | 0.04 |
| 55 | 0.24 | 0.05 | 0.21 | 0.11 |
| 56 | 0.07 | 0.01 | 0.11 | 0.02 |
| 57 | 0.07 | 0.01 | 0.09 | 0.06 |
| 58 | 0.04 | 0.01 | 0.10 | 0.14 |
| 59 | 0.16 | 0.03 | 0.34 | 0.18 |

TABLE 6-continued

| Compound Number | TEAD1 TAZ HTRF combined: $EC_{50}$ (μM) | TEAD2 TAZ HTRF combined: $EC_{50}$ (μM) | TEAD3 TAZ HTRF combined: $EC_{50}$ (μM) | TEAD4 TAZ HTRF combined: $EC_{50}$ (μM) |
|---|---|---|---|---|
| 60 | 0.04 | 0.01 | 0.22 | 0.51 |
| Final product obtained using Enantiomer A from Step 4, Example 54 | 0.24 | 0.04 | 0.26 | 0.48 |
| Final product obtained using Enantiomer B from Step 4, Example 54 | 0.17 | 0.04 | 0.25 | 1.65 |
| Enantiomer A, Example 55 | 0.11 | 0.01 | 0.11 | 0.46 |
| Enantiomer B, Example 55 | 0.09 | 0.02 | 0.10 | 0.14 |
| Final product obtained using Enantiomer A from Step 1, Example 56 | 0.32 | 0.06 | 0.43 | 2.25 |
| Final product obtained using Enantiomer B from Step 1, Example 56 | 0.36 | 0.07 | 0.94 | 2.10 |
| 67 | 0.22 | 0.05 | 0.20 | 4.00 |
| 68 | 0.27 | 0.06 | 0.59 | 4.95 |
| 69 | 0.05 | 0.01 | 0.12 | 0.13 |
| 70 | 0.02 | 0.01 | 0.03 | 0.97 |
| 71 | 0.05 | 0.01 | 0.05 | 3.00 |
| 72 | 0.08 | 0.02 | 0.17 | 0.03 |
| 73 | 0.11 | 0.02 | 0.16 | 0.08 |
| Enantiomer A, Example 63 | 0.13 | 0.04 | 0.20 | 1.55 |
| Enantiomer B, Example 63 | 0.14 | 0.03 | 0.16 | 0.59 |

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

What is claimed is:

1. A compound of formula (I):

(I)

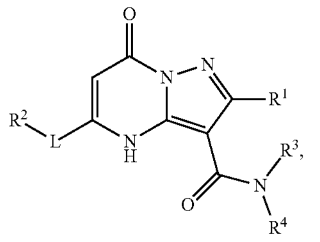

or a pharmaceutically acceptable salt, stereoisomer, tautomer, or deuterated analog thereof, wherein:

$R^1$ is selected from the group consisting of $C(O)N(R^a)(R^b)$, $C_{6-20}$aryl, 5-20 membered heteroaryl, 5-20 membered heterocyclyl, and $C_{1-6}$alkyl, wherein the $C_{6-20}$aryl, 5-20 membered heteroaryl and 5-20 membered heterocyclyl of $R^1$ are independently optionally substituted with one or more substituents selected from the group consisting of halo, OH, cyano, $C_{1-6}$alkyl, $C_{1-6}$haloalkyl, $C_{1-6}$alkoxy, $C_{3-8}$cycloalkyl, and $C_{6-10}$aryl, and wherein the $C_{1-6}$alkyl of $R^1$ is optionally substituted with one or more substituents selected from the group consisting of halogen, OH, cyano, $C_{1-6}$alkyl, $C_{1-6}$haloalkyl, $C_1$-6alkoxy, $C_{3-8}$cycloalkyl, and $C_{6-10}$aryl;

$R^a$ and $R^b$ are each independently H or $C_{1-6}$alkyl, wherein the $C_{1-6}$alkyl is optionally substituted with one or more substituents selected from the group consisting of halo, OH, cyano, $C_1$-6alkyl, $C_{1-6}$haloalkyl, and $C_{1-6}$alkoxy, or $R^a$ and $R^b$ are taken, together with the atoms to which they attached, to form a 3-10 membered heterocyclyl, wherein the 3-10 membered heterocyclyl is optionally substituted with one or more substituents selected from the group consisting of halo, OH, cyano, $C_{1-6}$alkyl, $C_{1-6}$haloalkyl, and $C_{1-6}$alkoxy;

L is absent or is $*—O—CH_2—**$, $*—CH_2—O—$, or —O—, wherein  denotes the point of attachment to the $R^2$ moiety and * denotes the point of attachment to the remainder of the molecule;

$R^2$ is $C_{2-12}$alkyl, $C_{2-12}$alkenyl, or $C_{6-10}$aryl, wherein the $C_{2-12}$alkyl, $C_{2-12}$alkenyl, and $C_{6-10}$aryl of $R^2$ are independently optionally substituted with one or more substituents selected from the group consisting of halo, OH, cyano, $C_{1-6}$alkyl, $C_{1-6}$haloalkyl, $C_{1-6}$alkoxy, $C_{6-10}$aryl, and $C_{3-10}$cycloalkyl, wherein the $C_{1-6}$alkyl, $C_{1-6}$alkoxy, and $C_{3-10}$cycloalkyl are independently optionally further substituted with one or more halo, $C_{1-6}$haloalkyl, $C_{6-10}$aryl, or $C_{3-10}$cycloalkyl; and $R^3$ and $R^4$ are each independently $C_{1-6}$alkyl, wherein the $C_{1-6}$alkyl is optionally substituted with one or more substituents selected from the group consisting of halo, OH, cyano, $C_{1-6}$alkyl, $C_1$-haloalkyl, and $C_{1-6}$alkoxy, or $R^3$ and $R^4$, together with the atoms to which they are attached, form a 3-10 membered heterocyclyl, wherein the 3-10 membered heterocyclyl is optionally substituted with one or more substituents selected from the group consisting of halo, OH, cyano, and $C_{1-6}$alkyl, wherein the $C_1$-6alkyl is further optionally substituted with one or more substituents selected from the group consisting of halo, OH, cyano, $C_{1-6}$alkyl, $C_{1-6}$haloalkyl, and $C_{1-6}$alkoxy.

2. The compound of claim 1, wherein the compound of formula (I) is a compound of formula (IA):

(IA)

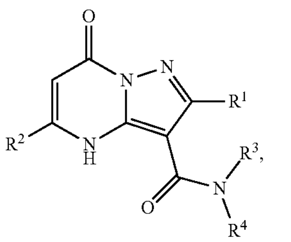

or a pharmaceutically acceptable salt, stereoisomer, tautomer, or deuterated analog thereof.

3. The compound of claim 1, wherein $R^3$ and $R^4$, together with the atoms to which they are attached, form a 3-10 membered heterocyclyl, wherein the 3-10 membered heterocyclyl is optionally substituted with one or more substituents selected from the group consisting of halo, OH, cyano and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy.

4. The compound of claim 3, wherein the compound of formula (I) is a compound of formula (IB):

(IB)

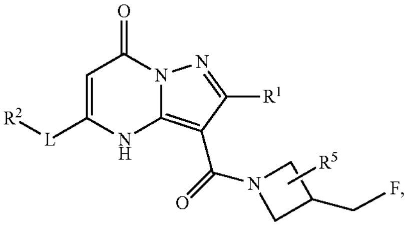

or a pharmaceutically acceptable salt, stereoisomer, tautomer, or deuterated analog thereof, wherein $R^5$ is selected from the group consisting of H, halo, OH, cyano, and $C_{1-6}$alkyl, wherein the $C_{1-6}$alkyl is further optionally substituted with one or more substituents selected from the group consisting of halo, OH, cyano, $C_{1-6}$alkyl, $C_{1-6}$haloalkyl, and $C_{1-6}$alkoxy.

5. The compound of claim 4, wherein $R^5$ is H.

6. The compound of claim 5, wherein the compound of formula (IB) is:

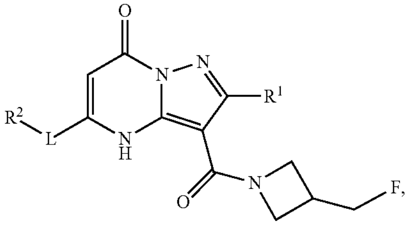

or a pharmaceutically acceptable salt, stereoisomer, tautomer, or deuterated analog thereof.

7. The compound of claim 6, wherein the compound is selected from the group consisting of:

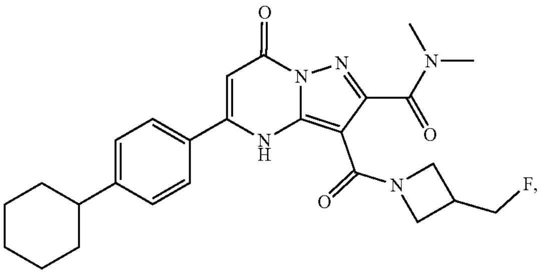

-continued

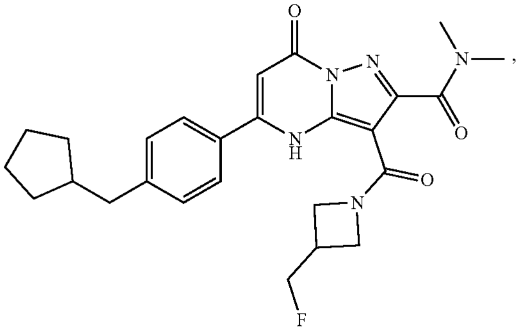

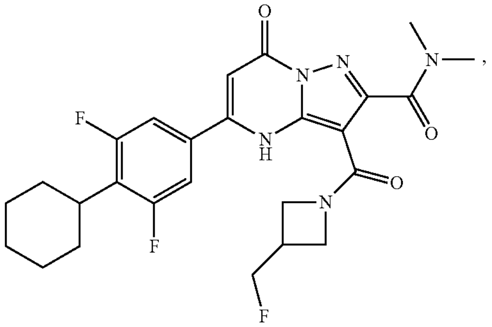

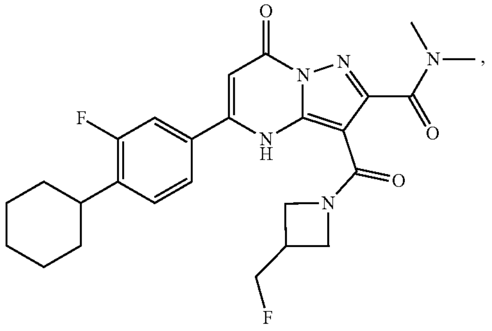

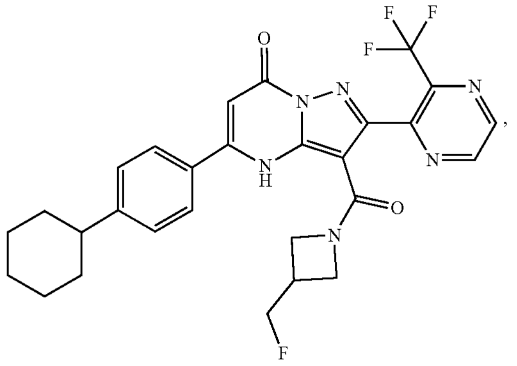

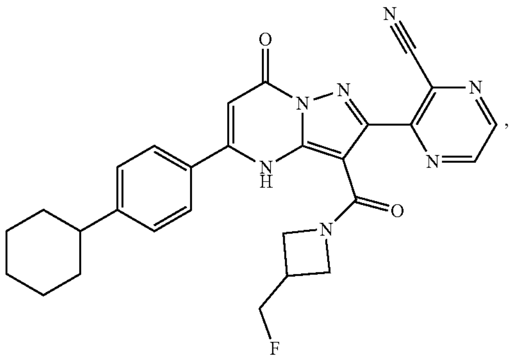

-continued
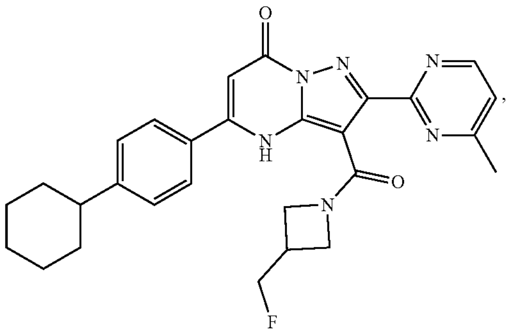
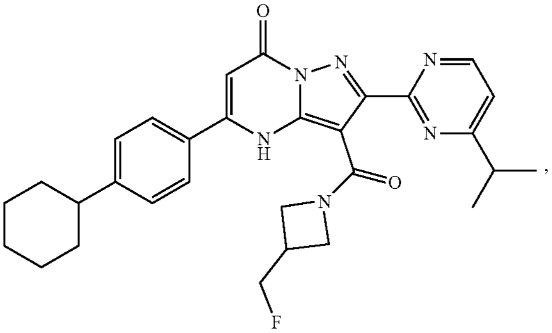
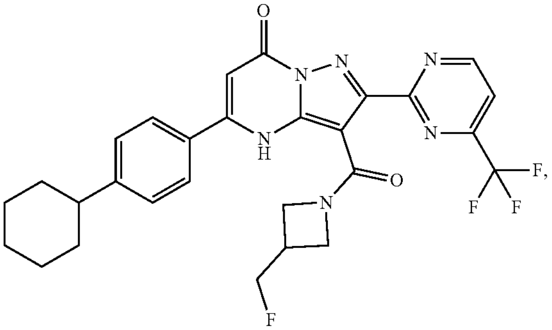
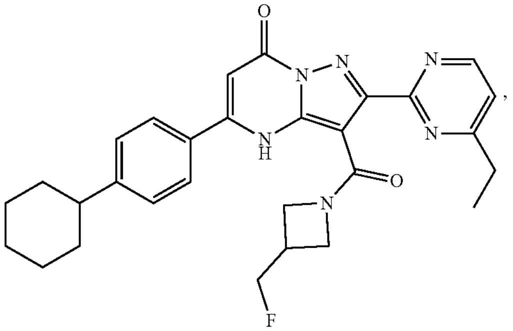
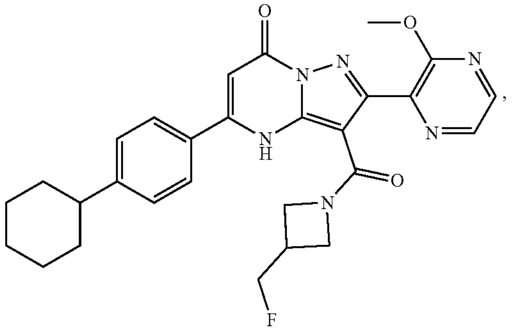
-continued
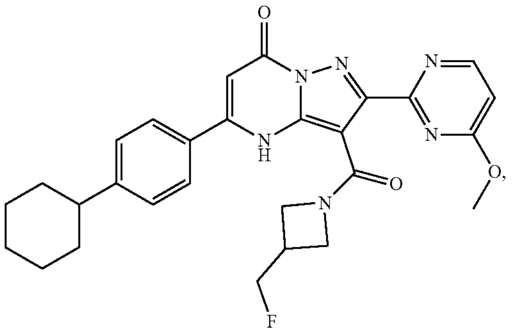
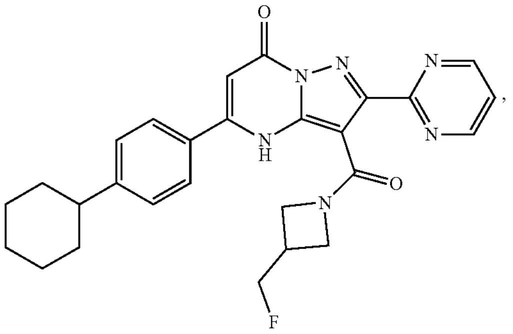
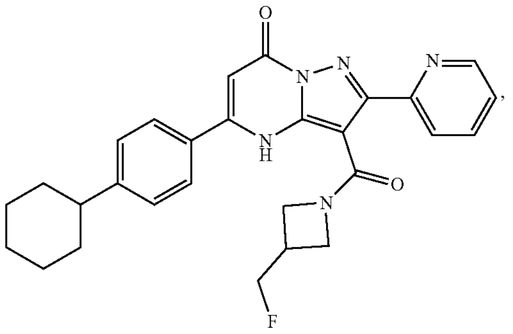
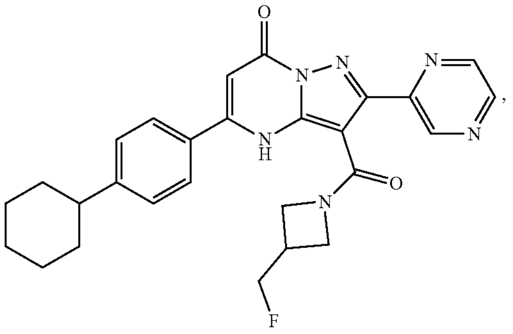
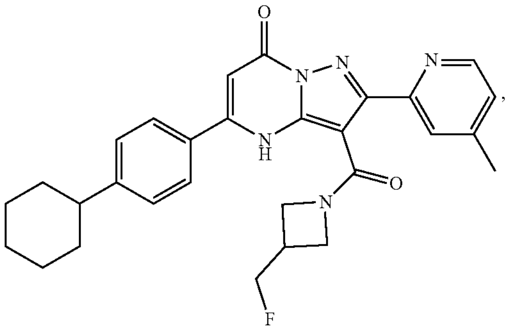

-continued
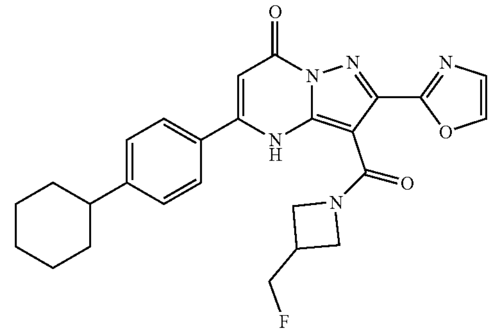,
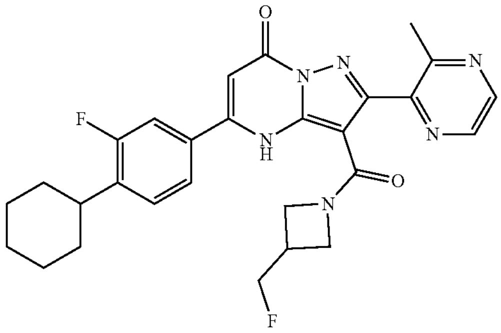,
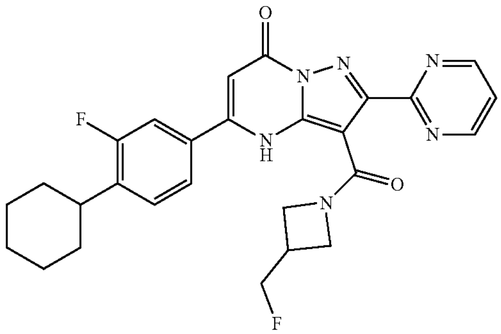,
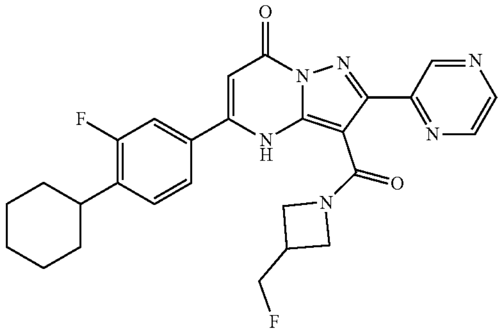,
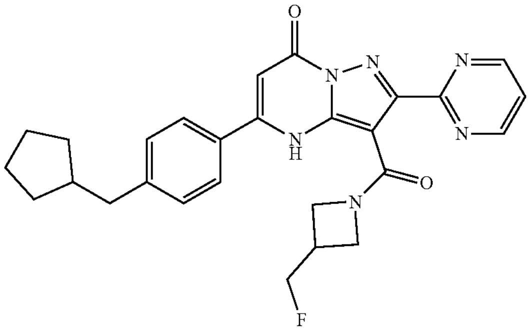,
-continued
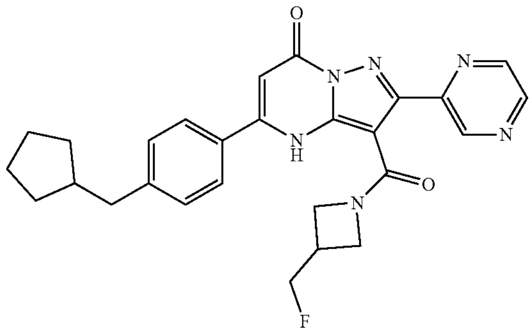,
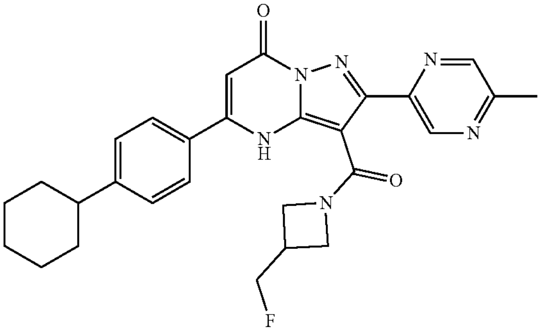,
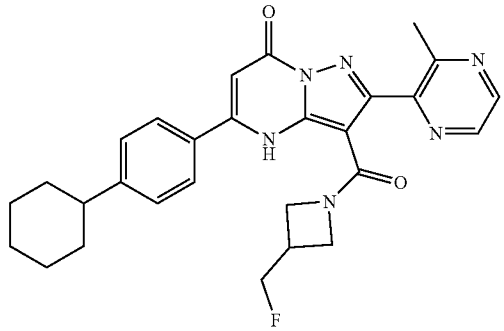,
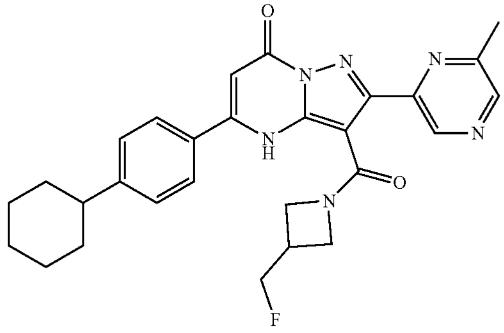,
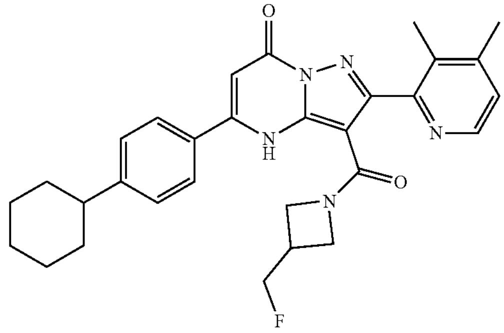

-continued
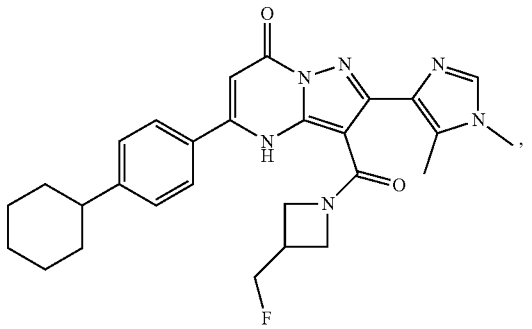
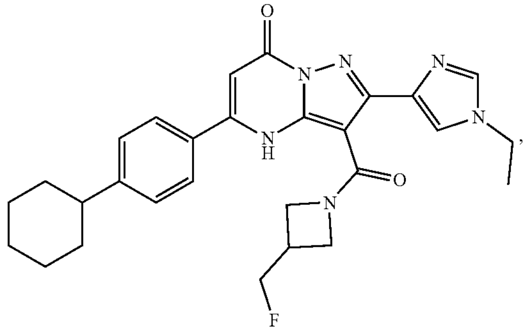
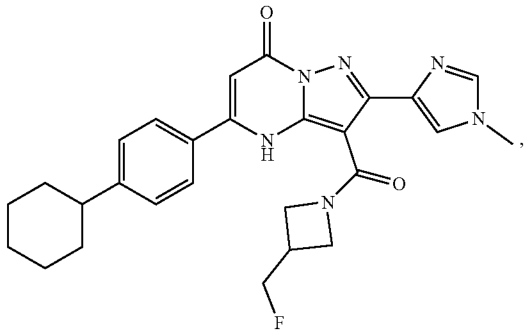
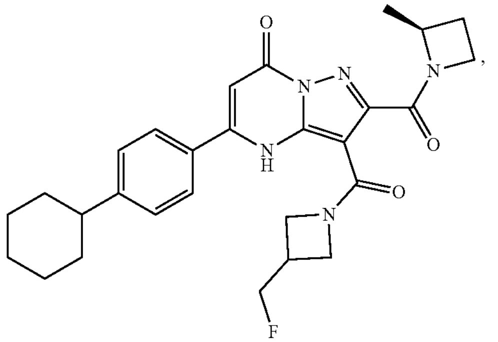
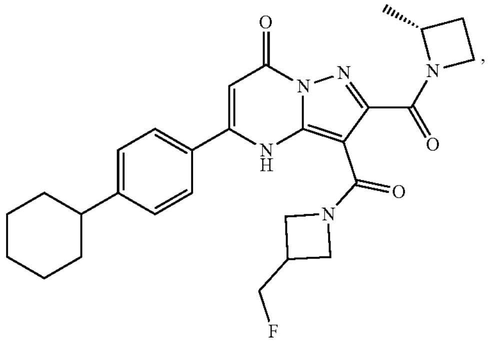
-continued
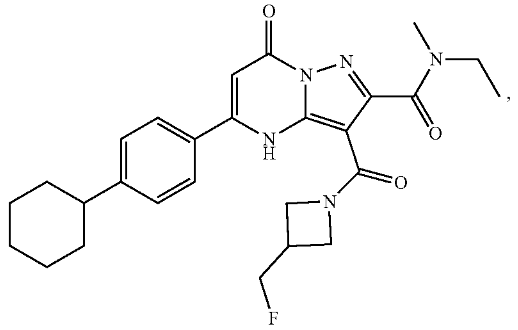
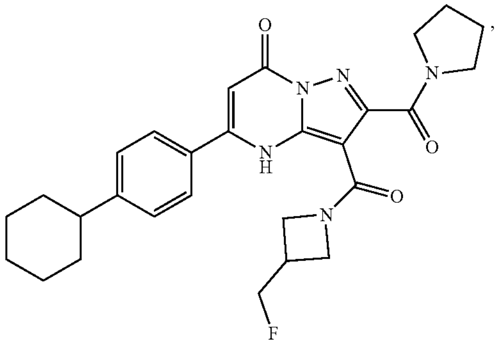
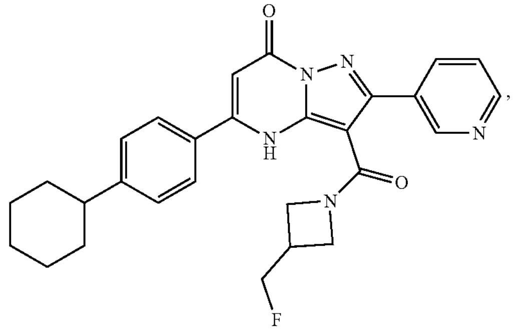
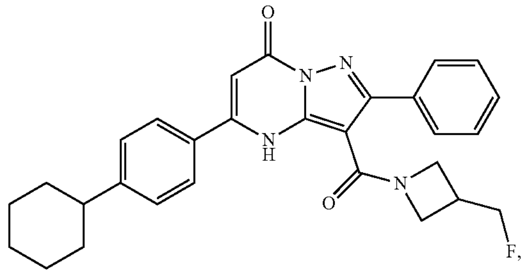
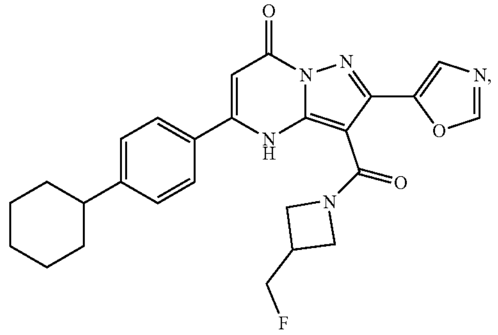

-continued
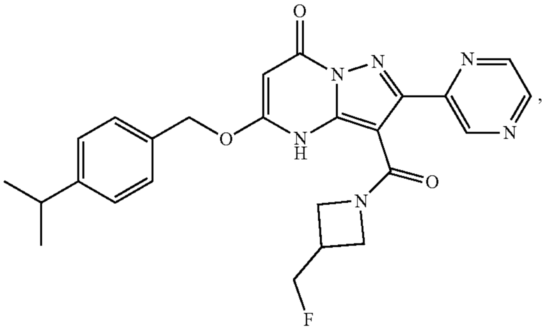
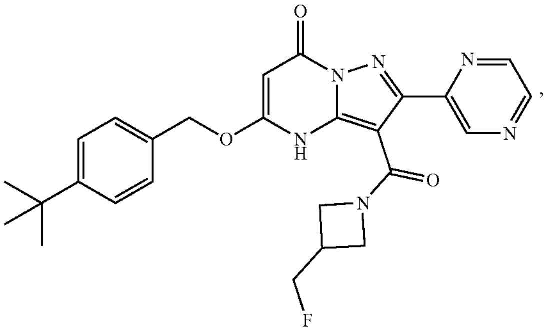
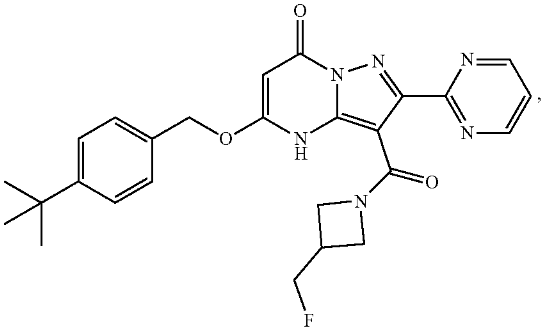
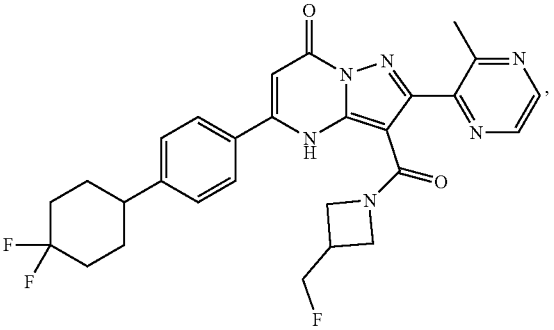
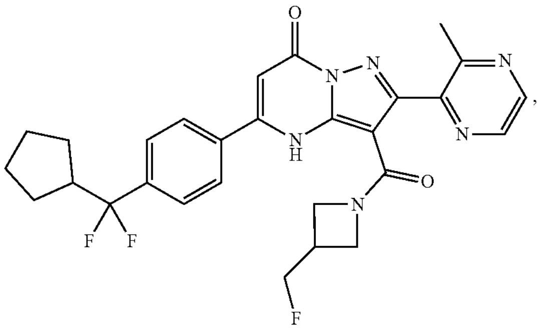
-continued
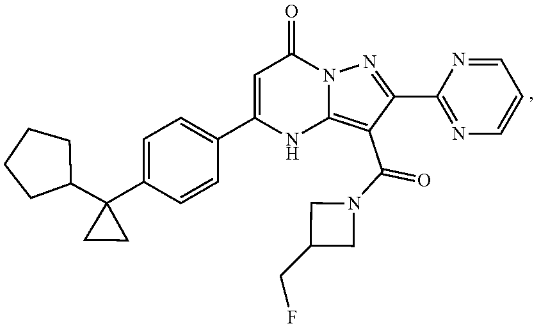
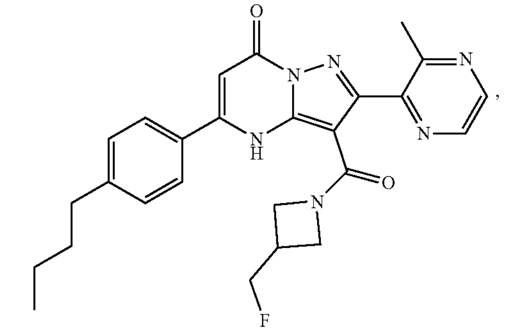
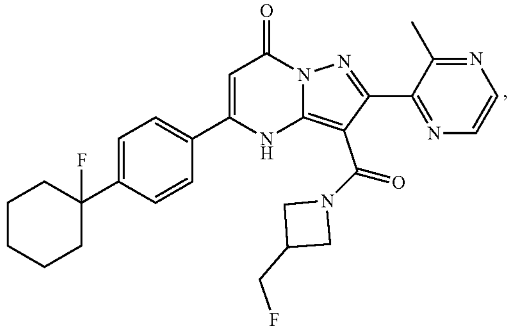
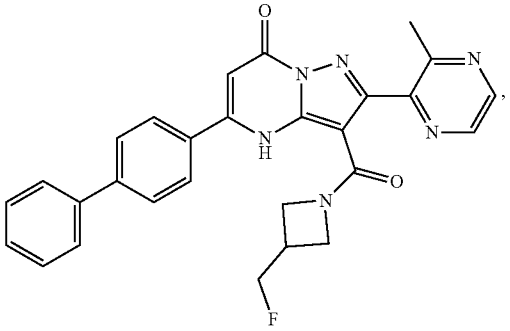
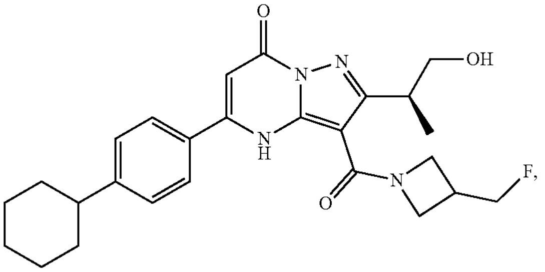

-continued

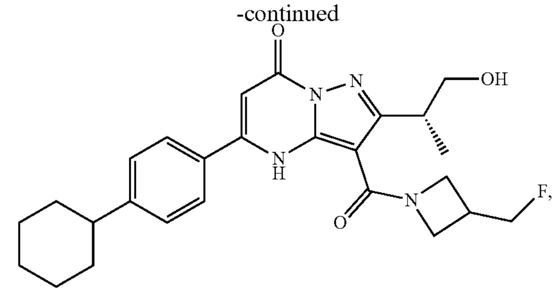

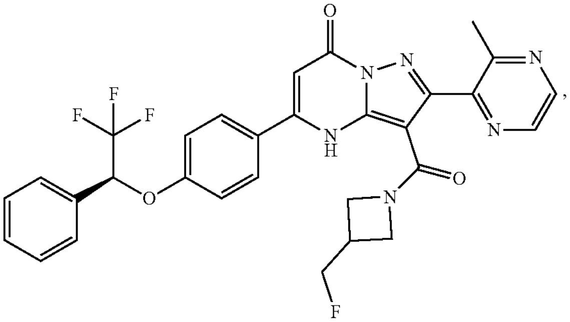

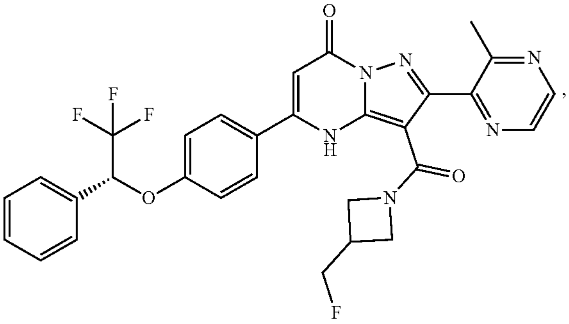

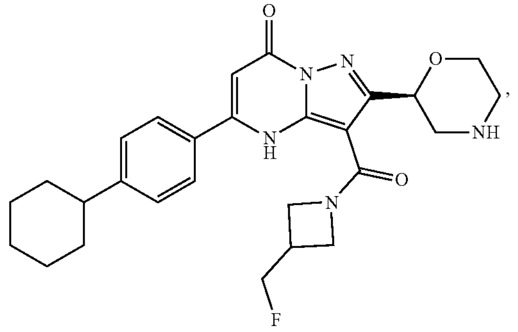

and

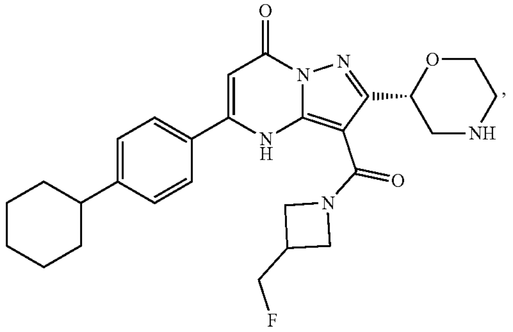

or a pharmaceutically acceptable salt, stereoisomer, tautomer, or deuterated analog thereof.

8. The compound of claim 4, wherein $R^5$ is methyl.

9. The compound of claim 8, wherein the compound of formula (IB) is:

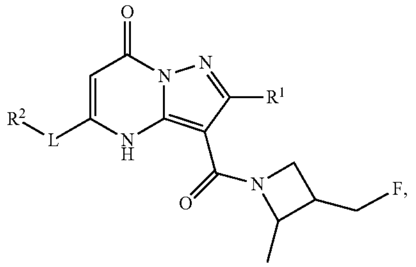

or a pharmaceutically acceptable salt, stereoisomer, tautomer, or deuterated analog thereof.

10. The compound of claim 9, wherein the compound is selected from the group consisting of:

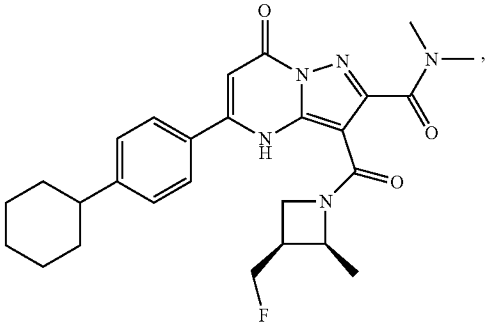

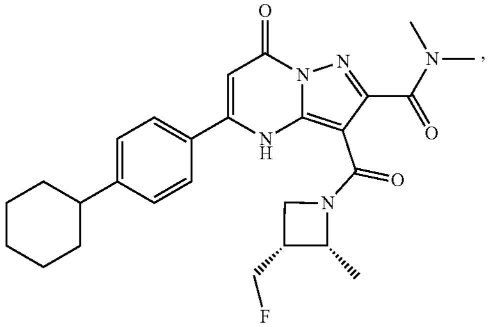

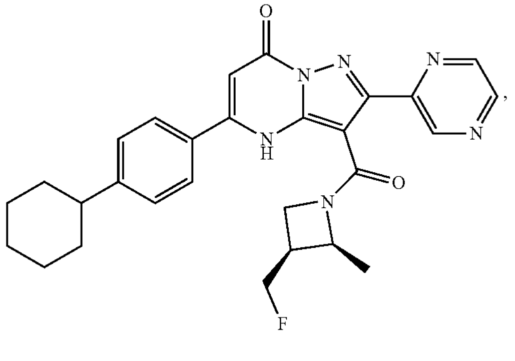

-continued
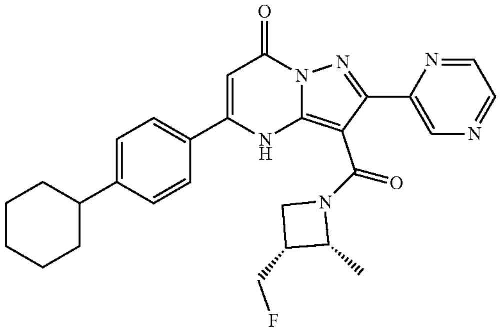
,
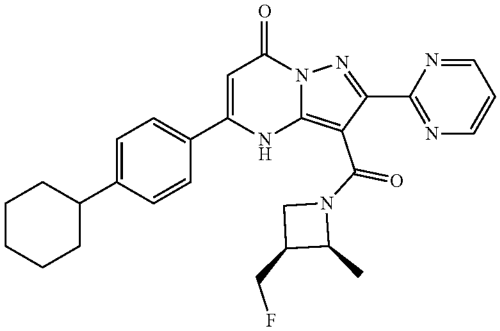
,
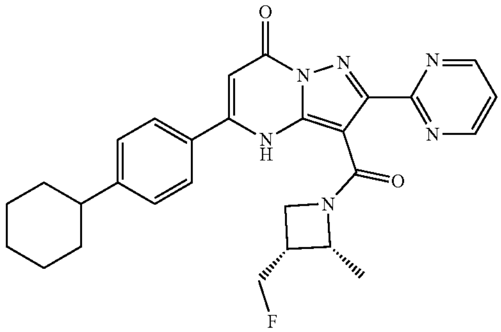
,
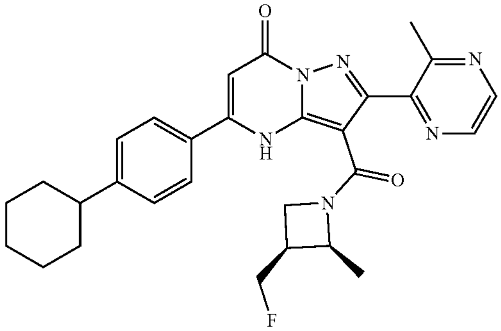
,
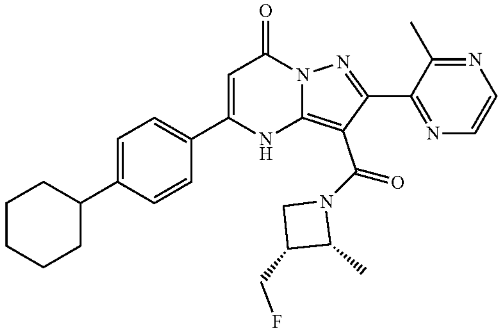
,
-continued
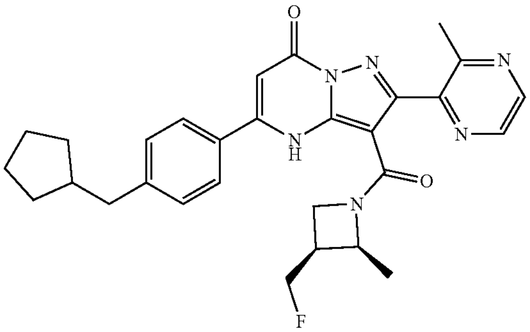
,
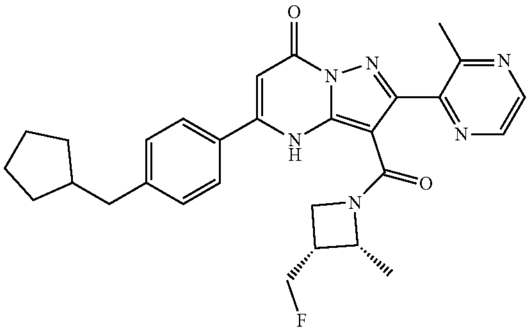
,
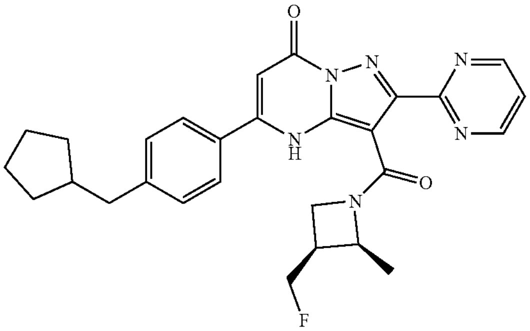
,
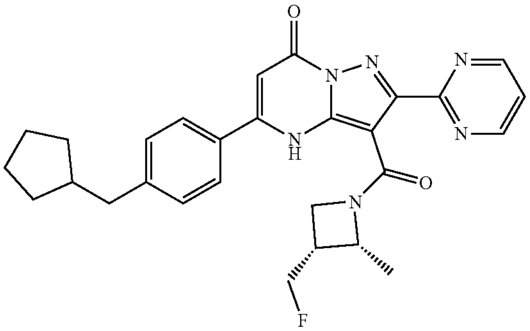
,
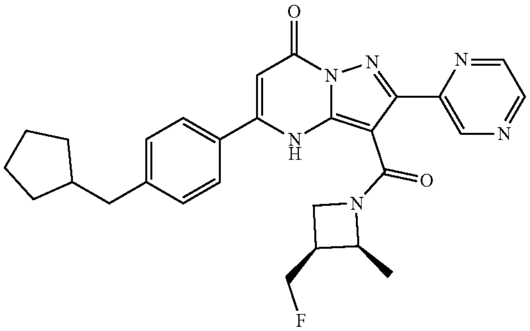
, -continued

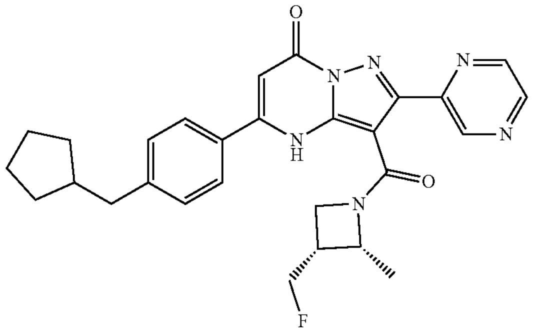
,

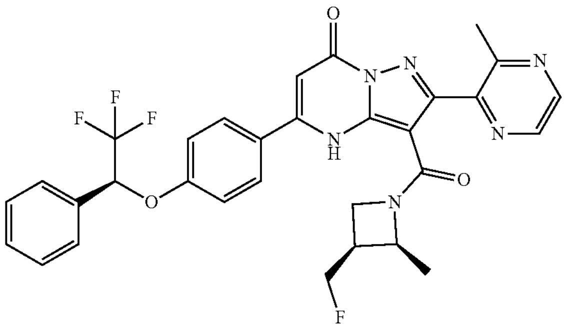
,

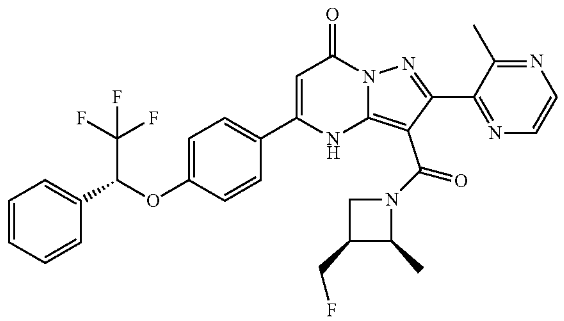
,

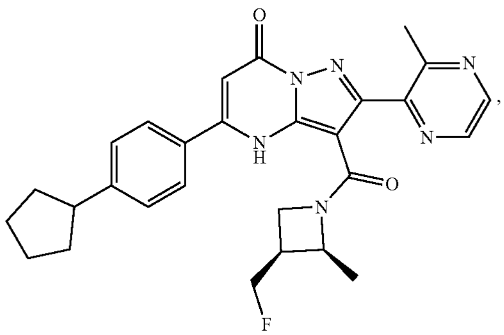
,

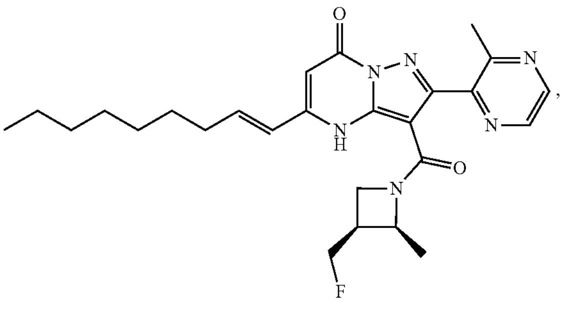
,

-continued

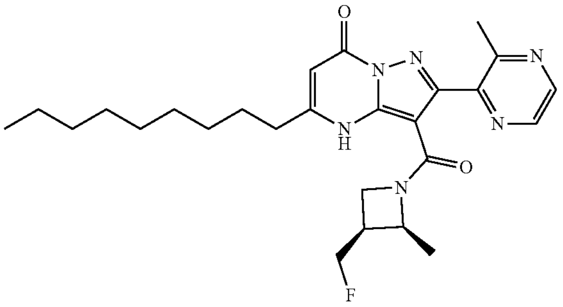
,

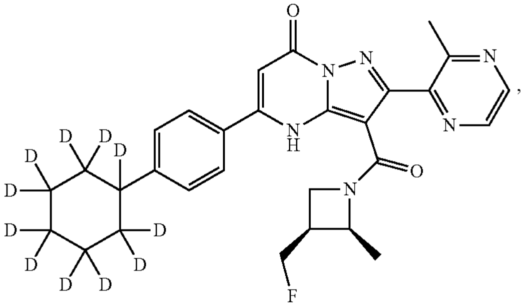
, and

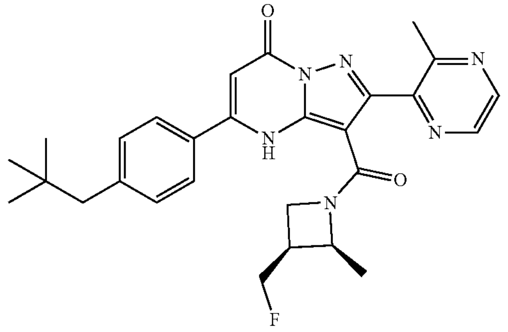
, or a pharmaceutically acceptable salt, stereoisomer, tautomer, or deuterated analog thereof.

11. The compound of claim 1, wherein $R^1$ is a 6-membered heteroaryl.

12. The compound of claim 1, wherein $R^2$ is $C_6$aryl, wherein the $C_6$aryl is optionally substituted with one or more substituents selected from the group consisting of halo, OH, cyano, $C_{1-6}$alkyl, $C_{1-6}$haloalkyl, $C_{1-6}$alkoxy, $C_{6-10}$aryl, $C_{3-10}$cycloalkyl, wherein the $C_{3-10}$cycloalkyl is optionally further substituted with one or more halo or $C_{3-10}$cycloalkyl.

13. The compound of claim 1, wherein the compound of formula (I) is a compound of formula (IC):

(IC)

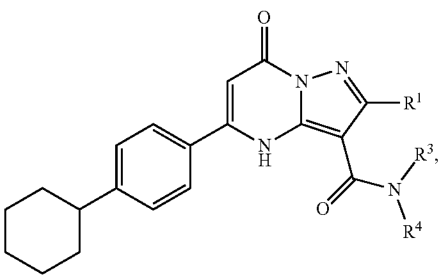

or a pharmaceutically acceptable salt, stereoisomer, tautomer, or deuterated analog thereof.

14. The compound of claim 1, wherein the compound of formula (I) is a compound selected from the group consisting of
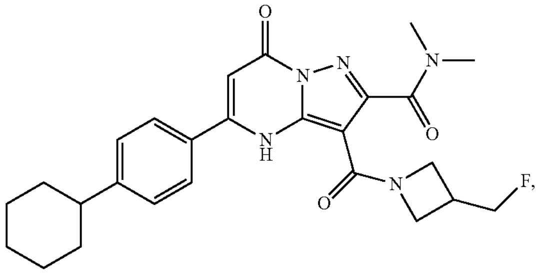
,
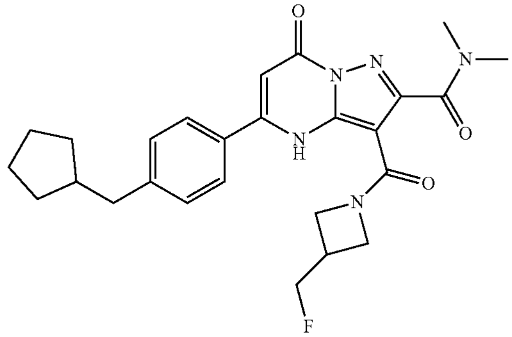
,
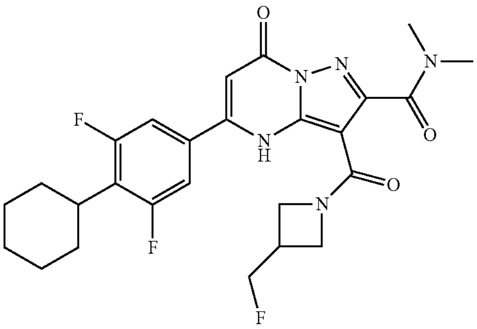
,
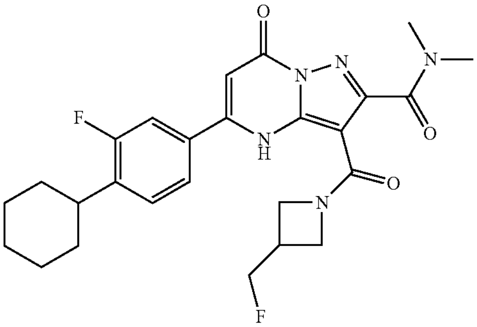
,
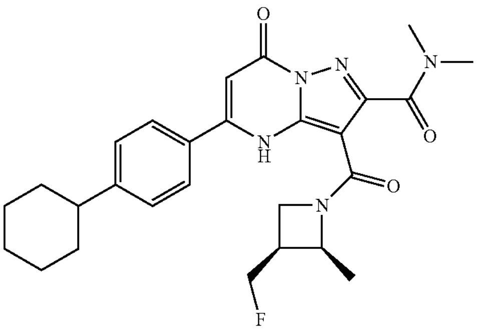
,
-continued
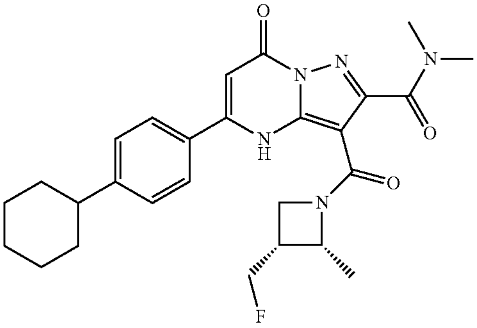
,
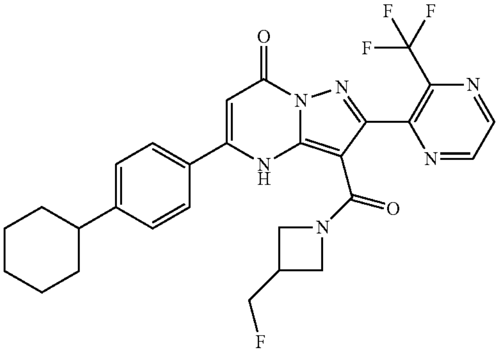
,
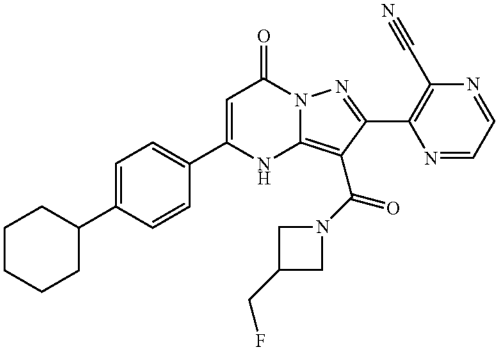
,
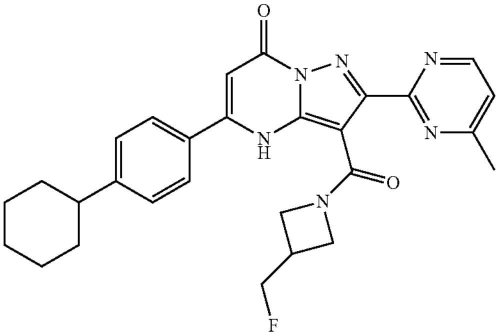
,
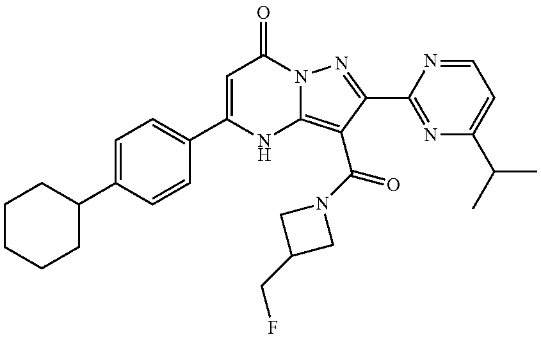
, -continued
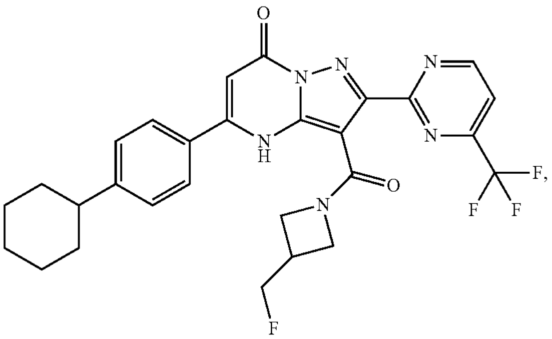
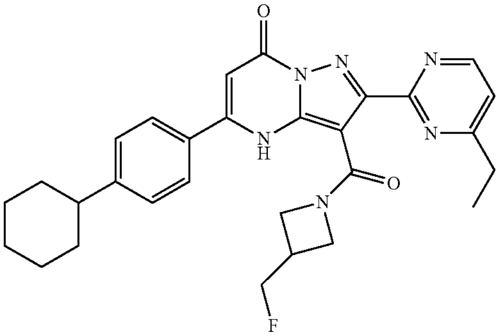
,
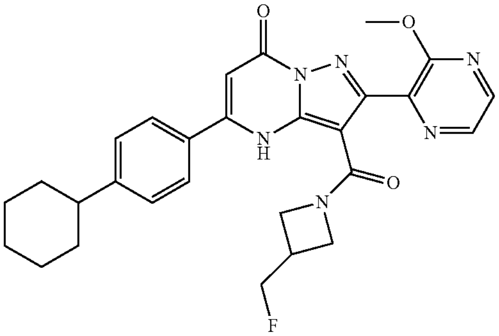
,
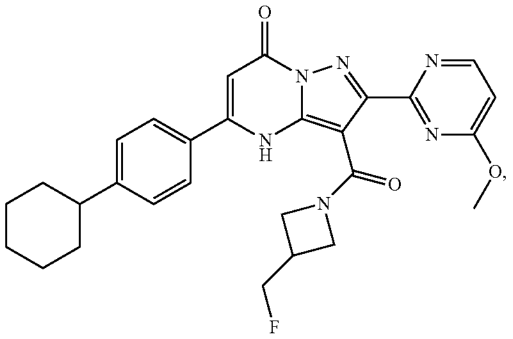
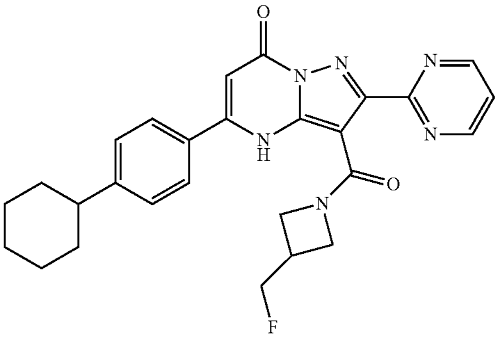
,
-continued
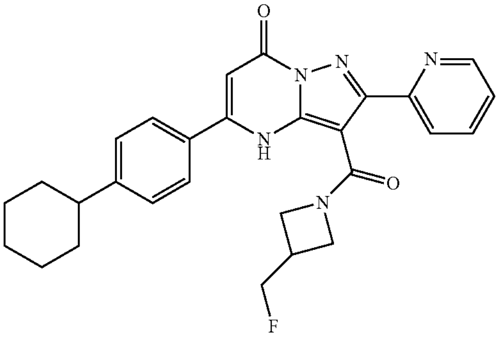
,
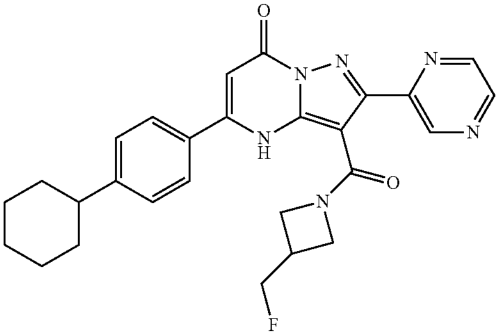
,
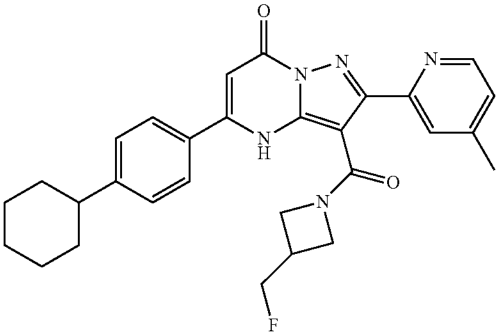
,
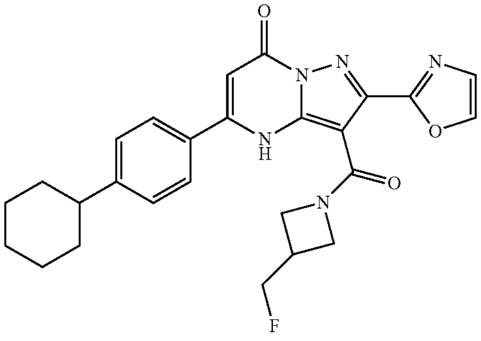
,
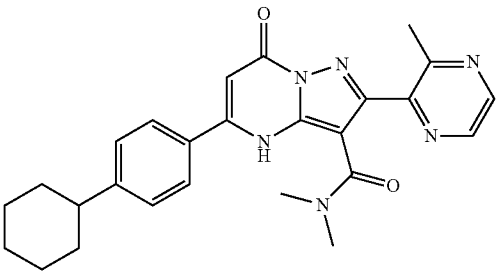
, -continued
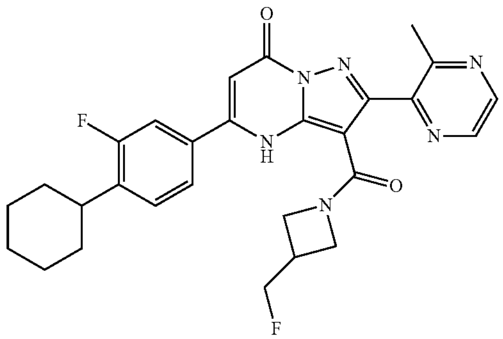
,
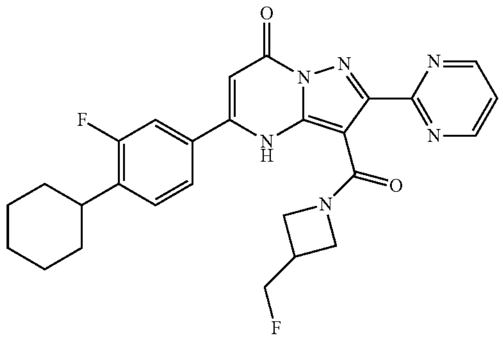
,
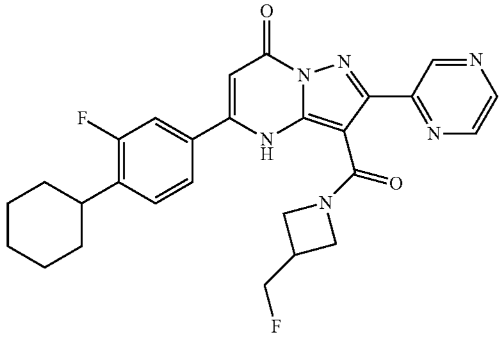
,
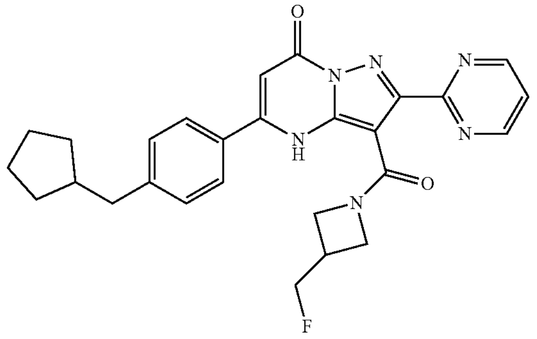
,
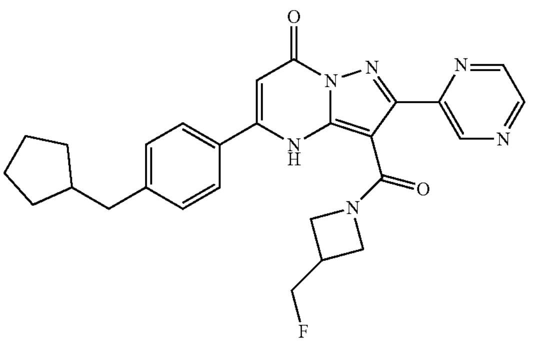
,
-continued
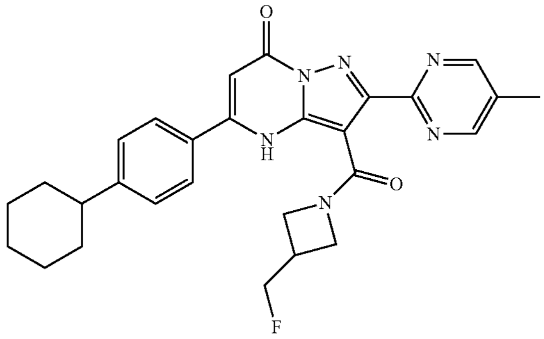
,
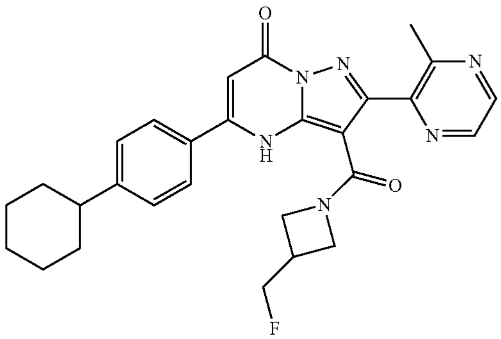
,
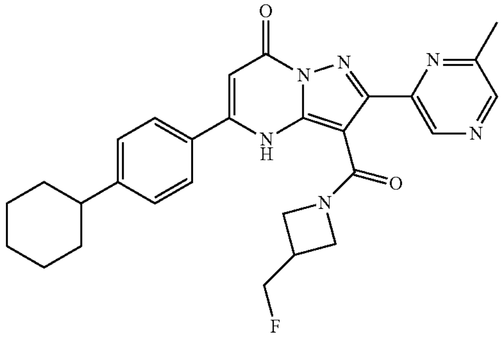
,
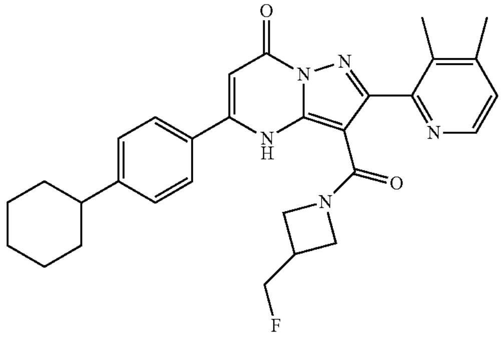
,
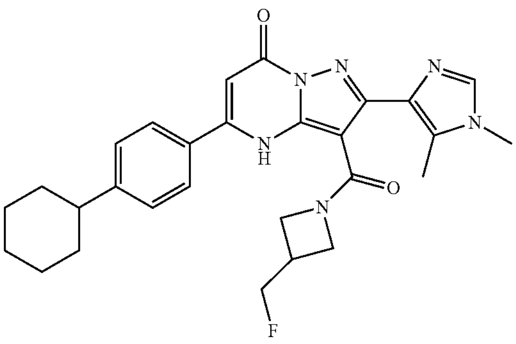
, -continued
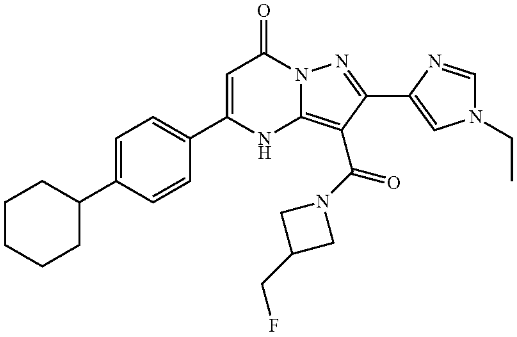
,
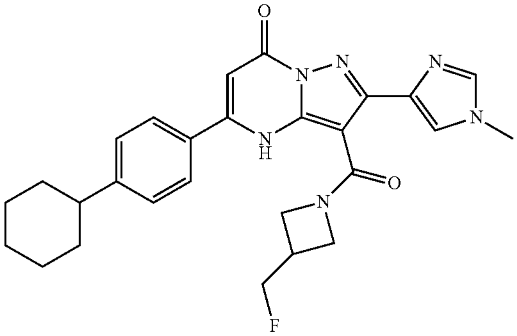
,
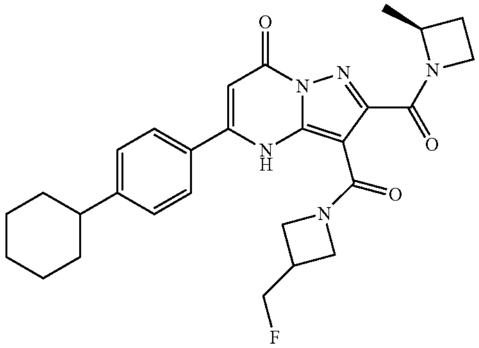
,
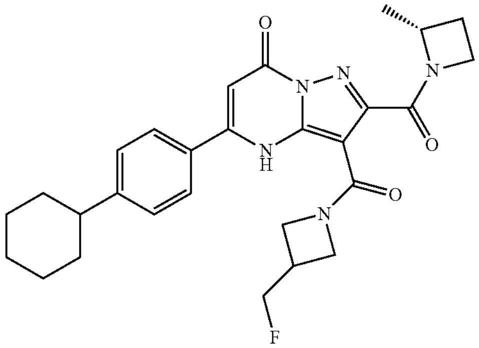
,
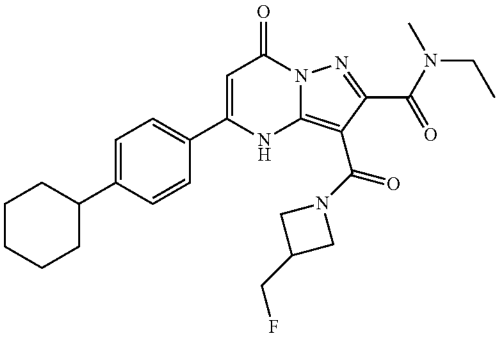
,
-continued
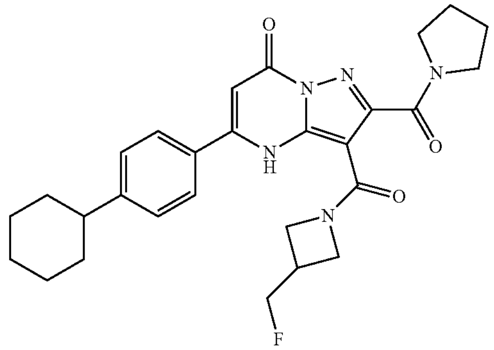
,
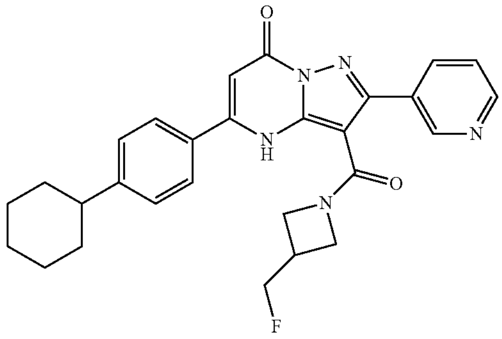
,
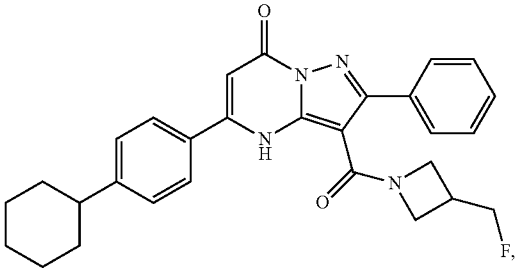
,
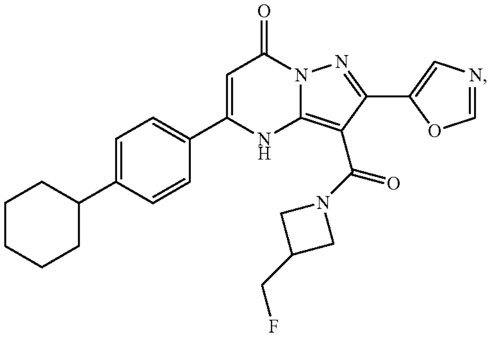
,
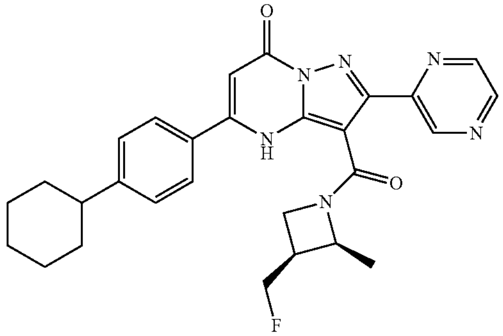
, -continued
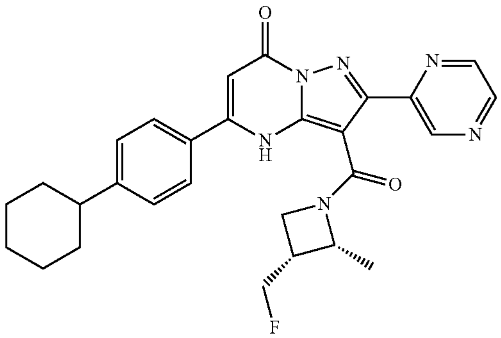
,
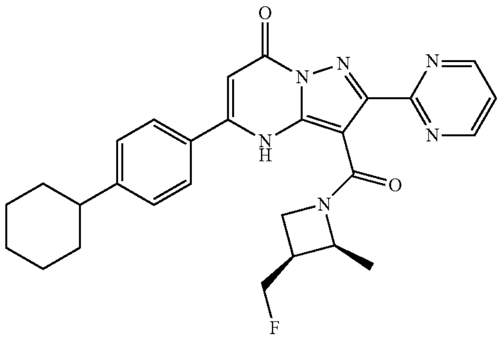
,
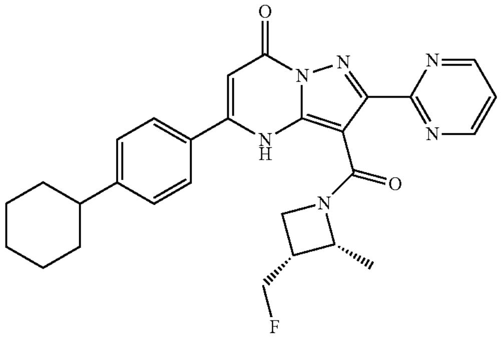
,
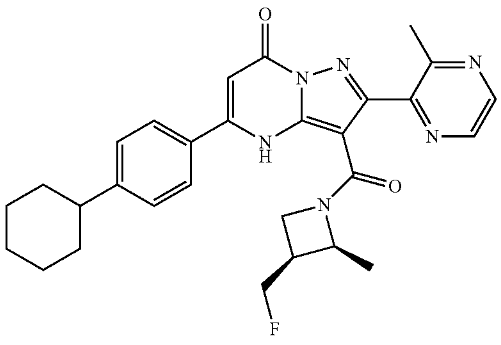
,
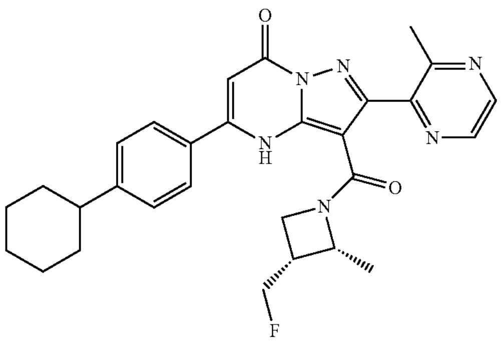
,
-continued
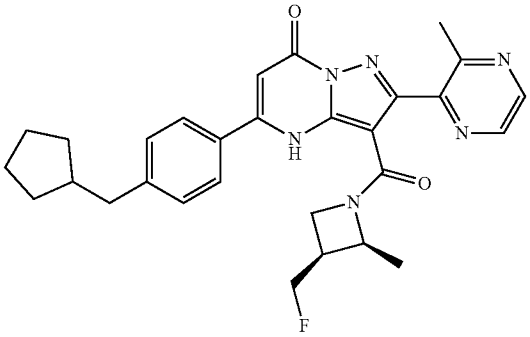
,
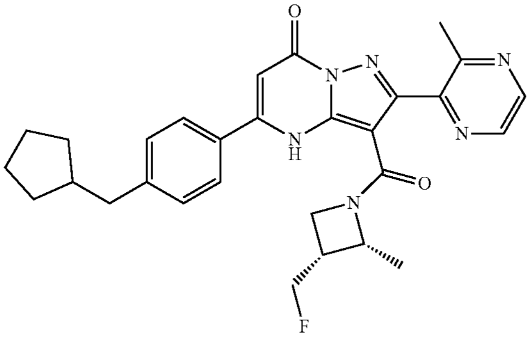
,
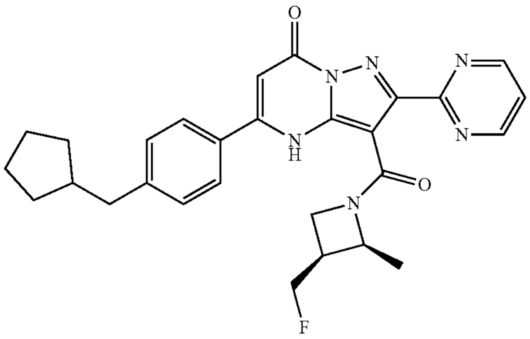
,
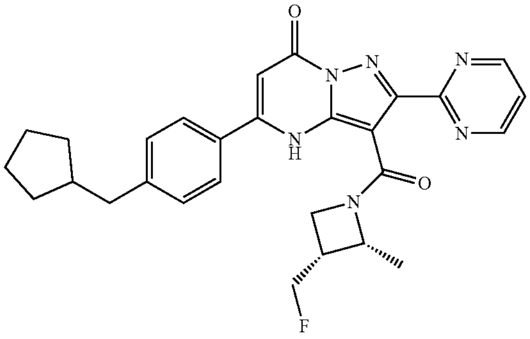
, -continued
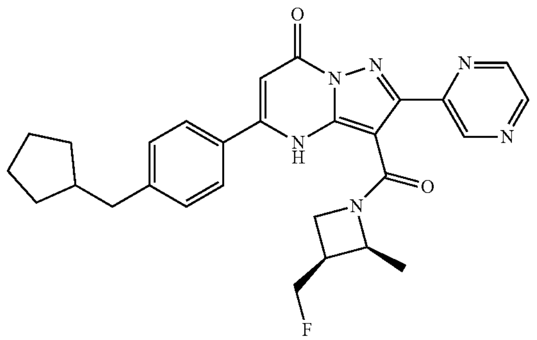
,
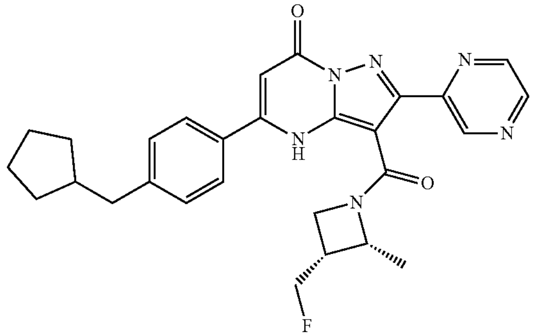
,
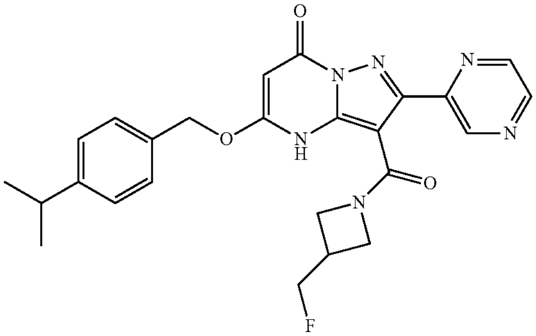
,
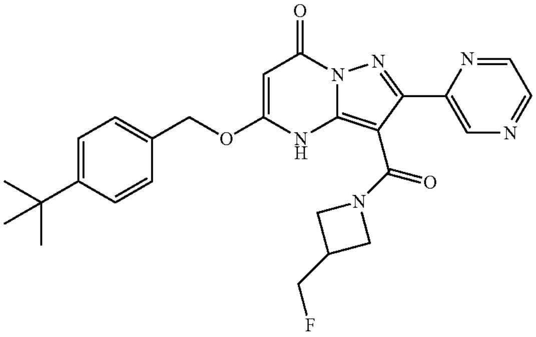
,
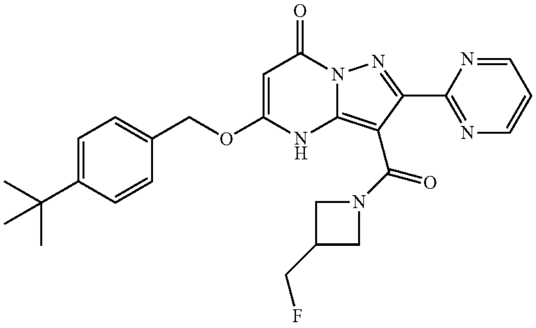
,
-continued
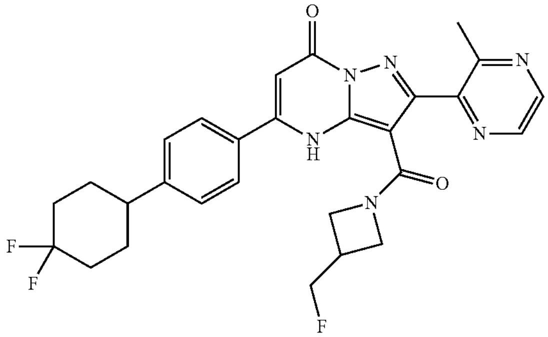
,
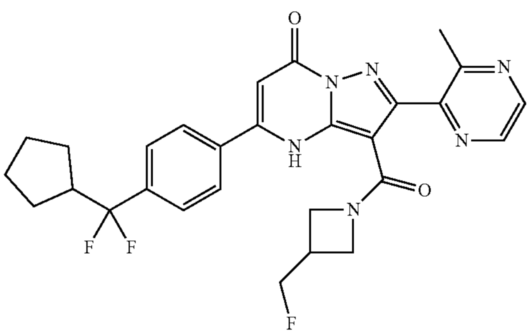
,
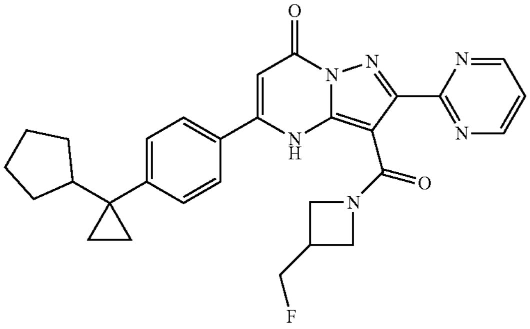
,
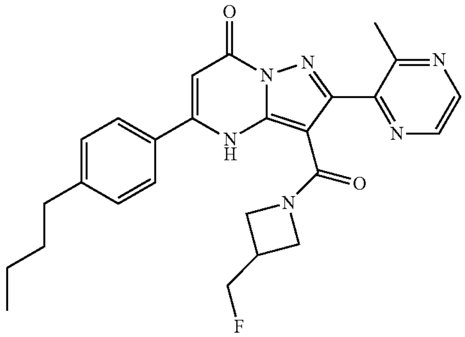
,

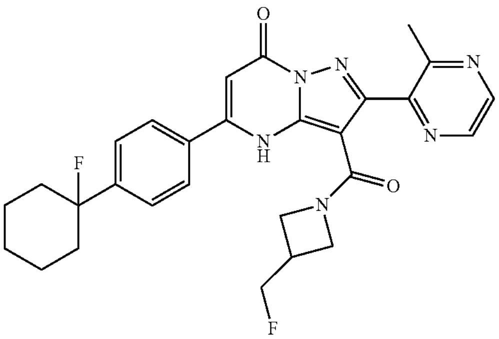
,
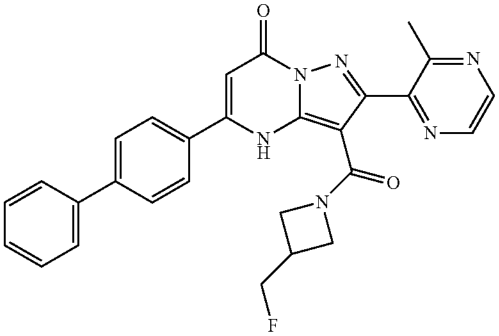
,
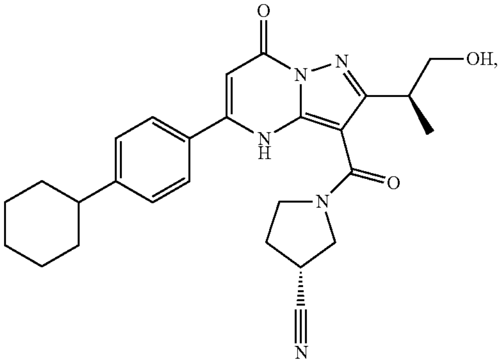
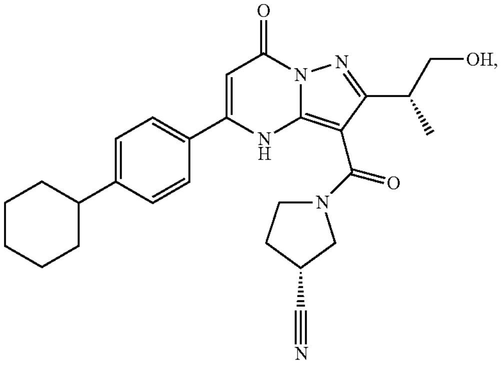
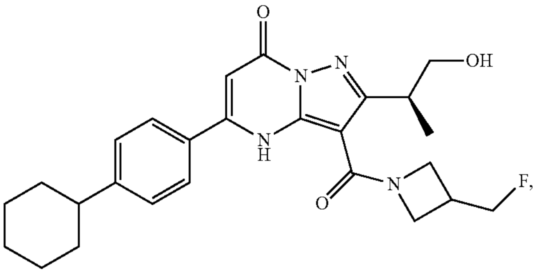
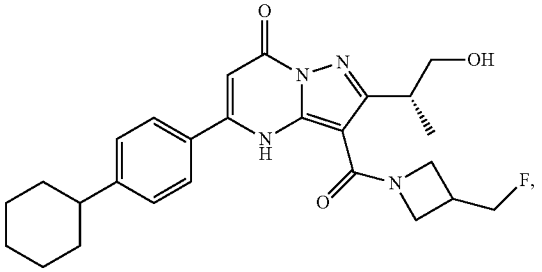
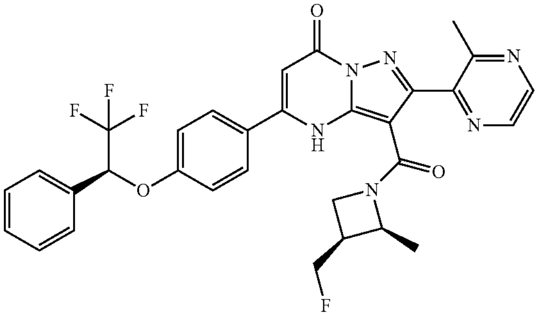
,
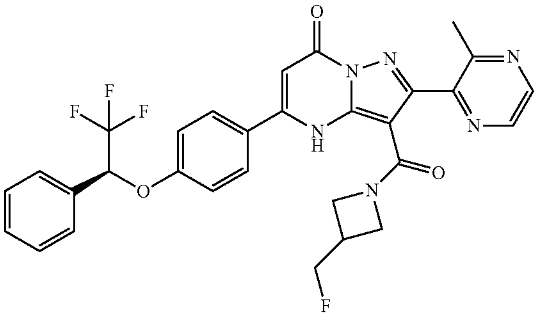
,
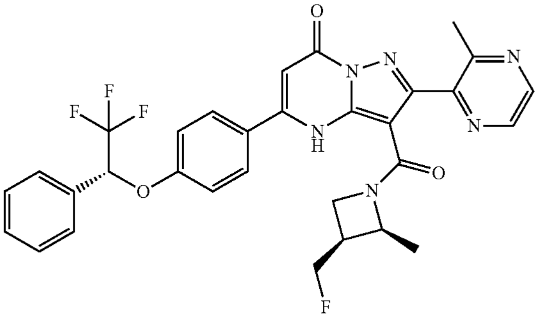
,
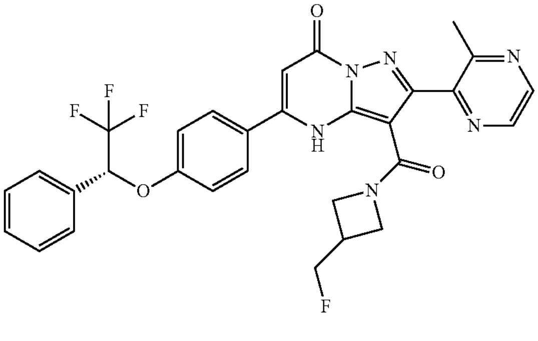
, -continued

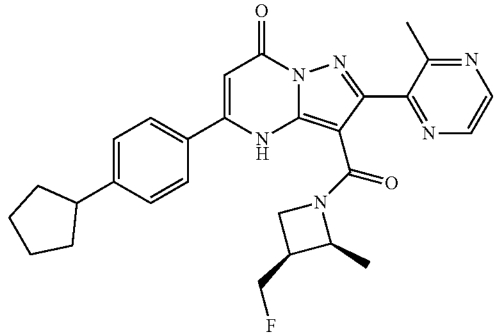

,

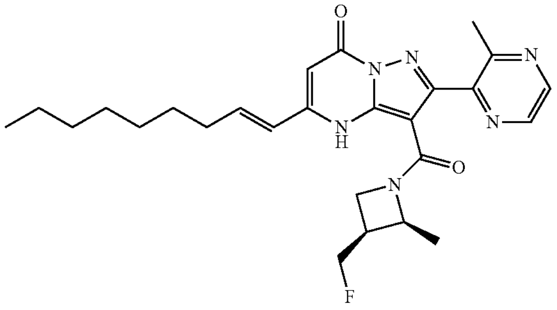

,

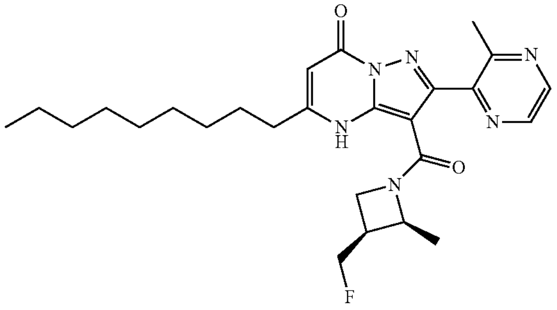

,

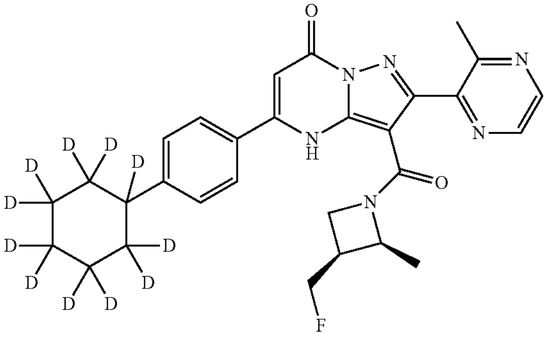

,

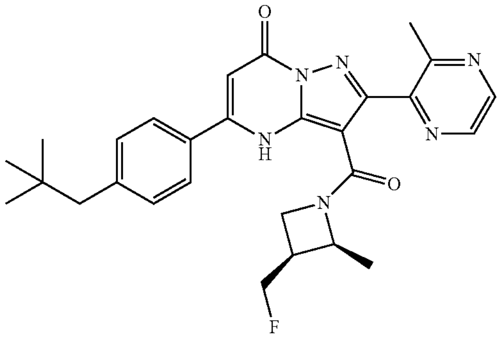

,

-continued

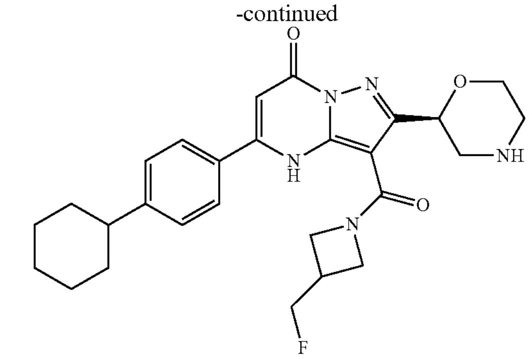

,

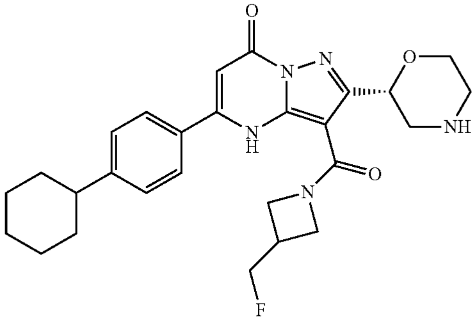

and and

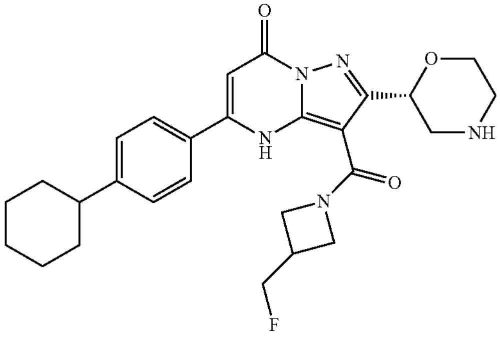

or a pharmaceutically acceptable salt, stereoisomer, tautomer, or deuterated analog thereof.

15. The compound of claim 1, wherein the compound of formula (I) is a compound selected from the group consisting of 5-(4-cyclohexylphenyl)-3-[3-(fluoromethyl) azetidine-1-carbonyl]-N,N-dimethyl-7-oxo-4H-pyrazolo [1,5-a] pyrimidine-2-carboxamide, 5-[4-(cyclopentylmethyl) phenyl]-3-[3-(fluoromethyl) azetidine-1-carbonyl]-N,N-dimethyl-7-oxo-4H-pyrazolo [1,5-a]pyrimidine-2-carboxamide, 5-(4-cyclohexyl-3,5-difluoro-phenyl)-3-[3-(fluoromethyl) azetidine-1-carbonyl]-N,N-dimethyl-7-oxo-4H-pyrazolo [1,5-a]pyrimidine-2-carboxamide, 5-(4-cyclohexyl-3-fluoro-phenyl)-3-[3-(fluoromethyl) azetidine-1-carbonyl]-N,N-dimethyl-7-oxo-4H-pyrazolo [1,5-a]pyrimidine-2-carboxamide, 5-(4-cyclohexylphenyl)-N,N-dimethyl-7-oxo-3-[3-(fluoromethyl)-2-methyl-azetidine-1-carbonyl]-4H-pyrazolo [1,5-a]pyrimidine-2-carboxamide, 5-(4-cyclohexylphenyl)-N,N-dimethyl-7-oxo-3-[3-(fluoromethyl)-2-methyl-azetidine-1-carbonyl]-4H-pyrazolo [1,5-a]pyrimidine-2-carboxamide, 5-(4-cyclohexylphenyl)-3-[3-(fluoromethyl) azetidine-1-carbonyl]-2-[3-(trifluoromethyl) pyrazin-2-yl]-4H-pyrazolo [1,5-a]pyrimidin-7-one, 3-[5-(4-cyclohexylphenyl)-3-[3-(fluoromethyl) azetidine-1-carbonyl]-7-oxo-4H-pyrazolo [1,5-a]pyrimidin-2-yl] pyrazine-2-carbonitrile, 5-(4-cyclohexylphenyl)-3-[3-(fluoromethyl) azetidine-1-carbonyl]-2-(4-methylpyrimidin-2-yl)-4H-pyrazolo [1,5-a]pyrimidin-7-one, 5-(4-cyclohexylphenyl)-3-[3-(fluoromethyl) azetidine-1-carbonyl]-2-(4-isopropylpyrimidin-2-yl)-4H-pyrazolo [1,5-a]pyrimidin-7-one, 5-(4-cyclohexylphenyl)-3-[3-(fluoromethyl) azetidine-1-carbonyl]-2-[4-(trifluoromethyl)pyrimidin-2-yl]-4H-pyrazolo [1,5-a]pyrimidin-7-one, 5-(4-cyclohexylphenyl)-2-(4-ethylpyrimidin-2-yl)-3-[3-(fluoromethyl) azetidine-1-carbonyl]-4H-pyrazolo [1,5-a]pyrimidin-7-one, 5-(4-cyclohexylphenyl)-3-[3-(fluoromethyl) azetidine-1-carbonyl]-2-(3-methoxypyrazin-2-yl)-4H-pyrazolo [1,5-a]pyrimidin-7-one, 5-(4-cyclohexylphenyl)-3-[3-(fluoromethyl) azetidine-1-carbonyl]-2-(4-methoxypyrimidin-2-yl)-4H-pyrazolo [1,5-a]pyrimidin-7-one, 5-(4-cyclohexylphenyl)-3-[3-(fluoromethyl) azetidine-1-carbonyl]-2-pyrimidin-2-yl-4H-pyrazolo [1,5-a]pyrimidin-7-one, 5-(4-cyclohexylphenyl)-3-[3-(fluoromethyl) azetidine-1-carbonyl]-2-(2-pyridyl)-4H-pyrazolo [1,5-a]pyrimidin-7-one, 5-(4-cyclohexylphenyl)-3-[3-(fluoromethyl) azetidine-1-carbonyl]-2-pyrazin-2-yl-4H-pyrazolo [1,5-a]pyrimidin-7-one, 5-(4-cyclohexylphenyl)-3-[3-(fluoromethyl) azetidine-1-carbonyl]-2-(4-methyl-2-pyridyl)-4H-pyrazolo [1,5-a] pyrimidin-7-one, 5-(4-cyclohexylphenyl)-3-[3-(fluoromethyl) azetidine-1-carbonyl]-2-oxazol-2-yl-4H-pyrazolo [1,5-a]pyrimidin-7-one, 5-(4-cyclohexylphenyl)-N,N-dimethyl-2-(3-methylpyrazin-2-yl)-7-oxo-4H-pyrazolo [1,5-a]pyrimidine-3-carboxamide, 5-(4-cyclohexyl-3-fluoro-phenyl)-3-[3-(fluoromethyl) azetidine-1-carbonyl]-2-(3-methylpyrazin-2-yl)-4H-pyrazolo [1,5-a]pyrimidin-7-one, 5-(4-cyclohexyl-3-fluoro-phenyl)-3-[3-(fluoromethyl) azetidine-1-carbonyl]-2-pyrimidin-2-yl-4H-pyrazolo [1,5-a]pyrimidin-7-one, 5-(4-cyclohexyl-3-fluoro-phenyl)-3-[3-(fluoromethyl) azetidine-1-carbonyl]-2-pyrazin-2-yl-4H-pyrazolo [1,5-a]pyrimidin-7-one, 5-[4-(cyclopentylmethyl) phenyl]-3-[3-(fluoromethyl) azetidine-1-carbonyl]-2-pyrimidin-2-yl-4H-pyrazolo [1,5-a]pyrimidin-7-one, 5-[4-(cyclopentylmethyl) phenyl]-3-[3-(fluoromethyl) azetidine-1-carbonyl]-2-pyrazin-2-yl-4H-pyrazolo [1,5-a]pyrimidin-7-one, 5-(4-cyclohexylphenyl)-3-[3-(fluoromethyl) azetidine-1-carbonyl]-2-(5-methylpyrazin-2-yl)-4H-pyrazolo [1,5-a]pyrimidin-7-one, 5-(4-cyclohexylphenyl)-3-[3-(fluoromethyl) azetidine-1-carbonyl]-2-(3-methylpyrazin-2-yl)-4H-pyrazolo [1,5-a]pyrimidin-7-one, 5-(4-cyclohexylphenyl)-3-[3-(fluoromethyl) azetidine-1-carbonyl]-2-(6-methylpyrazin-2-yl)-4H-pyrazolo [1,5-a]pyrimidin-7-one, 5-(4-cyclohexylphenyl)-2-(3,4-dimethyl-2-pyridyl)-3-[3-(fluoromethyl) azetidine-1-carbonyl]-4H-pyrazolo [1,5-a]pyrimidin-7-one, 5-(4-cyclohexylphenyl)-2-(1,5-dimethylimidazol-4-yl)-3-[3-(fluoromethyl) azetidine-1-carbonyl]-4H-pyrazolo [1,5-a]pyrimidin-7-one, 5-(4-cyclohexylphenyl)-2-(1-ethylimidazol-4-yl)-3-[3-(fluoromethyl) azetidine-1-carbonyl]-4H-pyrazolo [1,5-a]pyrimidin-7-one, 5-(4-cyclohexylphenyl)-3-[3-(fluoromethyl) azetidine-1-carbonyl]-2-(1-methylimidazol-4-yl)-4H-pyrazolo [1,5-a]pyrimidin-7-one, 5-(4-cyclohexylphenyl)-3-[3-(fluoromethyl) azetidine-1-carbonyl]-2-[2-methylazetidine-1-carbonyl]-4H-pyrazolo [1,5-a]pyrimidin-7-one, 5-(4-cyclohexylphenyl)-3-[3-(fluoromethyl) azetidine-1-carbonyl]-2-[2-methylazetidine-1-carbonyl]-4H-pyrazolo [1,5-a]pyrimidin-7-one, 5-(4-cyclohexylphenyl)-N-ethyl-3-[3-(fluoromethyl) azetidine-1-carbonyl]-N-methyl-7-oxo-4H-pyrazolo [1,5-a]pyrimidine-2-carboxamide, 5-(4-cyclohexylphenyl)-3-[3-(fluoromethyl) azetidine-1-carbonyl]-2-(pyrrolidine-1-carbonyl)-4H-pyrazolo [1,5-a]pyrimidin-7-one, 5-(4-cyclohexylphenyl)-3-[3-(fluoromethyl) azetidine-1-carbonyl]-2-(3-pyridyl)-4H-pyrazolo [1,5-a]pyrimidin-7-one, 5-(4-cyclohexylphenyl)-3-[3-(fluoromethyl) azetidine-1-carbonyl]-2-phenyl-4H-pyrazolo [1,5-a]pyrimidin-7-one, 5-(4-cyclohexylphenyl)-3-[3-(fluoromethyl) azetidine-1-carbonyl]-2-oxazol-5-yl-4H-pyrazolo [1,5-a]pyrimidin-7-one, 5-(4-cyclohexylphenyl)-2-pyrazin-2-yl-3-[3-(fluoromethyl)-2-methyl-azetidine-1-carbonyl]-4H-pyrazolo [1,5-a]pyrimidin-7-one, 5-(4-cyclohexylphenyl)-2-pyrazin-2-yl-3-[3-(fluoromethyl)-2-methyl-azetidine-1-carbonyl]-4H-pyrazolo [1,5-a]pyrimidin-7-one, 5-(4-cyclohexylphenyl)-2-pyrimidin-2-yl-3-[3-(fluoromethyl)-2-methyl-azetidine-1-carbonyl]-4H-pyrazolo [1,5-a]pyrimidin-7-one, 5-(4-cyclohexylphenyl)-2-pyrimidin-2-yl-3-[3-(fluoromethyl)-2-methyl-azetidine-1-carbonyl]-4H-pyrazolo [1,5-a]pyrimidin-7-one, 5-(4-cyclohexylphenyl)-2-(3-methylpyrazin-2-yl)-3-[3-(fluoromethyl)-2-methyl-azetidine-1-carbonyl]-4H-pyrazolo [1,5-a]pyrimidin-7-one, 5-(4-cyclohexylphenyl)-2-(3-methylpyrazin-2-yl)-3-[3-(fluoromethyl)-2-methyl-azetidine-1-carbonyl]-4H-pyrazolo [1,5-a]pyrimidin-7-one, 5-[4-(cyclopentylmethyl) phenyl]-2-(3-methylpyrazin-2-yl)-3-[3-(fluoromethyl)-2-methyl-azetidine-1-carbonyl]-4H-pyrazolo [1,5-a]pyrimidin-7-one, 5-[4-(cyclopentylmethyl) phenyl]-2-(3-methylpyrazin-2-yl)-3-[3-(fluoromethyl)-2-methyl-azetidine-1-carbonyl]-4H-pyrazolo [1,5-a]pyrimidin-7-one, 5-[4-(cyclopentylmethyl) phenyl]-2-pyrimidin-2-yl-3-[3-(fluoromethyl)-2-methyl-azetidine-1-carbonyl]-4H-pyrazolo [1,5-a]pyrimidin-7-one, 5-[4-(cyclopentylmethyl) phenyl]-2-pyrimidin-2-yl-3-[3-(fluoromethyl)-2-methyl-azetidine-1-carbonyl]-4H-pyrazolo [1,5-a]pyrimidin-7-one, 5-[4-(cyclopentylmethyl) phenyl]-2-pyrazin-2-yl-3-[3-(fluoromethyl)-2-methyl-azetidine-1-carbonyl]-4H-pyrazolo [1,5-a]pyrimidin-7-one, 5-[4-(cyclopentylmethyl) phenyl]-2-pyrazin-2-yl-3-[3-(fluoromethyl)-2-methyl-azetidine-1-carbonyl]-4H-pyrazolo [1,5-a]pyrimidin-7-one, 3-[3-(fluoromethyl) azetidine-1-carbonyl]-5-[(4-isopropylphenyl) methoxy]-2-pyrazin-2-yl-4H-pyrazolo [1,5-a]pyrimidin-7-one, 5-[(4-tert-butylphenyl) methoxy]-3-[3-(fluoromethyl) azetidine-1-carbonyl]-2-pyrazin-2-yl-4H-pyrazolo [1,5-a]pyrimidin-7-one, 5-[(4-tert-butylphenyl) methoxy]-3-[3-(fluoromethyl) azetidine-1-carbonyl]-2-pyrimidin-2-yl-4H-pyrazolo [1,5-a]pyrimidin-7-one, 5-[4-(4,4-difluorocyclohexyl)phenyl]-3-[3-(fluoromethyl) azetidine-1-carbonyl]-2-(3-methylpyrazin-2-yl)-4H-pyrazolo [1,5-a]pyrimidin-7-one, 5-[4-[cyclopentyl(difluoro)methyl] phenyl]-3-[3-(fluoromethyl) azetidine-1-carbonyl]-2-(3-methylpyrazin-2-yl)-4H-pyrazolo [1,5-a]pyrimidin-7-one, 5-[4-(1-cyclopentylcyclopropyl)phenyl]-3-[3-(fluoromethyl) azetidine-1-carbonyl]-2-pyrimidin-2-yl-4H-pyrazolo [1,5-a]pyrimidin-7-one, 5-(4-butylphenyl)-3-[3-(fluoromethyl) azetidine-1-carbonyl]-2-(3-methylpyrazin-2-yl)-4H-pyrazolo [1,5-a]pyrimidin-7-one, 5-[4-(1-fluorocyclohexyl)phenyl]-3-[3-(fluoromethyl) azetidine-1-carbonyl]-2-(3-methylpyrazin-2-yl)-4H-pyrazolo [1,5-a]pyrimidin-7-one, 3-[3-(fluoromethyl) azetidine-1-carbonyl]-2-(3-methylpyrazin-2-yl)-5-(4-phenylphenyl)-4H-pyrazolo [1,5-a]pyrimidin-7-one, 1-[5-(4-cyclohexylphenyl)-7-oxo-2-[2-hydroxy-1-methyl-ethyl]-4H-pyrazolo [1,5-a]pyrimidine-3-carbonyl] pyrrolidine-3-carbonitrile, 1-[5-(4-cyclohexylphenyl)-7-oxo-2-[2-hydroxy-1-methyl-ethyl]-4H-pyrazolo [1,5-a]pyrimidine-3-carbonyl] pyrrolidine-3-carbonitrile, 5-(4-cyclohexylphenyl)-3-[3-(fluoromethyl) azetidine-1-carbonyl]-2-[2-hydroxy-1-methyl-ethyl]-4H-pyrazolo [1,5-a]pyrimidin-7-one, 5-(4-cyclohexylphenyl)-3-[3-(fluoromethyl) azetidine-1-carbonyl]-2-[2-hydroxy-1-methyl-ethyl]-4H-pyrazolo [1,5-a]pyrimidin-7-one, 2-(3-methylpyrazin-2-yl)-3-[3-(fluoromethyl)-2-methyl-azetidine-1-carbonyl]-5-[4-[2,2,2-trifluoro-1-phenyl-ethoxy] phenyl]-4H-pyrazolo [1,5-a]pyrimidin-7-one, 3-[3-(fluoromethyl) azetidine-1-carbonyl]-2-(3-methylpyrazin-2-yl)-5-[4-[2,2,2-trifluoro-1-phenyl-ethoxy] phenyl]-4H-pyrazolo [1,5-a]pyrimidin-7-one, 2-(3-methylpyrazin-2-yl)-3-[3-(fluoromethyl)-2-methyl-azetidine-1-carbonyl]-5-[4-[2,2,2-trifluoro-1-phenyl-ethoxy] phenyl]-4H-pyrazolo [1,5-a]pyrimidin-7-one, 3-[3-(fluoromethyl) azetidine-1-carbonyl]-2-(3-methylpyrazin-2-yl)-5-[4-[2,2,2-trifluoro-1-phenyl-ethoxy] phenyl]-4H-pyrazolo [1,5-a]pyrimidin-7-one, 5-(4-cyclopentylphenyl)-2-(3-methylpyrazin-2-yl)-3-[3-(fluoromethyl)-2-methyl-azetidine-1-carbonyl]-4H-pyrazolo [1,5-a]pyrimidin-7-one, 2-(3-methylpyrazin-2-yl)-3-[3-(fluoromethyl)-2-methyl-azetidine-1-carbonyl]-5-[non-1-enyl]-4H-pyrazolo [1,5-a]pyrimidin-7-one, 2-(3-methylpyrazin-2-yl)-5-nonyl-3-[3-(fluoromethyl)-2-methyl-azetidine-1-carbonyl]-4H-pyrazolo [1,5-a]pyrimidin-7-one, 2-(3-methylpyrazin-2-yl)-3-[3-(fluoromethyl)-2-methyl-azetidine-1-carbonyl]-5-[4-(1,2,2,3,3,4,4,5,5,6,6-undecadeuteriocyclohexyl)phenyl]-4H-pyrazolo [1,5-a] pyrimidin-7-one, 5-[4-(2,2-dimethylpropyl)phenyl]-2-(3-methylpyrazin-2-yl)-3-[3-(fluoromethyl)-2-methyl-azetidine-1-carbonyl]-4H-pyrazolo [1,5-a]pyrimidin-7-one, and 5-(4-cyclohexylphenyl)-3-[3-(fluoromethyl) azetidine-1-carbonyl]-2-[morpholin-2-yl]-4H-pyrazolo [1,5-a]pyrimidin-7-one, or a pharmaceutically acceptable salt, stereoisomer, tautomer, or deuterated analog thereof.

16. A pharmaceutical composition comprising a compound of claim 1, and a therapeutically inert carrier.

17. A method for the therapeutic treatment of cancer in a subject, which method comprises administering to said subject an effective amount of a compound of claim 1.

18. The method of claim 17, wherein the cancer is a solid tumor.

19. The method of claim 17, wherein the cancer is selected from the group consisting of lung, liver, ovarian, breast and squamous cancer.

20. A method of preparing a compound of claim 1, comprising reacting

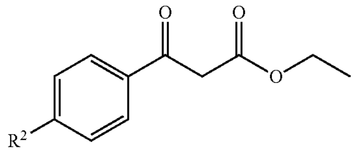

with

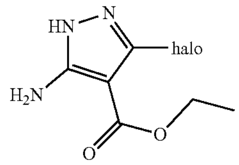

to form

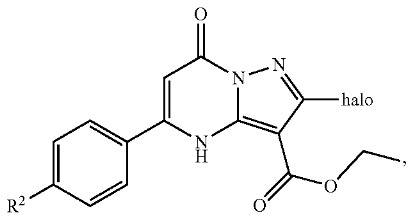

wherein $R^2$ is halo, OH, cyano, or optionally substituted $C_{1-6}$alkyl, $C_{1-6}$haloalkyl, $C_{1-6}$alkoxy, $C_{6-10}$aryl or $C_{3-10}$cycloalkyl.

21. The compound 5-(4-cyclohexylphenyl)-3-(3-(fluoromethyl) azetidine-1-carbonyl)-2-(3-methylpyrazin-2-yl) pyrazolo [1,5-a]pyrimidin-7 (4H)-one.

* * * * *